United States Patent
Vandekerckhove et al.

(10) Patent No.: US 6,908,740 B2
(45) Date of Patent: Jun. 21, 2005

(54) METHODS AND APPARATUS FOR GEL-FREE QUALITATIVE AND QUANTITATIVE PROTEOME ANALYSIS, AND USES THEREFORE

(76) Inventors: Joel Vandekerckhove, Rode Beukendreef 27, B-8210 Loppem (BE); Kris Gevaert, Narcislaan 179, B-9240 Zele (BE)

(*) Notice: Subject to any disclaimer, the term of this patent is extended or adjusted under 35 U.S.C. 154(b) by 108 days.

(21) Appl. No.: 10/394,980

(22) Filed: Mar. 21, 2003

(65) Prior Publication Data

US 2004/0005633 A1 Jan. 8, 2004

Related U.S. Application Data

(63) Continuation of application No. PCT/EP02/03368, filed on Mar. 22, 2002
(60) Provisional application No. 60/323,999, filed on Sep. 20, 2001, provisional application No. 60/318,749, filed on Sep. 12, 2001, and provisional application No. 60/278,171, filed on Mar. 22, 2001.

(51) Int. Cl.$^7$ ............... G01N 33/53; C12Q 1/37; C12Q 1/00; A23J 1/00; C07K 1/00
(52) U.S. Cl. ............... 435/7.1; 435/23; 435/24; 435/4; 435/803; 435/287.2; 530/417; 530/300
(58) Field of Search ............... 435/7.1, 23, 24, 435/4, 803, 287.2; 530/417, 300

(56) References Cited

U.S. PATENT DOCUMENTS

2004/0005633 A1 * 1/2004 Vandekerckhove et al. .. 435/7.1

OTHER PUBLICATIONS

Zhang et al,"Fabrication of Isotopically labeled peptides in quantitative proteomics",Nov. 1, 2001,Analytical Chemistry, 73(21),pp. 5142,(Abstract Only).*

* cited by examiner

Primary Examiner—Louise N. Leary
(74) Attorney, Agent, or Firm—Lahive & Cockfield, LLP; DeAnn F. Smith, Esq.

(57) ABSTRACT

Methods and apparatus for qualitative and quantitative proteome analysis are provided. The methods and apparatus allow for the isolation of a subset of peptides out of complex mixtures of peptides. The isolation is based on a specific chemical and/or enzymatic alteration of one or more types of peptides. This alteration modifies the biophysical, chemical or any other biochemical property of the affected types of peptides (e.g., net electrical charge and/or hydrophobicity) in such way that the altered peptides can be separated from the unaltered peptides.

4 Claims, 25 Drawing Sheets

Figure 3 A - C
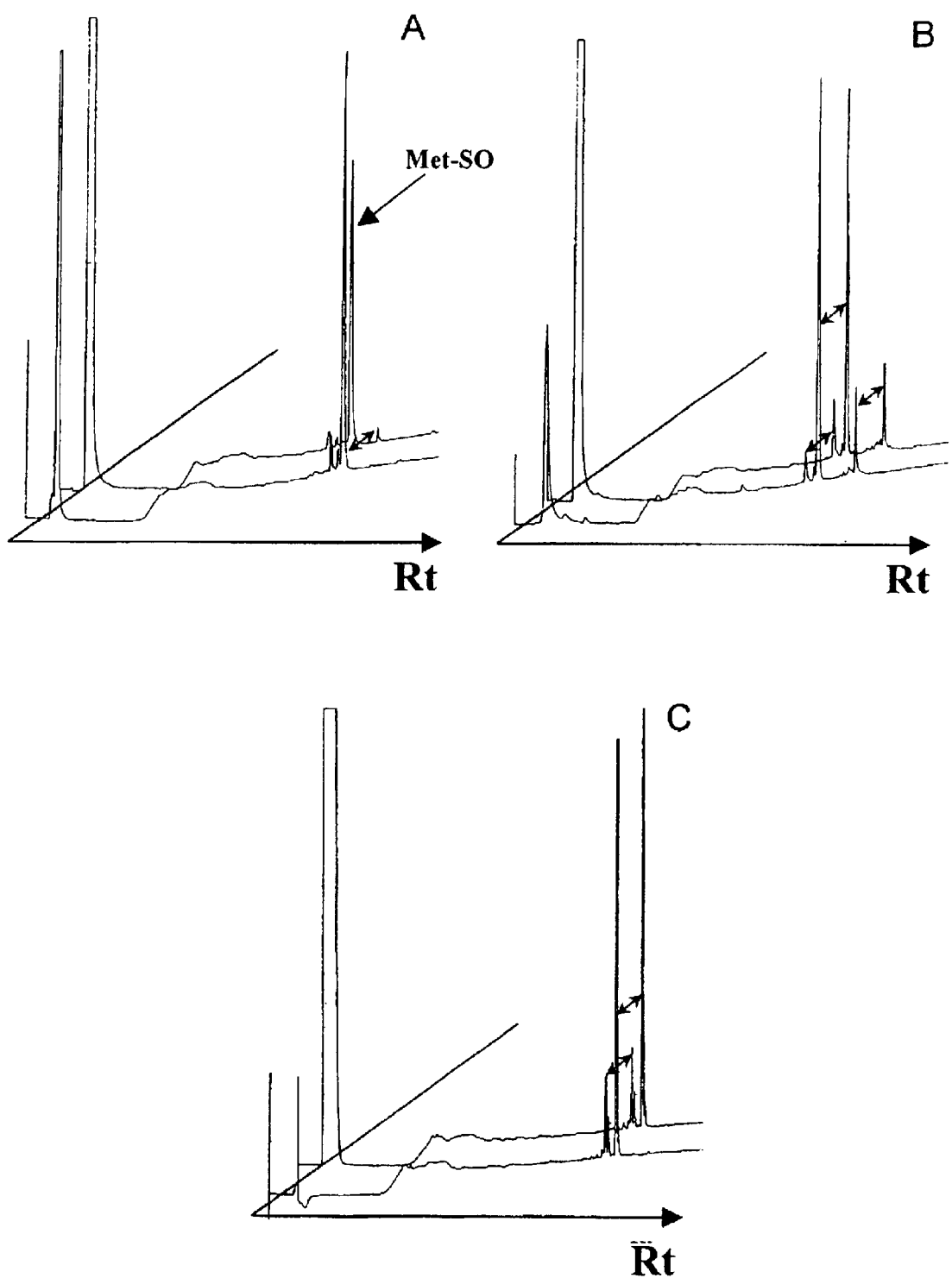

Are not changed and will therefore elute at the same position.
Notice that *in vivo* blocked proteins can be distinguished from chemically modified $NH_2$- termini Will be more hydrophobic and are therefore retained Sample 1:

Sample 2:

Mix the two samples and sort for the methionine-containing peptides:

The heavy and light peptides are chemically extremely similar and will elute at the same time. They will also ionize in an identical manner. Measure the ratio of heavy/light peptide ions by MS.

METHODS AND APPARATUS FOR GEL-FREE QUALITATIVE AND QUANTITATIVE PROTEOME ANALYSIS, AND USES THEREFORE

RELATED APPLICATIONS

The present application claims priority from U.S. provisional patent application Ser. No. 60/323,999, filed on Sep. 20, 2001, and from U.S. provisional patent application Ser. No. 60/318,749, filed on Sep. 12, 2001. The present application also claims priority from U.S. provisional patent application Ser. No. 60/278,171, filed on Mar. 22, 2001. The present application additionally claims priority from PCT application no. PCT/EP02/03368, filed Mar. 22, 2002. All of the above applications are expressly incorporated by reference.

SUMMARY OF THE INVENTION

Methods and apparatus for qualitative and quantitative proteome analysis are provided. The methods and apparatus allow for the isolation of a subset of peptides out of complex mixtures of peptides. The isolation is based on a specific chemical and/or enzymatic alteration of one or more types of peptides. This alteration modifies the biophysical, chemical or any other biochemical property of the affected types of peptides (e.g., net electrical charge and/or hydrophobicity) in such way that the altered peptides can be separated from the unaltered peptides.

In one embodiment, this alteration is applied in between a first chromatographic separation of the complex mixture of peptides and a second chromatographic separation of the altered complex mixture, using the same type of chromatographic separation in the first and second separation. The "same type of chromatographic separation" means that both the first and the second chromatographic separations are based on hydrophobicity or both the first and the second chromatographic separation are based on ion exchange. The methods of the present invention therefore utilize a first separation step whereby complex mixtures of peptides are separated in fractions on the basis of their elution or migration patterns. Subsequently, each fraction is subjected to a specific alteration reaction which may be chemically or enzymatically or chemically and enzymatically driven. Each fraction is then re-subjected to a second separation. Based on the i) type of alteration and ii) the separation conditions, the altered subset of peptides in each fraction will elute or migrate separated from the unaltered peptides.

In addition, the present invention provides an apparatus for performing the methods in a selective and efficient manner, using either a single column system or a multi-column system of identical or similar columns, which may be run either in an exclusive parallel, exclusive serial or in a combined serial/parallel mode. The isolated peptides may then be gradually and serially released and passed to analytical systems for identification.

BACKGROUND OF THE INVENTION

The proteome has been defined as the entire complement of proteins expressed by a cell, tissue type or organism, and accordingly, proteomics is the study of this complement expressed at a given time or under certain environmental conditions. Such a global analysis requires that thousands of proteins be routinely identified and characterized from a single sample. Two-dimensional polyacrylamide gel electrophoresis (2D-PAGE) is considered an important tool for proteomics, producing separations that display up to thousands of protein spots on the 2D-gel. Proteins in a gel can be detected by the use of various stains, allowing to a certain extent, quantification and comparison among gels from different samples. Identification of proteins is possible, for example, by excising a protein spot and digesting the spot with a protease of well-known specificity. The peptides resulting from such cleavage have particular masses which subsequently may be determined by mass spectrometry. These data are compared with the masses of peptides in databases. The latter masses are in silico data which are obtained by computing the molecular weight of each protein and its cleavage fragments starting from for instance DNA sequence data. When a spectrometrically, accurately determined mass of a peptide matches with the mass of an in silico peptide, this is often sufficient to annotate the peptide to its parent protein. Or, vice versa, a particular protein in a sample can be identified by identifying one or more of its constituent peptide fragments (so called peptide mass fingerprinting).

However, 2D-PAGE is sequential, labour intensive, and difficult to automate. In addition, specific classes of proteins, such as membrane proteins, very large and small proteins, and highly acidic or basic proteins, are difficult to analyze using this method. Another significant flaw lies in its bias toward highly abundant proteins, as lower abundant regulatory proteins (such as transcription factors and protein kinases) are rarely detected when total cell lysates are analyzed.

Because of such shortcomings, scientists have searched for alternative approaches to analyze the proteome without the need to purify each protein to homogeneity. These technologies are referred to herein as "gel-free systems" and do not use a gel separation step. The peptide mass fingerprinting approach has taught us that proteins can be identified on the basis of the mass of one or more of their constituting peptides. One approach to analyse proteins in a biological sample has been to proteolyse the proteins and to determine the mass of the resulting peptides. In so far the sample only contains a small amount of different proteins, the number of resulting peptides is small and can be identified by separating the peptides chromatographically followed by analysis with mass spectrometry. In most complex biological samples, the proteolysis of the proteins will produce thousands of peptides and this overwhelms the resolution capacity of any known chromatographic system. It results in the co-elution and therefore inefficient separation and isolation of individual peptides. In addition, the resolving power of mass spectrometry coupled with such chromatography is not sufficient to adequately determine the mass of the individual peptides. One approach to improve the resolution of complex mixtures of peptides is to make use of multidimensional chromatography such as the recently described process of direct analysis of large protein complexes (DALPC) (Link et al. (1999) The DALPC process uses the independent physical properties of charge and hydrophobicity to resolve complex peptide mixtures via a combination of strong cation exchange—and reversed-phase chromatography. While this strategy improves the separation of the complex mixture in its individual components, the resolving power of this approach is still largely insufficient to reproducibly identify the constituting peptides in biological samples. Further disadvantages of the DALPC method are the incompatibility with the analysis of low-abundance proteins and the fact that the method cannot be used quantitatively.

A second recently described approach, the ICAT-method, is based on the use of a combination of new chemical reagents named isotope-coded affinity tags (ICATs) and tandem mass spectrometry (Gygi et al (1999) ). The ICAT-method is based on the modification of cysteine-containing proteins by an iodacetate derivative carrying a biotin label. After enzymatically cleaving the modified proteins into peptides only the cystein-modified, labeled peptides are pulled down with streptavidine-coated beads in an affinity purification step. The affinity purification step reduces the complexity of the original peptide mixture making the separation of the constituting peptides via liquid chromatography combined with mass spectrometry a more feasible and realistic objective. However, disadvantages are that an affinity purification step generally necessitates the use of greater amounts of starting material because of the loss of material during the purification step. In addition, the ICAT label is a relatively large modification (~500 Da) that remains on each peptide throughout the MS analysis complicating the database-searching algorithms especially for small peptides. The method also fails for proteins that contain no cysteine residues. Moreover, due to an affinity purification step the modified peptides are generated at once and are liberated in a so-called compressed mixture. This means that there is no optimal chromatographic separation and a less efficient mass spectrometric detection of the modified peptides. Similarly, two other publications (Geng el al., 2000 and Ji et al., 2000) use affinity chromatography to select a subset of peptides and use isolated signature peptides to identify the corresponding parent proteins.

The present invention describes a novel gel-free methodology for qualitative and quantitative proteome analysis without the need for multidimensional chromatography and without the use of affinity tags. The methodology is very flexible, can be applied to a plethora of different classes of peptides and is even applicable to biological samples comprising small numbers of cells.

DETAILED DESCRIPTION OF THE INVENTION

Figure 1:
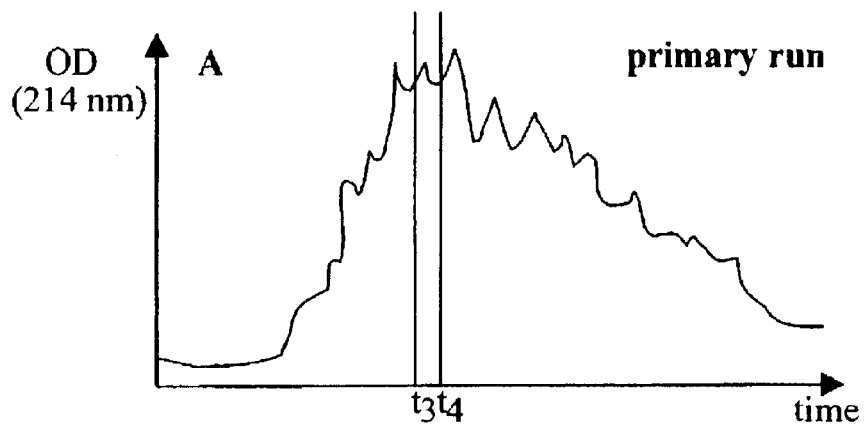
FIG. 1: Schematic demonstrating the direct peptide sorting process and indicating the different parameters used to describe the sorting process. (A) The total protein peptide mixture separated in the primary run; $t_3$ and $t_4$ indicate the time interval taken for a given fraction ($w_1$). (B) Flagged peptides display hydrophilic shifts between $\delta_{min}$ and $\delta_{max}$. They elute between time intervals $t_1$ and $t_2$ in window $w_2$. (C) Flagged peptides are more hydrophobic, show hydrophobic shifts between $\delta'_{min}$ and $\delta'_{max}$, elute between times $t_5$ and $t_6$ in window $w_2'$.
Figure 1:
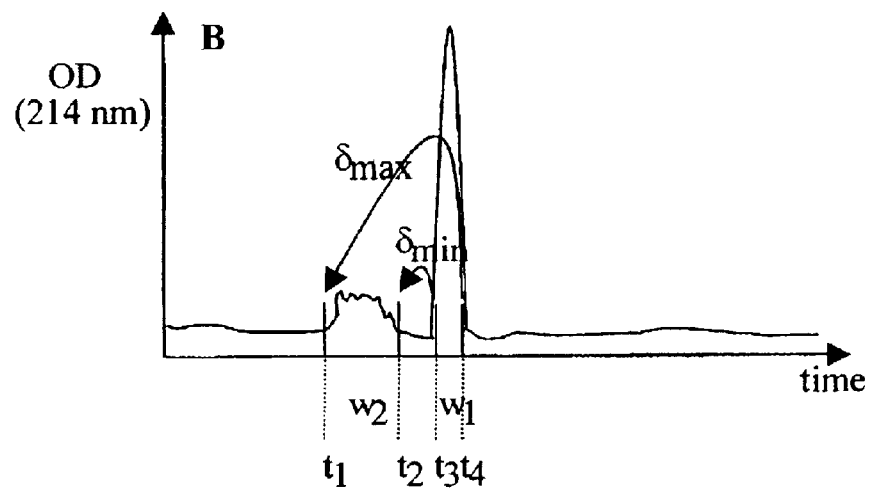
Figure 1:
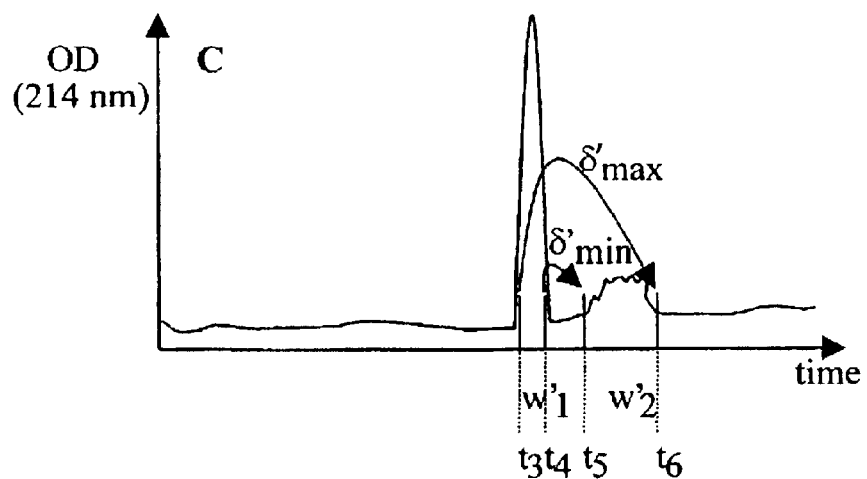

The present invention provides a method and an apparatus for the isolation and identification of a subset of peptides from a complex mixture of peptides.

The method utilizes a combination of two chromatographic separations of the same type, separated by a step in which a selected population of the peptides is altered in such a way that the chromatographic behaviour of the altered peptides in the second chromatographic separation differs from the chromatographic behaviour of its unaltered version.

To isolate a subset of peptides out of a protein peptide mixture, the current invention can be applied in two action modes. In a first mode a minority of the peptides in the protein peptide mixture are altered and the subset of altered peptides is isolated. In this action mode the altered peptides are called flagged peptides. In a second, reverse mode, the majority of the peptides in the protein peptide mixture are altered and the subset of unaltered peptides is isolated. In this action mode the unaltered peptides are called the identification peptides.

In one embodiment, the invention provides for a method for the isolation of a subset of peptides out of a protein peptide mixture, comprising the steps of: (a) separating the protein peptide mixture into fractions of peptides via chromatography; (b) chemically, or enzymatically, or chemically and enzymatically, altering at least one amino acid of at least one of the peptides in each fraction, thereby generating a subset of altered peptides; and (c) isolating said altered or so-called flagged peptides out of each fraction via chromatography, wherein the chromatography of steps (a) and (c) is performed with the same type of chromatography.

In another embodiment, the invention provides a method for the isolation of a subset of peptides out of a protein peptide mixture, comprising the steps of a) an initial separation of the protein peptide mixture in fractions via chromatography, b) chemically or enzymatically or chemically and enzymatically altering at least one amino acid in the majority of the peptides in each fraction, thereby generating a subset of unaltered peptides, and c) isolating said unaltered or so-called identification peptides via a second chromatography whereby the chromatography of the initial and the second separation step is performed with the same type of chromatography.

The same type of chromatography means that the type of chromatography is the same in both the initial separation and the second separation. The type of chromatography is for instance in both separations based on the hydrophobicity of the peptides. Similarly, the type of chromatography can be based in both steps on the charge of the peptides and the use of ion-exchange chromatography. In still another alternative, the chromatographic separation is in both steps based on a size exclusion chromatography or any other type of chromatography.

The first chromatographic separation, before the alteration, is hereinafter referred to as the "primary run" or the "primary chromatographic step" or the "primary chromatographic separation" or "run 1". The second chromatographic separation of the altered fractions is hereinafter referred to as the "secondary run" or the "secondary chromatographic step" or the "secondary chromatographic separation" or "run 2".

In a preferred embodiment of the invention the chromatographic conditions of the primary run and the secondary run are identical or, for a person skilled in the art, substantially similar. Substantially similar means for instance that small changes in flow and/or gradient and/or temperature and/or pressure and/or chromatographic beads and/or solvent composition is tolerated between run 1 and run 2 as long as the chromatographic conditions lead to an elution of the altered peptides that is predictably distinct from the non-altered peptides and this for every fraction collected from run 1.

As used herein, a "protein peptide mixture" is typically a complex mixture of peptides obtained as a result of the cleavage of a sample comprising proteins. Such sample is typically any complex mixture of proteins such as, without limitation, a prokaryotic or eukaryotic cell lysate or any complex mixture of proteins isolated from a cell or a specific organelle fraction, a biopsy, laser-capture dissected cells or any large protein complexe such as ribosomes, viruses and the like. It can be expected that when such protein samples are cleaved into peptides that they may contain easily up to 1.000, 5.000, 10.000, 20.000, 30.000, 100.000 or more different peptides. However, in a particular case a "protein peptide mixture" can also originate directly from a body fluid or more generally any solution of biological origin. It is well known that, for example, urine contains, besides proteins, a very complex peptide mixture resulting from proteolytic degradation of proteins in the body of which the peptides are eliminated via the kidneys. Yet another illustration of a protein peptide mixture is the mixture of peptides present in the cerebrospinal fluid.

More generally speaking, the invention applies to any complex mixture of peptides. As used herein, a "complex mixture of peptides" refers to a mixture of more than 100 different peptides, typically more than 500 different peptides and even more typically more than 1.000 different peptides. In the present invention the wording "protein peptide mixture" and "complex mixture of peptides" are used interchangeable.

Also as used herein, "a subset of peptides" out of a protein peptide mixture means a certain fraction of the total number of peptides present in the protein peptide mixture. Such fraction is certainly less than 50% of the initial number of peptides and will represent typically less than 20%, and even more typically less than 10% of the initial number of peptides in the protein peptide mixture.

The term "altering" or "altered" or "alteration" as used herein in relation to a peptide, refers to the introduction of a specific modification in an amino acid of a peptide, with the clear intention to change the chromatographic behaviour of such peptide containing said modified amino acid. An "altered peptide" as used herein is a peptide containing an amino acid that is modified as a consequence of an alteration.

Such alteration can be a stable chemical or enzymatical modification. Such alteration can also introduce a transient interaction with an amino acid. Typically an alteration will be a covalent reaction, however, an alteration may also consist of a complex formation, provided the complex is sufficiently stable during the chromatographic steps.

Typically, an alteration results in a change in hydrophobicity such that the altered peptide migrates different from its unaltered version in hydrophobicity chromatography. Alternatively, an alteration results in a change in the net charge of a peptide, such that the altered peptide migrates different from its unaltered version in an ion exchange chromatography, such as an anion exchange or a cation exchange chromatography. Also, an alteration may result in any other biochemical, chemical or biophysical change in a peptide such that the altered peptide migrates different from its unaltered version in a chromatographic separation. The term "migrates differently" means that a particular altered peptide elutes at a different elution time with respect to the elution time of the same non-altered peptide.

Altering can be obtained via a chemical reaction or an enzymatic reaction or a combination of a chemical and an enzymatic reaction. A non-limiting list of chemical reactions include alkylation, acetylation, nitrosylation, oxidation, hydroxylation, methylation, reduction and the like. A non-limiting list of enzymatic reactions includes treating peptides with phosphatases, acetylases, glycosidases or other enzymes which modify co- or post-translational modifications present on peptides. The chemical alteration can comprise one chemical reaction, but can also comprise more than one reaction (e.g. a β-elimination reaction and an oxidation) such as for instance two consecutive reactions in order to increase the alteration efficiency. Similarly, the enzymatic alteration can comprise one or more enzymatic reactions.

Another essential feature of the alteration in the current invention is that the alteration allows the isolation of a subset of peptides out of protein peptide mixture. A chemical and/or enzymatic reaction which results in a general modification of all peptides in a protein peptide mixture will not allow the isolation of a subset of peptides. Therefore an alteration has to alter a specific population of peptides in a protein peptide mixture to allow for the isolation of a subset of peptides in the event such alteration is applied in between two chromatographic separations of the same type.

One approach to be able to isolate a subset of peptides composed of flagged peptides is to target the alteration to a rare amino acid. A rare amino acid is considered as an amino acid that is not too abundantly present in the complex mixture of peptides. For example, if the specific amino acid would be represented too abundantly in the peptide mixture (e.g. in more than 50% of the peptides), then too many peptides would be selected and efficient separation and isolation of flagged peptides would again become impossible. Preferably less than 30%, 25%, 20%, 15%, 10%, 5%, 1%, 0.1%, 0.01% or even less of the peptides from the complex mixture of peptides are selected.

In a preferred embodiment, the specific amino acid selected for alteration comprises one of the following amino acids: methionine (Met), cysteine (Cys), histidine (His), tyrosine (Tyr), lysine (Lys), tryptophan (Trp), arginine (Arg), proline (Pro) or phenylalanine (Phe).

Alternatively, the alteration is specifically targeted to a population of amino acids carrying a co- or posttranslational modification. Examples of such co- or posttranslational modifications are glycosylation, phosphorylation, acetylation, formylation, ubiquitination, pyrroglutamylation, hydroxylation, nitrosylation, ε-N-acetylation, sulfation, $NH_2$-terminal blockage. Examples of modified amino acids altered to isolate a subset of peptides according to the current invention are phosphoserine (phospho-Ser), phospho-threonine (phospho-Thr), phospho-histidine (phosho-His), phospho-aspartate (phospho-Asp) or acetyl-lysine.

A further non-limiting list of examples of amino acids that can be altered and can be used to select a subset of peptides are other modified amino acids (e.g. a glycosylated amino acid), artificially incorporated D-amino acids, seleno-amino acids, amino acids carrying an unnatural isotope and the like. An alteration can also target a particular residue (e.g. a free $NH_2$-terminal group) on one or more amino acids or modifications added in vitro to certain amino acids.

In a preferred embodiment of the invention, the amino acid selected to be altered should be rare, but nevertheless present in the vast majority of the proteins in the sample comprising proteins. This embodiment allows to isolate flagged peptides representing the vast majority of proteins in the sample. The vast majority of the proteins should contain at least one and preferably two, three or a limited number of residues of the selected amino acid. For example Cysteine is a rare amino acid and only 14.55% of the proteins and/or open reading frames from E. coli genomic sequences do not contain Cys. These numbers are 11.34% for Trp, 4.12% for His and 0.32% for Met respectively. The latter increases to 3.17%, after omitting the initiator methionine, which is frequently processed. A similar theoretical analysis using other genomic sequences stored in the Swiss-Prot database (release 39.0) is summarized in Table I. These studies reveal that among the rare amino acids, methionine represents an excellent protein representativity in species as diverse as mammals, yeast and E. coli. More than 96% of the proteins contain at least one internal methionine. This number is consistently lower for cysteine which is, depending on the organism, present in 85% to 95% of the predicted proteins. These values are in line with the results of earlier studies based on the fragment corrected SWISS-PROT and SWISS-NEW annotated database, using 72,101 sequences indicated 2.3% of the proteins did not contain Met, while 12.8% of the proteins were lacking Cys (Vuong et al., 2000). In addition, these studies revealed a more homogeneous distribution of Met than Cys over the different proteins. Methionine is an amino acid that is preferably targeted for alteration in the current invention. Cysteine, histidine and tryptophane are also preferred amino acids. Other less frequently observed amino acids such as lysine, phenylalinine and tyrosine can also be used in the invention. The choice of an amino acid to alter also depends upon the complexity and origin (e.g. plants, animals, bacteria, or viruses) of the sample proteins. For example, in plants, methionine is an underrepresented amino acid and, therefore, it is more appropriate to select an amino acid such as cysteine as a specific amino acid to alter.

Alternatively the specific chemical and/or enzymatic reaction has a specificity for more than one amino acid residue (e.g. both phosphoserine and phosphothreonine or the combination of methionine and cysteine) and allows separation of a subset of peptides out of a protein peptide mixture. Typically the number of selected amino acids to be altered will however be one, two or three. In another aspect, two different types of selected amino acids can be altered in a protein peptide mixture and a subset of flagged peptides containing one or both altered amino acids can be isolated.

In yet another aspect, the same peptide mixture can be altered first on one amino acid, a subset of flagged peptides can be isolated and, subsequently, a second alteration can be made on the remaining previously unaltered sample and another subset of flagged peptides can be isolated.

The current invention requires that the alteration is effective in each of the peptide fractions from the primary run. Thus, in each fraction obtained from the primary chromatographic step, the flagged peptides have to migrate distinctly from the unaltered peptides in the secondary chromatographic step. The alteration of an amino acid in a flagged peptide induces a shift in the elution of said flagged peptide. Depending on the type of applied alteration, the shift may be caused by a change in the hydrophobicity, the net charge and/or the affinity for a ligand (e.g. a metal ion) of the flagged peptides. This shift is called δp and is specific for every individual flagged peptide. In the example of a change in hydrophobicity, δp-values can be expressed as changes in the hydrophobic moment, or as a percentage of organic solvents in chromatographic runs, but most practically in time units under given chromatographic/electrophoretic conditions. Thus δp is not necessary identical for every flagged peptide and lies in-between $\delta_{max}$ and $\delta_{min}$ (see FIG. 1). δp is affected by a number of factors such as the nature of the induced alteration, the nature of the colunm stationary phase, the mobile phase (buffers, solvents), temperature and others. All δp values taken together delineate the extremes of $\delta_{max}$ and $\delta_{min}$ (see FIG. 1). Given $t_1$ and $t_2$, the times delineating the beginning and the end of the interval of the shifted flagged peptides, and $t_3$ and $t_4$, the times enclosing the fraction taken from the primary run, then $\delta_{min}$ (the minimal shift) will be determined by $t_3-t_2$, while $\delta_{max}$ (the maximal shift) will be determined by $t_4-t_1$. Window $w_1$ is the fraction window taken from the primary run $w_1=t_4-t_3$. Window $w_2$ is the window in which the flagged peptides will elute $w_2=t_2-t_1$. Thus: $\delta_{min}=t_3-t_2$; $\delta_{max}=t_4-t_1$; $w_1=\delta_{max}+t_1-\delta_{min}-t_2$ and $w_2=t_2-t_1=\delta_{max}-\delta_{min}-w_1$. Important elements in the sorting process are: $\delta_{min}$, delineating the distance between the unaltered and the least shifted of the flagged peptides in a given fraction and $w_2$, the time-window in which flagged compounds are eluted. The word 'sorted' is in this invention equivalent to the word 'isolated'.

$\delta_{min}$ has to be sufficient to avoid that flagged peptides elute within window $w_1$ (and as such would overlap with the unaltered peptides), and this rule should apply for every fraction collected from the primary run. Preferentially $\delta_{min}$ should be w1 or larger in order to minimize overlap between flagged and unaltered peptides. For instance, if w1=1 minute, $\delta_{min}$ should by preference be 1 minute or more.

Avoiding overlap or co-elution of flagged peptides improves the possibility of identifying an optimal number of individual peptides. From this perspective, the size of window $w_2$ has an impact on the number of peptides that can be identified. Larger values of $w_2$ result in a decompression of the flagged peptide elution time, providing a better isolation of flagged peptides and a better opportunity for analysis by gradually presenting the compounds for identification to analysers such as mass spectrometers. While window $w_2$ may be smaller than $w_1$, in a preferred embodiment, $w_2$ will be larger than $w_1$. For instance if $w_1$=1 minute, $w_2$ can be 1 minute or more. It is preferred that the size of $w_2$, and the value of $\delta_{min}$ and $\delta_{max}$ are identical or very similar for every fraction collected from the primary run. It is however self-evident that minor contaminations of unaltered peptides in the elution window of the flagged peptides is not preferred, but it is acceptable.

Manipulation of the values of $\delta_{min}$, $\delta_{max}$ and $w_2$ to obtain optimal separation of the flagged peptides from the unaltered peptides in each primary run fraction is part of the current invention and comprises, among others, the right combination of the amino acid(s) selected for alteration, the type of alteration, and the chromatographic conditions (type of column, buffers, solvent, etc.).

While the aspects of the hydrophilic shift have been worked out herein above, a similar description could also be provided where a hydrophobic shift was induced in order to separate the flagged peptides from the non-altered peptides. Here $t_3$ and $t_4$ define window $W_1$ in which the unaltered peptides elute, while $t_5$ and $t_6$ define the window $w_2$ in which the flagged peptides elute. The maximum hydrophobic shift $\delta_{max}=t_6-t_3$, the minimum shift=$t_5-t_4$ (FIG. 1C). It will be appreciated that similar calculations for conditions in which fractions are pooled may be used.

It is obvious for a person skilled in the art that the same approach can be applied to isolate flagged peptides with for instance ion exchange chromatography, or other types of chromatography.

In one embodiment, the invention provides a method for the isolation of methionine-containing peptides out of a protein peptide mixture, comprising the steps of (a) separating the protein peptide mixture into fractions via a primary run, (b) chemically altering methionine in the peptides of each peptide fraction and (c) isolating the flagged methionine-containing peptides via a secondary run. In a particular embodiment the primary and secondary run are chromatographic separations based on hydrophobicity and the alteration of methionine induces a hydrophilic shift in the flagged methionine-containing peptides. In a further particular embodiment the hydrophobic chromatography is performed with a reverse phase column and the alteration of methionine is obtained with a mild oxidation. In yet another embodiment the primary run and secondary run are based on ion exchange chromatography and the alteration of methionine is a chemical reaction with an alkylhalide such as methyliodide. This reaction induces a change in charge on the flagged peptides and allows to separate the flagged peptides in the secondary run on an ion exchange column.

In another embodiment the invention provides a method for the isolation of phosphorylated peptides out of protein peptide mixture comprising the steps of (a) separating the protein peptide mixture into fractions via a primary run, (b) enzymatically and/or chemically altering the phosphopeptides in each of the fractions and (c) isolating the flagged phosphopeptides via a secondary run. In a particular embodiment the primary and secondary run are chromatographic separations based on hydrophobicity and the alteration of the phosphopeptides is a treatment with phosphatases. The dephosphorylated flagged peptides undergo a hydrophobic shift and can therefore be isolated from the bulk of unaltered peptides in each fraction via a secondary run on a hydrophobic column. It will be appreciated that specific phosphatases can be used to isolate specific phosphopeptides. A phospatase specific for phosphotyrosines can be used to isolate peptides containing a phosphorylated tyrosine.

In yet another embodiment the invention provides a method for the isolation of flagged peptides altered on methionine and/or cysteine out of a protein peptide mixture comprising the steps of (a) separating the protein peptide mixture into fractions via a primary run, (b) chemically altering the methionine- and cysteine-residues in the peptides present in each of the fractions and (c) isolating the flagged methionine- and cysteine-peptides via a secondary run. In yet another embodiment the invention provides a method for the isolation of flagged peptides altered on cysteine out of a sample comprising proteins comprising the steps of (a) oxidizing the protein sample (b) generating a protein peptide mixture, (c) separating the protein peptide mixture into fractions via a primary run, (d) chemically altering the cysteine-residues present in the peptides in each of the fractions and (e) isolating the flagged cysteine-peptides via a secondary run. In yet another embodiment the invention provides a method for the isolation of flagged peptides altered on phospho-serine and/or phospho-threonine out of a sample comprising proteins comprising the steps of (a) oxidizing the protein sample, (b) separating the protein peptide mixture into fractions via a primary run, (c) enzymatically altering the peptides comprising phospho-serine and/or phospho-threonine in each of the fractions and (d) isolating the flagged phospho-serine and phospho-threonine peptides via a secondary run.

In yet another embodiment the invention provides a method for the isolation of a subset of peptides out of a protein peptide mixture comprising the steps of (a) separating the protein peptide mixture into fractions via a primary run, (b) adding a chelating agent to each of the primary fractions and (c) isolating the chelated peptides via a secondary run. Said chelating compounds can be small complex-forming molecules, co-factors, antibodies and the like.

In yet another embodiment the invention provides a method for the isolation of phosphorylated peptides out of a protein peptide mixture comprising the steps of (a) separating the protein peptide mixture into fractions via a primary run, (b) adding at least one chelating compound to said primary fractions and (c) isolating the phosphorylated peptides via a secondary run. In a specific embodiment the chelating compound used for the isolation of phosphorylated peptides comprises $Fe^{3+}$ and iminodiacetate.

In yet another embodiment the invention provides a method to isolate a subset of peptides out of a protein peptide mixture comprising the steps of (a) separating the protein peptide mixture into fractions via a primary run, (b) chemically or enzymatically adding a bulky and voluminous entity to at least one amino acid in at least one of the peptides in each fraction and (c) isolating said flagged peptides out of each fraction via a secondary run, whereby the primary and secondary run are performed on a size exclusion column under identical or substantially similar conditions.

In yet another embodiment the invention provides a method for the isolation of glycosylated peptides out of a protein peptide mixture comprising the steps of (a) separating the protein peptide mixture into fractions via a primary run, (b) chemically and/or enzymatically altering the glycosylation structures present on the peptides in each of the fractions and (c) isolating the flagged peptides comprising altered glycosylation structures via a secondary run. In a specific embodiment the alteration of the glycosylation structures can, for instance, be a chemical and/or enzymatic deglycosylation or, alternatively, the glycosylgroups may be converted into moieties with different biophysical or biochemical properties such that they can be separated from the otherwise co-eluting non-altered peptides. For example, sialylated glycosyl chains can be desialylated by neuraminidase treatment, resulting in shifts on a chromatographic medium.

In yet another embodiment the invention provides a method for the isolation of $\epsilon$-N-acetylated peptides out of a protein peptide mixture comprising the steps of (a) separating the protein peptide mixture into fractions via a primary run, (b) enzymatically deacetylating the ε-N-acetylated peptides in each of the fractions and (c) isolating the flagged deacetylated peptides via a secondary run.

As mentioned before, the isolation of a subset of flagged peptides with the method provided by the current invention requires that only a subpopulation of peptides is altered in the protein peptide mixture. In several applications the alteration can be directly performed on the peptides. However, (a) pretreatments of the proteins in the sample and/or (b) pretreatments of the peptides in the protein peptide mixture allow to broaden the spectrum of classes of peptides which can be isolated with the invention. To illustrate the principle, an example of how cysteine-containing peptides can be isolated is described. It is clear that peptides containing one or more cysteines can be converted in a more hydrophilic flagged peptide via a chemical reaction with for instance acrylamide. This chemical alteration converts cysteine into the more hydrophilic S-propionamido-cysteine. This cysteine-derivative can be converted in an even more hydrophilic version via an oxidation reaction. Such oxidation converts the S-propionamido-cysteine to S-propionamido-cysteinesulfoxide. Flagged peptides containing S-propionamido-cysteine-sulfoxide derivatives show such a significant hydrophilic shift that they can easily be isolated from the bulk of the non-altered peptides using the current invention. However, applying the above chemical alteration not only alters the cysteine-containing peptides but also alters the methionine-containing peptides (since the oxidation also converts the methionine in its more hydrophilic methionine-sulfoxide derivative). In consequence two types of flagged peptides are simultaneously generated by the alteration and will also be simultaneously isolated. To avoid such simultaneous isolation of Cys peptides and Met peptides a pretreatment step is introduced.

In one particular embodiment, before being cleaved into their constituting peptides, the proteins in the mixture are oxidized. This pretreatment results in the oxidation of methionines to their methionine-sulfoxide derivative. Subsequently the proteins are precipitated and reduced to convert disulfide bridges into thiol groups. The protein peptide mixture resulting from the cleavage of the proteins is then, according to the invention, subjected to the primary run and the fractions are chemically altered with acrylamide followed by an oxidation. Since the methionines have already been oxidized during the pretreatment step, only the Cys-containing peptides will now be altered. The flagged S-propionamido-cysteinesulfoxide peptides are isolated applying the secondary run, without noticeable contamination with Met-peptides.

This example illustrates that selectivity of the alteration reaction towards a selected amino acid (or modified amino acid or amino acid residue, etc.) can be obtained by pretreating the proteins in the sample prior to the primary run. Such pretreatment can equally well be directed to the peptides in the protein peptide mixture, prior to the primary run. In a particular case a pretreatment could also be carried out during the primary run. The invention thus further provides a method for the isolation of flagged peptides from a protein peptide mixture comprising a) a pretreatment of the proteins in the sample and/or the peptides in the protein peptide mixture in order to prevent that unwanted amino acids are co-altered in step (c); (b) separating the protein peptide mixture into fractions via a primary run; (c) chemically and/or enzymatically altering at least one amino acid in at least one peptide in each fraction and (d) isolating the flagged peptides via a secondary run. Such pretreatment may comprise one or more chemical and/or enzymatic reactions.

In a particular embodiment flagged peptides can be isolated that are derived form proteins with a free $NH_2$-terminus. The latter method comprises the following steps: (a) the sample comprising proteins is pretreated in order to derivatize cysteine-side chains and convert lysine into homoarginine, (b) the alfa-$NH_2$-groups are converted into a thiocarbamoyl derivative, (c) a protein peptide mixture is prepared, (d) the newly generated $NH_2$-groups in the mixture are blocked, (e) the mixture is treated with an acid inducing the loss of the $NH_2$-terminal residue of peptides that were blocked in step b), (f) the pretreated protein peptide mixture is separated in a first chromatographic run, (g) the newly generated $NH_2$-groups are altered with an acetylating compound and thereby a subset of flagged peptides is generated and (h) said flagged peptides are isolated in a secondary chromatographic step. In a particular case step d) of the latter embodiment can be carried out with trinitrobenzenesulfonic acid (TNBS). In another particular case step e) is carried out with TFA.

As mentioned above, in a reverse action mode, the invention provides for a method to isolate identification peptides from a protein peptide mixture. In this embodiment, the minority of the peptides in the protein peptide mixture remain unaltered, while the bulk of the peptides become altered. The altered peptides acquire properties which change their chromatographic behaviour, while the identification peptides are not altered and retain their original chromatographic behaviour. So, the identification peptides elute at the same time during the secondary run as they did during the primary run, while the altered peptides are shifted forward or backwards. This allows to separate in each fraction the identification peptides from the altered peptides and to isolate the identification peptides.

Similarly to the situation with the flagged peptides as described herein above, the current invention requires that the alteration is effective in each of the peptide fractions from the primary run. Thus, in each fraction obtained from the primary chromatographic step, the altered peptides have to migrate distinctly from the identification peptides in the secondary chromatographic step. Depending on the type of applied alteration, the shift may for instance be caused by a change in the hydrophobicity or the net charge. This shift is called $\delta p$ and is specific for every individual altered peptide. In the example of a change in hydrophobicity, $\delta p$-values can be expressed as changes in the hydrophobic moment, or as a percentage of organic solvents in chromatographic runs, but most practically in time units under given chromatographic/electrophoretic conditions. Thus $\delta p$ is not necessarily identical for every altered peptide and lies in-between $\delta_{max}$ and $\delta_{min}$. $\delta p$ is affected by a number of factors such as the nature of the induced alteration, the nature of the column stationary phase, the mobile phase (buffers, solvents), temperature and others. In an example where the peptides in a fraction from the primary run elute in window w1, the identification peptides will elute in about the same window w1 during the secondary run. In a preferred embodiment $\delta_{min}$ has to be sufficient to avoid that altered peptides elute within window $w_1$ (and as such would overlap with the identification peptides). This rule should apply for every fraction collected from the primary run. Preferentially $\delta_{min}$ should be w1 or larger in order to minimize overlap between altered and identification peptides. For instance, if w1=1 minute, $\delta_{min}$ should by preference be 1 minute or more. It is however self-evident that minor contaminations of altered peptides in the elution window of the identification peptides is not preferred, but it is acceptable. Manipulation of the values of $\delta_{min}$ to obtain optimal separation of the identification peptides from the altered peptides in each primary run fraction is part of the current invention and comprises, among others, the right combination of the amino acid(s) selected to become altered, the type of alteration, and the chromatographic conditions (type of column, buffers, solvent, etc.). It is obvious for a person skilled in the art that the same approach can be applied to isolate identification peptides with for instance ion exchange chromatography or other types of chromatography.

The present invention therefore further provides in a method for the isolation of a subset of peptides from a protein peptide mixture, comprising the steps of: (a) separating the protein peptide mixture into fractions of peptides via chromatography; (b) chemically and/or enzymatically altering at least 50%, by preference 60%, more preferably 70%, even more preferably 80% and most preferably more than 90% of the peptides in each fraction; and (c) isolating the identification peptides via chromatography, wherein the chromatography of step (a) and (c) is performed with the same type of chromatography. Similarly to the approach with flagged peptides, the alteration between the primary and the secondary run can for instance be an alteration of an amino acid, of a modified amino acid (glycosylated, phosphorylated, acetylated, etc.), of a modification added in vitro to certain amino acids and/or of a particular residue on one or more amino acids.

As mentioned before, the isolation of a subset of identification peptides with the method provided by the current invention requires that the majority of peptides is altered in the protein peptide mixture. In several applications the alteration can be directly performed on the peptides. However, (a) pretreatments of the proteins in the sample and/or (b) pretreatments of the peptides in the protein peptide mixture allow to broaden the spectrum of classes of peptides which can be isolated with the invention. In a particular case a pretreatment could also be carried out during the primary run.

To illustrate the principle, an example of how aminoterminally blocked peptides (id est peptides derived from the aminoterminal end of proteins which are in vivo blocked at their amino terminus) can be isolated is described. Aminoterminally blocked peptides can be isolated according to the current invention via (a) separating the protein peptide mixture via chromatography; (b) altering the free amino-terminal group of the peptides (those peptides derived from an aminoterminally blocked protein do not have a free amino terminal group) and; (c) separating the aminoterminally blocked identification peptides from the bulk of the altered peptides via chromatography, whereby the chromatography in step (a) and (c) is performed with the same type of chromatography. While this approach allows to isolate many of the aminoterminally blocked peptides, the population of aminoterminally blocked peptides which also contain a lysine will not be selected in the procedure. Lysines also have a free aminogroup and the alteration in step (b) will therefore also alter those aminoterminally blocked peptides containing a lysine. The population of blocked aminoterminally peptides which also contain a lysine will thus be altered and will therefore not be part of the identification peptides and will not be isolated. To avoid the loss of this population, a pretreatment step is introduced, which converts, prior to the primary run, the protein lysine $\epsilon$—$NH_2$-groups to a blocked amino group. In a particular embodiment, the lysines with a free $\epsilon$—$NH_2$-group are converted into homo-arginine, followed by digestion with trypsin which cleaves the protein at homo-arginine and generates a free $\alpha$-amino acid at these positions. In consequence, blocked aminoterminally peptides containing a lysine are no longer altered and will be isolated as identification peptides.

This example illustrates that the selectivity of the alteration reaction towards a selected amino acid (or modified amino acid or amino acid residue) is enhanced by pretreating the proteins in the sample prior to the primary run. Such pretreatment can equally well be directed to the peptides in the protein peptide mixture. The invention thus further provides a method for the isolation of identification peptides from a protein peptide mixture comprising a) a pretreatment of the proteins in the sample and/or the peptides in the protein peptide mixture; (b) separating the protein peptide mixture into fractions via a primary run; (c) chemically and/or enzymatically altering at least one amino acid in the majority of peptides in each fraction and (d) isolating the identification peptides via a secondary run. Such pretreatment may comprise one or more chemical and/or enzymatic reactions.

The invention further provides a method to isolate the amino-terminal blocked peptides of the proteins in a sample comprising proteins comprising the steps of: (1) conversion of the protein lysine $\epsilon$—$NH_2$-groups into guanidyl groups or other moieties, (2) digestion of the protein sample in such a way that the proteins are cleaved at homo-arginine and generate a free $\alpha$-amino acid at these positions, (3) fractionation of the protein peptide mixture in a primary run, (4) altering the free amino-terminal groups of the peptides in each fraction with a hydrophobic, hydrophilic or charged component, and (5) isolating the non-altered identification peptides in a secondary run.

In yet another embodiment, the invention provides a method to isolate the amino-terminal peptides of the proteins in a sample comprising proteins. This method comprises the steps of: (1) the conversion of the protein lysine $\epsilon$—$NH_2$-groups into guanidyl groups or other moieties, (2) the conversion of the free $\alpha$-amino-groups at the amino terminal side of each protein, yielding a blocked (not further reactive) group, (3) digestion of the protein sample yielding peptides with newly generated free $NH_2$-groups, (4) fractionation of the protein peptide mixture in a primary run, (5) altering said free $NH_2$-groups of the peptides in each fraction with a hydrophobic, hydrophilic or charged component and (6) isolating the non-altered identification peptides in a secondary run. This approach makes it possible to specifically isolate the amino terminal peptides of the proteins in the protein sample, comprising both those amino terminal peptides with a free and those with a blocked $\alpha$-amino acid group. Performing step two in the above protocol in such a way that the free $\alpha$-amino groups are blocked with an isotopically labeled residue allows one to distinguish the in vivo blocked aminoterminal peptides from the aminoterminal peptides with a free $NH_2$-group. An application of the latter embodiment is the study of internal proteolytic processing of proteins between two different samples comprising proteins (see e.g. example 8).

In yet another embodiment of the reversed action mode, the chemical or enzymatic alteration between the primary and the secondary run is targeted to amino acids that are present in the large majority of peptides. Such abundant amino acids are present in at least 50% of the peptides, preferably in more than 75% of the peptides and more preferably in more than 90% of the peptides.

In another embodiment the identification peptides are the COOH-terminal (carboxy-terminal) peptides of the proteins.

In yet another embodiment the invention provides a method to isolate a subset of peptides out of a protein peptide mixture comprising the steps of (a) separating the protein peptide mixture into fractions via a primary run, (b) chemically or enzymatically adding a bulky and voluminous entity to at least one amino acid in the majority of the peptides in each fraction and (c) isolating said identification peptides out of each fraction via a secondary run, whereby the primary and secondary run are performed on a size exclusion column under identical or substantially similar conditions.

The method according to the invention allows, in each of the fractions, the separation of the flagged peptides from the bulk of the unaltered peptides and finally results in the isolation of a specific subset of flagged peptides from the complete protein peptide mixture. As mentioned above, such flagged peptides can for instance be peptides containing one or more methionines, peptides containing one or more cysteines, peptides containing one or more methionines and/or one or more cysteines, phosphopeptides, peptides fosforylated on tyrosines, peptides containing an $\epsilon$—N-acetylated cysteine, etc. Flagged peptides are highly representative of the originating proteins and as such flagged peptides serve as identification elements for their corresponding proteins. The present invention therefore further provides a method to identify a subset of peptides and their corresponding proteins in a sample comprising proteins. Thereto the isolation of flagged peptides according to any of the embodiments of the invention is further coupled to a peptide analysis.

Similarly, the method according to the invention allows, in each of the fractions, the separation of the identification peptides from the bulk of the altered peptides and finally results in the isolation of a specific subset of identification peptides from the complete protein peptide mixture. As mentioned above, such identification peptides can for instance be amino-terminal peptides, amino-terminally blocked peptides, carboxy-terminal peptides. Identification peptides are highly representative of the originating proteins and as such identification peptides serve as identification elements for their corresponding proteins. The present invention therefore further provides a method to identify a subset of peptides and the corresponding proteins in a sample comprising proteins. Thereto the isolation of identification peptides according to any of the embodiments of the invention is further coupled to a peptide analysis.

In a preferred approach peptide analysis of flagged or identification peptides is performed with a mass spectrometer. However, flagged or identification peptides can also be further analysed and identified using other methods such as electrophoresis, activity measurement in assays, analysis with specific antibodies, Edman sequencing, etc.

An analysis or identification step can be carried out in different ways. In one way, flagged peptides or identification peptides eluting from the chromatographic columns are directly directed to the analyzer. In an alternative approach, flagged peptides or identification peptides are collected in fractions. Such fractions may or may not be manipulated before going into further analysis or identification. An example of such manipulation consists out of a concentration step, followed by spotting each concentrate on for instance a MALDI-target for further analysis and identification.

In a preferred embodiment flagged peptides or identification peptides are analysed with high-throughput mass spectrometric techniques. The information obtained is the mass of the flagged or identification peptides. When the peptide mass is very accurately defined, such as with a Fourrier transform mass spectrometer (FTMS), using an internal calibration procedure (O'Connor and Costello, 2000), it is possible to unambiguously correlate the peptide mass with the mass of a corresponding peptide in peptide mass databases and as such identify the flagged peptide or identification peptide. The accuracy of some conventional mass spectrometers is however not sufficient to unambiguously correlate the spectrometrically determined mass of each peptide with its corresponding peptide and protein in sequence databases. To increase the number of peptides that can nevertheless be unambiguously identified, data about the mass of the peptide are complemented with other information. In one embodiment the peptide mass as determined with the mass spectrometer is supplemented with the proven knowledge (for instance proven via neutral loss of 64 amu's in the case of methionine sulfoxide flagged peptides) that each flagged peptide contains one or more residues of the altered amino acid and/or with the knowledge that the peptide was generated following digestion of a sample comprising proteins using a cleavage protease with known specificity. For example trypsin has the well known property of cleaving precisely at the sites of lysine and arginine, yielding peptides which typically have a molecular weight of between about 500 to 5,000 dalton and having C-terminal lysine or arginine amino acids. This combined information is used to screen databases containing information regarding the mass, the sequence and/or the identity of peptides and to identify the corresponding peptide and protein.

In another embodiment the method of determining the identity of the parent protein by only accurately measuring the peptide mass of at least one flagged peptide or identification peptide can be improved by further enriching the information content of the selected flagged peptides or identification peptides. As a non-limiting example of how information can be added to the flagged or identification peptides, the free $NH_2$-groups of these peptides can be specifically chemically changed in a chemical reaction by the addition of two different isotopically labeled groups. As a result of this change, said peptides acquire a predetermined number of labeled groups. Since the change agent is a mixture of two chemically identical but isotopically different agents, the flagged peptides or identification peptides are revealed as peptide twins in the mass spectra. The extent of mass shift between these peptide doublets is indicative for the number of free amino groups present in said peptide. To illustrate this further, for example the information content of flagged peptides can be enriched by specifically changing free $NH_2$-groups in the peptides using an equimolar mixture of acetic acid N-hydroxysuccinimide ester and trideuteroacetic acid N-hydroxysuccinimide ester. As the result of this conversion reaction, peptides acquire a predetermined number of $CH_3$—CO ($CD_3$—CO) groups, which can be easily deduced from the extent of the observed mass shift in the peptide doublets. As such, a shift of 3 amu's corresponds with one $NH_2$-group, a 3 and 6 amu's shift corresponds with two $NH_2$-groups and a shift of 3, 6 and 9 amu's reveals the presence of three $NH_2$-groups in the peptide. This information further supplements the data regarding the peptide mass, the knowledge about the presence of one or more residues of the altered amino acid and/or the knowledge that the peptide was generated with a protease with known specificity.

A yet further piece of information that can be used to identify flagged peptides or identification peptides is the Grand Average of hydrophaticity (GRAVY) of the peptides, reflected in the elution times during chromatography. Two or more peptides, with identical masses or with masses that fall within the error range of the mass measurements, can be distinguished by comparing their experimentally determined GRAVY with the in silico predicted GRAVY.

Any mass spectrometer may be used to analyze the flagged or identification peptides. Non-limiting examples of mass spectrometers include the matrix-assisted laser desorption/ionization ("MALDI") time-of-flight ("TOF") mass spectrometer MS or MALDI-TOF-MS, available from PerSeptive Biosystems, Framingham, Mass.; the Ettan MALDI-TOF from AP Biotech and the Reflex III from Brucker-Daltonias, Bremen, Germany for use in post-source decay analysis; the Electrospray Ionization (ESI) ion trap mass spectrometer, available from Finnigan MAT, San Jose, Calif.; the ESI quadrupole mass spectrometer, available from Finnigan MAT or the GSTAR Pulsar Hybrid LC/MS/MS system of Applied Biosystems Group, Foster City, Calif. and a Fourrier transform mass spectrometer (FTMS) using an internal calibration procedure (O'Connor and Costello, 2000).

Protein identification software used in the present invention to compare the experimental mass spectra of the peptides with a database of the peptide masses and the corresponding proteins are available in the art. One such algorithm, ProFound, uses a Bayesian algorithm to search protein or DNA database to identify the optimum match between the experimental data and the protein in the database. ProFound may be accessed on the World-Wide Web at <http//prowl.rockefeller.edu> and <http//www.proteometrics.com>. Profound accesses the non-redundant database (NR). Peptide Search can be accessed at the EMBL website. See also, Chaurand P. et al. (1999) *J. Am. Soc. Mass. Spectrom* 10, 91, Patterson S. D., (2000), *Am. Physiol. Soc.,* 59–65, Yates J R (1998) *Electrophoresis,* 19, 893). MS/MS spectra may also be analysed by MASCOT (available at http://www.matrixscience.com, Matrix Science Ltd. London).

In another preferred embodiment isolated flagged peptides or identification peptides are individually subjected to fragmentation in the mass spectrometer. In this way information about the mass of the peptide is further complemented with (partial) sequence data about the flagged peptide or identification peptide. Comparing this combined information with information in peptide mass and peptide and protein sequence databases allows to identify the flagged or identification peptides. In one approach fragmentation of the flagged or identification peptides is most conveniently done by collision induced dissociation (CID) and is generally referred to as $MS^2$ or tandem mass spectrometry. Alternatively, flagged peptide ions or identification peptide ions can decay during their flight after being volatilized and ionized in a MALDI-TOF-MS. This process is called post-source-decay (PSD). In one such mass spectrometric approach, selected flagged peptides or identification peptides are transferred directly or indirectly into the ion source of an electrospray mass spectrometer and then further fragmented in the MS/MS mode. Thus, in one aspect, partial sequence information of the flagged peptides or identification peptides is collected from the $MS^n$ fragmentation spectra (where it is understood that n is larger or equal to 2) and used for peptide identification in sequence databases described herein.

In a particular embodiment additional sequence information can be obtained in MALDI—PSD analysis when the alfa-$NH_2$-terminus of the peptides is altered with a sulfonic acid moiety group. Flagged peptides carrying an $NH_2$-terminal sulfonic acid group are induced to particular fragmentation patterns when detected in the MALDI-TOF-MS mode. The latter allows a very fast and easy deduction of the amino acid sequence. In particular, example 6b describes a procedure how $NH_2$-terminal flagged peptides are isolated from proteins with a free $NH_2$-terminus.

The present invention further provides a method for the identification of one or more proteins in a sample comprising proteins. On the one hand it is known that cleavage of a sample comprising proteins results in a protein peptide mixture comprising thousands of peptides and this overwhelms the resolving power of the currently available chromatographic systems and mass spectrometry systems. On the other hand it is known that a protein can be identified based on the identification of one or more of its constituting peptides. The current invention provides methods to isolate and identify a spectrum of different types of flagged peptides or identification peptides from a protein peptide mixture. Every set of flagged peptides or identification peptides represents a subset of the peptides in the protein peptide mixture. This simplification of the original peptide mixture significantly reduces the co-elution of peptides in the secondary run and results in an efficient identification of the flagged or identification peptides with analysers such as mass spectrometers or others. Since flagged peptides or identification peptides are most often unique identification elements for their corresponding parent proteins, identification of flagged peptides or identification peptides allows the identification of the proteins in the original sample comprising proteins. So, the task of identifying proteins in a sample comprising proteins by isolating and identifying one or more of their composite peptides becomes possible with the methods of the present invention.

The present invention therefore further provides a method to identify proteins in a sample comprising proteins, comprising the steps of (a) separating the protein peptide mixture into fractions of peptides via chromatography; (b) chemically and/or enzymatically altering at least one amino acid of at least one of the peptides in each fraction, thereby generating a subset of altered peptides; (c) isolating the flagged peptides out of each fraction via a secondary run; (d) identifying the flagged peptides and their corresponding proteins.

The present invention therefore also further provides a method to identify proteins in a sample comprising proteins, comprising the steps of (a) separating the protein peptide mixture into fractions of peptides via chromatography; (b) chemically and/or enzymatically altering at least one amino acid of the majority of the peptides in each fraction, thereby generating a subset of unaltered peptides; (c) isolating the identification peptides out of each fraction via a secondary run; (d) identifying the identification peptides and their corresponding proteins.

It is obvious for a person skilled in the art that these embodiments of the invention are equally applicable when there is a pretreatment of the proteins or the peptides prior to step (a), as also described hereabove. It is equally obvious for a person skilled in the art that, starting from the known identity of a flagged peptide or an identification peptide, the identity of the corresponding protein can be easily determined by screening peptide, protein and DNA sequence databases. Both the databases and the software to screen are available in the art.

Flagged peptides that can be used according to the invention to identify proteins in a sample comprising proteins are for instance: methionine-containing peptides, cysteine-containing peptides, histidine-containing peptides, tyrosine-containing peptides, lysine-containing peptides, tryptophane-containing peptides, arginine-containing peptides, proline-containing peptides, phenylalanine-containing peptides or a combination of two or more of these flagged peptides.

Other flagged peptides can be used according to the invention to identify the presence of co- or posttranslationally modified proteins in a sample comprising proteins. The present invention for instance provides a method to identify the phosphorylated proteins in a sample comprising proteins. In one approach peptides containing a phosphorylated amino acid are therefore altered and isolated as flagged peptides according to the invention. Subsequently identification of these flagged peptides and their correlating proteins results in the identification of the phosphorylated proteins (or the phosphoproteome) in a sample. The present invention also provides methods to identify other types of co- or posttranslationally modified proteins in a sample comprising proteins such as glycosylated proteins, tyrosine-phosphorylated proteins, serine- and/or threonine phosphorylated proteins, acetylated proteins, ε-N-acetylated proteins, sulfated proteins, etc.

Identification peptides that can be used according to the invention to identify proteins in a sample are for instance the amino-terminal peptides of the proteins. The masses of each of these peptides can be determined using mass spectrometry. Combining the mass of such peptides with the knowledge that such peptide is an aminoterminal peptide is, for the large majority of the peptides, sufficient to unambiguously identify the corresponding parent proteins. In a further embodiment of this aspect of the invention, databases only containing the masses of aminoterminal peptides are designed and the masses of the isolated aminoterminal identification peptides are probed against these databases. In this approach there is a very high probability that an isolated identification peptide matches uniquely with a mass in the restricted databases. Moreover, this approach considerably reduces the complexity of the peptide-based proteome approach and significantly increases the speed of analysis.

It is further important to mention that the invention allows the identification of a whole range of proteins in a sample comprising proteins, varying for instance from high to low abundant, from acidic to basic, from small to large, from soluble to membrane proteins. Furthermore, the invention provides a method to identify proteins in a sample comprising proteins, starting from very small amounts of cells. The methods provided by the invention are so efficient and sensitive that it is for instance possible to identify several hundreds to more than thousand proteins starting from as few a 50,000 human cells. Even with a smaller number of cells as starting material, it is still possible to identify hundreds of proteins in a sample comprising proteins. Obviously, the methods of the invention can also be applied to large numbers of cells.

Other identification peptides can for instance be used to identify aminoterminally blocked proteins or proteolytically cleaved proteins.

In another embodiment, the present invention provides a method to determine the relative amount of one or more proteins in two or more samples comprising proteins. The method comprises the use of differentially isotopically labeled flagged peptides or identification peptides. In this method, the two samples are treated in such a way that the flagged or identification peptides isolated from one sample contain one isotope and the flagged or identification peptides isolated from a second sample contain another isotope of the same element.

The method comprises the steps of (a) labeling the peptides present in a first sample with a first isotope; (b) labeling the peptides present in a second sample with a second isotope; (c) combining the protein peptide mixture of the first sample with the protein peptide mixture of the second sample; (d) separating the protein peptide mixture into fractions of peptides via chromatography; (e) chemically, or enzymatically, or chemically and enzymatically, altering at least one amino acid of at least one of the peptides in each fraction; (f) isolating the flagged peptides out of each fraction via chromatography, wherein the chromatography is performed with the same type of chromatography as in step (d); (g) performing mass spectrometric analysis of the isolated flagged peptides; (h) calculating the relative amounts of the flagged peptides in each sample by comparing the peak heights of the identical but differential isotopically labeled flagged peptides; and (i) determining the identity of the flagged peptide and its corresponding protein.

The same approach can be followed with the reverse mode action, wherein the method comprises the steps of (a) labeling the peptides present in a first sample with a first isotope; (b) labeling the peptides present in a second sample with a second isotope; (c) combining the protein peptide mixture of the first sample with the protein peptide mixture of the second sample; (d) separating the protein peptide mixture into fractions of peptides via chromatography; (e) chemically, or enzymatically, or chemically and enzymatically, altering at least one amino acid in the majority of the peptides in each fraction; (f) isolating the identification peptides out of each fraction via chromatography, wherein the chromatography is performed with the same type of chromatography as in step (d); (g) performing mass spectrometric analysis of the isolated identification peptides; (h) calculating the relative amounts of the identification peptides in each sample by comparing the peak heights of the identical but differential isotopically labeled identification peptides; and (i) determining the identity of the identification peptide and its corresponding protein.

It is obvious that the same approach can be followed in combination with a pretreatment step as mentioned hereabove. The method is also applicable if the chromatographic separations in step (d) and (f) are identical or substantially similar. It is also obvious that, instead of mixing the peptides from both samples in step (c), peptides from a first and a second sample can be separately subjected to steps (d) and/or (e) and/or (f) and become combined in step (d) or (e) of (f) or (g).

The differential isotopic labeling of the peptides in a first and a second sample can be done in many different ways available in the art. A key element is that a particular peptide originating from the same protein in a first and a second sample is identical, except for the presence of a different isotope in one or more amino acids of the peptide. In a typical embodiment the isotope in a first sample will be the natural isotope, referring to the isotope that is predominantly present in nature, and the isotope in a second sample will be a less common isotope, hereinafter referred to as an uncommon isotope. Examples of pairs of natural and uncommon isotopes are H and D, $O^{16}$ and $O^{18}$, $C^{12}$ and $C^{13}$, $N^{14}$ and $N^{15}$. Peptides labeled with the heaviest isotope of an isotopic pair are herein also referred to as heavy peptides. Peptides labeled with the lightest isotope of an isotope pair are herein also referred to as light peptides. For instance, a peptide labeled with H is called the light peptide, while the same peptide labeled with D is called the heavy peptide. Peptides labeled with a natural isotope and its counterparts labeled with an uncommon isotope are chemically very similar, separate chromatographically in the same manner and also ionize in the same way. However, when the peptides are fed into an analyser, such as a mass spectrometer, they will segregate into the light and the heavy peptide. The heavy peptide has a slightly higher mass due to the higher weight of the incorporated, chosen isotopic label. Because of the minor difference between the masses of the differentially isotopically labeled peptides the results of the mass spectrometric analysis of isolated flagged or identification peptides will be a plurality of pairs of closely spaced twin peaks, each twin peak representing a heavy and a light peptide. Each of the heavy peptides is originating from the sample labeled with the heavy isotope; each of the light peptides is originating from the sample labeled with the light isotope. The ratios (relative abundance) of the peak intensities of the heavy and the light peak in each pair are then measured. These ratios give a measure of the relative amount (differential occurrence) of that peptide (and its corresponding protein) in each sample. The peak intensities can be calculated in a conventional manner (e.g. by calculating the peak height or peak surface). As herein described above, the flagged or identification peptides can also be identified allowing the identification of proteins in the samples. If a protein is present in one sample but not in another, the isolated flagged or identification peptide (corresponding with this protein) will be detected as one peak which can either contain the heavy or light isotope. However, in some cases it can be difficult to determine which sample generated the single peak observed during mass spectrometric analysis of the combined sample. This problem can be solved by double labeling the first sample, either before or after the proteolytic cleavage, with two different isotopes or with two different numbers of heavy isotopes. Examples of labeling agents are acylating agents.

Incorporation of the natural and/or uncommon isotope in peptides can be obtained in multiple ways. In one approach proteins are labeled in the cells. Cells for a first sample are for instance grown in media supplemented with an amino acid containing the natural isotope and cells for a second sample are grown in media supplemented with an amino acid containing the uncommon isotope. In one embodiment the differentially isotopically labeled amino acid is the amino acid that is selected to become altered. For instance, if methionine is the selected amino acid, cells are grown in media supplemented either with unlabeled L-methionine (first sample) or with L-methionine which is deuterated on the Cβ and Cγ position and which is therefore heavier by 4 amu's (second sample).

Mixing of the proteins/peptides from both samples can be done at different time points. The mixing can be done at the level of the sample (e.g. mixing an equal number of cells from both samples) or proteins can be isolated separately from sample 1 and sample 2 and subsequently mixed or proteins from sample 1 are digested into peptides and proteins from sample 2 are digested into peptides and the peptides originating from sample 1 and sample 2 are mixed, etc. Whatever the mixing procedure, the current invention is further used to isolate the flagged methionine-peptides out of the protein peptide mixture. Methionine-peptides will be isolated independent from their isotopic constitution and analysis of the methionine peptide in a mass spectrometer as described supra allows determining the relative amount of their corresponding protein in sample 1 and sample 2.

Incorporation of the differential isotopes can also be obtained by an enzymatic approach. For instance labeling can be carried out by treating one sample comprising proteins with trypsin in "normal" water ($H_2{}^{16}O$) and the second sample comprising proteins with trypsin in "heavy" water ($H_2{}^{18}O$). As used herein "heavy water" refers to a water molecule in which the O-atom is the $^{18}O$-isotope. Trypsin shows the well-known property of incorporating two oxygens of water at the COOH-termini of the newly generated sites. Thus in sample one, which has been trypsinized in $H_2{}^{16}O$, peptides have "normal" masses, while in sample two peptides (except for most of the COOH-terminal peptides) have a mass increase of 4 amu's corresponding with the incorporation of two $^{18}O$ atoms This difference of 4 amu's is sufficient to distinguish the heavy and light version of the flagged peptides or identification peptides in a mass spectrometer and to accurately measure the ratios of the light versus the heavy peptides and thus to determine the ratio of the corresponding peptides/proteins in the two samples. The present invention therefore further provides a method to determine the relative amount of at least one protein in at least two samples comprising the steps of: a) digesting the proteins of a first sample with trypsin in the presence of $H_2{}^{16}O$ and digesting the proteins of a second sample with trypsin in the presence of $H_2{}^{18}O$; b) combining the two trypsin digested protein peptide mixtures; c) subjecting the combined mixture to a primary run (because the differentially isotopically labeled peptides have the same chromatographic behaviour, they separate in the same fractions); d) chemically and/or enzymatically altering at least one amino acid of at least one peptide in each fraction; e) isolating the flagged peptides or the identification peptides via a secondary run (because the differentially isotopically labeled flagged or identification peptides have the same chromatographic behaviour, they sort in the same fractions); f) analysing the isolated peptides in a mass spectrometer; g) calculating the relative amounts of the corresponding heavy and light peptides by comprising their peak hights and h) identifying the peptides and their corresponding proteins.

Incorporation of the differential isotopes can further be obtained with multiple labelling procedures based on known chemical reactions that can be carried out at the protein or the peptide level. For example, proteins can be changed by the guadinylation reaction with O-methylisourea, converting $NH_2$-groups into guanidinium groups, thus generating homoarginine at each previous lysine position. Proteins from a first sample can be reacted with a reagent with the natural isotopes and proteins from a second sample can be reacted with a reagent with an uncommon isotope. Peptides could also be changed by Shiff's-base formation with deuterated acetaldehyde followed by reduction with normal or deuterated sodiumborohydride. This reaction, which is known to proceed in mild conditions, may lead to the incorporation of a predictable number of deuterium atoms. Peptides will be changed either at the α—$NH_2$-group, or ε—$NH_2$ groups of lysines or on both. Similar changes may be carried out with deuterated formaldehyde followed by reduction with deuterated $NaBD_4$, which will generate a methylated form of the amino groups. The reaction with formaldehyde could be carried out either on the total protein, incorporating deuterium only at lysine side chains or on the peptide mixture, where both the α—$NH_2$ and lysine-derived $NH_2$-groups will be labeled. Since arginine is not reacting, this also provides a method to distinguish between Arg- and Lys-containing peptides.

Primary amino groups are easily acylated with, for example, acetyl N-hydroxysuccinimide (ANHS). Thus, one sample can be acetylated with normal ANHS whereas a second sample can be acylated with either $^{13}CH_3CO$—NHS or $CD_3CO$—NHS. Also the ε—$NH_2$ group of all lysines is in this way derivatized in addition to the amino-terminus of the peptide. Still other labelling methods are for example acetic anhydride which can be used to acetylate hydroxyl groups and trimethylchlorosilane which can be used for less specific labelling of functional groups including hydroxyl groups and amines.

In yet another approach the primary amino acids are labelled with chemical groups allowing to differentiate between the heavy and the light peptides by 5 amu, by 6 amu, by 7 amu, by 8 amu or even by larger mass difference. Examples of such compounds are mentioned in example 16. Alternatively, the differential isotopic labelling is carried out at the carboxy-terminal end of the peptides, allowing the differentiation between the heavy and light variants by more than 5 amu, 6 amu, 7 amu, 8 amu or even larger mass differences. Since the methods of the present invention do not require any prior knowledge of the type of proteins that may be present in the samples, they can be used to determine the relative amounts of both known and unknown proteins which are present in the samples examined.

The methods provided in the present invention to determine relative amounts of at least one protein in at least two samples can be broadly applied to compare protein levels in for instance cells, tissues, or biological fluids (e.g. nipple aspiration fluid, saliva, sperm, cerebrospinal fluid, urine, serum, plasma, synovial fluid), organs, and/or complete organisms. Such a comparison includes evaluating subcellular fractions, cells, tissues, fluids, organs, and/or complete organisms which are, for example, diseased and non-diseased, stressed and non-stressed, drug-treated and non drug-treated, benign and malignant, adherent and non-adherent, infected and uninfected, transformed and untransformed. The method also allows to compare protein levels in subcellular fractions, cells, tissues, fluids, organisms, complete organisms exposed to different stimuli or in different stages of development or in conditions where one or more genes are silenced or overexpressed or in conditions where one or more genes have been knocked-out.

In another embodiment, the methods described herein can also be employed in diagnostic assays for the detection of the presence, the absence or a variation in expression level of one or more protein markers or a specific set of proteins indicative of a disease state (e.g., such as cancer, neurodegenerative disease, inflammation, cardiovascular diseases, viral infections, bacterial infections, fungal infections or any other disease). Specific applications include the identification of target proteins which are present in metastatic and invasive cancers, the differential expression of proteins in transgenic mice, the identification of proteins that are up- or down-regulated in diseased tissues, the identification of intracellular changes in cells with physiological changes such as metabolic shift, the identification of biomarkers in cancers, the identification of signalling pathways.

Quantitative analysis of large sets of proteins in different samples can be performed with both flagged peptides and identification peptides. In a typical example flagged peptides based on an alteration of methionine, or cysteine, or histidine or a combination of two of these amino acids will be used. In another typical example identification peptides based on amino-terminal peptides or carboxy-terminal peptides are used. Further the invention can be used to achieve the proteome-wide, qualitative and quantitative analyses of the state of modification of proteins. For example, in several signal transduction pathways serine-, threonine- and tyrosine-residues, present in proteins, often become phosphorylated. In one specific embodiment the differentially isotopically labeled flagged peptides are flagged peptides selected on the presence of a phospho-amino acid. Comparison of the relative abundance of the heavy and light flagged peptides allows the comparison of the relative abundance of phosphorylated proteins in two samples comprising proteins. In yet another embodiment, the differentially isotopically labeled flagged peptides are flagged peptides selected on the presence of a phosphoserine and/or phosphothreonine or phosphotyrosine. In yet another embodiment, the differentially isotopically labeled flagged peptides are flagged peptides selected on the presence of ε-N-acetylated lysine-containing peptides. In still another embodiment the differentially isotopically labeled flagged peptides are flagged peptides selected on the presence of a glycosyl group.

The present invention further provides a method to quantitate the amount of one or more proteins in a single sample comprising proteins. The method comprises the steps of: (a) preparing a protein peptide mixture; (b) adding to the mixture a known amount of a synthetic reference peptide labeled with an isotope distinguishable form the reference peptide isotope; (c) separating the mixture into fractions of peptides via chromatography; (d) chemically, or enzymatically, or chemically and enzymatically, altering at least one amino acid of at least one of the peptides in each fraction; (e) isolating the flagged peptides out of each fraction via chromatography, wherein the chromatography is performed with the same type of chromatography as in step (c); (f) performing mass spectrometric analysis of the flagged peptides; and (g) determining the amount of the protein present in the sample by comparing the peak heights of the synthetic reference peptide to the reference peptide.

The same method can be applied with the reverse mode action, wherein the method comprises the steps of: (a) preparing a protein peptide mixture; (b) adding to the mixture a known amount of a synthetic reference peptide labeled with an isotope distinguishable form the reference peptide isotope; (c) separating the mixture into fractions of peptides via chromatography; (d) chemically, or enzymatically, or chemically and enzymatically, altering at least one amino acid in the majority of the peptides in each fraction; (e) isolating the identification peptides out of each fraction via chromatography, wherein the chromatography is performed with the same type of chromatography as in step (c); (f) performing mass spectrometric analysis of the identification peptides; and (g) determining the amount of the protein present in the sample by comparing the peak heights of the synthetic reference peptide to the reference peptide.

It is obvious that the same methods can be followed in combination with a pretreatment step as mentioned herein above. The methods are also applicable if the chromatographic separations in step (c) and (e) are identical are substantially similar.

"Reference peptides" as used herein are peptides whose sequence and/or mass is sufficient to unambiguously identify its parent protein By preference, peptide synthesis of equivalents of reference peptides is easy. For the sake of clarity, a reference peptide as used herein is the native peptide as observed in the protein it represents, while a synthetic reference peptide as used herein is a synthetic counterpart of the same peptide. Such synthetic reference peptide is conveniently produced via peptide synthesis but can also be produced recombinantly. Peptide synthesis can for instance be performed with a multiple peptide synthesizer. Recombinant production can be obtained with a multitude of vectors and hosts as widely available in the art. Reference peptides by preference ionize well in mass spectrometry. A non-limiting example of a well ionizing reference peptide is a reference peptide which contains an arginine. By preference a reference peptide is also easy to isolate as flagged peptide or as identification peptide. In the latter preferred embodiment the reference peptide is simultaneously also a flagged peptide or an identification peptide.

A reference peptide and its synthetic reference peptide counterpart are chemically very similar, separate chromatographically in the same manner and also ionize in the same way. The reference peptide and its synthetic reference peptide counterpart are however differentially isotopically labeled. In consequence, in a preferred embodiment whereby the reference peptide is also a flagged or identification peptide, the reference peptide and its synthetic reference peptide counterpart are altered in a similar way and are isolated in the same fraction of the primary and the secondary run and in an eventual ternary run. However, when a reference peptide and its synthetic reference peptide are fed into an analyzer, such as a mass spectrometer, they will segregate into the light and heavy peptide. The heavy peptide has a slightly higher mass due to the higher weight of the incorporated chosen heavy isotope.

Because of this very small difference in mass between a reference peptide and its synthetic reference peptide, both peptides will appear as a recognizable closely spaced twin peak in a mass spectrometric analysis. The ratio between the peak heights or peak intensities can be calculated and these determine the ratio between the amount of reference peptide versus the amount of synthetic reference peptide. Since a known absolute amount of synthetic reference peptide is added to the protein peptide mixture, the amount of reference peptide can be easily calculated and the amount of the corresponding protein in the sample comprising proteins can be calculated.

There are several methods known in the art to differentially isotopically label a reference peptide and its synthetic reference peptide. In a first approach, the reference peptide carries the uncommon isotope and the synthetic counterpart carries the natural isotope. In this approach the synthetic reference peptides can be efficiently chemically synthesized with their natural isotopes in large-scale preparations. To label the reference peptide with an uncommon isotope, any of the hereabove mentioned methods to differentially isotopically label a peptide with an uncommon isotope can be applied (in vivo labelling, enzymatic labelling, chemical labelling, etc.). One example of in vivo labelling is to incorporate the commercially available deuterated methionine $CH_3$—$SCD_2$—$CD_2$—CH—$(NH_2)$—COOH, adding 4 amu's to the total peptide mass. Alternatively, synthetic reference peptides could also contain deuterated arginine $H_2NC$—(NH)—NH—$(CD_2)_3$—CD—$(NH_2)$—COOH) which would add 7 amu's to the total peptide mass. It should be clear to one of skill in the art that every amino acid of which deuterated or $^{15}N$ or $^{13}C$ forms exist can be considered in this protocol. Another example of this approach is to proteolyse the sample comprising proteins with trypsin in the presence of $H_2^{18}O$, but many other methods can be used. Thus, in a preferred embodiment, the quantitative analysis of at least one protein in one sample comprising proteins comprises the steps of: a) preparing a protein peptide mixture wherein the peptides carry an uncommon isotope (e.g. a heavy isotope); b) adding to the protein peptide mixture a known amount of a synthetic reference peptide carrying natural isotopes (e.g. a light isotope); c) the protein peptide mixture, also containing the synthetic reference peptide, is separated in fractions via a primary chromatographic separation; d) chemical and/or enzymatic alteration of at least the reference peptide and its synthetic reference peptide counterpart; e) isolation of the flagged reference peptide and the flagged synthetic reference peptide via a secondary chromatographic separation; f) determination by mass spectrometry of the ratio between the peaks heights of the reference peptide versus the synthetic reference peptides and g) calculation of the amount of protein, represented by the reference peptide, in the sample comprising proteins.

In another preferred embodiment the reference peptide is simultaneously an identification peptide. The above method can equally well be applied to this approach, but in step d) the reference peptide and its synthetic reference peptide will remain unaltered and in step e) the identification peptides (including the reference peptide and its synthetic reference peptide) are isolated.

In another preferred embodiment, the quantitative determination of at least one protein in one single sample, comprises the steps of: a) the digestion with trypsin of said protein mixture in $H_2^{18}O$ into peptides; b) the addition to the resulting protein peptide mixture of a known amount of at least one synthetic reference peptide carrying natural isotopes; c) the fractionation of the protein peptide mixture in a primary chromatographic separation; d) the chemical and/or enzymatic alteration of each fraction on one or more specific amino acids (both the peptides from the protein peptide mixture and the synthetic reference peptides containing the specific amino acid will be altered); e) the isolation of the flagged peptides via a second chromatographic separation (these flagged peptides comprise both the biological reference peptide and their synthetic reference peptide counterparts); f) the mass spectrometric analysis of the flagged peptides and the determination of the relative amounts of the reference peptide and its synthetic reference peptide counterpart. Again, a similar approach can be followed with reference peptides which are simultaneously identification peptides.

Also, the above methods can equally be applied in a mode whereby a reference peptide is labelled with the natural isotope and its synthetic reference peptide counterpart is labelled with an uncommon isotope.

The above methods of the present invention to quantify the amount of protein in a sample comprising proteins can be used to quantify from one up to hundreds of proteins in the sample. For every protein to be quantified, there is a need for at least one and preferably two or more reference peptides. In a particular embodiment, each synthetic reference peptides is added in an amount equimolar to the expected amount of its reference peptide counterpart.

The methods provided in the present invention to quantify at least one protein in a sample comprising proteins can be broadly applied to quantify proteins of different interest. For example, diagnostic assays can be developed by which the level of one or more proteins is determined in a sample by making use of the present invention.

In another example reference peptides can be used to quantify specific known splice variants of particular proteins in a sample. If a particular splice variant is known from a specific protein and said splice variant is aimed to be detected then a synthetic reference peptide can be synthesized that only corresponds with said splice variant of a particular protein. Indeed, it often happens that due to exon skipping new junctions are formed and as such a specific reference peptide can be chosen that not occurs in the parent protein and only occurs in the splice variant. However, in many cases it is advised to choose two or more reference peptides in order to distinguish between the parent protein and the splice variant of interest. Also it is common that a particular splice variant is expressed together with the parent protein in the same cell or tissue and thus both are present in the sample. Often the expression levels of the particular splice variant and the parent protein are different. The detection and the abundance between the reference peptides can be used to calculate the expression levels between the splice variant and its parent protein. In yet another example, it is well known that drugs can highly influence the expression of particular proteins in a cell. With the current method it is possible to accurately measure the amount of one or a set of proteins of interest under different experimental conditions. As such, equivalent technologies such as genomic applications can be applied on the protein level comprising pharmacoproteomics and toxicoproteomics. Though gene markers of disease have received significant attention with the sequencing of the human genome, protein markers are more useful in many situations. For example a diagnostic assay based on reference peptides representing protein disease markers can be developed basically for any disease of interest. Most conveniently such disease markers can be quantified in cell, tissue or organ samples or body fluids comprising for instance blood cells, plasma, serum, urine, sperm, saliva, nipple aspiration fluid, synovial fluid or cerebrospinal fluid. Reference peptides for protein disease markers can then according to the present invention for example be used for monitoring if the patient is a fast or slow disease progressor, if a patient is likely to develop a certain disease and even to monitor the efficacy of treatment. Indeed, in contrast to genetic markers, such as SNPs, levels of protein disease markers, indicative for a specific disease, could change rapidly in response to disease modulation or progression. Reference peptides for protein disease markers can for instance also be used according to the present invention for an improved diagnosis of complex genetic diseases such as for example cancer, obesity, diabetes, asthma and inflammation, neuropsychiatric disorders, including depression, mania, panic disorder and schizophrenia. Many of these disorders occur due to complex events that are reflected in multiple cellular and biochemical pathways and events. Therefore many proteins markers may be found to be correlated with these diseases. The present invention allows to follow one to several hundreds of protein disease markers simultaneously. The identification and the possibility of relative and absolute quantification of protein markers, using the current invention, could lead to a more accurate diagnostic subclassification.

In another embodiment, the invention is directed to a peptide sorter device that is able to carry out the method of the invention. As described herein, methods to analyze protein peptide mixtures or complex peptide mixtures may comprise two consecutive chromatographic steps: a primary chromatographic step using the complete protein peptide mixture which divides said mixture into fractions, and a second chromatographic step that is performed after the chemical and/or enzymatic alteration of at least one specific amino acid present in the peptides in the fractions. As described herein, the term "peptide sorter" refers to a device that efficiently separates the flagged peptides from the non-altered peptides according to the invention or that alternatively efficiently separates the identification peptides from the altered peptides according to the invention. In a preferred aspect, identical or very similar chromatographic conditions are used in the two chromatographic steps such that during the second run (i) the non-altered peptides stay at their original elution times and the flagged peptides are induced to undergo a shift in the elution time or (ii) in the reversed mode, the identification peptides stay at their original elution times and the bulk of the altered peptides are induced to undergo a shift in the elution time. As described herein, a peptide sorter particularly refers to the pooling of fractions obtained after run 1 and the optimal organisation of the second chromatographic step (e.g., the step in which the flagged peptides are separated from the non-altered peptides or alternatively, the step in which the identification peptides are separated from the altered peptides, to speed up the isolation of the flagged peptides (or identification peptides) out of each of the run 1 fractions).

One approach to isolate and identify flagged peptides isolated from a protein peptide mixture, is to independently collect every fraction from the primary chromatographic separation, to carry out the chemical and/or enzymatic alteration in each of the fractions and to rerun every fraction independently in the same chromatographic conditions and on the same or substantially similar column. Subsequently the flagged peptides of each independently run secondary run are collected and passed to an analytical instrument such as a mass spectrometer. However, such approach requires a considerable amount of chromatography time and occupies important machine time on the mass spectrometer. In order to obtain a more efficient and economic use of both the chromatographic equipment and the mass spectrometer, the present invention provides the use of peptide sorters allowing the pooling of several fractions of the primary chromatographic separation while avoiding elution overlap between flagged peptides originating from different fractions, and between flagged peptides from one fraction and unaltered peptides from one or more other fractions or in the reversed mode the invention provides the use of peptide sorters allowing the pooling of several fractions of the primary chromatographic separation while avoiding elution overlap between identification peptides originating from different fractions, and between identification peptides from one fraction and altered peptides from one or more other fractions.

The general principle of the system for sorting peptides can be illustrated as follows. In each fraction obtained from the primary chromatographic step, flagged peptides elute distinct from the unaltered peptides. In case the alteration of the amino acid(s) in the flagged peptides induces a shift in the elution of the flagged peptides with a lower limit of $\delta_{min}$ and an upper limit of $\delta_{max}$, then the elution window of each fraction isolated from the primary chromatographic run ($w_1$) may be equal to $\delta_{min}$ but is preferentially less then or equal to $\delta min/2$ in order to allow distinct elution of a maximum number of flagged peptides and unaltered peptides within one fraction. The primary run is divided in fractions, here designated as window w1, situated between times t3 and t4. In a non-limiting example w1 is taken as 1 min (FIG. 1A). An example of a chromatographic shift, due to the conversion of the peptides to their altered derivatives is represented in FIG. 1B. Thus the concept is illustrated by arbitrarily selecting a 1 min fraction eluting between t3 and t4. Peptides from this fraction, which have been altered, will show a hydrophilic shift expressed as $\delta p$ (the shift for each altered peptide). Since the effect of the alteration is not always identical for every peptide derived from the selected fraction, $\delta p$ will show different values for every altered peptide and will therefore vary between two extreme values: $\delta min$ and $\delta max$ (thus $\delta min \leq \delta p \leq \delta max$). Given t1 and t2, the times at which the sorted flagged peptides start and stop to elute respectively; and t3 and t4 being the times enclosing the selected fraction, then $\delta min = t3 - t2$ and $\delta max = t4 - t1$. Thus the window in which the sorted peptides elute (w2) is expressed in terms of the hydrophilic shift and the selected fraction size (w1), $w2 = t2 - t1$ or $w2 = \delta max - \delta min - w1$ (eq. 1)

Figure 2:
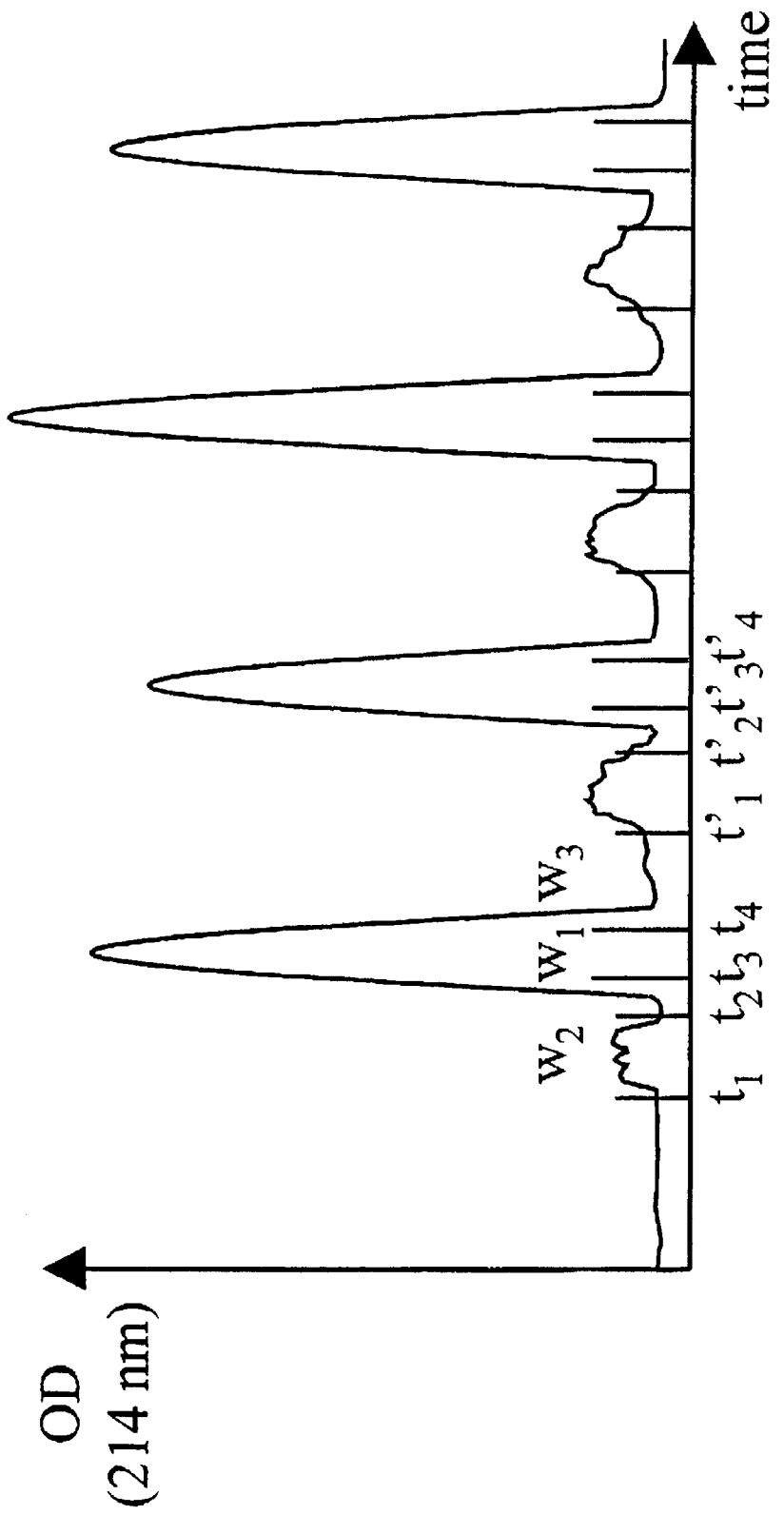
FIG. 2: Four fractions from the primary run (FIG. 1A) were pooled and subjected to the alteration process. They are subjected to the secondary run and the flagged peptides are eluting between $t_1$ and $t_2$, $t'_1$ and $t'_2$, $t''_1$ and $t''_2$ and $t'''1$ and $t'''_2$ respectively. The fractions are combined such that the sorted peptides do not overlap with the unaltered peptides from the previous fraction. By pooling fractions, the number of secondary runs is reduced.

When several fractions of the primary run are combined (pooled), then it is important that during the second run with the pooled fractions, the sorted flagged peptides from one selected fraction do not co-elute with the unaltered peptides of one of the previous fractions. This is schematically represented in FIG. 2. Thus t'1 should start at a time difference w3, measured from t4. Since there is always some spreading noticed of unaltered peptides during the secondary run, w3 should not be taken as zero. This means that t'3 being the elution time of the next fraction will be expressed as:

$$t'3 = t3 + w1 + w3 + w2 + \delta min$$

or $t'3 = t3 + w1 + w3 + w2 + \delta max - w1 - w2$ or $t'3 = t3 + w3 + \delta max$ or $t'3 - t3 = \Delta t = w3 + \delta max$ (eq. 2)

Thus the space between two consecutive fractions that can preferentially be pooled is determined by the spacing between the unaltered peptides of a given fraction and the flagged peptides of the next fraction and $\delta max$. Thus when $\delta max = 7$ min and $w3 = 5$ min then the fractions of the primary run that can be preferentially combined for the secondary run are separated by 12 min (e.g. fractions 10, 22, 34, etc. if w1 equals 1 minute). These values apply when $\delta max$ and $\delta min$ remain constant throughout the entire gradient. Depending on the chromatographic conditions, the $\delta p$ values might slightly vary throughout the fractions. It has for instance been observed that for the altered methionine-peptides, the hydrophilic shifts are in some circumstances slightly smaller for the more hydrophobic peptides than for the more hydrophilic ones, eluting at earlier times. In the TFA/acetonitrile system, this regression is limited and can therefore easily be corrected for. However, in other chromatographic conditions this regression is more pronounced and is therefore taken into account. A correction factor $\lambda n$ (as illustrated in Example 18) is therefore provided. $\lambda n$ is the correction factor for the $\delta p$'s at a given fraction ($\eta$) in which the concentration of solvent B is given as concBn. In case there is a linear correlation between $\lambda n$ and ConcBn, this will be expressed as $\lambda n = a \cdot ConcBn + b$ (eq. 3). Using the TFA/acetonitrile system described in Example 18, a C18 RP—HPLC column and hydrophilic shifts due to oxidation of methionine peptides, it was determined that $a = -0.002$ and $b = 1.002$. Thus in this example of fraction containing 10% of solvent B, $\lambda 10 = -0.002 \cdot 10 + 1.002 = 1$ and of fraction containing 50% of solvent B, $\lambda 50 = -0.002 \cdot 50 + 1.002 = 0.902$. This means that when in the fraction with 10% of solvent B, $\delta min = 2$ min and $\delta max = 7$ min, w2 will be 7 min−2 min−1 min=4 min. This value for w2 in the combined or pooled mode in the fraction containing 50% of solvent B will be w2c=7 min.0.902−2 min.0.902−1=3.51 min Thus in order to adjust the sorting system, $\delta max$ and $\delta min$ are determined for the early eluting fractions and for the late eluting fractions respectively, and the collecting times are then set as $\delta max$ taken from the earlier fractions, and $\delta min$ taken from the later fractions. Thus w2c: $\delta max$. $\lambda$ (early fractions)−$\delta min$. $\lambda$(late fractions)−w1 (eq. 4)

In one example:

$$w2c = 7 \text{ min} - 1.8 \text{ min} - 1 \text{ min} = 4.2 \text{ min}$$

Next to the use of a constant w2c-value throughout the entire sorting process, the regression of $\delta max$ and $\delta min$ may also be used to select the fractions of the primary run in order to reach a better sorting efficiency. This could be the case when the shifts are strongly affected in the course of the gradient of solvent B. Assuming values a and b of equation 3 are $a = -0.02$ and $b = 1.2$ and $\delta min = 2$ min and $\delta max = 7$ min, then the shifts at fraction 10 (10% of solvent B) will be $\delta max = 7$ min, and w2=4 min. When $\delta max$ and $\delta min$ would not be affected during the run, then the next fraction should be at 22 min. However, assuming values for a and b of equation 3 are $a = -0.02$ and $b = 1.2$, then $\lambda 22 = -0.02 \times 22 + 1.2 = 0.776$ and $\delta max 22 = 7 \times 0.76 = 5.32$ min. With t'3=10 min+5 min+5,32 min=20,32 min. Thus the next fraction could now be fraction 21 instead of fraction 22, and the new $\lambda 21$ would then be: $\lambda 21 = 0.78$ and $\delta max 21 = 7 \times 0.78 = 5.46 = 5.46$ min. Thus t'3 could be taken at least at time 10 min+5 min+5.46 min=20.46 min. Given that the next fraction selected is fraction 21, it is possible to recalculate which next fraction will most closely follow the previous one. This is fraction 31, for which $\lambda 31$ will be: 0.58 and $\delta max = 4.06$ min. Thus t"3 will be: t"3=21 min+5 min+4.06 min=30.1 min. Following the same calculations one can now include fraction 39, for which $\lambda 39 = 0.42$ and $\delta max = 2.94$ min. Thus t'"3=31 min+5 min+2.94 min=38.94 min, ect. To illustrate the principle of the peptide sorter, an illustrative example is worked out for flagged peptides and fractions isolated with an elution window $w_1$ equalling x/2 and with no regression (a constant shift throughout the entire gradient is assumed). If the total run 1 elution window of all peptides originating from the protein peptide mixture equals 20x, than 40 fractions with an x/2 window (first fraction: 0 to x/2; second fraction: x/2 to x; third fraction: x to 3x/2, . . . ) are collected. In the simplest approach, every fraction is individually subjected to the chemical and/or enzymatic amino acid alteration step and the peptides are subjected to run 2 under chromatographic conditions substantially similar to run 1. Run 2 separates the flagged peptides from the unaltered peptides.

To limit the chromatography and analysis time, the procedure has been optimised by pooling fractions obtained from run 1. Pooling may be performed with the primary fractions prior to the altering reaction or may be performed with the altered fractions. An altered fraction is a fraction wherein the peptides have been subjected to a chemical and/or enzymatic alteration according to the invention.

In the example pooling is done with fractions prior to the altering reaction. After the primary chromatographic run, the following fractions are pooled: fraction 1 (0 to x/2), with fractions 8 (7x/2 to 4x), 15 (7x to 15x/2), 22 (21x/2 to 11x), 29 (14x to 29x/2), and 36 (35x/2 to 18x). Similarly, fraction 2 is pooled with fractions 9, 16, 23, 30 and 37; fraction 3 is pooled with fractions 10, 17, 24, 31 and 38; fraction 4 is pooled with fractions 11, 18, 25, 32 and 39; fraction 5 is pooled with fractions 12, 19, 26, 33 and 40; fraction 6 is pooled with fractions 13, 20, 27 and 34; and fraction 7 is pooled with fractions 14, 21, 28 and 35. The 7 pools are chemically and/or enzymatically altered on at least one specific amino acid and each of the seven pools are separately subjected to run 2 under chromatographic conditions substantially similar to the primary chromatographic separation. Thanks to the selection of the right combination of fractions in each pool, the flagged peptides are eluting in windows distinct from the time in which the unaltered peptides are known to elute, and there is also no overlap between flagged peptides originating from different fractions in the same pool. In a non-limiting example where the alteration of the specific amino acid in the flagged peptides induces a forward shift on a hydrophobic separation column, with the shift varying in value between x and 2x (this implies that the values for $\delta min = x/2$, $\delta max = 5x/2$, $w1 = x/2$ and w3=7x/2), the flagged peptides in the first pool will, for instance, be collected in the fractions [−2x to −x/2], [3x/2 to 3x], [5x to 13x/2], [17x/2 to 10x], [12x to 27x/2] and [31x/2 to 17x]. A similar approach is followed for the pools two to seven. Therefore, in this example, instead of 40 reruns, only 7 secondary runs with the pools need to be run. The flagged peptides eluting during this secondary run can, for instance, be passed directly into the ion source of an on line connected mass spectrometer for immediate identification. The above pooling strategy is a non-limiting example. It will be clear to those skilled in the art that similar strategies can be developed to create more or fewer pools and that similar strategies can be applied to identification peptides. The choice of the number of pools will among others depend on (i) the interval shift δp induced by the chemical or enzymatic alteration, ii) the elution window of the fractions collected from the primary chromatographic separation and iii) the need to optimise the chromatography time and the analysis time. The current invention also provides the use of a parallel column sorter. With a parallel column sorter, the method based on a single column is executed with a number of columns operating in parallel (i.e., synchronously). The parallel sorter contains a number of identical columns which are run in exactly the same conditions (flow rate, gradient, etc.).

The general principle of a parallel sorter can be explained by the following non-limited example, whereby 12 pools of peptide fractions are generated, and δp is between x/2 and 5x/2 and is the hydrophilic shift between the flagged peptides and the non-altered peptides. If the total elution window of all peptides originating from the primary chromatographic run equals 20x, then 40 fractions with an x/2 window are collected. Thus, after the primary chromatographic run, the following fractions can be pooled: fraction 1 (0 to x/2), with fractions 13 (6x to 13x/2), 25 (12x to 25x/2,) and 37 (18x to 37x/2). Similarly, fraction 2 is pooled with fractions 14, 26 and 38; fraction 3 is pooled with fractions 15, 27 and 39; fraction 4 is pooled with fractions 16, 28 and 40; fraction 5 is pooled with fractions 17 and 29; fraction 6 is pooled with fractions 18 and 30; fraction 7 is pooled with fractions 19 and 31; fraction 8 is pooled with fractions 20 and 32; fraction 9 is pooled with fractions 21 and 33; fraction 10 is pooled with fractions 22 and 34; fraction 11 is pooled with fractions 23 and 35; and fraction 12 is pooled with fractions 24 and 36. The 12 pools are then chemically and/or enzymatically altered on at least one selected amino acid In an alternative approach each fraction is first subjected to the alteration and pooling is performed with the altered fractions. Table II, contains calculations of the theoretical shifts of the 12 flagged peptide pools. If each of the 12 altered pools (id est a pool containing altered fractions) are subjected to run 2, under chromatographic conditions equal or at least very similar to the primary chromatographic separation, on a single column sorter, then there is each time an "empty" elution window of 9x/2 between the fractions (present in one pool) comprising flagged peptides. This empty elution window of 9x/2 is a "dead interval" for the chromatographic separation as well as for the analyzer, because no flagged peptides will elute in this elution window, and consequently, no flagged peptides can be sent to a suitable analyzer. A parallel column sorter is most conveniently a device where 2, 3, 4 or more columns perform a secondary chromatographic run at the same time in substantially similar conditions (flow rate, gradient, etc.) and wherein the exit of the parallel sorter is directly connected with an analyzer. A parallel column sorter divides the chromatographic separation time which is normally needed for a series of serial single columns by approximately the number of columns which are used in said parallel sorter. In a non-limiting example where a parallel column sorter consists of 3 columns, the altered pools are rerun in parallel with a preferred combination of altered pools. Thus, the advantage of using a parallel column sorter is not only that the overall peptide sorting time can be significantly reduced, but also that there are a limited number of dead intervals between the selection of flagged peptides from the altered fractions so that the detection of the flagged peptides can occur in a continuous manner. As illustrated in Table II, for the non-limited example described above, a preferred combination of altered pools is when the altered pools 1, 5, and 9 are loaded on three parallel columns in a first run, altered pools 2, 6, and 10 are loaded on three parallel columns in a second run, altered pools 3, 7, and 11 are loaded on three parallel columns in a third run, and altered pools 4, 8, and 12 are loaded on three parallel columns in a forth run. With the above combination of altered pools there exists a nearly perfect alignment between the intervals in which the flagged peptides elute from the parallel columns in each of the four runs. When column I, II and III are started at the same time, flagged peptides from column I, pool 1, fraction 1 will elute first at a window −2x to −x/2. The next flow of flagged peptides comes from column II, pool 5, fraction 5; These flagged peptides will elute at a window 0 to 3x/2. These are subsequently followed by flagged peptides from column III, pool 9, fraction 9 which elute at a window 2x to 7x/2. The subsequent flagged peptides elute form column I, pool 1, fraction 13 at a window 4x to 11x/2, and so on . . . (to avoid a possible overlap between the flagged peptides from the different pools, a window of x/2 has been introduced in between each two flagged peptide elution windows). In the peptide sorter, the flagged peptides eluting from column I, II and III are passed continuously to an analyser such as a mass spectrometer. The fact that the flagged peptides in each run elute without interruption leads to a continuous flow of peptides into the analyzer. Once the first run has been completed, the second run can be started, followed by the third and the fourth run. The above pooling strategy is a non-limiting example. It will be clear to those skilled in the art that other combinations of numbers of pools and parallel columns can lead to similar results, i.e., a continuous chromatographic elution of flagged peptides immediately coupled to a continuous analysis of the peptides in for instance a mass spectrometer. The choice of the number of pools and columns will among others depend on i) the interval δp induced by the chemical or enzymatic alteration, ii) the elution window of the fractions collected from the primary chromatographic separation and iii) the need to optimise the chromatography time and the analysis time. It will also be clear to those skilled in the art that this parallel column approach can also be applied to isolate identification peptides.

In another aspect of the invention, a multi-column peptide sorter is provided. Such a multi-column peptide sorter is created and essentially exists of a number of parallel column sorters that are operating in a combined parallel and serial mode. Such parallel sorter essentially comprises y times a set of z columns, wherein the z columns are connected in parallel. In a non-limiting example, a multi-column sorter where y=3 and z=3 is a nine-column sorter. Such a nine-column sorter operates with three sets of each time three columns connected in parallel. The three parallel column sets are designated as A, B, and C. The individual columns of A are designated as I, II, and III; the individual columns of B are designated as I', II'; and III'; and the individual columns of C are designated as I", II" and III". One set of parallel columns operates with a delay (named θ) versus the previous set. Therefore, the parallel sorter B starts with a delay of θ with respect to the parallel sorter A, and the parallel sorter C starts with a delay of θ after the start of the parallel sorter B, and with a delay of 2θ after the start of the parallel sorter A. It is important to note that in the multi-column sorter, only one run 1 fraction of altered peptides is processed at a given time per column. Thus, in the example of a nine-column sorter, nine fractions of flagged peptides (or identification peptides) are processed simultaneously. This differs from the two previous described sorters (i.e., a one column peptide sorter and a parallel sorter) where several altered fractions are strategically pooled and loaded simultaneously. As only one fraction of flagged peptides (or identification peptides) is processed at the time on the multi-column sorter, the control of the flow rate accuracy (i.e., in the secondary chromatographic step) is not as important as in the previous sorters. Another advantage of the multi-column sorter is that it is well adapted to separate flagged peptides from non-altered peptides in cases where the chromatographic shift of flagged peptides varies significantly throughout the different fractions. Equally, the multi-column sorter is well adapted to separate identification peptides from altered peptides.

The mechanism of a multi-column peptide sorter is explained as a non-limited example for a nine-column peptide sorter whereby the elution windows of the altered fractions as represented in Table II are used. On column I altered fraction 1 is loaded, on column II altered fraction 13 is loaded, and on column III altered fraction 25 is loaded. System B (columns I', II', and III') is loaded with altered fractions 2, 14 and 26, respectively, and system C (columns I", II", and III'") is loaded with altered fractions 3, 15 and 27, respectively. As can be observed in Table II, when the 3 columns of system A are started simultaneously, the 3 columns of system B all start with a delay θ=3x/2 and the 3 columns of system C all start with a delay 2θ=3x (with respect to system A), there is a minimal amount of dead time during the elution of the flagged peptides. When the multi-column peptide sorter is for instance run according to the above settings, flagged peptides from system A, column I, fraction 1 will elute first at a predetermined window −2x to −x/2, followed by flagged peptides from system B, column I', fraction 2 eluting at a window 0 to 3x/2, subsequently followed by flagged peptides from system C, column I", fraction 3 eluting at a window 2x to 7x/2, subsequently followed by flagged peptides from system A, column II, fraction 13 eluting at a window 4x to 11x/2, and so on. Furthermore, the complete sorting of the fractions presented in Table II can be carried out in five runs: Run 1: system A (1,13,25), system B (2,14,26), system C (3,15,27); Run 2: system A (4,16,28), system B (5,17,29), system C (6,18,30); Run 3: system A (7,19,31), system B (8,20,32), system C (9,21,33); Run 4: system A (10,22,34), system B (11,23,35), system C (12,24,36); and Run 5: system A (37), system B (38), system C (39,40). It will be clear to those skilled in the art that other combinations of parallel and serial columns can lead to similar results and that the multi-column peptide sorter can be equally well applied to isolate identification peptides. The choice of the number of columns, their arrangement and the fractions loaded on the columns will among others depend on (i) the interval δp induced by the chemical or enzymatic alteration, ii) the elution window of the fractions collected from the primary chromatographic separation and iii) the need to optimise the chromatography time and the analysis time.

It will further be clear to a person skilled in the art that peptide sorters that carry out the method of the current invention could also be performed in a fully automated manner, using commercially available auto-injectors, HPLC-equipment and automated fraction collectors. Therefore, the present examples of peptide sorters should not be considered as exhaustive. Several variants, including electrophoretic and ion-exchange chromatography systems, are equally feasible. For the sake of completeness, peptide sorters to sort identification peptides can be designed based on the same principles.

The illustrative embodiment further provides a system for performing the above-described method of proteome analysis in a selective and efficient manner. As discussed, a primary chromatographic column performs an initial separation of the complex peptide mixture. The primary chromatographic column separates the complex peptide mixture into at least two fractions under a defined set of conditions. For example, the primary chromatographic column separates the protein peptide mixture by eluting the column with a predetermined solvent gradient and a predetermined flow rate. The fractions resulting from the primary chromatographic separation may be strategically pooled to combine a plurality of fractions having distinct elution times into a plurality of pooled fractions, as described above. The pooled fractions may be subsequently altered to result in a set of altered peptides and a set of non-altered peptides for each fraction. According to an alternate embodiment, the fractions are first altered using the methods described above and then strategically pooled into a set of pooled fractions, wherein each fraction in a pooled fraction comprises a set of altered peptides and a set of non-altered peptides. In a secondary chromatographic separation, the altered peptides are separated from the unaltered peptides. The isolated peptides may then be analyzed to identify a protein.

Figure 9:
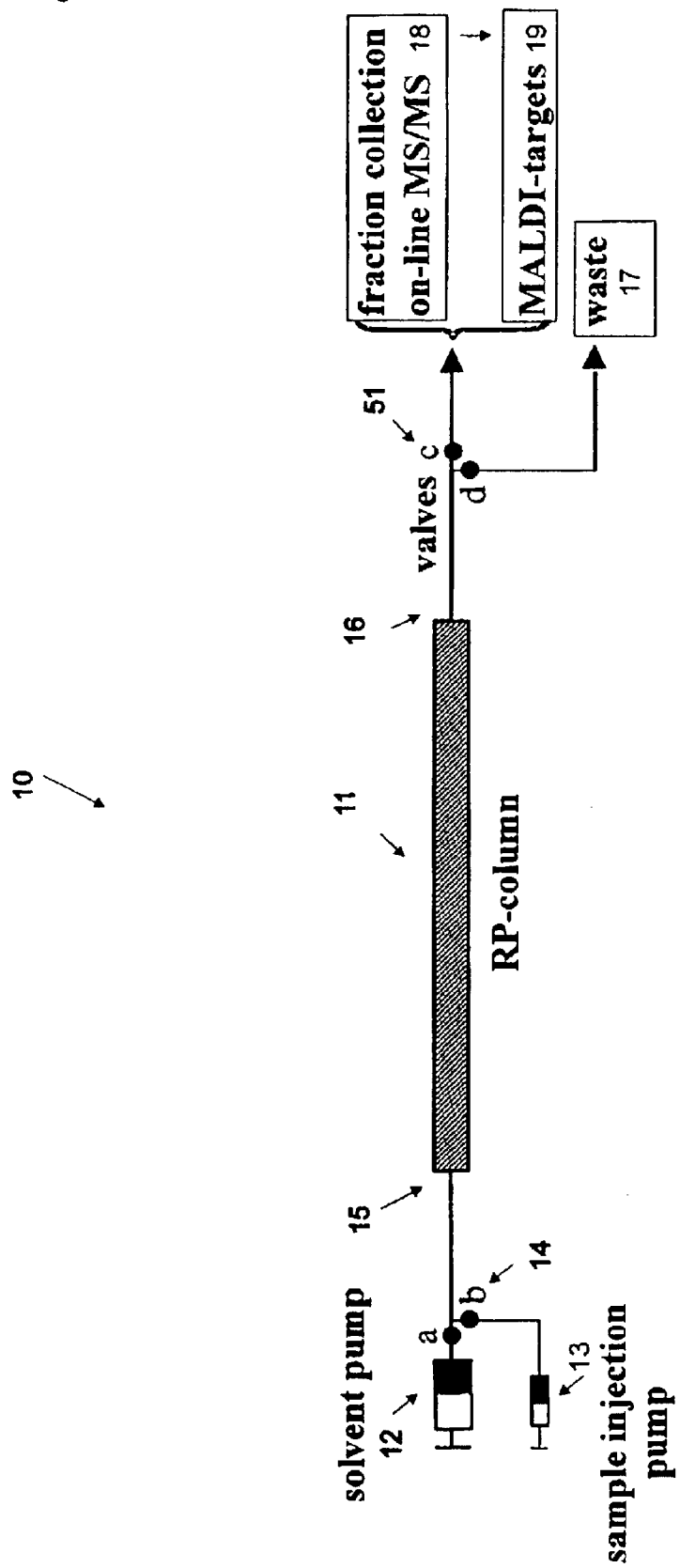
FIG. 9: The single column Peptide Sorter: Peptide sorting takes place during the secondary runs, after alterations were carried out on fractions of the primary runs. Peptide fractions from the primary run were combined as stipulated in Table IVA and loaded via the sample injector. All conditions (RP-sorbents, flow rates, gradients, solvents, etc.) were kept identically in the primary as well as during the secondary runs. In the single column version, all peptides pass the same column. After sample loading, a gradient is created using conventional commercially available high-pressure HPLC pump systems (here referred as solvent pumps). The valves are automatically steered (a and b are high-pressure valves; c and d are low-pressure valves) directing the solvent flows in the desired direction, either to the analytical instruments (fraction collector, mass-spectrometer or MALDI-targets) or the waste.

The secondary chromatographic separation may be performed using a single column peptide sorter 10, as illustrated in FIG. 9. According to the illustrative embodiment, the single column peptide sorter 10 operates in sequence with a primary chromatographic column and comprises a secondary chromatographic column 11. According to the illustrative embodiment, the secondary chromatographic column 11 is substantially identical in type, size, shape and other parameters to the primary chromatographic column. The illustrative secondary chromatographic column 11 further performs under substantially similar chromatographic conditions. For example, according to the illustrative embodiment, the secondary chromatographic column is eluted with an identical or substantially similar solvent gradient to the solvent gradient used to effect separation in the primary chromatographic column and an identical or substantially similar flow rate. The illustrative peptide sorter 10 further includes a solvent system including a solvent pump 12 connected to at least one solvent reservoir. The solvent pump 12 provides the predetermined solvent gradient to the secondary column 10. A sample injector 13 is provided for introducing a fraction or a pooled fraction to the column for separation. The peptide sorting system 10 further includes a set of inlet valves 14 for controlling and directing solvent and sample flow to the secondary column inlet 15. The peptide sorting system 10 of FIG. 9 further includes a set of outlet valves 51 for controlling flow from the outlet 16 of the secondary column 10 and directing eluate from the secondary column 10 between a waste receptacle 17, a fraction collector 18 and/or an ion-source of an on-line connected analyzer 19. A valve control system 50 is provided to controlling and guiding the operation of the valves 14, 51. According to the illustrative embodiment, the analyzer 19 comprises a mass spectrometer, though one skilled in the art will recognize that any suitable analyzer for identifying a protein, such as those described herein may be utilized. As discussed, altered peptides elute distinctly from the non-altered peptides in the secondary column 10, allowing isolation and identification of the altered peptides to occur. It is clear for a person skilled in the art that the same principles (column) can be used to separate identification peptides from altered peptides.

While the column utilized to effect the secondary chromatographic step is illustrated as separate and distinct from the primary column, one skilled in the art will recognize that a single column may be utilized to perform the primary and secondary chromatographic steps of the illustrative embodiment. For example, the complex mixture may be separated into fractions using a given chromatographic column. The given column may be cleaned and subsequently re-used for the secondary chromatographic step.

According to an alternate embodiment, the separation of the altered fractions may be performed using a parallel column peptide sorting system, as illustrated in FIGS. 12a and 12b. As discussed, the complex mixture is first separated using a primary chromatography column, altered using methods described above and strategically pooled before or after the step of altering. The altered and pooled fractions then undergo a second chromatographic step to effect separation of altered and non-altered peptides. The parallel column peptide sorting system 20 illustrated in FIG. 12a significantly improves the efficiency and speed of the secondary chromatographic step. As illustrated, the parallel column system 20 comprises a plurality of substantially identical secondary chromatography columns 21a, 21b, 21c connected in parallel. The secondary chromatography columns 21a, 21b, 21c of the parallel column system 20 are identical or substantially similar in size, shape and other chromatographic parameters to the primary chromatographic column used to perform a primary separation of a complex mixture. According to the illustrative embodiment, the peptide sorting system comprises three secondary columns. However, one skilled in the art will recognize that any suitable number of chromatography columns connected in parallel may be utilized and that the present invention is not limited to the illustrative embodiment of three columns. The same mechanical principles can also be applied to isolate identification peptides.

As shown in FIG. 12a, the parallel column system 20 includes a set of solvent systems 22a, 22b, 22c corresponding to each column 21a, 21b, 21c, respectively. Each solvent pump is connected a set of solvent reservoirs and provides a predetermined solvent gradient to the corresponding secondary column. The parallel column peptide sorting system 20 further comprises a sample injector 23 coupled to the inlets 25a, 25b, 25c of the secondary columns 22a, 22b, 22c for introducing a sample to the one or more of the secondary columns. A set of inlet valves 24 are provided for controlling and directing solvent and sample flow to a selected secondary column. A set of outlet valves 53 are provided for controlling and directing eluate from the outlets 26a, 26b, 26c of the secondary columns 20a, 20b, 20c between a waste receptacle 27, a fraction collector 28 and/or an ion-source of an on-line connected analyzer 29, such as a mass spectrometer. A valve control system 55 is provided to controlling and guiding the operation of the valves 24, 53.

According to an alternate embodiment of the parallel column peptide sorting system, shown in FIG. 12b, a single solvent pump 58 is utilized to provide a solvent gradient to the secondary parallel columns 20a', 20b', 20c' in peptide sorting system 20'. The peptide sorting system of FIG. 12b is substantially similar to the peptide sorting system of FIG. 12a, with the exception of the solvent system. As illustrated, a single solvent pump 58 is utilized to pump a solvent mixture from solvent reservoirs to the parallel secondary columns. In the embodiment illustrated in FIG. 12b, a controlled splitter system, comprising a set of flow rate regulators 59, is utilized to control and direct the flow of solvent from the solvent pump 58 to the parallel secondary columns 20a', 20b', 20c'.

Figure 13:
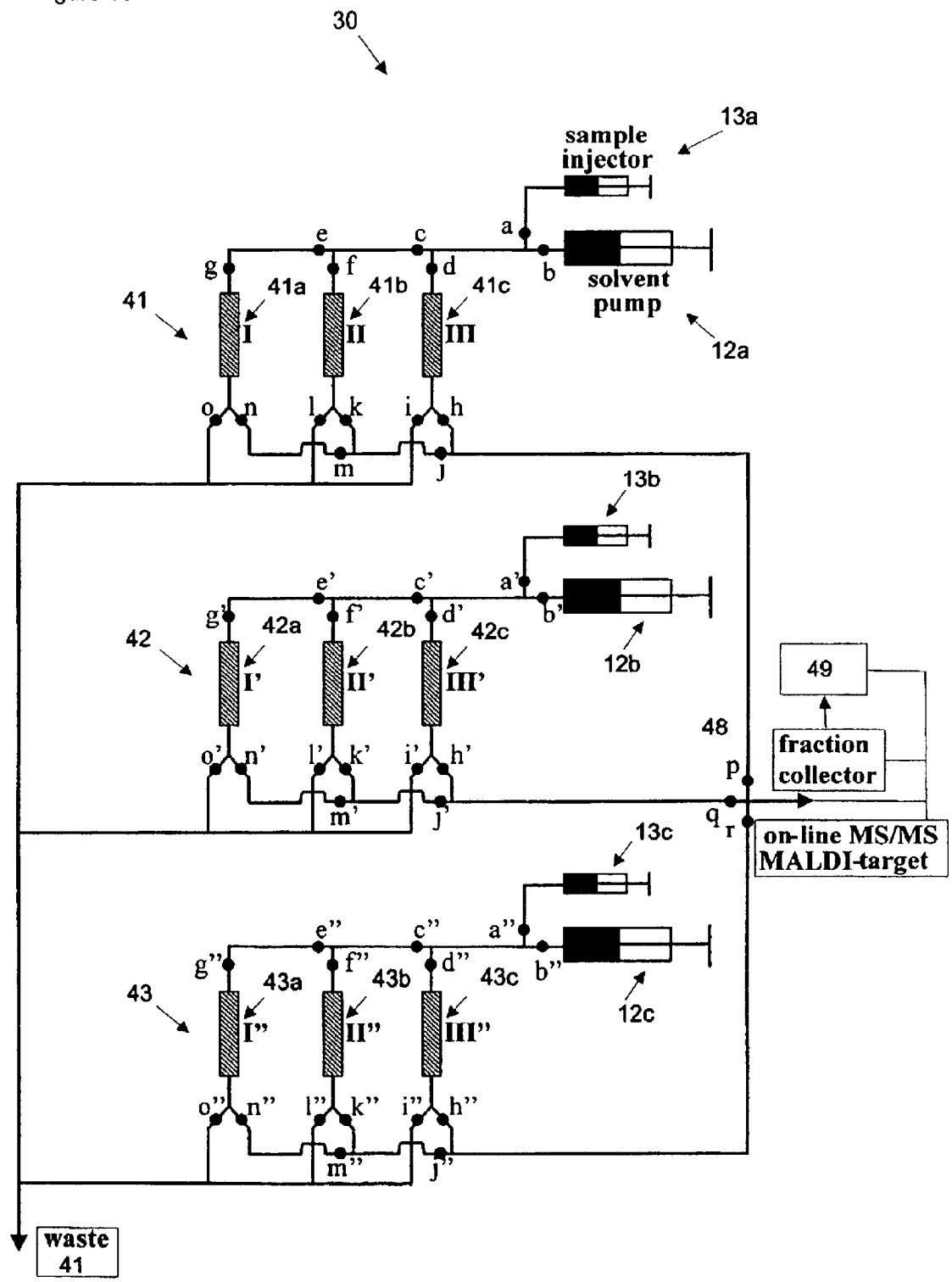
FIG. 13: The nine-column Peptide Sorter: This system differs from the previous apparatus in several aspects: i) one fraction of the primary run is each time loaded on one column, ii) each of the columns are smaller than the column of the primary run and may consist of disposable material and iii) they are operated in a combined serial/parallel mode in such a manner that every column is fully developed before the gradient is directed towards the next column. Since the columns are smaller, operation times may be decreased. Valves a–g, which control the inlet of the columns are high-pressure valves. Valves h–o and p–r control the outlet flows of the different columns either to the waste or the analyzing systems, could be low-pressure dead-volume valves. Columns I, II and II are developed with the same solvent gradient, the first part of the gradient being directed towards column I, the second part used for column II and the third part directed to column III (for details see Example 13). The segregation of the flagged and unaltered peptides is steered by valve setting which can be operated using a PC. The nine-column sorter operates with three sets of each three columns, running with a delay versus the previous set, in the examples described here, the delay was set at three minutes: B starting three minutes later than A and C starting three minutes after the start of B. Eluting peptides derived from each of the column sets are directed by valves p–r towards the analytical tools as described above.

According to yet another embodiment, shown in FIG. 13, an alternative peptide sorting system 30 for performing the secondary chromatographic step of the invention comprises a plurality of parallel column sets operating in a combined serial/parallel mode. According to the illustrative embodiment, the peptide sorting system 30 of FIG. 13 comprises a plurality of serially connected secondary column sets 41, 42, 43. Each secondary column set 41, 42, 43 comprises a plurality of secondary columns 41a, 41b, 41c, 42a, 42b, 42c, 43a, 43b, 43c connected in parallel. One skilled in the art will recognize that the illustrative peptide sorting system is not limited to illustrated number of columns and column sets and that any suitable number of parallel columns and serial column sets may be utilized to perform the secondary chromatographic step of the illustrative embodiment.

In the peptide sorting system 30 of FIG. 13, a single altered fraction of peptides produced from the primary chromatographic run is processed at a given time per column. The fractions are loaded one at a time on a selected column and a solvent gradient is provided to each respective column to effect separation of the altered peptides in each fraction from the non-altered peptides. A sample injector 13a, 13b, 13c is provided and connected to each secondary column set 41, 42, 43, respectively, for introducing a peptide fraction to a selected secondary column in the secondary column set. A solvent system, including a solvent pump 12a, 12b, 12c, is provided and connected to each secondary column set 41, 42, 43, respectively, for providing a predetermined solvent gradient at a predetermined time to the respective column set. A set of inlet valves 44 control and direct the flow of solvent from the solvent pumps and the flow of sample from the sample injectors to the inlets of the secondary columns in the secondary column sets 41, 42, 43. The outlets of the secondary columns 41a, 41b, 41c, 42a, 42b, 42c, 43a, 43b, 43c are connected to and direct eluate from the secondary columns to a waste receptacle 47, a fraction collector 48 and/or an ion-source of an on-line connected analyzer 49. A valve control system 50 is provided to controlling and guiding the operation of the valves 14, 51.

The solvent pumps 12a, 12b, 12c are configured to initiate a predetermined solvent gradient for the respective column set 41, 42, 43 at a selected time period. For example, the first solvent pump 12a initializes a first suitable solvent gradient in the column set 41 at a first predetermined time to effect separation of each fraction in the secondary columns 41a, 41b, 41c of the first set 41. The solvent gradient is developed over each secondary column 41a, 41b, 41c in the first set. After a selected delay, the second solvent pump 12b initializes an identical or substantially identical solvent gradient in the second set of secondary columns 42 at a second predetermined time. The second solvent system develops the solvent gradient over each secondary column 42a, 42b, 42c to effect separation of each fraction in the secondary columns 42a, 42b, 42c in the second set 42. Finally, after a selected delay, the third solvent pump 12c initializes an identical or substantially identical solvent gradient in the third set of secondary columns 43 to effect separation of a third set of fractions. The described configuration provides a continuous stream of separated and isolated peptides to the fraction collector 48 and/or the ion-source of the on-line connected analyzer 49 to identify an altered peptide in the fraction and a protein corresponding to the altered peptide.

The peptide sorting system 30 of FIG. 13 may be implemented using a set of secondary columns 41a, 41b, 41c, 42a, 42b, 42c, 43a, 43b, 43c that are substantially smaller than the primary column. The secondary columns 41a, 41b, 41c, 42a, 42b, 42c, 43a, 43b, 43c may also be formed of less expensive, disposable materials. In this manner the peptide sorting system 30 of the illustrative embodiment not only significantly improves the speed and efficiency of the proteome analysis of the present invention, the illustrative peptide sorting system 30 further reduces the cost of performing the analysis. The above mechanical principle can be used to separate flagged peptides from non-altered peptides or to separate identification peptides from altered peptides.

Thus in another embodiment the invention provides a system for sorting peptides comprising a) a primary chromatographic column for separating a protein peptide mixture into a plurality of fractions under a defined set of conditions and whereby each fraction is subsequently subjected to an alteration of at least one amino acid to generate flagged peptides and wherein the altered fractions are pooled into a set of pooled fractions, each pooled fraction comprising at least two altered fractions and b) a set of secondary chromatographic columns comprising a first secondary chromatographic column for separating a first pooled fraction and at least a second secondary chromatographic column arranged in parallel with the first secondary chromatographic column for separating a second pooled fraction, wherein the set of secondary chromatography columns perform isolation of the flagged peptides under substantially identical conditions as the defined set of conditions, whereby there is no elution overlap between i) the flagged peptides from different fractions within one pool or between pools and ii) the flagged peptides and the unaltered peptides.

In yet another embodiment the invention provides a system for sorting peptides comprising: a primary chromatographic column for separating a protein peptide mixture into a plurality of fractions under a defined set of conditions and whereby each fraction is subsequently subjected to an alteration of at least one amino acid to generate altered peptides and unaltered peptides and wherein the altered fractions are pooled into a set of pooled fractions, each pooled fraction comprising at least two altered fractions and a set of secondary chromatographic columns comprising a first secondary chromatographic column for separating a first pooled fraction and at least a second secondary chromatographic column arranged in parallel with the first secondary chromatographic column for separating a second pooled fraction, wherein the set of secondary chromatography columns perform isolation of the identification peptides under substantially identical conditions as the defined set of conditions, whereby there is no elution overlap between i) the identification peptides from different fractions within one pool or between pools and ii) the identification peptides and the altered peptides.

In another embodiment the system further comprises an outlet to the set of second chromatography columns for collecting eluate from the first secondary chromatographic column and the second secondary chromatographic column.

In another embodiment the system further comprises an analyzer connected to the outlet.

In another embodiment the system further comprises a waste receptacle connected to the outlet for collecting a waste product from the set of secondary chromatography columns.

In yet another embodiment the system further comprises a sample injector coupled to the set of secondary chromatography columns for injecting a pooled fraction into one of the first secondary column and the second secondary column.

In yet another embodiment the system further comprises a set of sample injection valves for directing the pooled fraction from the sample injector to one of the first secondary column and the second secondary column.

In yet another embodiment the system further comprises a solvent system for providing a solvent gradient to the set of secondary chromatographic columns.

In yet another embodiment said solvent system comprises a first solvent pump for providing a solvent gradient to the first secondary chromatographic column and a second solvent pump for providing a solvent gradient to the second secondary chromatographic column.

In yet another embodiment said solvent system comprises: a solvent pump connected to the first secondary chromatographic column and the second secondary chromatographic column; a controlled splitter system comprising a first flow rate regulator for regulating a solvent flow to the first secondary chromatographic column and a second flow rate regulator for regulating a solvent flow to the second secondary chromatographic column.

In yet another embodiment the system further comprises a fraction collector for collecting an eluate from the set of secondary chromatographic columns.

In yet another embodiment the system further comprises a valve control system for controlling the set of sample injection valves.

In yet another embodiment in said system the first and second secondary chromatographic columns are substantially identical to the primary column.

In yet another embodiment in said system a first solvent gradient is applied to the primary column to effect separation of the protein peptide mixture and a second solvent gradient that is substantially identical to the first solvent gradient is applied to the secondary columns to effect separation of the pooled fractions.

In another embodiment the invention provides a peptide sorting system, comprising a first chromatographic column set comprising a first chromatographic column and a second chromatographic column arranged substantially in parallel with the first chromatographic column, a first sample injector for providing a sample to the first chromatographic column set, a first solvent system for providing a predetermined solvent gradient to the first chromatographic column set at a first predetermined time, a second chromatographic column set comprising a third chromatographic column and a fourth chromatographic column arranged in parallel with the third chromatographic column, a second sample injector for providing a sample to the second chromatographic column set, and a second solvent system for providing the solvent gradient to the second chromatographic column set at a second predetermined time subsequent to the first predetermined time.

In yet another embodiment this sorting system further comprises a waste receptacle connected to the outputs of the first and second chromatographic column sets for collecting a waste product the chromatographic columns. In yet another embodiment this sorting system further comprises a fraction collector connected to the outputs of the first and second chromatographic column sets for collecting elute from the column at predetermined time intervals. In yet another embodiment this sorting system further comprises an analyzer connected to the outputs of the first and second chromatographic column. In yet another embodiment this sorting system further comprises a set of inlet valves connected to the inlets of the chromatographic columns for controlling the inlets of the chromatographic columns. In yet another embodiment the sorting system further comprises a set of outlet valves connected to the outlets of the chromatographic columns for directing an eluate from the columns to one of a waste receptacle, a fraction collector and an analyzer. In yet another embodiment the system further comprises a valve control system for controlling the set of inlet valves and the set of outlet valves.

In another embodiment the invention provides a method of separating peptides, comprising the steps of: providing a set of fractions of a protein peptide mixture; providing a peptide sorting system comprising a first set of parallel chromatography columns and a second set of parallel chromatography columns, loading the first set of columns with a first set of fractions of the protein peptide mixture; loading the second set of columns with a second set of fractions of the protein peptide mixture; providing a solvent gradient in the first set of columns at a first predetermined time to initialize separation of the first set of fractions; and providing the solvent gradient in the second set of columns at a second predetermined time subsequent to the first predetermined time to initialize separation of the second set of fractions. In yet another embodiment the method further comprises the step of directing an eluate from the first set of columns to one of a waste receptacle, a fraction collector and an analyzer. In yet another embodiment the method further comprises the step of directing an eluate from the second set of columns to one of a waste receptacle, a fraction collector and an analyzer.

In another embodiment the invention provides a method of isolating a flagged peptide from a protein peptide mixture, comprising the steps of: (a) providing a primary chromatography column for separating the protein peptide mixture; (b) injecting the protein peptide mixture into the primary chromatography column to separate the protein peptide mixture into a set of fractions under a defined set of conditions; (c) altering at least one of the fractions in the set of fractions to form a set of altered fractions, wherein an altered fraction comprises a subset of flagged peptides and a subset of unaltered peptides; (d) pooling a first altered fraction and a second altered fraction to form a first pooled fraction, wherein there is no elution overlap between i) the flagged peptides from the first and second altered fractions and ii) the flagged peptides and the unaltered peptides of said fractions; (e) pooling a third altered fraction and a fourth altered fraction to form a second pooled fraction, wherein there is no elution overlap between i) the flagged peptides from the third and fourth altered fractions and ii) the flagged peptides and the unaltered peptides of said fractions; (f) providing a first secondary chromatography column for separating a subset of flagged peptides from a subset of unaltered peptides; and (g) separating the first pooled fraction using the secondary chromatography column under the defined set of conditions to isolate the subsets of flagged peptides in the first altered fraction and the second altered fraction.

In another embodiment the invention provides a method of isolating an identification peptide in a protein peptide mixture, comprising the steps of: (a) providing a primary chromatography column for separating the protein peptide mixture; (b) injecting the protein peptide mixture into the primary chromatography column to separate the protein peptide mixture into a set of fractions under a defined set of conditions; (c) altering at least one of the fractions in the set of fractions to form a set of altered fractions, wherein an altered fraction comprises a subset of altered peptides and a subset of identification peptides; (d) pooling a first altered fraction and a second altered fraction to form a first pooled fraction, wherein there is no elution overlap between i) the altered peptides from the first and second altered fractions and ii) the altered peptides and the identification peptides of said fractions; (e) pooling a third altered fraction and a fourth altered fraction to form a second pooled fraction, wherein there is no elution overlap between i) the identification peptides from the third and fourth altered fractions and ii) the altered peptides and the identification peptides of said fractions; (f) providing a first secondary chromatography column for separating a subset of altered peptides from a subset of identification peptides, and (g) separating the first pooled fraction using the secondary chromatography column under the defined set of conditions to isolate the subsets of identification peptides in the first altered fraction and the second altered fraction.

In yet another embodiment the previous methods further comprise the step of separating the second pooled fraction using the first secondary chromatography column under the defined set of conditions to isolate the subsets of flagged or identification peptides in the third altered fraction and the fourth altered fraction.

In yet another embodiment the previous methods further comprise the steps of: (h) providing a second secondary chromatography column arranged substantially in parallel with the first secondary chromatography column for separating a subset of altered peptides from a subset of unaltered peptides in a fraction; and (i) separating the second pooled fraction using the second secondary chromatography column under the defined set of conditions to isolate the subsets of altered peptides in the third altered fraction and the second altered fraction.

In yet another embodiment the previous methods further comprise the step of directing the flagged or identification peptides to an analyzer.

In yet another embodiment the previous methods further comprise the step of identifying an identification or flagged peptide and its corresponding protein using the analyser in combination with a database searching.

In what follows, a more informative description of several of the different steps of the invention is presented.

I. Preparation of a Protein Peptide Mixture

Protein peptide mixtures originating from a sample comprising proteins (the protein peptide mixtures) are obtained by methods described in the art such as chemical or enzymatic cleavage or digestion. In a preferred aspect, the proteins are digested by a proteolytic enzyme. Trypsin is a particularly preferred enzyme because it cleaves at the sites of lysine and arginine, yielding charged peptides which typically have a length from about 5 to 50 amino acids and a molecular weight of between about 500 to 5,000 dalton. Such peptides are particularly appropriate for analysis by mass spectroscopy. A non-limited list of proteases which may also be used in this invention includes *Lysobacter enzymogenes* endoproteinase Lys-C, *Staphylocolococus aureus* endoproteinase Glu-C (V8 protease), *Pseudomonos fragi* endoproteinase Asp-N and clostripain. Proteases with lower specificity such as *Bacillus subtilis* subtilisin, procain pepsin and *Tritirachium album* proteinase K may also be used in this invention.

Alternatively, chemical reagents may also be used to cleave the proteins into peptides. For example, cyanogen bromide may be used to cleave proteins into peptides at methionine residues. Chemical fragmentation can also be applied by limited hydrolysis under acidic conditions. Alternatively, BNPS-skatole may be used to cleave at the site of tryptophan. Partial $NH_2$-terminal degradation either using chemically induced ladders with isothiocyanate or using aminopeptidase treatment can be used as well.

II. Chromatography

As used herein, the term "chromatographic step" or "chromatography" refers to methods for separating chemical substances and are vastly available in the art. In a preferred approach it makes use of the relative rates at which chemical substances are adsorbed from a moving stream of gas or liquid on a stationary substance, which is usually a finely divided solid, a sheet of filter material, or a thin film of a liquid on the surface of a solid. Chromatography is a versatile method that can separate mixtures of compounds even in the absence of detailed previous knowledge of the number, nature, or relative amounts of the individual substances present. The method is widely used for the separation of chemical compounds of biological origin (for example, amino acids, fragments of proteins, peptides, proteins, phospholipids, steroids etc.) and of complex mixtures of petroleum and volatile aromatic mixtures, such as perfumes and flavours. The most widely used columnar liquid technique is high-performance liquid chromatography, in which a pump forces the liquid mobile phase through a high-efficiency, tightly packed column at high pressure. Recent overviews of chromatographic techniques are described by Meyer M., 1998, ISBN: 047198373X and Cappiello A. et al. (2001) Mass Spectrom. Rev. 20(2): 88–104, incorporated herein by reference. Other recently developed methods described in the art and novel chromatographic methods coming available in the art can also be used. Some examples of chromatography are reversed phase chromatography (RP), ion exchange chromatography, hydrophobic interaction chromatography, size exclusion chromatography, gel filtration chromatography or affinity chromatography such as immunoaffinity and immobilized metal affinity chromatography.

Chromatography is one of several separation techniques. Electrophoresis and all variants such as capillary electrophoresis, free flow electrophoresis etc. is another member of this group. In the latter case, the driving force is an electric field, which exerts different forces on solutes of different ionic charge. The resistive force is the viscosity of the non-flowing solvent. The combination of these forces yields ion mobilities peculiar to each solute. Some examples are sodium dodecyl sulfate polyacrylamide gel electrophoresis (SDS-PAGE) and native gel electrophoresis. Capillary electrophoresis methods include capillary gel electrophoresis, capillary zone electrophoresis, capillary electrochromatography, capillary isoelectric focussing and affinity electrophoresis. These techniques are described in McKay P., An Introduction to Chemistry, Science Seminar, Department of Recovery Sciences, Genentech, Inc. incorporated herein by reference.

III. Buffers

The methods of the invention require compatibility between the separation conditions in the primary run, the reaction conditions in the alteration step, the separation condition in the secondary run and the conditions to analyse the eluting flagged or identification peptides in analysers such as mass spectrometers. As mentioned before, the combination of the chromatographic conditions in the primary and secondary run and the chromatographic shifts induced by the alteration reaction is determining the possibility to isolate the flagged or identification peptides out of each fraction obtained from a protein peptide mixture in the primary run. As also mentioned before, in a preferred embodiment the chromatographic conditions of the primary run and the secondary run are the same or substantially similar.

In a further preferred embodiment, buffers and or solvents used in both chromatographic steps are compatible with the conditions required to allow an efficient proceeding of the chemical and/or enzymatic reactions in the alteration step in between the two chromatographic steps. In a particular preferred embodiment the nature of the solvents and buffer in the primary run, the secondary run and the alteration step are identical or substantially similar. In a further preferred embodiment said buffers and solvents are compatible with the conditions required to perform a mass spectrometric analysis. Defining such buffers and solvents needs tuning and fine-tuning [and such conditions are not available in the prior art]. Examples to illustrate this tuning are for instance described in example 9.

For some embodiments of the invention with particular types of flagged peptides or identification peptides it is very difficult if not impossible to design one set of identical or substantially similar buffers and/or solvents which can be used throughout the procedure of primary run, alteration step, secondary run and analysis.

For instance, the chemical and/or enzymatic reaction to alter the peptides in the alteration step may request specific reaction conditions which are not compatible with the buffers used in the primary and/or secondary run. In these cases the buffer/solvent conditions in the fractions are changed before the alteration step and/or after the alteration step which changing is performed with methods described in the art such as for example an extraction, a lyophilisation and redisolving step, a precipitation and redisolving step, a dialysis against an appropriate buffer/solvent or even a fast reverse phase separation with a steep gradient.

Another complication may be the composition of the buffer/solvent present in the protein peptide mixture before starting the primary run. Application of a pre-treatment step as mentioned herein above may request specific buffer/solvent conditions which are not compatible with the buffer/solvent to perform the primary run. Alternatively, the conditions for the preparation/isolation of proteins from their biological source may result in the contamination of the protein mixtures or protein peptide mixtures with compounds which negatively interfere with the primary run. In these situations the buffer/solvent composition of the protein mixture or the protein peptide mixture is changed to make them compatible with the primary run. Such changing is performed with methods described in the art such as for example an extraction, a lyophilisation and redisolving step, a precipitation and redisolving step, a dialysis against an appropriate buffer/solvent or even a fast reverse phase separation with a steep gradient.

In yet another embodiment of the invention the buffer/solvent of the secondary run is not compatible with performing the analysis of the eluting flagged peptides or identification peptides. In such cases, the buffer/solvent in the fractions collected from the secondary run is changed to make the conditions compatible with the analysis with for instance a mass spectrometer. Such changing is performed with methods described in the art such as for example an extraction, a lyophilisation and redisolving step, a precipitation and redisolving step, a dialysis against an appropriate buffer/solvent or even a fast reverse phase separation with a steep gradient. Alternatively, the fractions with the flagged peptides or identification peptides can be collected and recombined for a third series of separations, hereinafter referred to as a ternary run. Said ternary run is designed in such a way that the eluting flagged or identification peptides can be analysed with a mass spectrometer. An example of the strategy and the pooling strategy is for instance described in example 18.

Equivalents

Those skilled in the art will recognize, or be able to ascertain using no more than routine experimentation, many equivalents to the specific embodiments of the invention described herein. For example chromatography can be substituted in many cases by electrophoresis. Electrophoretic techniques include (capillary) gel electrophoresis, (capillary) electrochromatography, (capillary) isoelectric focussing and affinity electrophoresis. In yet another equivalent example, an alteration could also be a physical alteration. For instance, exposing peptides to an elevated temperature can result in the (partial) unfolding of temperature sensitive peptides and, as a consequence, these peptides will acquire another chromatographic behaviour.

For instance, the present invention provides a method to isolate a subset of peptides out of a protein peptide mixture, comprising the steps of: (a) initially separating the protein peptide mixture into fractions of peptides via chromatography, (b) exposing each fraction to an elevated temperature and (c) isolating the physically altered peptides via a second chromatography whereby the chromatography of the initial and the second separation step is performed with the same type of chromatography and whereby the chromatographic conditions in both separations are preferentially the same or substantially similar. In a reverse mode, the peptides which are unaltered after exposure to an elevated temperature are isolated in step c). In a particular embodiment, the exposure to an elevated temperature can even be applied during the secondary run instead of before the secondary run.

Another possibility is than run 1 or run 2 are carried out in the presence of a magnetic field. This magnetic field then specifically influences the elution or migration of peptides sensitive to magnetism. For instance, magnetic particles coated with specific antibodies directed against phophotyrosine could be added to a protein peptide mixture. The phosphotyrosine-containing peptides will be specifically affected under the influence of a magnetic field.

EXAMPLES

Example 1

Specific Chemical Alteration of Methionine-Residues

Figure 3:
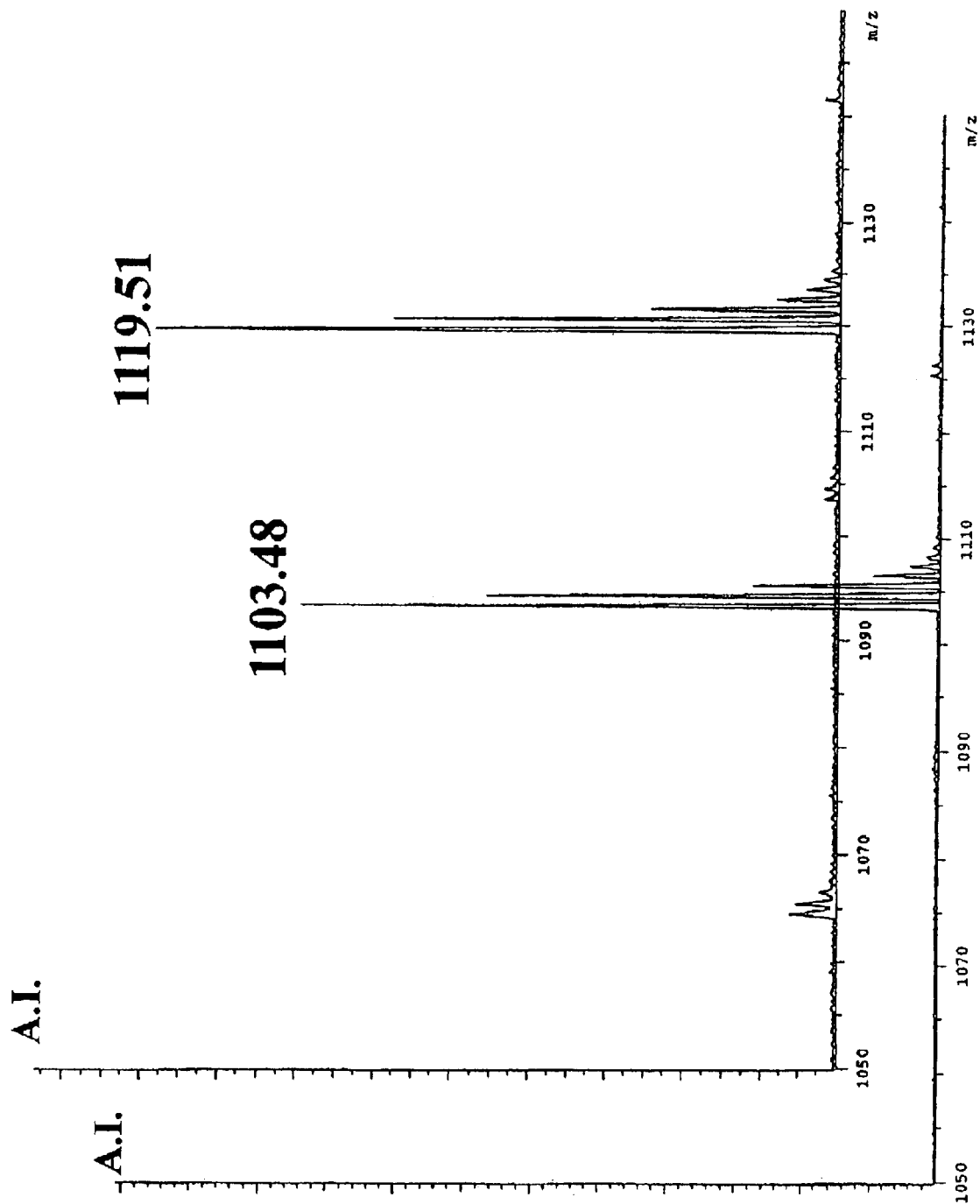
FIG. 3: 214 nm UV-absorbance profiles of RP-HPLC separations of NH$_2$—YSFV<u>M</u>TAER—COOH (A), NH$_2$—YSFV<u>C</u>TAER—COOH (B) and NH$_2$—YSFV<u>W</u>TAER—COOH (C), before (lower trace) and after treatment (upper trace) with 0.5% H$_2$O$_2$ in 1% TFA at 30° C. for 30 min. MALDI-RETOF-MS spectra of the eluting control and H$_2$O$_2$-treated peptides (respectively lower trace vs. upper trace) are shown in panels D–F.
Figure 3:
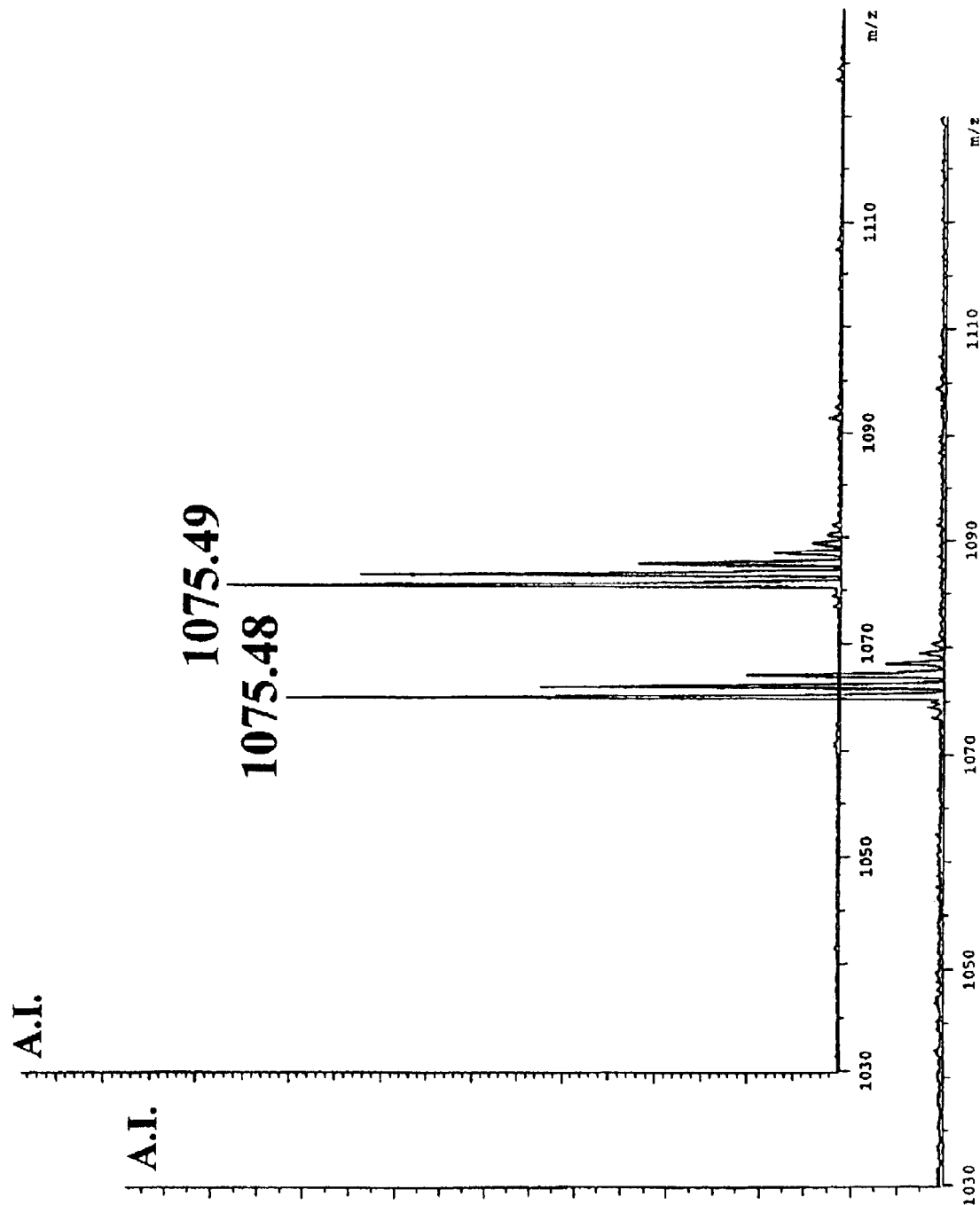
Figure 3:
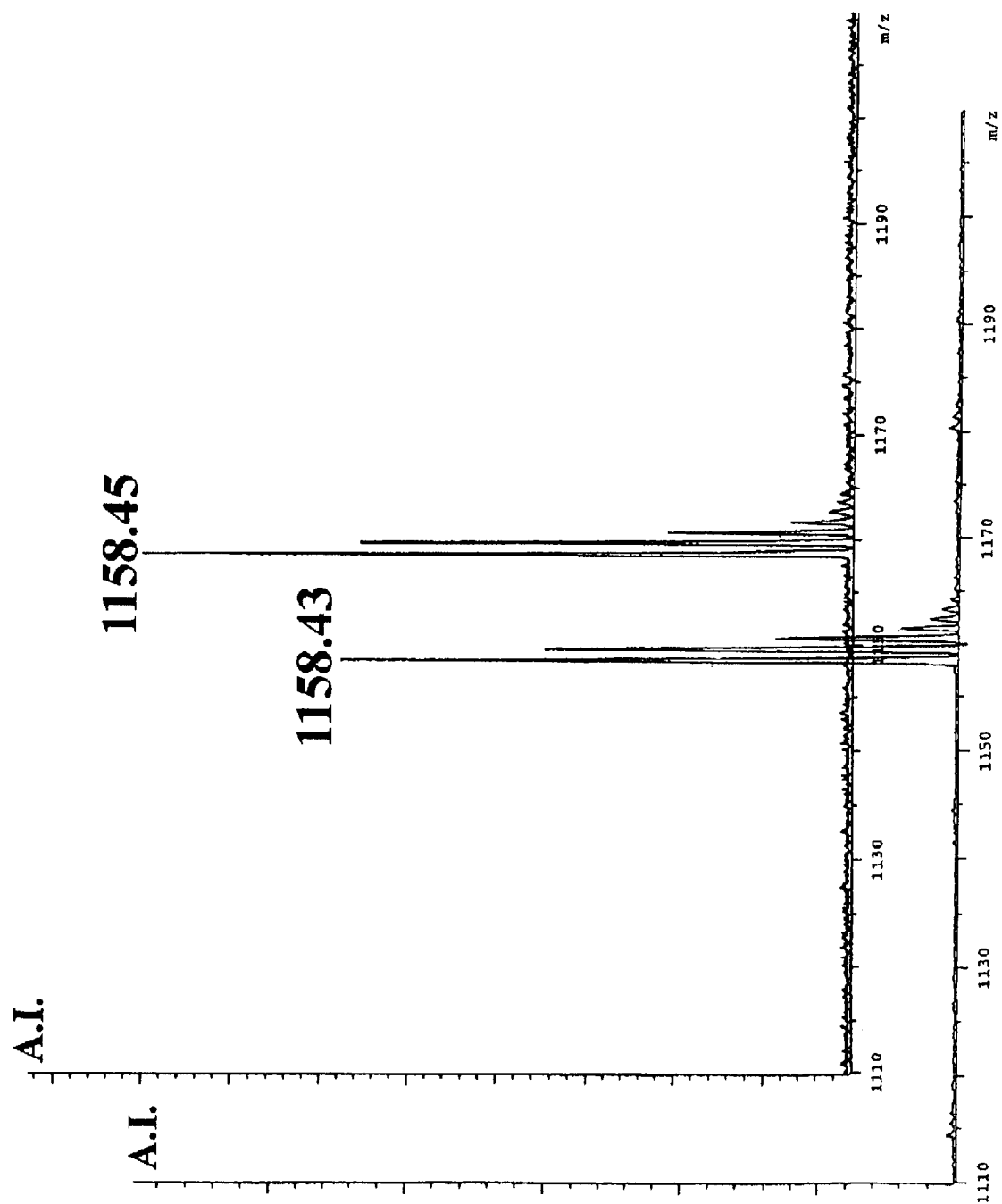

A protein peptide mixture was generated according to the method described in the invention and the relatively rare amino acid methionine was selected for alteration. As documented in the literature, one approach to alter methionine is by chemical oxidation, which can lead to sulfoxide-formation and to sulfone-formation. Peptides comprising methionine can be converted into their sulfone derivatives by using strong oxidizing conditions such as with performic acid or other per-acids (Toennies and Homiller, 1942 and Hirs, 1956). It is known that the stronger oxidizing conditions are rather harsh and not selective enough. The formation of methionine-sulfoxide proceeds upon contact of methionine with the air. However, in the presence of 0.5% $H_2O_2$ at room temperature and low pH (1% TFA), this reaction is completed in less than 30 minutes. Interestingly, under these mild conditions, it was observed that both cysteine and tryptophan, two other residues that are very sensitive to oxidation, are poorly oxidized or not oxidized at all. This conclusion was reached by oxidizing a large variety of Trp peptides, Cys peptides, and Met peptides, followed by HPLC-analysis and mass spectrometry of the reaction products. An illustrative example of the specificity of the reaction is shown in FIG. 3. Both methionine alterations (the sulfoxide- and the sulfone-derivative) are more hydrophilic (the sulfone derivative to a lesser extent than the sulfoxide derivative) than the non-altered methionine. The specific mild chemical oxidation of peptides containing methionine-residues, towards methionine-sulfoxide, was preferentially exploited in this invention because of the specificity of the alteration for methionine and because of the optimal properties to separate flagged peptides from non-altered peptides. The experiments demonstrate that, under the conditions of the invention, this methionine alteration can be efficiently used to largely separate the methionine-sulfoxide altered peptides from the non-altered peptides in a complex mixture of peptides or a protein peptide mixture. An important element of the invention is the strong decrease of the hydrophobicity when peptides are converted from the methionine to their methionine-sulfoxide forms. This is illustrated by a shift in the elution of the oxidized peptides towards lower concentrations of the organic solvent during reversed-phase chromatography (here referred to as the frontal or hydrophilic shift). Using different methionine-containing peptides and also using reversed phase chromatographic conditions, it is demonstrated that a large spectrum of peptides containing oxidized methionine can be efficiently separated from the pool of unaltered peptides. Depending on the chromatographic conditions, it is demonstrated that the hydrophilic shifts in the elution of the oxidized peptides can differ significantly. The results show that by using the right conditions, shifts from 3 min to more than 7 min in standard gradients towards lower modifier concentrations can be obtained. This is illustrated for one peptide run in different systems (Table III). Large shifts were systematically observed with the $NH_4Ac$/methanol system. Smaller, but still significant shifts, were noticed with the TFA/acetonitrile or HCOOH/acetonitrile combination. In principle, all systems indicated in Table III can be used in the sorting process. In all following examples we used the 0.1% TFA/acetonitrile or the 0.1% HCOOH/acetonitrile mixtures. It should be clear that the peptide sorting system does not exclude the use of other solvent systems. The HCOOH/acetonitrile combination is one approach which can be used when flagged peptides will be analyzed with electrospray MS. Interestingly, the hydrophilic shifts of flagged peptides (even when originating from the same fraction in the primary chromatographic run) are not identical and may even vary considerably. Thus the oxidation seems to have a variable effect which might be sequence dependent. More in particular, the methionine peptides which have been collected in a 1 min interval in the primary run, will now elute as their sulfoxide forms in a larger time interval (for instance in 4 minutes) in the secondary runs. This is an important advantage, because the selected methionine-containing peptides are eluting during the secondary run in a larger time interval and this significantly increases the resolving capacity of the separation system. In consequence, co-elution of flagged peptides decreases, the peptides elute more gradually, in a less compressed manner, allowing a better presentation for identification to the mass spectrometer.

An alternative approach to alter the methionine sidechains in peptides is the reaction with alkylhalides, such as methyliodide, resulting in the formation of the sulfonium ion (Rothgeb et al., 1977). This reaction proceeds slowly and reaches completion after more than eight hours. A protein peptide mixture is generated according to the method described in the invention. A primary run is for example performed with an anion-exchange column and fractions are collected. Said fractions are altered with for example methyliodide which specifically reacts with peptides comprising methionine residues. As a result peptides comprising methionine are altered (methionine-residues are altered into their sulfonium ions) and have a different charge and the resulting flagged peptides migrate differently from the unaltered peptides on ion-exchange columns. The chromatographic conditions of the first and secondary run are performed under identical or similar chromatographic conditions. More specifically, this alteration results in a faster elution rate of the flagged peptides when such peptides are passed over an anion-exchanger (e.g. MONO Q or DEAE-columns) or an decreased elution rate on a cation-exchanger (e.g. Mono S, phosphocellulose).

Example 2

Specific Chemical Alteration of Cysteine-Residues

Figure 4:
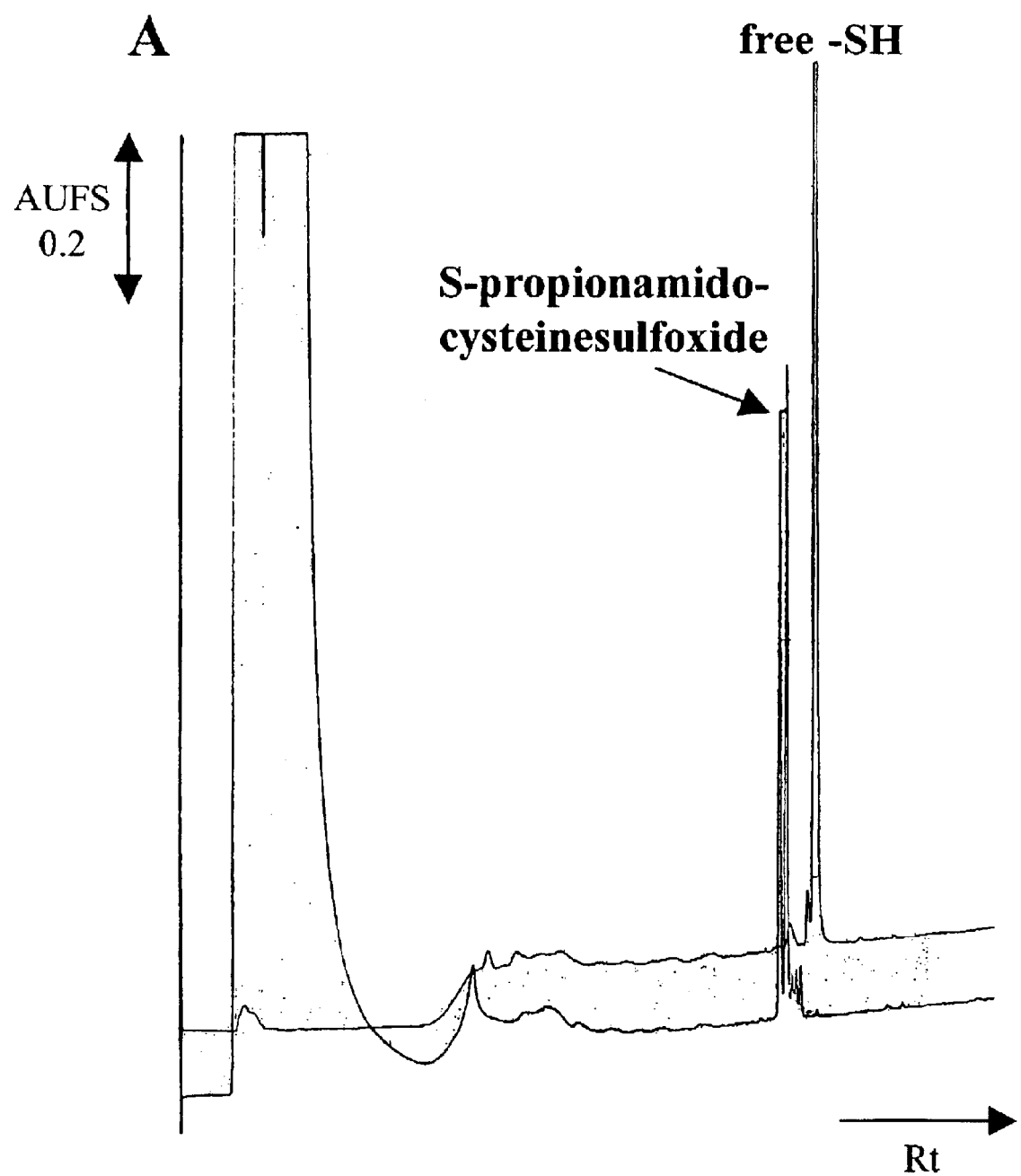
FIG. 4: (A) 214 nm UV absorbance profile of the peptide NH$_2$—YSFVCTAER—COOH, separated on a reversed-phase C18 HPLC-column. The peptide was altered by acrylamide followed by oxidation to its S-propionamido-cysteinesulfoxide derivative (lower trace) which, when run under the same HPLC-conditions shows a hydrophilic shift of about 2 min compared to the unaltered peptide (upper trace) Notice the presence of closely migrating enantiomeric doublet typical of the sulfoxide derivative in the TFA-acetonitrile system. (B) MALDI-RETOF-MS spectrum of the S-propionamido-cysteinesulfoxide derivative of the peptide NH$_2$—YSFVCTAER—COOH. Fragment ions arising from the rapid neutral loss of the altered side chain of the cysteine residue are indicated in blue and are of great help to identify the presence of a modified cysteine in the parent peptides.
Figure 4:
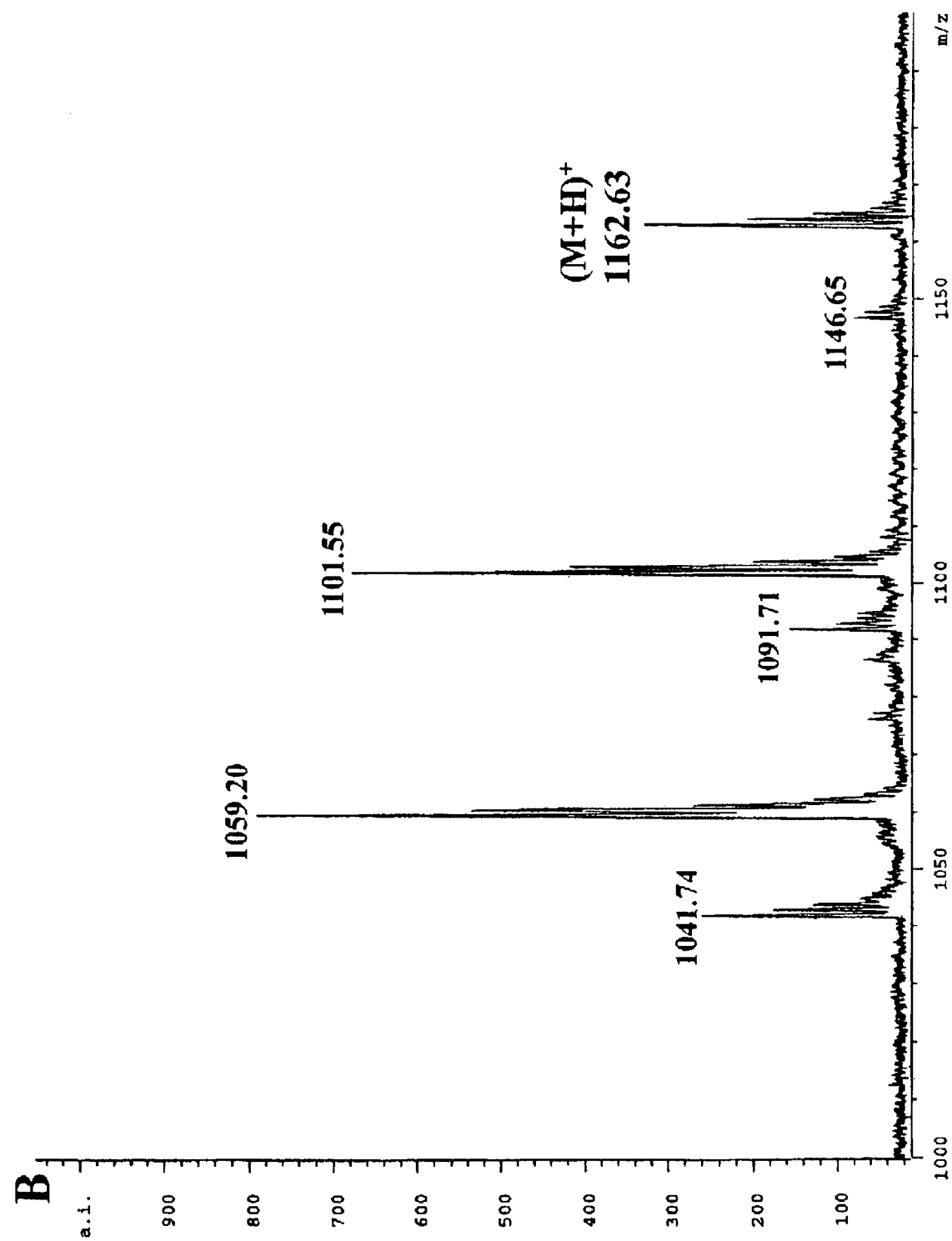

A protein peptide mixture is generated with one of the methods described herein before and a specific chemical alteration of cysteine residues is carried out. Said alteration is for instance based on the specific conversion of cysteine peptides into a more hydrophilic derivative, which undergoes a hydrophilic shift during reversed phase HPLC. Several reagents can fulfill these requirements. For instance, reactions with iodoacetamide, iodoacetate, ethyleneimine, bromoethylamine, acrylamide and 4-vinyl pyridine, all convert cysteine into compounds that behave more hydrophilic in reverse phase-conditions. In addition these compounds all undergo oxidation by $H_2O_2$ resulting in the formation of their corresponding sulfoxide derivatives, which are even more hydrophilic. It is important to mention that the shift due to oxidation is less pronounced here than in the case of the methionine oxidation. However, when combining the shifts between the free thiol cysteine derivative and its altered and oxidized counterpart, overall shifts of flagged peptides which are similar to those measured for methionine sulfoxide formation were obtained (FIG. 4). The following reaction scheme (i) shows an example how cysteine-residues can be specifically, chemically altered in such a way that the alteration can be used to separate flagged cys-peptides from non-altered peptides according to the invention. Thus the protocol is as follows: the protein mixture is dissolved in 8M urea in 1% TFA and first treated with $H_2O_2$ (1% final concentration) for 30 min at 25° C. resulting in sulfoxide formation of all methionine residues present in the protein mixture. The proteins are then precipitated overnight at −20° C. after addition of 4 volumes of ethanol. Precipitated proteins are recovered by centrifugation, washed once with 1 ml of ethanol-water (3:1, by volume). The washed protein pellet is redissolved in 8M urea, 0.1 M Tris-HCl pH 8.6 and a 2-fold molar excess of tributyl phosphine is added, converting all S—S bridges into thiol groups. Peptides are generated by specific cleavage (most conveniently trypsin is used) and the protein peptide mixture is separated by RP—HPLC (primary run) and collected in such number of fractions that allow during run 2 the separation of flagged peptides from non-altered peptides in each of the collected fractions. In each fraction, the cysteine residues are converted into their S-propionamide derivatives by reaction with acrylamide in buffer pH 8.6 (Sechi and Chait, 1998). This reaction is immediately followed by oxidation with $H_2O_2$ in 1% TFA, converting the S-propionamide derivatives in the more hydrophilic sulfoxide form. The latter are described below (i).

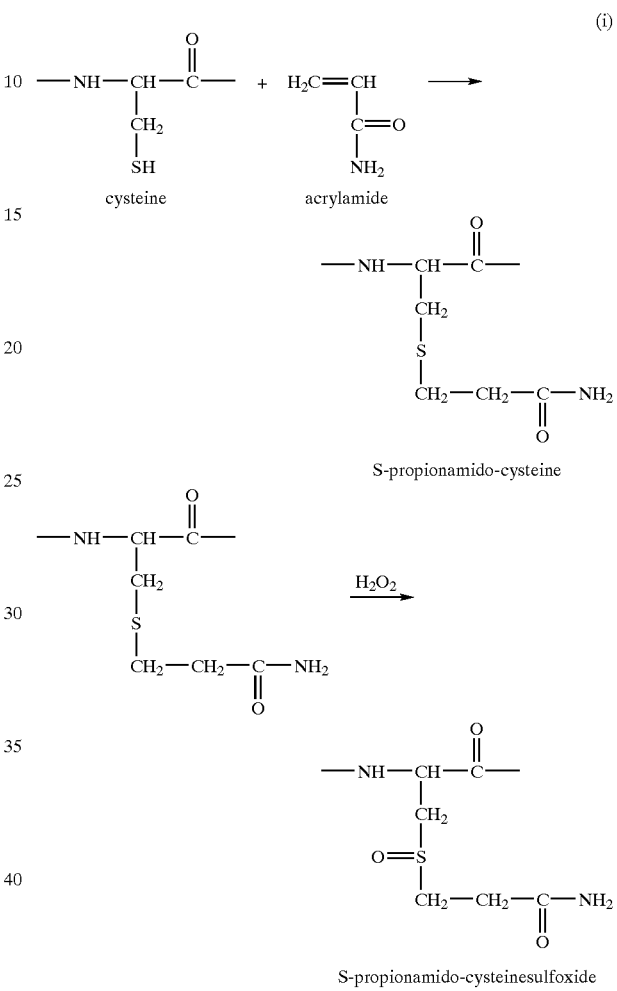

Both reactions reach completion within short time and no intermediate product can be detected (FIG. 4). Furthermore these reactions can be carried out sequentially, without removing the reagents at intermediate steps. Thus the entire mixture obtained after the last oxidation step, can be loaded on the RP-HPLC column and by using identical or very similar chromatographic conditions as during the primary run, the flagged peptides can be separated from the non-altered peptides. Subsequently the flagged peptides are passed to an analyzer such as a mass spectrometer to determine the identity of the flagged peptide and its corresponding protein. This procedure is repeated for each fraction collected during run 1. Peptide sorters consisting of multiple columns, in parallel and/or serial, can be used to optimize the time needed for the chromatographic separations and the analysis.

In an alternative version of the reaction sequence one can omit the protein pre-oxidation and precipitation step, starting with the cleavage of the proteins to generate a protein peptide mixture. Then the first oxidation step is carried out on the protein peptide mixture at acidic pH, followed by reduction at pH 8.6 with excess of $NaBH_4$, and the other alteration steps (reaction with acrylamide and oxidation) as described above. All these reactions can also be carried out in a continuous manner without intermediate purification steps.

Yet another alternative method to select for cysteine-containing peptides, involving a one step procedure, is based on the reaction with (5,5'-dithiobis(2-nitrobenzoate) or DTNB) converting SH-containing peptides to their mixed disulfide form. This reaction has been used to quantitatively measure the free SH-content of proteins and peptides. (Ellman, G. L. (1959). The reaction of a cysteine-containing peptide with DTNB is shown in (ii).

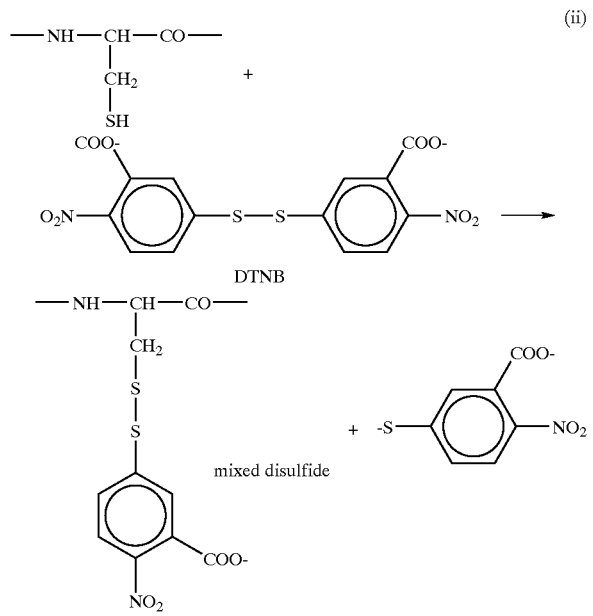

The mixed disulfide form of the peptide is more hydrophobic than its SH counterpart and elutes later in the peptide-sorting process. This method also allows to discriminate between free SH and disulfide peptides. Indeed, by omitting the reduction step, only peptides that carry a free SH are isolated with the current invention, while S—S peptides are not isolated. If however, the protein or peptide mixture is reduced prior to the primary run of the sorting process then the sum of SH and S—S peptides is sorted.

Example 3

Specific Chemical Alteration of the Sum of Methionine and Cysteine Residues

Figure 5:
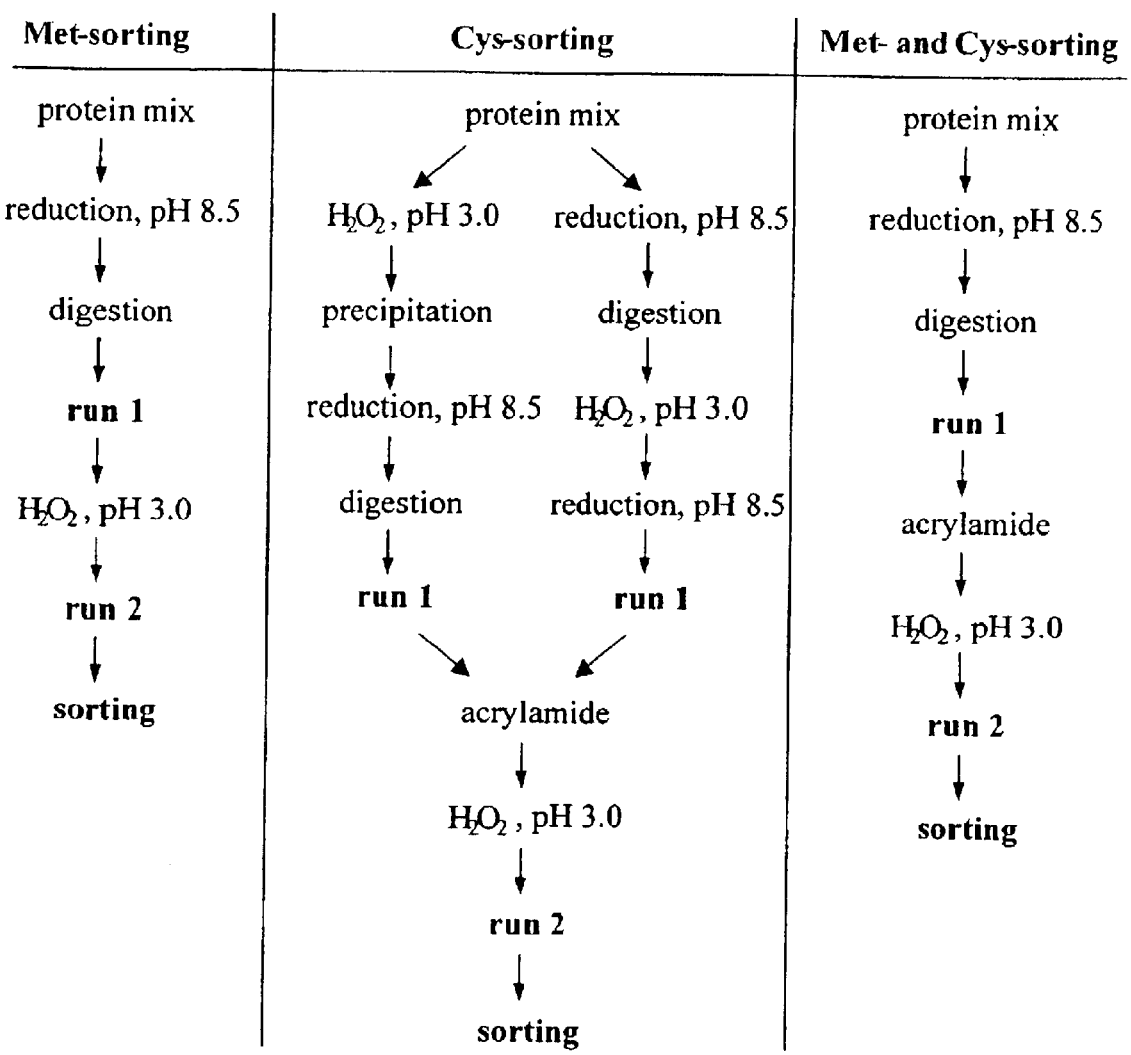
FIG. 5: Overview of the sequence of reactions used for the sorting of methionine, cysteine and the sum of cysteine and methionine containing peptides.

The procedure is identical to the procedure for specifically altering cysteine-residues (see Example 2) with the exception that the pre-oxidation step of the methionine residues is omitted. The reaction sequence starts with the reduction of a protein mixture with tributyl phosphine, followed by enzymatic or chemical cleavage. The protein peptide mixture is separated by RP—HPLC and each fraction is altered by reaction with acrylamide, immediately followed by oxidation with $H_2O_2$. The methionine-peptides are now oxidized together with the altered cysteine peptides and both types of flagged peptides show a hydrophilic shift when chromatographically separated using similar conditions as in the primary run. FIG. 5 summarizes the various reaction sequences in the Met-sorting, Cys-sorting and Met+Cys-sorting modes.

Example 4

Specific Alteration of Phosphoserine and Phosphothreonine-Peptides

A protein peptide mixture is generated as described herein before and a class of co- or post-translationally modified peptides is specifically isolated. Here an example is provided of a strategy to isolate phosphoserine- and phosphothreonine-containing peptides. Phosphoserine- and phosphothreonine-containing peptides are altered into their dehydroalanine and dehydroamino-2-butyric acid derivatives respectively by alkaline β-elimination of the phosphate moiety. Michael addition of ethanethiol converts the former into the S-ethylcysteine derivative and the latter into the β-methyl S-ethylcysteine derivative (Weckwerth et al. 2000). These thioether-containing amino acid derivatives are altered to their respective sulfoxide forms, following reaction with $H_2O_2$ which is similar to the oxidation of methionine residues. In order to avoid mixing with methionine-peptides and also to avoid β-elimination at cysteines during alkaline treatment, the protein mixture is first oxidized with performic acid, according to Hirs (1956). This step converts methionine into the sulfone form and cysteine residues into cysteic acid. After dialysis against distilled water, the protein mixture is digested with trypsin in 50 mM ammonium bicarbonate at 37° C., overnight at a trypsin/total protein ratio of 1:100. The tryptic digest (10 μl) is added to 50 μl of a 2:2:1:0.65 mixture of $H_2O$/DMSO/EtOH/5 M NaOH and 60 μl of ethanethiol is added. The reaction mixture is heated for 3 h at 50° C. and after cooling quenched by the addition of 60 μl of 20% acetic acid and 10 μl of acetonitrile. The protein peptide mixture is separated by reversed phase chromatography (run 1) in such number of fractions that will allow in run 2 the separation of flagged peptides from non-altered peptides in each of the collected fractions. In each fraction the peptides are oxidized with $H_2O_2$. Since methionine and cysteine have been oxidized in the earlier oxidation step, only the S-ethylcysteine and β-methyl-S-ethylcysteine are now oxidized to their sulfoxide derivative (see reaction equations iii and iv). These sulfoxide derivatives are significantly more hydrophilic. Each fraction is loaded on an RP—HPLC column and by using identical or similar chromatographic conditions as during run 1, the flagged peptides (S-ethylcysteine sulfoxide and β-methyl-S-ethylcysteine sulfoxide, respectively representing the phosphoserine and phosphothreonine containing peptides) are separated from the non-altered peptides. The flagged peptides are subsequently passed to an analyzer such as a mass spectrometer to identify the corresponding flagged peptide and its phosphorylated protein. In addition, a neutral loss scan of RSOH (here R=ethyl) (78 amu's) during mass spectrometric analysis allows a further verification of the authenticity of both types of the flagged peptides (Steen and Mann, 2000). The latter means that there exists an internal control for the authenticity of S-ethylcysteine sulfoxide and β-methyl-S-ethylcysteine sulfoxide, respectively representing the phosphoserine and phosphothreonine containing peptides, because of the observed neutral losses following measurement of said flagged peptides by mass spectrometry.

It is interesting to notice that the alkaline β-elimination reaction can also be carried out under milder alkaline conditions, using 0.5 M Li OH at 4° C., thus replacing the $H_2O$/DMSO/EtOH/5 M NaOH mixture given above (Sakaguchi et al., 2001).

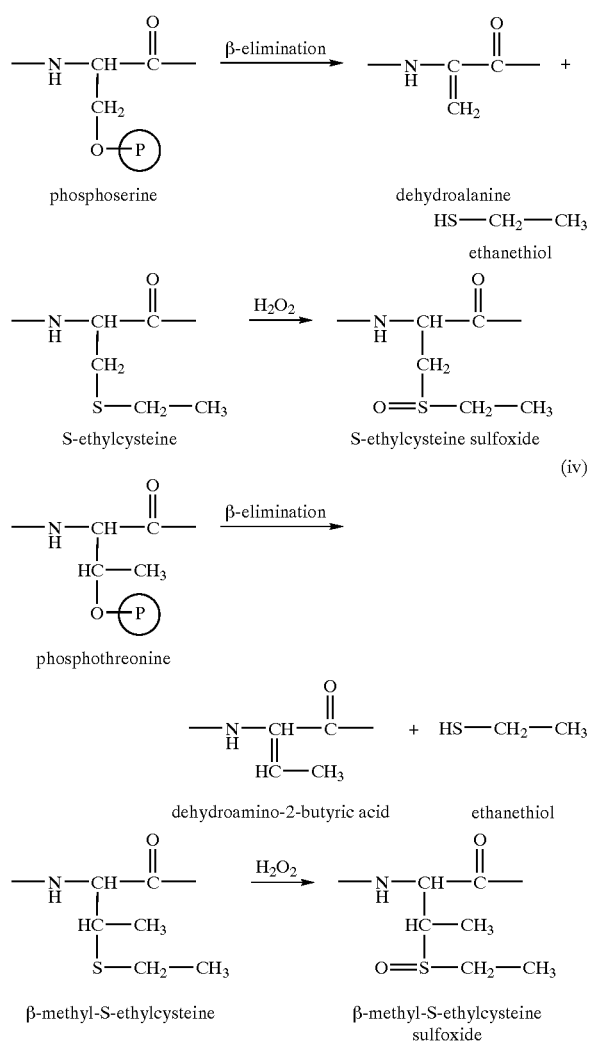

(iii) phosphoserine → dehydroalanine + ethanethiol

S-ethylcysteine → S-ethylcysteine sulfoxide (iv) phosphothreonine → dehydroamino-2-butyric acid + ethanethiol β-methyl-S-ethylcysteine → β-methyl-S-ethylcysteine sulfoxide An alternative phospho-peptide sorting system uses the hydrophobic difference between phosphorylated and dephosphorylated peptides by reversed phase chromatography at pH 5.0. The procedure outlined below is one example of such an approach. A protein peptide mixture is generated as described herein before. Peptides present in said mixture are now separated by RP-HPLC, using 10 mM $NH_4Ac$, pH 5.0/acetonitrile (or $NH_4AC$/methanol or other) as eluting solvent and collected in 1 min fractions. Peptides present in these fractions are treated with a general phosphatase (such as an alkaline phosphatase). The dephosphorylated peptides are less hydrophobic than their phosphorylated precursors and therefore undergo a hydrophobic shift during a secondary chromatographic separation under identical or substantially similar chromatographic conditions as run 1 and this allows their sorting. It is important to mention that the hydrophobic shift is more important at pH 5.0 than at lower pH-values, making the use of the 0.1% TFA or 0.1% HCOOH systems in the sorting process less attractive.

An interesting option is the use of separation systems particularly adapted for separation of phosphoryl-containing compounds. Such a system could for instance consist of the absobosphere nucleotide-nucleoside material (Alltech) combined with 60 mM $NH_4H_2PO_4$ and 5 mM tetrabutyl ammonium phosphate, pH 5.0 as solvent A and methanol (5 mM tetrabutylammonium phosphate) as solvent B.

Another way to sort for phophopeptides using a dephosphorylation method is based on the loss of the negatively charged phosphoryl group. In this case, runs 1 and 2 are carried out either on ion-exchange columns or by electrophoretic means. For instance, when runs 1 and 2 are carried out on a Mono Q-column or a DEAE-column at pH 6.0, then all dephosphorylated peptide species will display a forward shift because they are less strongly bound to the anion-exchanger. A similar effect may be obtained by the use of capillary-electrophoresis where the dephosphorylated peptide species will display an anodic shift, again leading to the sorting process.

It is important to stress that any sorting procedure, based on a dephosphorylation step which can be carried out either by enzymatic (e.g. general or specific phosphatases) or chemical (e.g. β-elimination in alkaline conditions) means, provides the possibility to select for a variety of phosphorylated species.

Yet another method to sort for phosphopeptides is based on the formation of a non-covalent complex between phosphopeptides and $Fe^{3+}$-chelates. A proteinpeptide mixture is generated as described herein before. Peptides present in said mixture are separated in run 1 by RP-HPLC, using 10 mM $NH_4Ac$, pH 5.0/acetonitrile (or $NH_4Ac$/methanol or other) as eluting solvent and collected in 1 minute time intervals. Peptides present in each of these fractions are separated in run 2 over the same chromatographic column but now in solvents containing iminodiacetate and $Fe^{3+}$, forming a dichelate complex with phosphopeptides. This complex elutes at a different position compared to that of the free phosphopeptides and allows isolation of the phosphopeptides. This differential chromatography again forms a platform for an efficient sorting process.

Example 5

Selection for ε-N-Acetylated Peptides

Acetylation of a certain number of lysine ε-amino groups of the nucleosomic histones H2A, H2B, H3 and H4 and possibly other factors modifies the chromatin structure and leads to an increase of transcriptional activity. Alterations in the degree of acetylation are likely to be associated with cellular proliferation and could be indicative for apoptosis, necrosis or for several other pathological situations. In addition the acetylation status can differentiate already at a very early stage between normal and neoplastic cells (e.g. in prostate cancer). Again the present invention can be used to selectively sort for the acetylated peptides using for instance deacetylation as the shifting principle for peptide sorting. One example of such strategy is provided below as an illustration. A protein peptide mixture from a nuclear extract is generated by trypsin cleavage of the isolated proteins. Trypsin cleaves at Arg and Lys, but not at the acetylated lysine side chain. The obtained peptide mixture is separated in run 1 by RP—HPLC using 0.1% TFA as solvent A and 0.09% TFA in 70% acetonitrile as solvent B with an increasing gradient of 1% solvent B/min and a flow rate of 80 μl/min (column 2.1 mm inner diameter and 250 mm length). Eluting peptides are collected in 1 min intervals. Every fraction is dried, redissolved in appropriate buffer and treated with a histone deacetylase (HDA). For instance, fully or partially purified preparations of the yeast Rpd3 (class I), the yeast HDA1 (class II) or the $NAD^+$-dependent Sir2 class proteins (for review see Furumai et al. 2001). Due to deacetylation, peptides become more hydrophilic and elute at lower acetonitrile concentrations. Due to this difference in hydrophilicity, and by applying the current invention, it is possible to separate the deacetylated peptides (flagged peptides) from the unaltered peptides during the secondary run. The shift in elution is comparable with the shifts measured for the alteration of methionine to methionine sulfoxide peptides. The nature of each of the flagged peptides and their corresponding proteins is for instance determined by using MS/MS or very accurate determination of the mass of each flagged peptide. This allows the identification of the proteins in the original protein-mixture.

To quantitatively determine the difference in ε-N-acetylated peptides between two samples (e.g. different cell types), protein peptide mixtures are generated by trypsin digestion either in $H_2^{16}O$ (sample 1) or $H_2^{18}O$ (sample 2). Both protein peptide mixtures are mixed before the primary run and further processed together as described above. A flagged peptide from any random protein X in sample 1 coelutes in the secondary run with the same flagged peptide from the same protein X in sample 2. Because flagged peptides from sample 1 and sample 2 respectively carry $^{16}O$ and $^{18}O$, they appear as twin peaks in a mass spectrometric analysis. The peak intensity or surface is calculated and the ratio of the flagged peptide containing twice $^{16}O$ versus the flagged peptide containing twice $^{18}O$ is proportional to the degree of acetylation of this peptide in both compared samples.

Example 6a

Selection of NH$_2$-Terminal Peptides Derived from in vivo NH$_2$-Terminally Blocked Proteins Another application of the present invention is the isolation of a subset of peptides which are derived from NH$_2$-terminally blocked proteins. Most of these may be acetylated peptides (eukaryotes) or formylated peptides (prokaryotes). To be able to only select NH$_2$-terminally blocked peptides and to avoid loss of amino-terminally blocked peptides comprising a lysine-residue, the sample comprising proteins is pretreated. In one approach, the sample is first guanidinated with O-methylisourea at pH 10, converting lysine side chains into their guanidinium derivatives. α-Amino groups react much more slowly with this reagent than do ε-amino groups (Plapp et al., 1971) and are therefore not or only to a minimal extent converted into their guanidinium derivatives.

Figure 6:
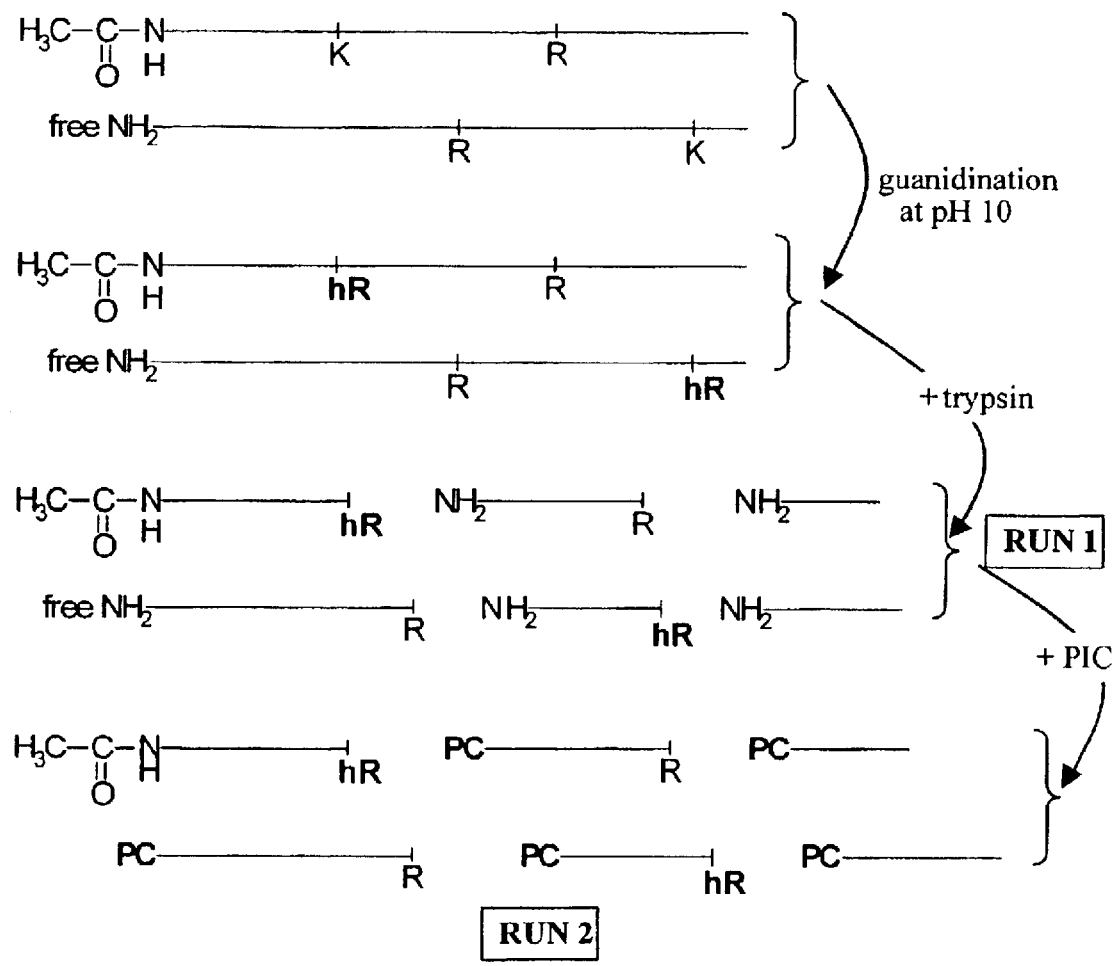
FIG. 6: Schematic description of the main steps in sorting the subset of NH$_2$-terminally blocked peptides. Critical amino acid residues are indicated. R=Arg, K=Lys, hR=homoArg, PIC=phenylisocyanate, PC=phenylcarbamyl. All PTC-peptides become more hydrophobic. The N-acetylated peptides are not changed and will elute in run 2 exactly as they did in run 1. The blocked peptides will thus segregate from the bulk of PTC-peptides.

According to the invention, the proteins are subsequently subjected to a trypsin digest. Trypsin cleaves both arginine and homoarginine albeit at a slower rate (the latter is derived from the guanidinated lysines) and the digest therefore generates a free α-amino group in every generated peptide, except in those containing the blocked protein amino terminus. The protein peptide mixture is now passed over a reversed phase column and separated in such number of fractions that allow, in each of the collected fractions, the separation of altered peptides from non-altered peptides during the secondary run. In each fraction, for instance, phenyl isocyanate (PIC) is added that reacts with the free NH$_2$-groups of the peptides. As a result all peptides with a free NH$_2$-group acquire a phenylcarbamoyl (PC) group, making the peptide more hydrophobic (FIG. 6). The peptides derived from NH$_2$-terminally blocked proteins are not altered. The peptide mixture is loaded on a RP-HPLC column and by using similar or identical chromatographic conditions as during run 1, the altered peptides are separated from the non-altered identification peptides (id est the amino terminally blocked peptides). Thus in this example, the bulk of the peptides is altered and is retarded (hydrophobic shift), while the subset of non-altered peptides elute in an unchanged position during the secondary runs. This is called the "reversed sorting procedure".

The extent of hydrophobic shifts can be altered by changing the chemical nature of the NH$_2$-terminal reacting derivatives. Methods known in the art describe a variety of isocyanate (IC) alteration reactions which can be used as an alternative to PIC in the sorting process described in this chapter. For instance reactions with trifluoroacetyl-IC, allyl-IC, naphthalene-IC, fluoresceine-IC, etc. can also be used. The hydrophobic shift of peptides with free α—NH$_2$-groups can also be obtained by any other quantitative alteration reaction which is specific for α—NH$_2$-groups. The list of reagents contains for instance acetyl-N-hydroxysuccinimide and all acylating reagents, F-moc-N-hydroxysuccinimide, trinitrobenzenesulfonic acid (TNBS) or nicotinoyl(oxy)succinimide. In the final choice of reagents and conditions it should be clear that the alteration reaction is limited to only the α—NH$_2$-groups and should alter at least 90%, by preference 95%, more preferably 99% and most preferred even a higher percentage of the peptides with a free NH$_2$ group.

Example 6b

Selection of NH$_2$-Terminal Peptides Derived from Proteins with a Free NH$_2$-Terminus This example shows how NH$_2$-terminal peptides derived from proteins with a free NH$_2$-terminus present in a protein peptide mixture can be sorted. A particular advantage of this method relies on the fact that the flagged peptides can be obtained with a sulfonic acid group attached at their NH$_2$-terminus that are ideally suited for high throughput MALDI—PSD analysis (Keough T. et al. (1999). The sample comprising proteins is first treated with tributylphosphine, followed by iodoacetamide in protein denaturing buffers. This step leads to the derivatization of cysteine-side chains and is immediately followed by the guanidination reaction, converting lysines into homoarginines. The α—NH$_2$-groups are then blocked with an isothiocyanate-derivative such as phenylisothiocyantate (PITC) or the well-known soluble Braunitzer reagent (1,5-disulfonylnaphtalene-3-isothiocyanate). Thus the proteins present in the mixture have now been derivatized at their SH-groups (as the acetamide derivatives), their ε—NH$_2$ groups (as homoarginine), and their α—NH$_2$ groups (as their thiocarbamoyl derivatives). Consecutive cleavage with trypsin now generates a new set of free alfa-NH$_2$-groups at each new cleavage site. These can be efficiently blocked by reaction with trinitrobenzenesulfonic acid (TNBS). The final pretreated protein peptide mixture now consists of four types of NH$_2$-terminally blocked peptides. First, peptides derived from in vivo blocked proteins: either α—NH$_2$-acetylated (eukaryotes) or formylated (prokaryotes) peptides, second, peptides blocked with TNBS, third, peptides blocked by pyroglutamic acid and which may originate spontaneously after trypsin cleavage in front of a glutamine residue and fourth, peptides blocked by a thiocarbamoyl (TC) derivative. The latter represent the subset of peptides, corresponding to the protein aminoterminal peptides. Of the four types of NH$_2$-terminal blocked peptides, only the TC-peptides are known to be sensitive to acid treatment and will loose the NH$_2$-terminal residue according to the well known Edman chemistry. Thus treatment of the peptide mixture with concentrated TFA removes the first amino acid of the TC-peptides generating a new free NH$_2$-terminus. At this moment the peptide mixture is separated in run 1 and collected in such number of fractions that allow, in each of the collected fraction, the separation of altered peptides from non-altered peptides during the secondary run. In each fraction, a NH$_2$-specific reagent is added, selectively altering the subset of peptides with free NH$_2$-group. Such reagent can either be TNBS or an acetylating compound leading to more hydrophobic peptides. In a particular embodiment this reagent however can also consist of the chemistry developed by Keough T. et al., 1999 or analogous compounds altering the peptides with a sulfonic acid moiety at the α—NH$_2$-group. These flagged peptides can again be selectively sorted using RP-chromatography, or ion-exchange chromatography procedures executed according to the invention. An important aspect of peptides carrying an NH$_2$-terminal sulfonic acid group is their particular fragmentation in conditions currently used in the MALDI-TOF-MS mode, allowing a very fast and easy deduction of the amino acid sequence, thus opening the way for efficient high throughput MALDI-based analysis and identification of the sorted peptides.

An example of the consecutive chemical or enzymatic steps leading to the sorting of the easily sequencable peptides derived from proteins with a free NH$_2$-terminus is summarized below:

Step 1: reduction followed by reaction with iodoacetamide

Step 2: conversion of lysine side chains into homoarginine

Step 3: conversion of free α—NH$_2$-groups in thiocarbamoyl derivatives

Step 4: precipitate modified proteins or purify by gel-filtration

Step 5: cleave with trypsin

Step 6: modify peptides with trinitrobenzenesulfonate

Step 7: treat with concentrated TFA

Step 8: dilute with water and separate protein peptide mixture in primary run

Step 9: alter peptides of each fraction with an NH$_2$-terminal blocking reagent, preferentially by sulfoacetylation Step 10: sort the flagged peptides in the secondary run Step 11: analyse flagged peptides by MALDI-PSD or ESI-CID or MALDI-CID Step 12: identify peptides based on the sequence produced by a series of y-ions This procedure may be particularly adapted to study internal cleavage of proteins (example 8) since these invariably lead to new NH$_2$-termini, which in general do not carry any known blocking group. It is also worthwhile to stress that this sorting process is again a direct approach, performing a positive selection for sulfoacetylated peptides, avoiding or minimizing contamination by non-altered peptides, even when the sulfo-acetylation reaction (here the alterating reaction) did not proceed to completeness.

Example 7

Selection of the NH$_2$-Terminal Peptides Derived from Proteins Present in a Complex Protein Mixture The technology in which one protein of a complex mixture such as a cell lysate is represented by one identification peptide (the NH$_2$-terminal peptide) is below referred to as individual peptide mass-based proteomics (IPMBP, see Example 10). The procedure starts with the conversion of the protein cysteines with iodoacetamide or similar SH-specific reagents known in the field. Then, the proteins are allowed to react with O-methylisourea, converting the E-lysine into their guanidinium derivatives (homoarginine). It is important to notice that the ε—NH$_2$-groups are changed, while the α—NH$_2$-groups of the proteins are not changed under the reaction conditions used. In a next step the proteins are acetylated with for example acetyl N-hydroxysuccinimide. In a next step, a protein peptide mixture is generated by for example trypsin cleavage and said protein peptide mixture is separated in a first chromatographic step. To each fraction trinitrobenzenesulfonic acid (TNBS) is added that reacts quantitatively with the free NH$_2$-groups on the peptides. It is important to remark that the peptides derived from the amino-terminus of a protein cannot react with this reagent because the NH$_2$-group of these peptides has previously been blocked with an acetyl-group. The peptides with a free NH$_2$-group acquire a trinitrobenzene group (TNB), making these peptides more hydrophobic. So, when the peptides from each fraction are separated on a RP-HPLC column run under similar chromatographic conditions as during run 1, the altered TNB containing peptides are separated from the non-altered identification peptides (id est, all aminoterminally blocked peptides). In this set-up the isolated non-altered identification peptides are derived from the amino-terminus of proteins and will contain an NH$_2$-terminal acetyl group (e.g. when eukaryotic cell extracts are used).

In another method, the protein mixture is pretreated by converting the protein cysteines into their carboxamido derivatives. In the next step the proteins are acetylated with acetyl-N-hydroxysuccinimide, both at their ε—NH$_2$ and α—NH$_2$-groups. Then a protein peptide mixture is generated by cleavage with trypsin. Since all lysine side chains have been acetylated before, cleavage by trypsine is predominantly at the COOH-terminus of arginine. All additional steps, including the peptide sorting process, are executed as above. This leads to the isolation of the amino-terminal peptides of all proteins present in the mixture. They are sorted as non-altered identification peptides.

In an alternative approach the proteins are acetylated with an equimolar mixture of acetyl- and trideuteroacetyl N-hydroxysuccinimide, which leads to a differential isotopic labeling of the protein free α—NH$_2$-termini. In a next step, the protein mixture is digested with trypsin and the protein peptide mixture is passed over a reversed phase column and separated in such number of fractions that allow, in each of the collected fractions, separation of altered peptides from non-altered peptides during run 2. To each fraction trinitrobenzenesulfonic acid (TNBS) is added that reacts quantitatively with the free NH$_2$-groups on the peptides. So, again when the peptides from each fraction are separated on a RP-HPLC column run under similar chromatographic conditions as during run 1, the altered TNB containing peptides are separated from the non-altered identification peptides. In this set-up peptides derived from proteins that were already blocked in vivo carry the CH$_3$—CO-group, while peptides derived from proteins with a free α—NH$_2$-group (which was altered in the course of our procedure) are now labeled with the doubly tagged CH$_3$—CO/CD$_3$-CO-moiety. The non-altered identification peptides from each fraction are passed to a mass spectrometer to determine the mass and sequence of each individual peptide. Importantly, this analysis simultaneously allows the distinction between peptides derived from proteins that were already blocked in vivo and peptides derived from proteins with a free α—$NH_2$-group, because the latter group of peptides will appear as doublets (separated by 3 amu's).

Alternatively TNBS is replaced in the process by phenylisocyanate (PIC) or similar compounds able to block free $NH_2$-groups. In case of $NH_2$-terminally formylated peptides, the same sorting procedure is followed. Thus formylated peptides are sorted together with the peptides that were labeled with the double $CH_3$—CO/$CD_3$-CO tags (see above). It is important to indicate that our sorting procedure also sorts peptides that carry pyroglutamic acid at their $NH_2$-terminus. Such peptides can be formed in the course of the enzymatic cleavage when $NH_2$-terminal glutamine is generated. Mass spectrometry in which peptide fragmentation is used, can distinguish between an $NH_2$-terminal acetyl and pyroglutamate, allowing to distinguish between the $NH_2$-terminal peptide and any internally generated peptide.

Example 8

Identification of Internally Proteolytically Processed Proteins in Total Cell Lysates and Localisation of the Processing Sites Using the Invention.

Often proteins are cleaved internally due to the action of specific proteases. This phenomenon is for instance observed at the onset of apoptosis due to the activation of caspases. Internal protein processing may also be an important step during normal cellular development and such processes may play an important physiological role. In addition protein cleavage in the precursor molecule is a process leading to maturation of a protein. Detection of these processes forms a fundamental element in modern proteomics. Our invention allows the identification both of the nature of the processed protein and the location of the processing site. A typical but not limiting experimental protocol is described below. First, proteins derived from a total cell lysate are reduced with tri-butylphosphine and the SH-groups are blocked with iodoacetate. This reaction is carried out under denaturing concentrations of guanidinium-HCl (6M) at pH 8.6. It is advised not to use urea-containing buffers for the reversed sorting methods (thus methods in which the unaltered peptides are selected as identification peptides). Indeed, prolonged contact with urea may lead to peptide carbamylation and such peptides would also be sorted as unwanted products. At this stage, excess of reagent and buffer are removed by precipitation in four volumes of ethanol at −20° C. overnight. The protein precipitate is recovered by centrifugation and redissolved in a small volume of 6 M guanidinium in phosphate buffer pH 8.5. Alternatively reagents and buffers can be removed by a gel-filtration step in 6 M guanidinium-HCl in phosphate buffer at pH 8.5. The acetyl- or nicotinoyl N-hydroxysuccinimide ester is added in order to convert the free $NH_2$-groups in their corresponding acetyl or nicotinoyl derivatives. Alternatively as in example 7 a 1/1 mixture of the acetyl and trideuteroacetyl derivative is used. In this second example a 1/1 mixture of H4 and D4-form of the nicotinoyl derivative is employed (Munchbach, M et al. (2000. The acetylation reaction is terminated by the addition of one molar excess of Tris-HCl pH 8.5 over the acetylation reagent, diluted to 1 M guanidinium-HCl or dialysed against 0.5% $NH_4HCO_3$ and then digested with trypsin. The resulting peptides are subjected to the primary chromatographic separation. Each fraction is then treated with a reagent that quantitatively reacts with the newly generated free peptide α—$NH_2$-groups (e.g. trinitrobenzene sulfonate, acetyl N-succinimide ester, phenylisocyanate etc.). A rerun of these treated fractions in a secondary run, now translocates all peptides which reacted in the last reaction step, towards more hydrophobic positions, while all peptides which were already blocked in vivo, or which were $NH_2$-terminally blocked via the pretreatment before the primary run or peptides with $NH_2$-terminal pyrrolidone carboxylic acid, are recovered as non-altered identification peptides in the same position as they eluted during the primary run. By comparing the peptide patterns of the protein lysate from two different samples, it is possible to identify peptides derived from newly generated $NH_2$-termini which are informative for both the nature of the processed protein and the exact cleavage site. The experiment outlined above can be varied in several ways, still keeping the general principle of sorting identification peptides. For instance, after converting the proteins with SH-reacting and $NH_2$-reacting compounds, proteins are digested with trypsin in $H_2^{16}O$ (sample 1) and $H_2^{18}O$ (sample 2). With this experiment a differential quantification of the extent of protein processing can be studied between two samples. Thus, after trypsin cleavage sample 1 and sample 2 are combined in equal ratios and said mixture is separated in a first chromatographic run. Each fraction is then treated with a reagent that reacts with the free alfa-$NH_2$ groups (e.g. trinitrobenzene sulfonate, acetyl N-succinimide ester, phenylisocyanate etc.). A rerun of these treated fractions in a secondary run, now translocates all peptides which reacted in the last reaction step, towards more hydrophobic positions, while all peptides which were already blocked in vivo, or which were $NH_2$-terminally blocked via the pretreatment before the primary run or peptides with $NH_2$-terminal pyrrolidone carboxylic acid, are recovered as non-altered identification peptides in the same position as they eluted during the primary run. The light ($^{16}O$) and heavy ($^{18}O$) peptides are chemically very similar and each peptide couple separates in the same manner and also ionise in the same way. During mass spectrometry the light and heavy peptide segregate because the heavy peptide has a mass increase of 4 amu's. This separation is sufficient to accurately measure the differential quantification of the extent of protein processing in the two samples.

Example 9

Buffer Systems

An important element of the invention is the choice of the peptide separation conditions in relation to and integrated with 1) the reaction conditions employed to alter the peptides and 2) the type of mass spectrometric approach which is used to analyse and to identify the flagged or the identification peptides. To illustrate this point, hereunder are described several examples of how to select for methionine-peptides from protein peptide mixtures, taking into account this integrity aspect of the procedure. In one example, the primary run is carried out in the TFA/acetonitrile system and the oxidation step is made in 1% TFA/$H_2O_2$. The secondary run is equally performed in the TFA/acetonitrile system, while the peptide mass measurements are made by MALDI-TOF-MS or by PSD-MALDI-RETOF-MS which is not sensitive to traces of TFA (see below). So, in this protocol, the counterion TFA is not changed from the start of the primary run throughout the procedure till the complete secondary run. In the event the identification of the flagged peptides or identification peptides is done by electrospray-ionisation (ESI-MS), then the TFA-system is not advised, as TFA is known to form ion-clusters, interfering with MS-measurements (Mirza and Chait, 1994). Therefore, as a second example, both the primary as well as the secondary runs are now carried out in a HCOOH/acetonitrile system, because this system allows efficient ionisation by ESI. However, the intermediate oxidation step to generate the sulfoxide-methionine peptides cannot be carried out in the presence of HCOOH because this leads to the formation of performic acid and thus to the conversion of methionine side chains in both the sulfoxide and sulfone derivatives. Thus the oxidation step here is carried out in a 1% TFA and 0.5% $H_2O_2$ mixture. In this case, the nature of the counterions between the two consecutive chromatographic steps and the alteration are not the same, potentially affecting the ion-paring effect during the secondary run. Here, due to the relatively low concentration of TFA the disturbing effect is not important. This could become a problem when the TFA concentration is increased or when counterions are used with stronger ion-pairing effect during the alteration step. In summary, it is preferred to keep the nature of the buffer unchanged throughout the primary and secondary runs, during the alteration step and during mass spectrometric analysis. If this cannot be done, or if the buffers in the chromatography process are different from solvents used in mass spectrometry, then a ternary chromatographic run could be carried out.

Along the same line, it may be important to take into account the buffer ions present in the protein peptide mixture before starting the primary run. Ideally, buffer ions in the protein peptide mixture should be the same as those used during the primary run and secondary run. In the event the buffer ions in the protein peptide mixture are too divergent, the necessary adaptation can be obtained with several methods available in the art. It can for instance be obtained by dialysing the protein mixture against appropriate buffers before trypsin digestion. Alternatively, a short reverse phase (RP)-separation with a steep gradient, could be added before starting the primary run. During this fast RP-separation, salts are removed and peptides are acquiring the correct counter ions which will be used in the primary and secondary runs. Peptides eluting from this fast RP-step are combined and lyophilised before being dissolved in the buffer suitable for the primary run. The procedure in which the peptide mixture is brought in the most ideal ion-condition is called here the conditioning step. An example where peptide-mixture conditioning is important is described below.

Human plasma is prepared by the addition of citrate buffer in order to inhibit clothing. When a tryptic digest of such total plasma protein preparation is directly subjected to the primary chromatographic step, the peptide separation will be influenced by the citrate originally present in the peptide mixture. When the unaltered peptides are now passed for the secondary run, where citrate is nearly absent, there might be an unwanted shift due to the change in ion-pairing. These kind of shifts are more important for the more hydrophilic peptides, eluting at the beginning of the gradient than for the late eluting hydrophobic peptides. The citrate effect in the primary run is avoided by first passing the protein peptide mixture over a fast RP-column using a steep gradient of organic solvent. Peptides eluting over the full gradient are all collected, dried by lyophilization or vacuum dried and redissolved in the appropriate buffer prior to the primary run. By conditioning the protein peptide mixture, one ensures the same or identical chromatographic conditions over the entire sorting procedure. The conditioning step is also important as a clean-up step removing compounds that may gradually contaminate the sorting columns.

Example 10

Individual Peptide Mass Based Proteomics (IPMBP)

According to the invention it is possible to select a subset of flagged peptides or identification peptides from a complex peptide mixture or a protein peptide mixture. Further to the invention the peptides and corresponding proteins are identified with a suitable analyzer such as a mass spectrometer. With a MALDI-TOF mass spectrometer the mass of said peptides is measured, however this is not always sufficient to unambiguously identify peptides and their corresponding proteins. In this example several approaches are described to increase the information content of the isolated flagged or identification peptides. This allows one to unambiguously determine the identification of an increasing number of said peptides via a simple determination of their mass with a mass spectrometer. This approach is designated as individual peptide mass based proteomics (IPMBP).

10.1 IPMBP on Endoproteinase-LysC-Generated Peptides

Making use of the invention allows one to select peptides containing one or more specimens of a specific amino acid. The knowledge that this amino acid has to be present in the selected peptide is used to increase the number of peptides that can be identified unambiguously. One approach is to build subdatabases only containing the masses of peptides known to contain at least one residue of the specific amino acid. For instance if methionine has been selected as the specific amino acid, a subdatabase with the masses of peptides containing at least one methionine is created and the mass of each methionine-containing flagged peptides is screened against this database.

Figure 7:
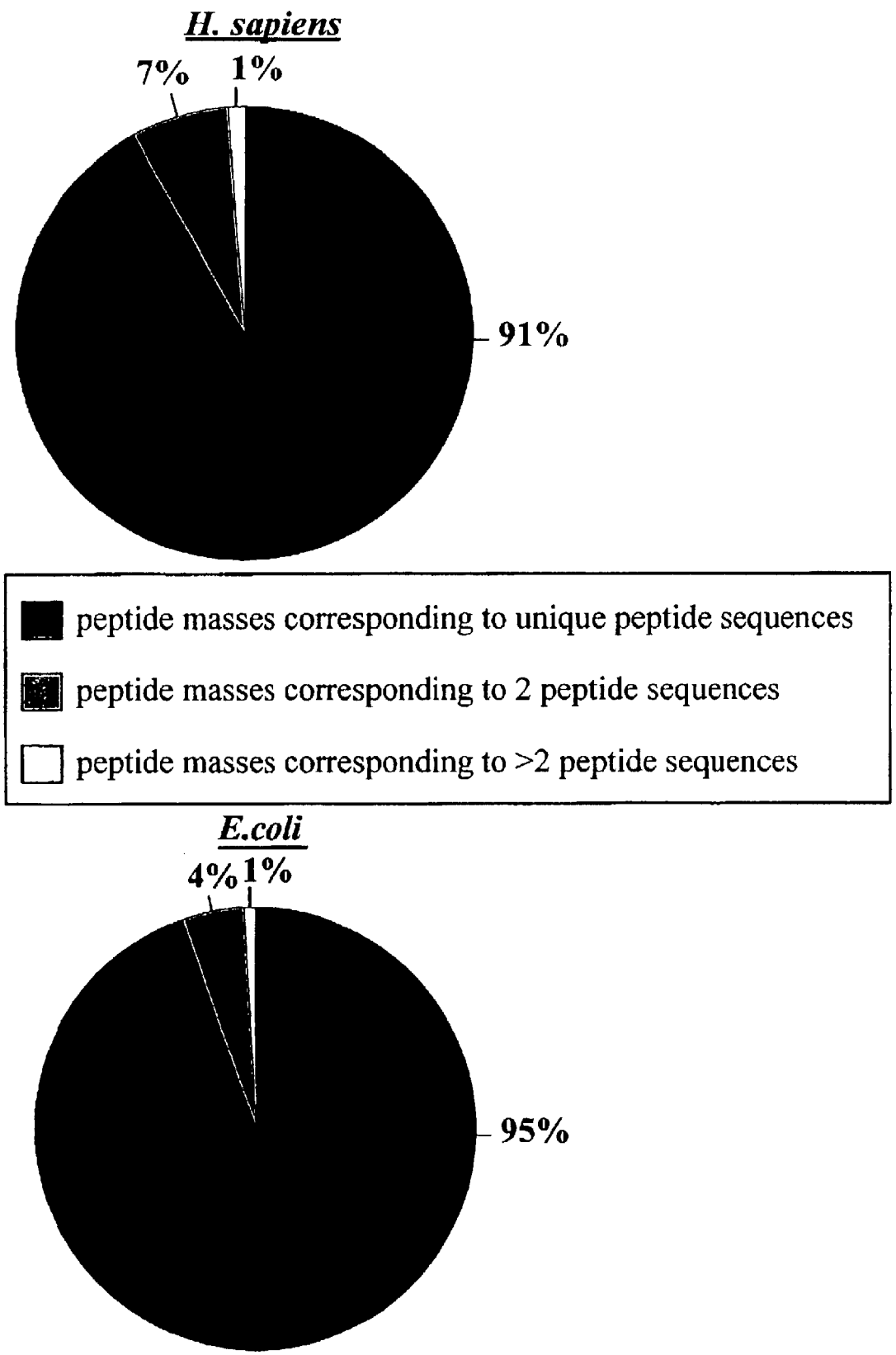
FIG. 7: Pie chart indicating the number of 'unique' peptide masses generated by an in silico endoproteinase Lys-C digestion on curated SwissProt protein entries of both human and E. coli origin. As can be seen in both cases more than 90% of the peptide masses (calculated to 0.001 Da accuracy) correspond to unique peptide sequences containing at least one methionine residue in the database and can thus be used to identify their parent proteins.

A further increase in the percentage of flagged peptides or identification peptides that is unambiguously determined is obtained by making use of specific proteases. In one example, endoproteinase-LysC is used. In this example a database was constructed containing all possible peptides derived by in silico endoproteinase-Lys-C digestion of human and E. coli proteins (extracted from the SwissProt database release 39.0). From this database a sub-database of peptides was created that met specific criteria: their monoisotopic mass should be between 700 Da and 4,000 Da and they should contain at least one methionine residue. The sub-database was indexed according to increasing peptide mass and then the number of peptides was calculated that could be used as unique identifiers for their parent proteins, i.e. peptides of which the mass, measured to three exact digits, correspond to a unique peptide sequence. From these calculations it was observed that 91% of the calculated human peptide masses and 95% of the calculated E. coli peptide masses serve as unique identifying peptides (FIG. 7). Similarly, the number of proteins in the databases that contained at least one of these unique identifiers was calculated, and it was observed that for both species more than 80% of the proteins can be identified this way. In order to use this strategy for high-throughput peptide-based proteomics, peptide masses need to be measured with very high accuracies. As recently published, such high mass accuracies could for instance well be within reach of a Fourrier transform mass spectrometer (FTMS) using an internal calibration procedure (O'Connor and Costello, 2000). As soon as this level of accuracy is not reached, a very rapid drop in the identification power can be expected. Likewise, from a statistics point of view, larger databases yield less unambiguous assignments than smaller ones. It is therefore preferable to direct IPMBP-search algorithms to a single species or organism. For these simulated experiments endoproteinase Lys-C, which generates on average larger peptides than for instance trypsin or chymotrypsin digestions was used. Use of the latter enzymes or combinations of different proteases, will result in peptide databases having a larger number of entries, thereby decreasing both the number of unique peptide masses and the number of proteins that can be uniquely identified by IPMBP.

10.2 Enrichment of the Information Content of the Peptides

In order to obtain more stringent criteria without using time-consuming MS/MS analysis, the information content of flagged peptides was further enriched by specifically changing free $NH_2$-groups in the peptide using an equimolar mixture of acetic acid N-hydroxysuccinimide ester and trideuteroacetic acid N-hydroxysuccinimide ester. As the result of this conversion reaction, flagged peptides or identification peptides acquire a predetermined number of $CH_3$—CO ($CD_3$—CO) groups depending on the number of free $NH_2$-groups in these peptides. The number of acquired groups can be easily deduced from the extent of the observed mass shift in the peptide doublets. For instance, a shift of 3 amu's corresponds with the presence of one $NH_2$-group, a 3 and 6 amu's shift with two $NH_2$-groups and a shift of 3, 6 and 9 amu's reveals the presence of three $NH_2$-groups in the peptide. Changing the free $NH_2$-groups is most conveniently carried out after protein digestion, but before the start of the primary run. The acetylation of the free $NH_2$-groups in the peptides increases the hydrophobicity of the peptides. Notwithstanding this effect, the extent of hydrophilic shifts ($\delta_{min}$ and $\delta_{max}$) obtained after for instance methionine oxidation (see example 1) are similar as when the peptides were not acetylated. The current invention can thus equally be applied in this approach. Using this approach, combined with the approach described hereabove, the following information can be obtained for each of the flagged peptides: (1) mass, determined by MS, (2) number of residues of a specific selected amino acid (e.g. methionine) and (3) number of free amino groups. This combined information significantly increases the number of flagged or identification peptides that can be unambiguously identified by screening databases and subdatabases as described hereabove.

Additionally, this approach can be used to determine the peptide ratio's present in two mixtures. In this example, peptides coming from one sample are acetylated with acetic acid N-hydroxysuccinimide ester and peptides from the second sample are acetylated with trideuteroacetic acid N-hydroxysuccinimide ester. The ratio of the two isot opic forms of each flagged peptide measured in mass spectra is subsequently used to make a quantitative comparison. In a differential quantitative method a similar approach was recently published by Brancia et al. (2001), who used O-methylisourea to determine the number of lysine residues in tryptic peptides and showed that this additional information improved the overall success of protein identification using conventional searching methods. The combination of this approach with the current invention further significantly improves the percentage of peptides that can be identified unambiguously.

An additional important piece of information is the elution or migration time of a given peptide in the separation system (e.g. during the primary run), because it will allow us to distinguish between peptides with identical or very similar masses but different hydrophobicities or net electric charges.

10.3 IPMBP by Selecting for $NH_2$-Terminal Tryptic Peptides

In the actual invention it is possible, for example to, sort for the $NH_2$-terminal peptides of $NH_2$-terminally blocked proteins (example 6a), but this idea is extended to the $NH_2$-terminal peptides of all proteins in a sample (example 7). In FIG. 6 a method is shown for the specific sorting of peptides derived from in vivo $NH_2$-blocked proteins (most likely $NH_2$-acetylated, $NH_2$-formylated or pyroglutamylated). Using a variation of this procedure (example 7), we are also able to specifically sort for the $NH_2$-terminal peptides from most, if not all, of the proteins present in a protein peptide mixture. This procedure also permits to distinguish between peptides derived from in vivo $NH_2$-terminally blocked proteins and from proteins with a free $NH_2$-terminus. Finally, the mass of these sorted $NH_2$-terminal peptides can easily be determined using for instance a mass spectrometer.

An important advantage of this approach is that it selects for the amino-terminal peptides of the proteins. As a consequence, the identification of the proteins corresponding with the peptides is significantly simplified because the search to correlate the peptide mass with masses of peptides stored in databases can now be limited to the masses of the amino-terminal peptides in the databases. As a result, for the large majority of peptides, it is possible to unambiguously correlate the peptide with its corresponding protein. In an ideal situation, every $NH_2$-terminal peptide can be considered as the only representative identification-peptide of its corresponding parent protein, reducing the protein identification problem mainly to a one protein-one peptide correlation. This means that for a mixture of 1,000 different proteins, we have to search for 1,000 different identification-peptides. There is some difficulty in verifying this assumption by simple computer simulation using genomic DNA sequences, because one does not always know the extent of processing at the $NH_2$-terminus during in vivo protein maturation. For instance, β-cytoplasmic actin is first synthesized as: Met-Cys-Asp-Asp-Asp-Ile-, but finally processed into Acetyl-Asp-Asp-Asp-Ile . . . , with consecutive removal of Met and Cys prior to the addition of an acetyl group (Redman and Rubenstein, 1984). The problem of "unpredictable" $NH_2$-terminal protein processing is solved by first selecting and then identifying every identification peptide by a MS/MS or PSD approach. These studies are not too complicated because the sorted $NH_2$-terminal peptides will contain either arginine or homoarginine (hArg) and this is known to ionize very efficiently and to produce mainly y-type fragment ions (Biemann, 1990) during MS/MS-analysis, thereby leading to easily interpretable spectra. As already mentioned in section 10.2, the elution or migration time of an identification peptide may be a valuable and sufficient additional parameter to be combined with its total mass in order to fully identify an identification peptide. Thus, the mass of every identification peptides combined with its chromatographic properties together with the information from which protein this specific peptide is derived is stored in a relational database. This means that in most cases it is possible to unambiguously correlate the mass of the identification peptide with its parent protein.

10.4 The use of IPMBP in a Quantitative Differential Proteome Approach.

Figure 8:
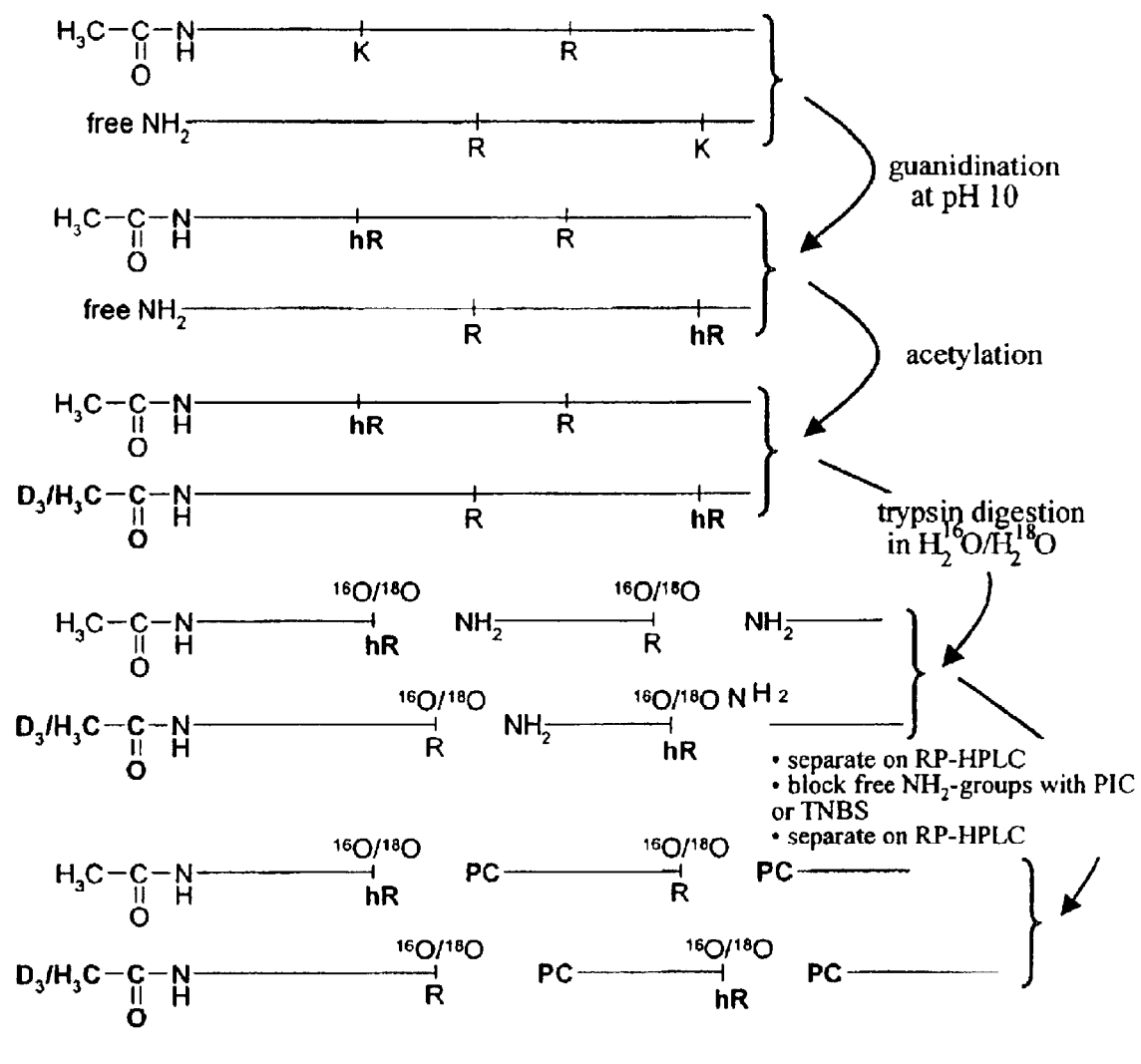
FIG. 8: Schematic summary of the reactions leading to a quantitative differential NH$_2$-terminal peptide-based proteome approach. Critical amino acid side chains are indicated. R=Arg, K=Lys, hR=homoArg, PIC=phenylisocyanate, PC=phenylcarbamyl, TNBS=trinitrobenzenesulfonate. $^{16}$O/$^{18}$O refers to the differential labeling obtained by digestion in H$_2$$^{16}$O or H$_2$$^{18}$O respectively.
Figure 8:
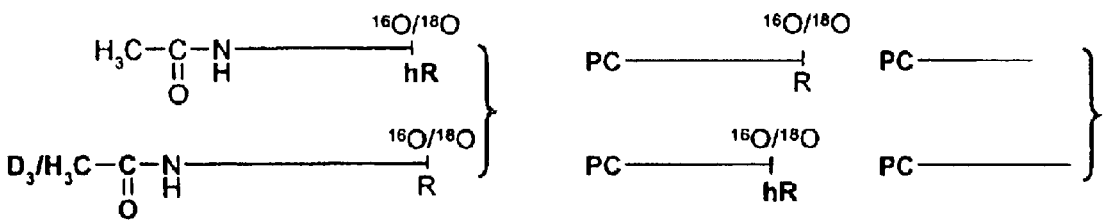

The procedure to use IPMBP in a quantitative proteome approach using identification peptides consists of the following steps: according to the procedure described in example 7 the proteins from protein peptide mixture 1 are first cysteine-modified and guandinated and then N-terminally acetylated. The proteins are then digested with trypsin in the presence of $H_2^{16}O$. The same procedure is carried out for protein peptide mixture 2, but now the trypsin digestion is carried out in the presence of $H_2^{18}O$. Trypsin not only catalysis the cleavage of its target peptide bonds, but also incorporates two oxygen atoms derived of water at the cleaved sites (see e.g. Schnölzer et al., 1996) (Rose et al., 1983) Thus peptides derived from protein peptide mixture 1 are COOH-terminally labeled with two $^{16}O$-isotopes, while peptides originating from protein peptide mixture 2 now carry two $^{18}O$-isotopes, differentiating the same peptide originating from the different mixtures by 4 amu's. Now the peptide mixtures are combined and passed over the first column (run 1). Peptides are again collected in fractions and labeled at their alfa-amino group by a specific reagent carrying a hydrophobic (or hydrophilic) group. Now peptides derived from $NH_2$-terminally blocked proteins (in vivo or in vitro) will not move in the second run and can be collected at the same elution time intervals as in run 1. In contrast, all altered peptides that have reacted at the $NH_2$-group after the primary run now undergo a hydrophobic/hydrophilic shift and segregate from the position that was taken before they were labeled. When hydrophilic reagents are used to alter the free alpha-amino groups, we observe a hydrophilic shift of the altered peptides, compared to the $NH_2$-terminally blocked peptides. However, since the peptide free alpha amino group is already hydrophilic, most blocking reagents lead to a more hydrophobic compound, which elute later than the free amino group peptide. Upon mass spectrometric analysis of the isolated identification peptides, we now detect two types of identification peptide doublets: those that segregate by 4 amu's (the difference between having two $^{16}O$ versus two $^{18}O$ isotopes) and that are derived from in vivo blocked proteins. The ratios of the peak intensities or peak surfaces reflect the relative ratios of the corresponding proteins in the two mixtures. The second type of doublets is separated by 7 amu's (the difference between having two $^{16}O$ versus two $^{18}O$ isotopes increased with the difference between having three H-atoms versus three D-atoms) and are derived from proteins in the samples that had a free $NH_2$-terminus. The ratios of the peak intensities or peak surfaces again reflect the relative ratios of the corresponding proteins in the two mixtures. The reaction scheme for the quantitative differential $NH_2$-terminal peptide approach is summarized in FIG. 8.

An alternative to the $^{16}O/^{18}O$ differential labeling method is the use of flagged or identification peptides that are chemically synthesized and contain at least one deuterated (or any type of heavy isotope $^{13}C$, $^{15}N$) amino acid, allowing sufficient segregation of the natural identification peptide versus the "heavy" synthesized identification peptide by mass spectrometry. The "heavy" peptides now serve as internal standards. Thus the synthetic peptide is added in known quantities to the protein peptide mixture and is sorted together with its natural counterpart. Comparison of the peptide peak ratios in the mass spectrometer allows a relative quantitative estimation of the natural identification peptide versus the added synthetic peptide.

Such isotopically labeled flagged or identification peptides could for instance contain deuterated Leucine (e.g. L-Leucine-$d_{10}$, producing a mass difference of 10 amu's), or deuterated methionine. The latter might be convenient when Met-containing peptides are sorted (see for instance examples 1, 18, 19 and 20).

Since the large majority of the tryptic peptides terminate with either Arginine or Lysine, and since chemical peptide synthesis starts from the COOH-terminus and proceeds towards the $NH_2$-terminus, all peptides could be synthesized starting with either deuterated lysine or deuterated arginine; while the other amino acids could be attached as their natural derivatives. In this case, a solid phase support could be used on which already deuterated lysine or deuterated arginine is connected via a cleavable linker arm with the solid phase support. Such solid phase resins could be used as general starting material from which any kind of heavy flagged or identification peptide could be synthesized by conventional solid phase peptide synthesis.

Example 11

A Peptide Sorter Device by Use of a Single Column System

Figure 10:
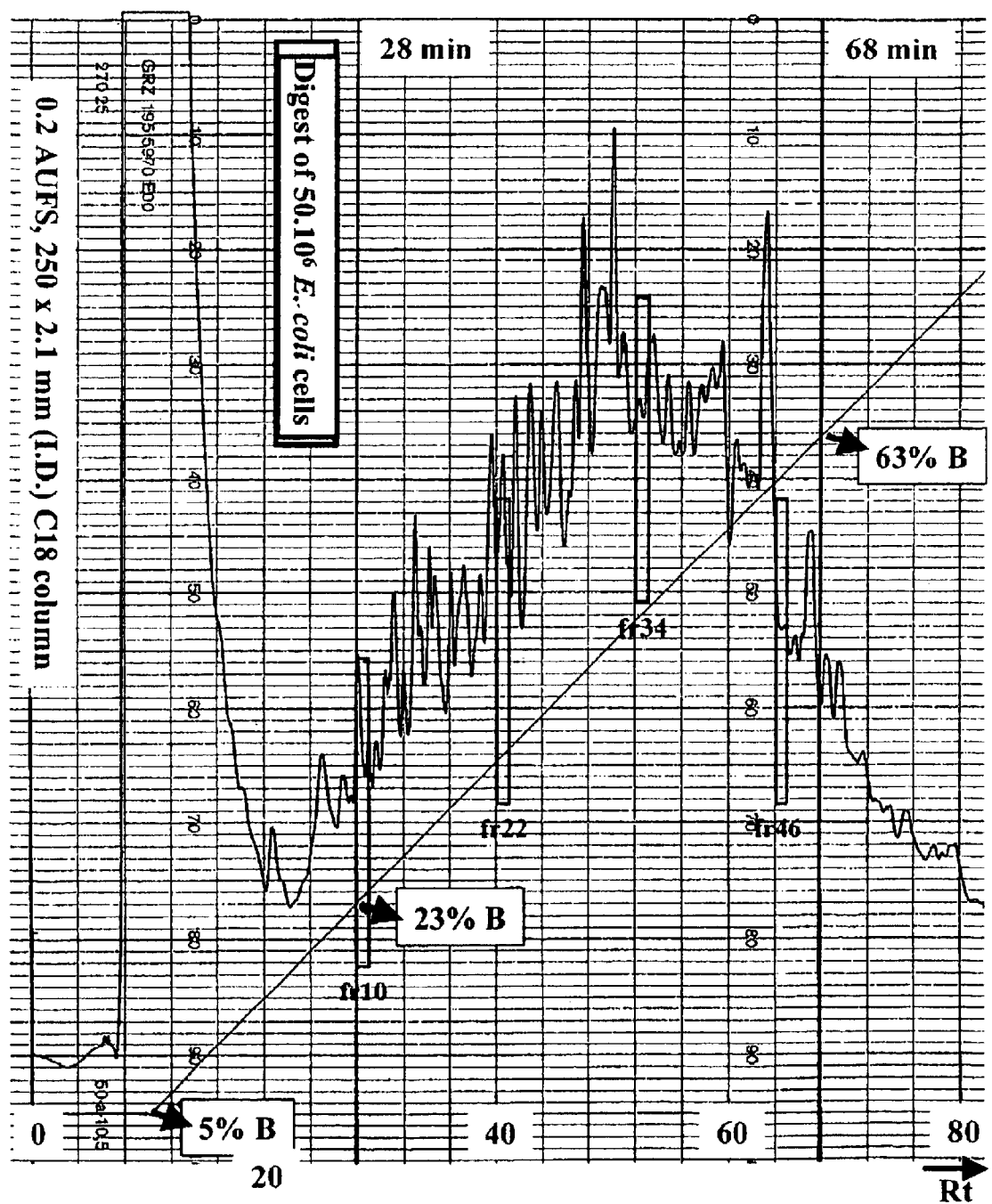
FIG. 10: 214 nm UV-absorbance profile of a RP-HPLC separation (2.1 i.d.×250 mm C18-column) of a total trypsin digest of a lysate of 50.10$^6$ E. coli cells. Tryptic peptides are eluted by employing an increasing linear gradient of 1% B/min with a constant flow of 80 µl/min, starting from 5% B (solvent B=70% acetonitrile in 0.09% TFA in water, solvent A is 0.1% TFA in water). Tryptic peptides eluting between 23% solvent B and 63% solvent B are collected in 40 fractions of 80 µl each. The first collected fraction is numbered 10, the last one is numbered 49 (see also Example 18). Fractions which were taken and further processed in FIG. 11 are indicated by blue open rectangular boxes.
Figure 11:
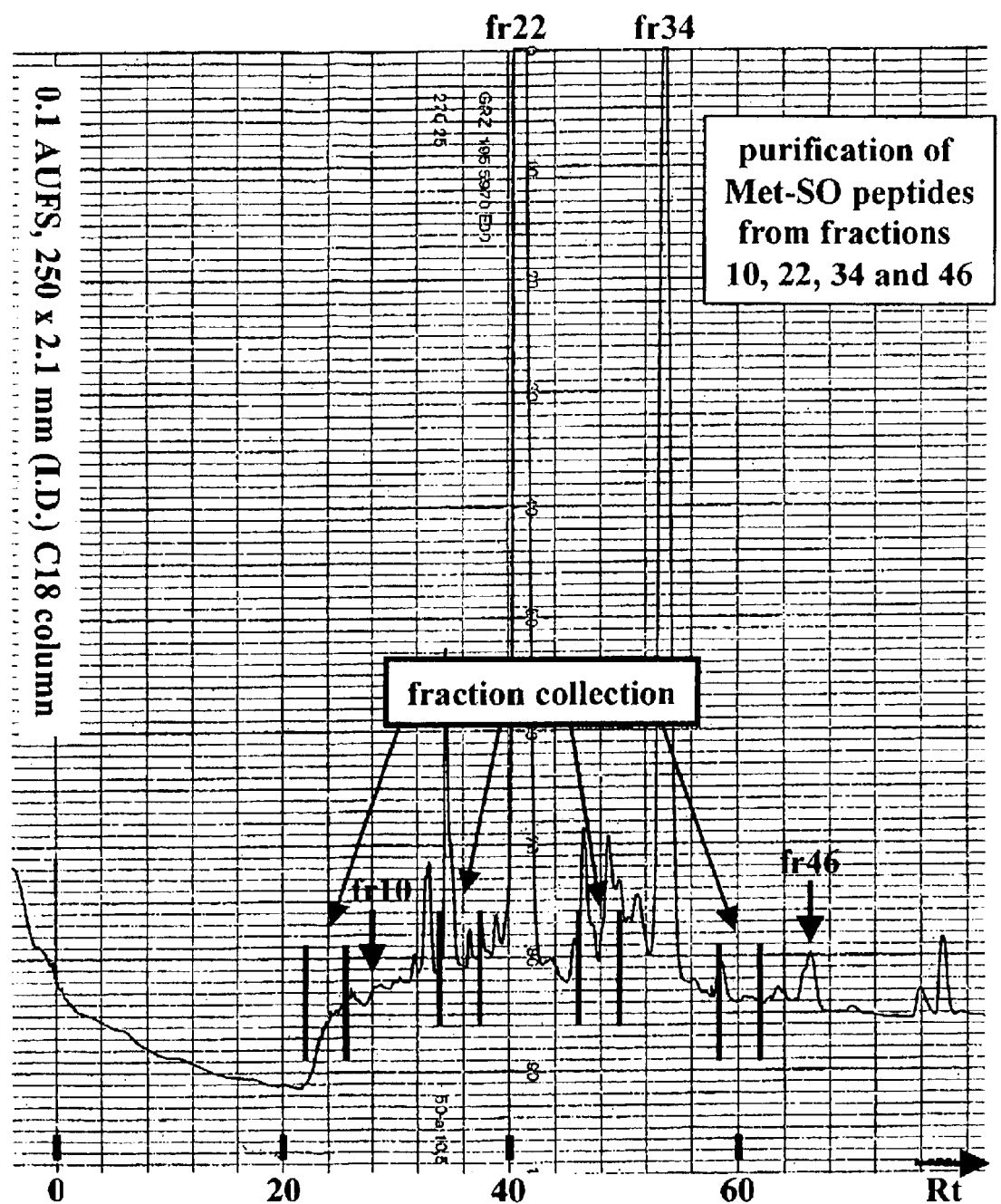
FIG. 11: 214 nm UV-absorbance profile showing the collection of methionine-sulfoxide peptides obtained following mild oxidation (using 0.5% $H_2O_2$ in 1% TFA) of the peptides present in fractions 10, 22, 34 and 46 (primary run). Collection of Met-SO peptides is started 6 min before the elution of the bulk of unmodified peptides and lasts 4 min. Chromatographic conditions were identical as those shown in FIG. 10. Fractions containing the unmodified peptides are indicated with blue arrows, the sorted peptides are delineated in red; 4–7, 16–19, 28–31 and 40–43 (Table IVA).

The basic protocol of the invention to isolate for example methionine-containing peptides out of a protein peptide mixture consists of two consecutive chromatographic steps: one RP-HPLC step of the protein peptide mixture, carried out in the solvent system that has been found to produce the most suitable shifts between the oxidized methionine-peptides and the non-altered peptides and which is also most compatible with either electrospray or MALDI-ionization procedures. The second RP—HPLC run which is performed after the oxidation step is made under the same or very similar chromatographic conditions, such that only the oxidized peptides shift forwards, while the non-altered peptides stay at their original elution times. This principle is used in several ways to separate methionine-peptides from the non-methionine peptides. Thus in a single column system, schematically represented in FIG. 9, the primary run (run 1) of the total cellular peptide mixture is made on a standard reversed phase column (e.g. a 2.1 mm I.D. ×25 cm C-18 RP-column, Vydac Separations Group, CA). This is referred to as the primary run and the UV-absorbance profile of peptides from an *E. coli* lysate is shown in FIG. 10. Following an initial isocratic washing step with 5% of solvent B for 10 min, the column is eluted with an acetonitrile gradient, increasing linearly at 1% of solvent B per minute during 95 min. Buffer A consists of 0.1% trifluoroacetic acid (TFA), while buffer B consists of 0.09% TFA in 70% acetonitrile. The flow is kept constant at a rate of 80 $\mu$l/min and fractions of 80 $\mu$l are collected in 0.5 ml Eppendorf tubes. In total 40 fractions are collected. The first fraction, which was collected, is called fraction nr. 10 (eluting between 18 and 19 min following the start of the gradient and corresponding with 23% of solvent B). The last collected fraction (eluting between 57 and 58 min following the start of the gradient and corresponding with 63% of solvent B) is given number 49. In this experimental set-up only the methionine-residues, present in the peptides in the fractions, are specifically chemically altered, peptides that contain oxidized methionine residues are here designated Met-SO peptides. The specific alteration is done as follows. Each fraction is vacuum dried and re-dissolved in the oxidation mixture, consisting of 1% TFA in water to which 30% stock solution of $H_2O_2$ was added to give a final concentration of 0.5% of $H_2O_2$. The oxidation is allowed to proceed for 30 min at 30° C. and the solution is then immediately loaded on the RP-column for the secondary runs. According to the invention it is highly preferable to rerun every fraction after oxidation in the same or very similar chromatographic conditions and on the same column. Using the same conditions in run 2, the Met-SO peptides elute between 6 and 2 min in front of the bulk of the unaltered peptides. One approach is to run every fraction separately and to do this for each of the 40 fractions. Such approach not only requires a considerable amount of HPLC-time, but it also occupies important machine time on the mass spectrometer. In order to obtain a more economic use of both the HPLC equipment and the mass spectrometer, and in order to speed up the whole process we reduced the number of separations by pooling several fractions of the primary run, avoiding overlapping of the forward shifting flagged peptides with the unaltered peptides from the previous fractions and avoiding overlapping of the flagged peptides from one fraction with the flagged peptides from another fraction. Before setting this protocol we measured the hydrophilic shifts of a significant number of synthetic methionine-containing peptides after oxidation and noticed that the large majority of the shifts was less than 6% but larger than 2% of solvent B; thus in a window between 6 and 2 min in the gradient used in our experiments (see also Table III). In the 2 min zone laying between the shifted peptides and the bulk of the peptide material, we noticed only very few methionine-peptides, but instead we already detected a few non-altered peptides, spreading from the large peak of bulk peptides. In order to avoid overlap in flagged peptide elution coming from two fraction in this particular experimental setting, there needs to be at least 6 minutes of elution difference between these two fractions (e.g. for fraction 10, this would have been fraction 17). However, for safety reasons, we added an additional 5 min elution time following the elution of the large peak fraction; before allowing the elution of the next group of oxidized methionine-peptides. This means that for the secondary runs we could combine fractions that were separated in the first run by intervals of 12 minutes. Thus we combined fraction 10 with fractions 22, 34 and 46. Similarly we combined fraction 11 with fractions 23, 35 and 47, etc. A complete list of fraction-pooling for the secondary runs is shown in Table IVA. The UV-absorbance profile of a typical secondary run (run 2A, combining fractions 10, 22 34 and 46) is shown in FIG. 11. The methionine SO-peptides were each time collected in the intervals between six and two minutes preceding the time in which the unaltered peptides were expected to elute. Thus in the example of run 2A above, oxidized peptides were collected in fractions 4–7, 16–19, 28–31 and 40–43 (Table IVA). The oxidized peptides in the remaining secondary runs were collected as further listed in Table IVA. Thus in total we have to carry out twelve such secondary separations consecutively, in order to cover all fractions from the primary run. Here it should be added that the time intervals and windows employed in the sorting process described here, are subject to changes depending on the chromatographic system selected or on the type of components that have to be sorted. For instance, in example 18 we describe a sorting process using different time intervals and windows to also sort for methionine peptides, but using the HCOOH/acetonitrile system. It is self evident that time intervals and windows have to be adapted to each particular question (e.g. sorting for phospho-peptides, sorting for N-ε-acetylated peptides, sorting for the $NH_2$-terminal peptides etc.).

The Met-SO peptides eluting during the secondary runs can either be directly passed into an ion source of an on-line connected mass spectrometer (e.g. an ESI-based mass spectrometer) or they can be collected in small aliquots for further MALDI-TOF/RETOF-MS analysis or directly spotted in small drops onto the MALDI-target plate for high throughput MALDI-MS analysis. Alternatively, the sorted Met-SO peptides can be collected in Eppendorf tubes and recombined for a possible third series of separations (here referred to as the ternary runs). The latter might be necessary when peptide sorting has been carried out in TFA-containing systems, while analysis is done by ESI-MS. Indeed TFA is known to cause ion clustering during electrospray, seriously impairing peptide detection and MS/MS analysis (Mirza and Chait, 1994). This is not the case when either 0.05% HCOOH or a 10 mM $NH_4Ac$ buffer at pH 5.7 are used as counter ions. It should be realized that the use of the latter systems can produce shifts in the peptide elution times when compared with the TFA-systems used in the previous runs, possibly leading to unwanted peak accumulation and thus risk of inefficient peptide identification. In Tables IVB and IVC we present two different schemes illustrating how the fractions derived from the secondary runs can be pooled to carry out a ternary run. In case identical counterions are used in the solvent throughout the different runs, we can combine fractions that elute one after the other. For instance fraction 4–7 of run 2A can be combined with fraction 8–11 of run 2E, fraction 12–15 of run 2I, fraction 16–19 of run 2A, fraction 20–23 of run 2E, fraction 24–27 of run 2I, fraction 28–31 of run 2A, fraction 32–35 of run 2E, fraction 36–39 of run 2I, fraction 40–43 of run 2A (marked in blue in Table IVB). The remaining fractions are combined in a similar way as shown in Table IVB, leading to four pools of which the components can be separated in four ternary runs; 3A, 3B, 3C and 3D. In case we use 0.05% HCOOH in the ternary runs it is advised to combine only half of the fractions each time. Thus for run 3'A we now pool fraction 4–7 of run 2A, with fraction 12–15 of run 2I, fraction 20–23 of run 2E, fraction 28–31 of run 2A and fraction 36–39 of run 2I. The other combinations are again listed in Table IVC and are separated in eight different ternary runs (3'A till 3'H). Still other combinations to pool fractions from the secondary runs in order to perform a tertiary run are possible. Although ternary runs as described above are important to obtain a better dispersion of the peptides over several runs, it is more efficient and faster to identify the peptides immediately when they elute the column in the course of the secondary runs. From a time perspective, the latter is not optimal with a single column peptide sorting device, because the Met-SO peptides elute at intervals separated by 8 min blocks where no collections are possible. These 8 min blocks can be filled up with two 4 min elutes when running three columns simultaneously. The design of such a three-column Peptide Sorter is described in the example 12.

In case the reversed sorting process is used, in which unaltered peptides are sorted and collected as identification peptides, while altered peptides, forming the majority of the peptides of the original protein peptide mixture, are discarded or used for other analysis, the following procedure is evident.

Using similar values of peptide shifts as those used in the example of the methionine oxidation used above, assuming that primary fractions of 1 min have been taken,($W_1$=1 min) assuming all altered peptides shift between 6 and 2 min in front of the elution position of the identification peptides; then we collect the identification peptides in the same time interval as where they were taken in the primary run, while the altered peptides eluting between −6 and −2 min are not analysed. It should be clear, that now the altered peptides form the bulk of peptides, while the non-altered peptides represent a minor fraction of the original mixture.

It is also important to indicate that there might be some broadening of the window in which unaltered peptides elute during the secondary run, due to the absence of large amounts of peptides in the secondary run. Therefore, unaltered identification peptides are better collected in a window, which is slightly wider than $w_1$: for instance 0.5 min before and behind the time intervals of $w_1$.

As in the example of the methionine oxidation, again, we can combine fractions 10, 22, 34 and 46 of the primary run. Now the altered peptides eluting in fraction 4–7, 16–19, 28–31 and 40–43 are discarded, while the identification peptides are now collected in fractions 9.5–11.5 min, 21.5–23.5 min, 33.5–35.5 min and 45.5–47.5 min.

The reversed sorting process can thus be carried out with the same apparatus as the normal sorting process, with minimal changes in the peptide collection program.

It should be clear again here to those skilled in the art that the shifting times can vary dependent of the chromatographic system and conditions and the used alteration chemistry or procedures.

Example 12

A Three-Column Peptide Sorting Device

Figure 12:
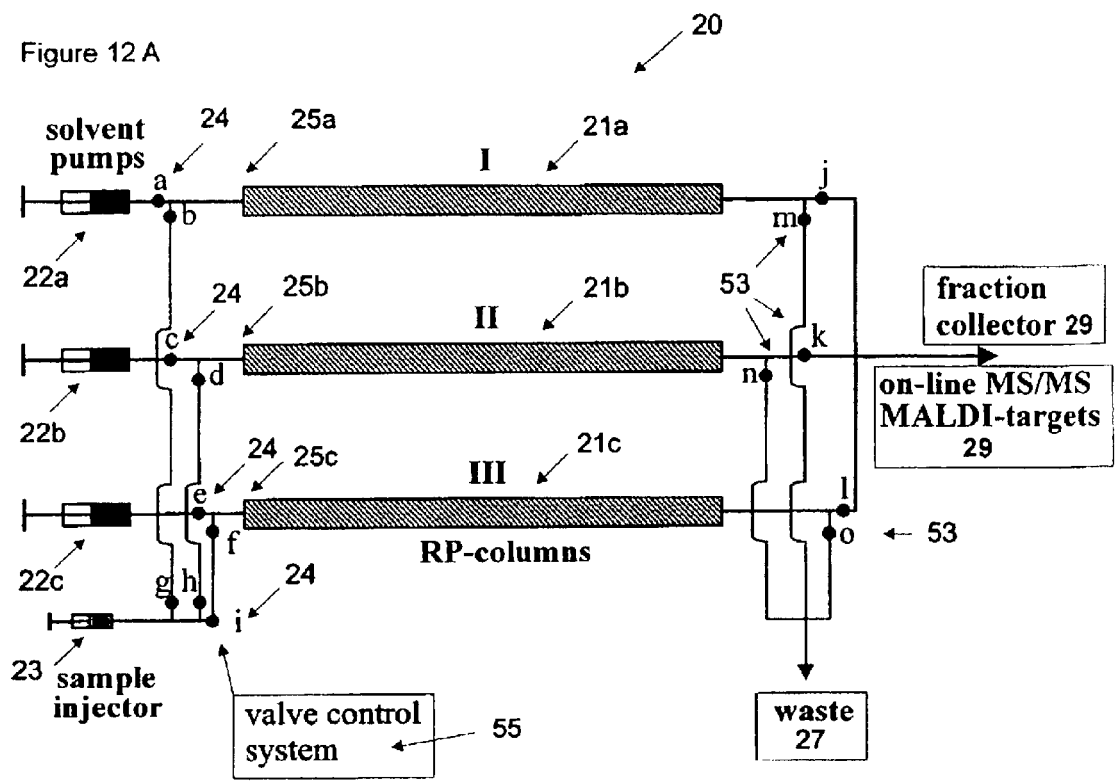
FIG. 12: The triple column Peptide Sorter: This system operates with three identical RP-columns connected in parallel. Also here, all conditions are kept identical not only among the parallel runs but also in comparison with the primary run. Fractions collected from the primary run, were combined, modified and distributed over each of the columns as stipulated in Table V. The solvent flows are kept constant throughout the three columns. This can be achieved by connecting each individual column to a high pressure pump system thereby using three such pumps (version A) or by using a single high pressure pump but controlling the flow rates towards each of the columns, using a controlled splitter system (version B). Such flow rate regulators are now commercially available (Valves a–i are high-pressure valves, valves j–o are low-pressure valves. These valves can be steered with a PC, allowing full-automated operation, including loading, separation and analysis (fraction collection, mass spectrometer or MALDI-target).
Figure 12:
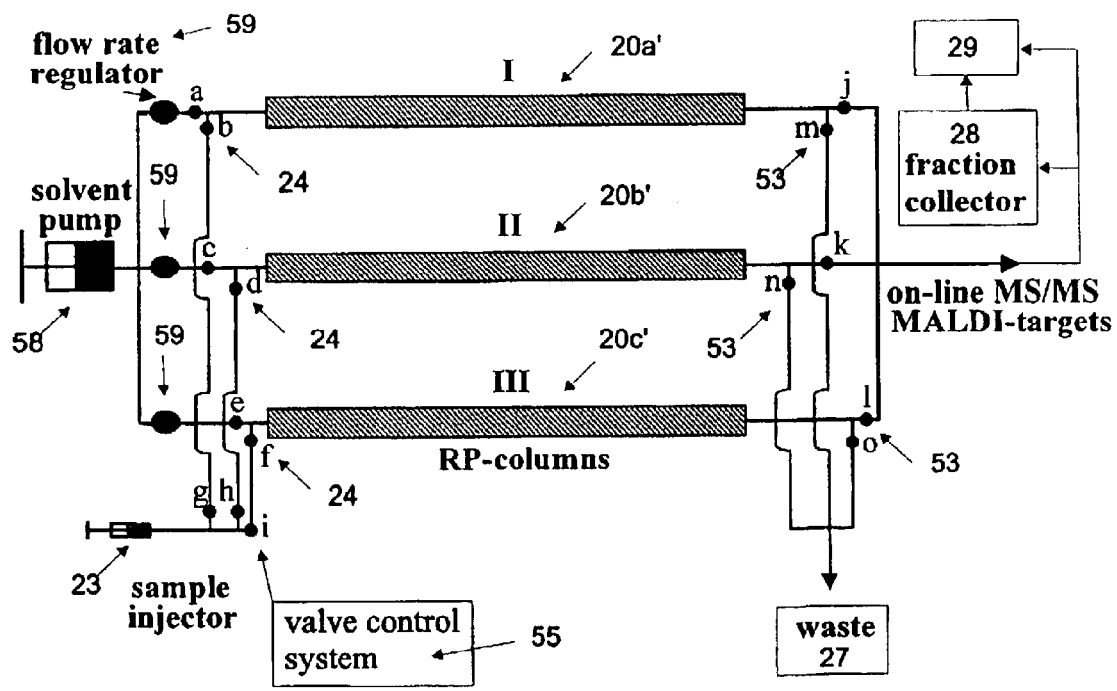

In order to reduce the overall peptide sorting time, the procedure followed in example 11 based on a single RP-HPLC column for all steps, is now executed with three columns operating in parallel and synchronously. A schematic view of such a sorting system is shown in FIG. 12. This peptide sorting device contains three identical RP-columns which are run in exactly the same conditions (flow rate, gradient, etc.). In order to achieve identical conditions, these columns are each connected with high-pressure pumps and solvent mixing devices, exactly controlling the flow-rates and gradients in the three columns (FIG. 12A). Alternatively the three columns are fed by a simple high-pressure pump, while the flow rates to each of the columns are monitored by a splitter valve able to control the flow rates (FIG. 12B). On column I we load fractions 10, 22, 34 and 46 from run 1. Exactly the same flow rate and gradient as in run 1 is created. The column is first washed with 0.1% TFA in 5% solvent B (e.g. 70% acetonitrile in 0.09% TFA) during 10 min. Then we continue the gradient as in run 1 with a gradient of 1% solvent B per minute. From min 4 till the end of min 7 (fractions 4–7 we collect the Met-SO peptides or we direct them into the ion-source of the MS-apparatus for analysis. Alternatively the 4–7 eluate is collected in small aliquots for instance by using a MicroBlotter (Applied Biosystems, Foster City, Calif., USA) for further analysis by MALDI-TOF-MS. From min 8–15 the eluate is again directed to the waste. At 16 min we collect the second boost of Met-SO peptides originating from fraction 22 in run 1. This collection or analysis is done during the interval from 16 to 19 min (fraction 16–19). Then again the eluate is discarded until the 28–31 min interval, during which we collect the third boost of Met-SO peptides which are originally derived from fraction 34. At 32 min the collection is stopped and the eluate is further directed into the waste. The gradient is continued as in run 1 with an additional collection of fractions 40–43 and completed 58 min after the start of the gradient followed by a re-equilibration step with 0.1% TFA for 30 min. Column II which has now been loaded with fractions 14, 26 and 38, is run in exactly the same conditions as described above for column I. Now the Met-SO peptides are saved in the time intervals 8–11, 20–23 and 32–35. Column III is loaded with fractions 18, 30 and 42, run in the same conditions and in the same synchrony as columns I and II. The Met-SO peptides now elute in the time intervals 12–15, 24–27 and 36–39. When the runs with the three columns are operating simultaneously we do not anymore observe dead intervals between the Met-SO peptide analyses. Indeed, as demonstrated in Table V we analyze the products of column I during min. 4–7, 16–19, 28–31 and 40–43, those of column II during min. 8–11, 20–23 and 32–35, while those of column III are saved during times min. 12–15, 24–27 and 36–39. These ten time intervals can be perfectly aligned resulting in a continuous flow of Met-SO peptides to the MS instruments. Again here, it is important to mention that the methionine peptides that were originally captured in a total of 10 min during the primary run, are now delivered after sorting to the MS-apparatus spread over a total time frame of 40 min, creating much better analytical conditions. In addition, it is also possible to reduce the flow-rate during the time interval in which the Met-SO peptides elute, so that the mass spectrometer can more efficiently select and analyze the eluting peptides. Thus we can use a kind of peak parking (Davis et al., 1995) procedure at the time the Met-SO peptides elute the sorting system. This needs the adaptation of the elution times in the other connected columns. The second triplicate run is now performed with combined fractions 11, 23, 35 and 47 separated on column I, with fractions 15, 27 and 39 on column II and with fractions 19, 31 and 43 on column III. Again the Met-SO peptides are collected in time intervals 5–8, 17–20, 29–32 and 41–44 for column I, intervals 9–12, 21–24 and 33–36 for column II and intervals 13–16, 25–28 and 37–40 for column III. All combinations of fractions of run 1 and the savings of Met-SO peptides are schematically represented in Table V. The valve operation throughout the full procedure is depicted in Table VI. Thus by using a tri-column peptide sorter we can now separate all Met-SO peptides from a complex mixture in a total of four secondary runs. Since every run will take about 120 min, including loading, washing, elution and re-equilibration, the entire Met-SO sorting step from a total cell lysate may be executed in approximately 500 min. This sorting process can be directly monitored using an on-line connected mass spectrometer. Alternatively, eluates of Met-SO peptides can be collected for further combination and analysis in ternary runs or eluates can be spotted in small aliquots on MALDI-targets that allow consecutive high throughput analysis. It should be mentioned that, in addition to the RP—HPLC chromatographic conditions used here, the same sorting process can be carried out with column systems allowing much faster elution times, thereby reducing the overall sorting process.

Example 13

A Nine-Column Peptide Sorting Device

A construction of a nine-column peptide sorting device is depicted in FIG. 13. The first three columns are connected with one gradient pump and one sample injector. There is a second and a third series of columns that are each connected with one gradient pump and one sample injector. The nine columns,—which can be small disposable columns—, are divided in three units. Unit A contains columns I, II and III, while units B and C include columns I', II', III' and I", II" and III" respectively. On column I we load fraction 12 of run 1, on column II, fraction 24 and on column III, fraction 36. Each loading procedure is followed by a wash step with solvent A for at least 10 min. Then the gradient is started (an increase of 1% solvent B per min). The gradient is first passed only over column I. This column is pre-conditioned between 0 and 5 min. The Met-SO peptides elute between 6 and 9 min and the column is washed between 10 and 16 min. At 17 min, valves are arranged such that the gradient now passes through column II that is first equilibrated for 1 min. The Met-SO peptides are collected between 18 and 21 min and the column is washed from 22 to 28 min. At 29 min the gradient is directed into column III which is pre-conditioned during one minute. The Met-SO peptides are eluted between 30 and 33 min, followed by a wash form 34 min till the end of the gradient. The system B (columns I', II'and III') is loaded with fractions 13, 25 and 37 respectively and developed with an identical program but with a delay of 3 min versus system A. Thus the Met-SO peptides sort at times 10–13 (I'), 22–23 (II') and 34–37 (III'). The same program is used for system C (columns I", II" and III") with fractions 14, 26 and 38 and a delay of 6 min versus system A. The corresponding Met-SO peptides are collected at the intervals 14–17 (I"), 26–29 (II") and 38–41 (III"). Thus in a one step procedure we sort the Met-SO peptides from nine fractions at once. An additional four such runs in which the fractions are loaded and collected as indicated in Table VII leads to a complete sorting of all the Met-SO peptides present in the original mixture. A full description of the valve settings during the complete run is provided in Table VIII. An important aspect of the nine-column peptide sorting device is that the column dimensions and the overall design of the system is different from that used in the primary run. Meaning that even when the RP-sorbents and solvent systems are kept identical, it is possible that different elution times occur. A solution for this problem is the use of a colored $(Ala)_n$-Arg synthetic mixture (see example 14) added to the peptide mixture. This allows to use the consecutive colored peaks as reference points, guiding fraction collection during the primary run. Thus fractions can be collected between two consecutive colored peaks or around the colored peaks. The same colored reference components can then be used as to guide fraction collection to the peptide sorters. The use of the nine-column peptide sorter in combination with reference compounds is particularly beneficial in the sorting process for $NH_2$-terminal peptides (see examples 6 and 7). In the latter the sorted peptides are not altered and stay together with the colored reference mixture while the bulk of non-sorted peptides is retarded and moves away from the colored references.

One run by this nine-column sorter is achieved in about 60 min., meaning that the complete sorting process is finished in ±300 min. or 5 h. It is important to mention here that small, and cheap columns can be used in this sorter. Since only one fraction is processed per column, flow rate accuracies are not as important as in systems where several fractions are loaded on one single column. All runs can also be done at lower pressure posing fewer demands for pumps and valves. The nine-column sorter is also better adapted for situations where hydrophilic shifts are either larger or smaller then those regularly measured during methionine sulfoxide formation. This may be the case when the methanol-chromatographic systems are used, or when cysteine derivatives are oxidized (see Table III). The different peptide sorters described here are limited examples that do not exclude the construction of similar sorters with a different number of columns.

Example 14

Calibration of Peptide Sorters

Figure 14:
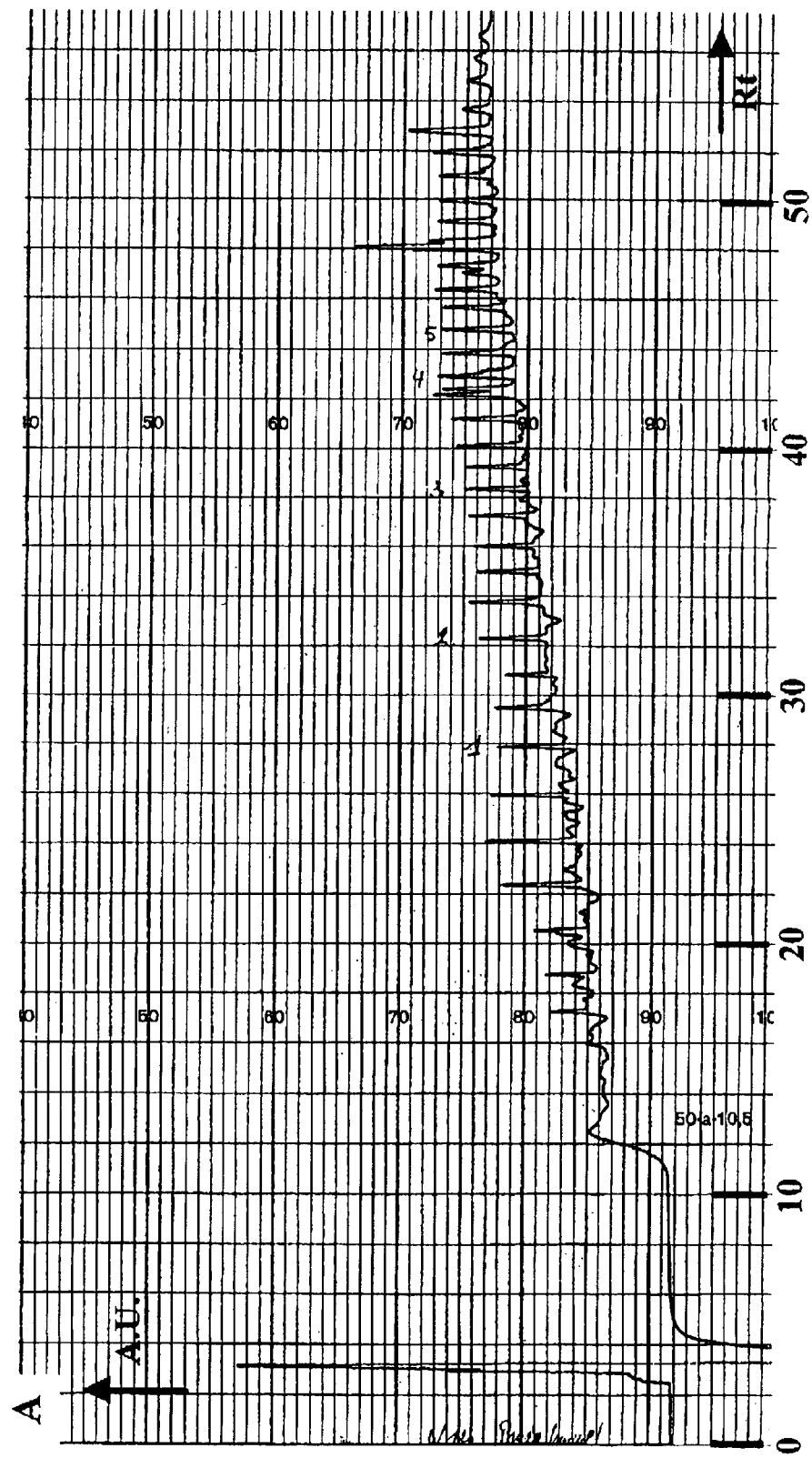
FIG. 14: (A) UV-absorption profile (214 nm) of an RP—HPLC separation of the peptide reference mixture $NH_2$—$Ala_n$-Arg-COOH (n=7 to 42). The components of this mixture differing in one additional alanine-residue can be clearly noticed. The separation was done on a 2.1 i.d. mm RP—HPLC C18-column using a linear acetonitrile gradient in 0.1% TFA. (B) MALDI-RETOF-MS spectrum revealing the different components present in this mixture, separated by 71 amu's.
Figure 14:
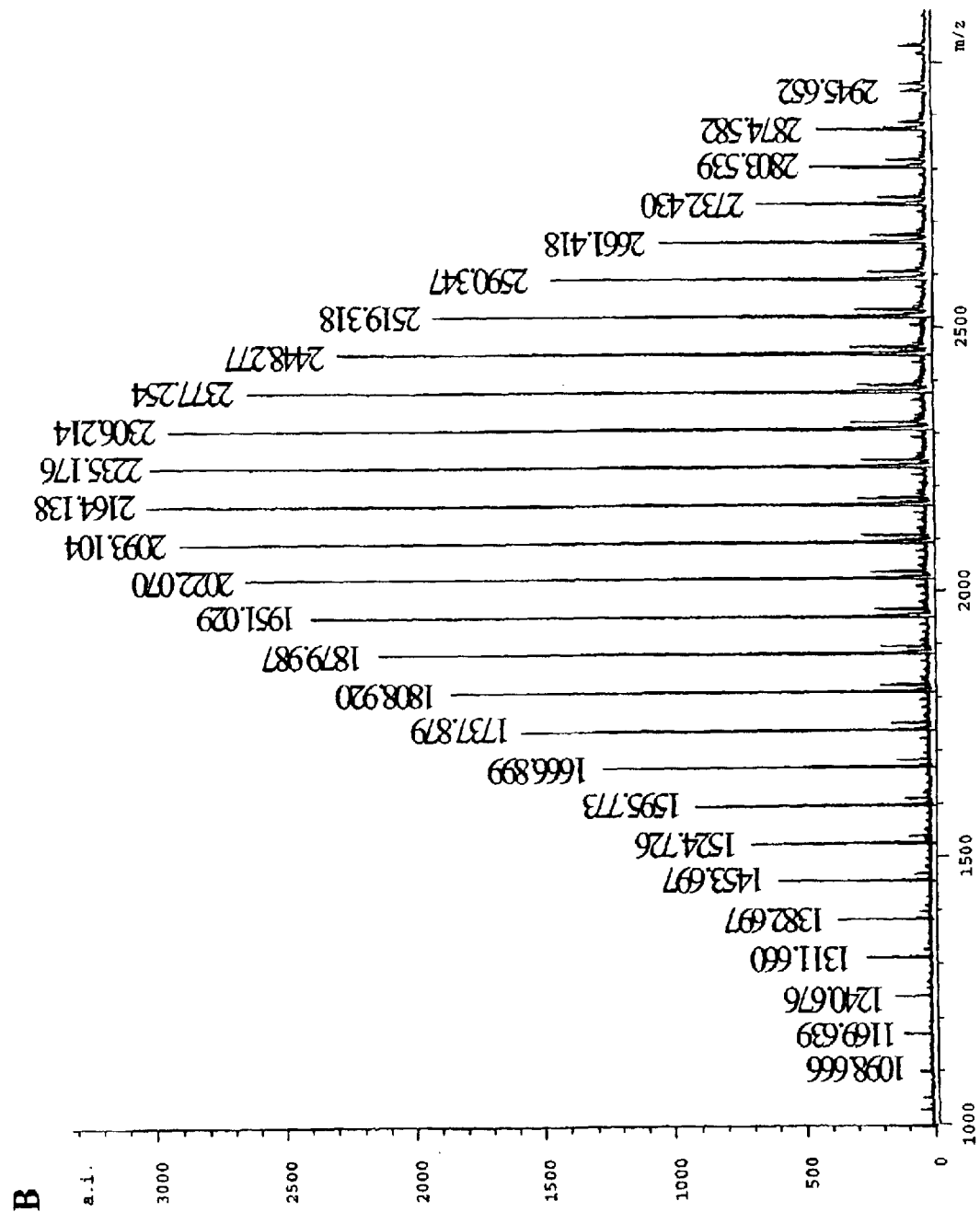

The efficiency and accuracy of the peptide sorters mainly depends on the reproducibility of the column separations. Thus for the installation but also for regular monitoring of the sorters, it is practical to use a peptide calibration mixture or a mixture of components covering the entire solvent gradient range and which can be monitored either by mass spectrometry, light-absorbance or by other means. As a non-limiting example we use here a chemically synthesized peptide mixture consisting of varying numbers of alanine to which a COOH-terminal arginine residue is attached ($Ala_n$-Arg, with n ranging from 7 to 42). This mixture is synthesized using conventional solid phase synthesis procedures (Merrifield, 1963). Using a mixture of 97% of Fmoc-Ala and 3% of tBoc-Ala for peptide elongation, premature stops are generated after each cycle in 3% of the growing peptide chain. This type of synthesis strategy yields a mixture in which every component differs from the other by the addition of one alanine yielding a set of peptides that show a contiguous change both in mass (71 amu's) and in hydrophobicity. Thus in the case of the above examples, a given elution window (w1) can also be characterized by one or more peptides from this mixture with well determined mass values. As a non-limited illustration the elution profile is shown of the $NH_2$—$Ala_n$-Arg-COOH mixture on a C18-RP-column using 0.1% TFA as ion and acetonitrile as modifier (FIG. 14A). A colored version of such a calibration compound can be obtained by synthesizing the poly-Ala-peptide with an additional lysine residue, allowing covalent attachment of a colored moiety via the epsilon-amino group; $Ala_n$-Lys-Gly-Arg.

This peptide calibration mixture is used to monitor the properties and characteristics of each column in the peptide sorter device and to calibrate the entire system. This can be done by mixing the calibration peptides with the peptide mixture derived from the sample, during the first run. Any adjustment of the elution profile of the calibration compound is carried out by conventional means well known in the field such as changing the modifier concentration, altering the elution gradient, changing the column temperature, adding ion-paring agents such as octylamine or dodecylsulfate or by adding tetrahydrofurane or propanol to solvent B etc. The same peptide calibration mixture is also used to calibrate the mass spectrometer in particular the MALDI-TOF-MS machines, in order to reach a high degree of accuracy (FIG. 14B).

Example 15

Identification of Peptides and Assignment of Parent Proteins

The flagged peptides or identification peptides eluting in a secondary run or from a ternary column system are passed directly into the ion source of an electrospray mass spectrometer and then further fragmented in the MS/MS mode. Partial sequence information is collected from the MS/MS fragmentation spectra and used for peptide identification in the sequence databases. Because flagged peptides are gradually eluted in run 2 over a broad time interval, there is minimal co-elution of these peptides and the resolving power of the MS/MS is significantly enhanced. (see for instance example 18). The current invention is also used to identify peptides by MALDI-TOF-MS. Indeed, high-throughput MALDI-TOF-MS techniques are employed to rapidly scan the flagged peptides or identification peptides. For this we for instance use the peptide-bead concentration method, where peptides are in batch adsorbed on POROS 50 R2 beads, transferred to the target disc and on-target desorbed with the MALDI matrix compounds (Gevaert et al. 1997 and Gevaert et al., 1998). The obtained information is limited to the total peptide masses, which is not always sufficient for unambiguous identification when it cannot be measured accurately. There are several ways to collect additional information that leads to more conclusive identification.

Figure 15:
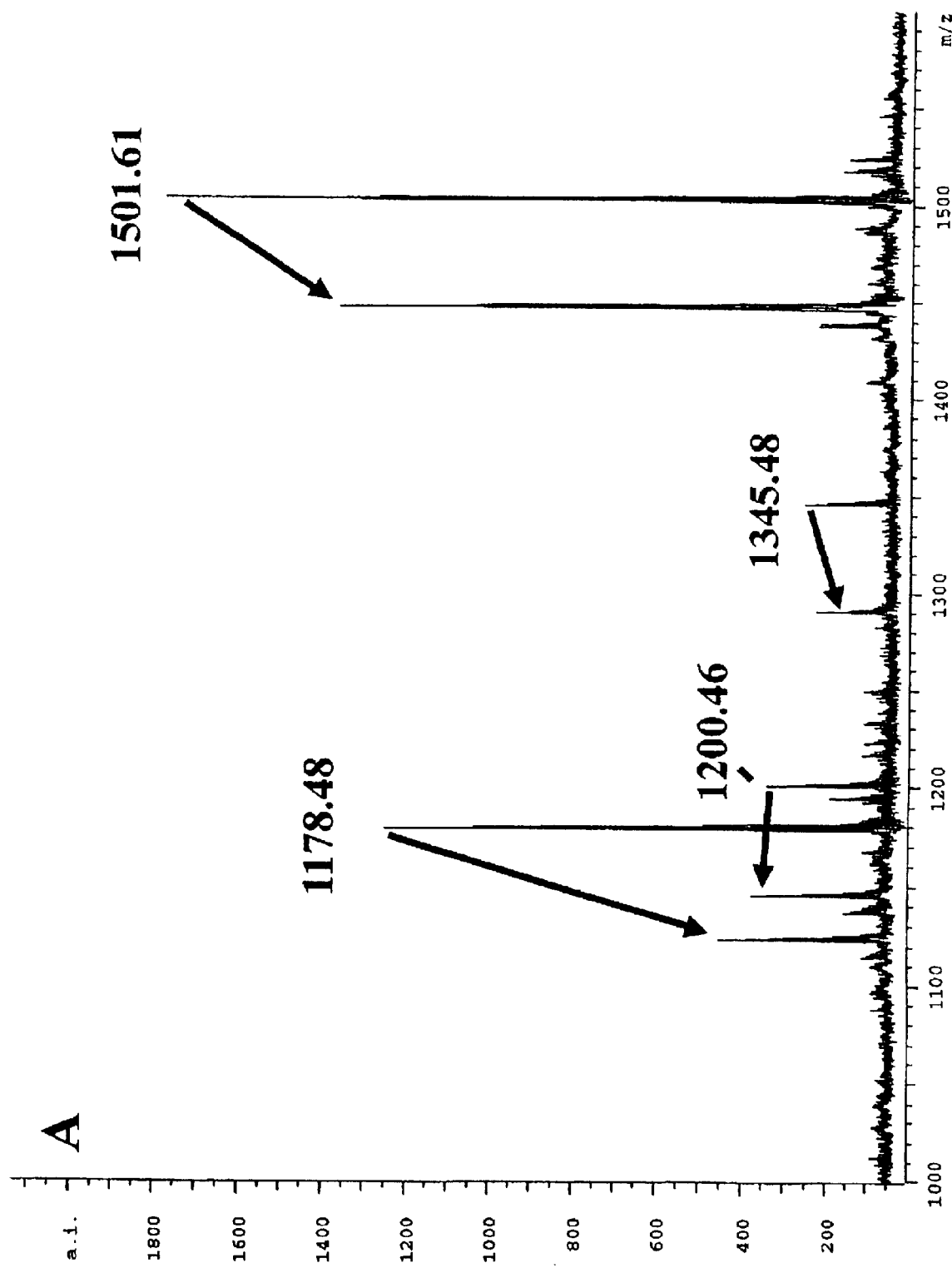
FIG. 15: MALDI-RETOF mass spectra of the peptides present in two fractions of collected Met-SO peptides (panels A and B). The masses of the identified Met-SO peptides are given and their characteristic fragmentation product with a loss of methanesulfenic acid observed in reflectron mode is indicated, giving a shorter fragment (indicated with a blue arrow).
Figure 15:
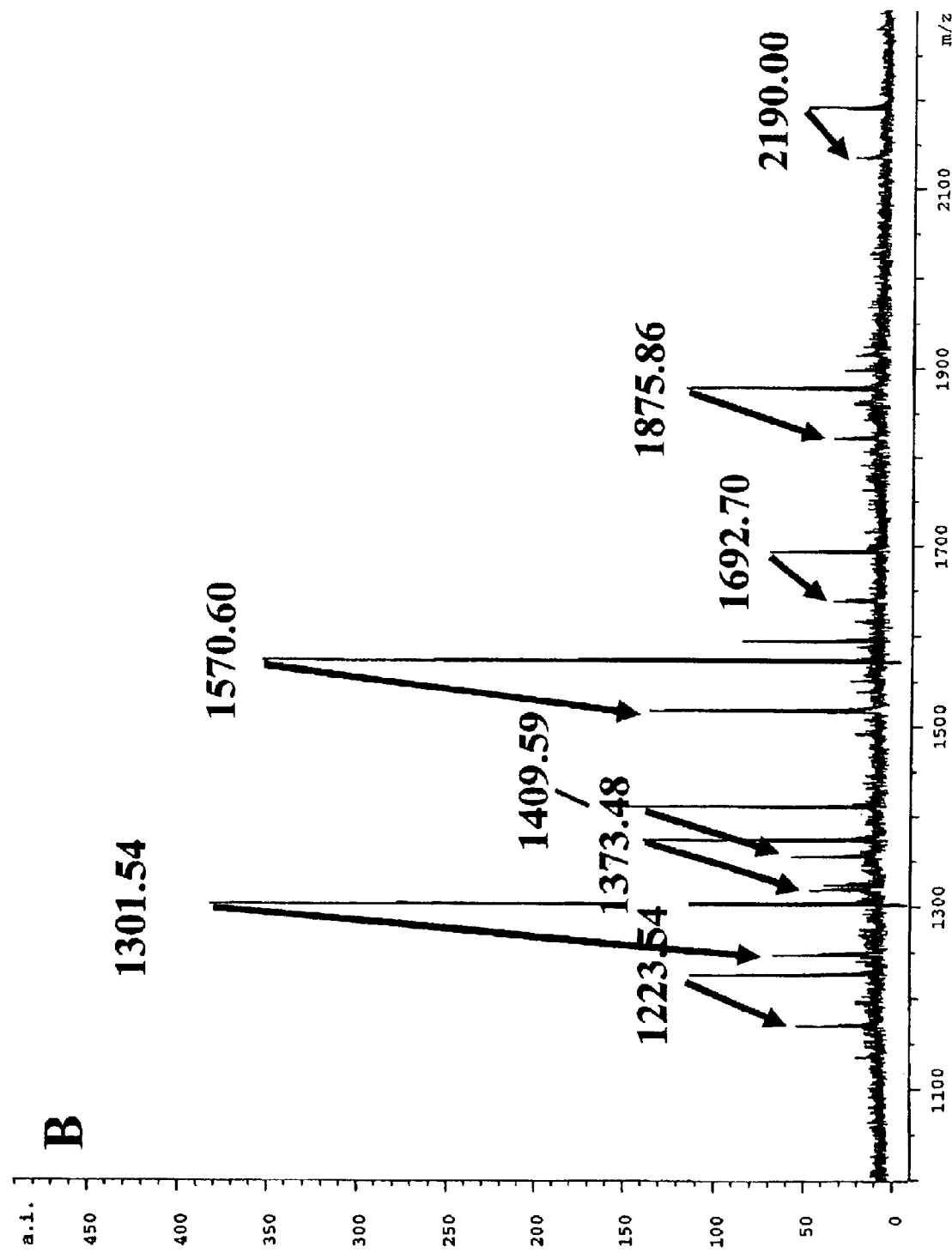

For instance, for Met-SO peptides one verifies if peptides contain Met-SO. These peptides are characterized by an efficient neutral loss of methanesulfenic acid (64 amu's) which is observed during mass spectrometric analysis (FIG. 15). Following the methanesulfenic acid loss, peptides seem to have lost their vibration energy giving them an apparent stability in MALDI—PSD analysis. It is therefore nearly impossible to generate interpretable post source decay (PSD) spectra from Met-SO peptides, thereby loosing a tool for peptide identification using MALDI-mass spectrometry. There are several ways to circumvent the PSD-problem.

First, the Met-SO peptides can be back-reduced to their original structure by treating them with reducing agents such as N-(methyl)mercaptoacetamide (Houghten and Li, 1981). Secondly and more conveniently, the Met-SO peptides are additionally oxidized to their corresponding sulfone derivatives using performic acid (Hirs, 1956) or a longer incubation with $H_2O_2$ (for instance 24 h at room temperature). Both, the methionine sulfone and methionine-peptides yield much better MALDI—PSD spectra than the corresponding sulfoxides. At this stage it is worth noting that little neutral loss is observed for the sulfone-peptides, yielding better PSD-spectra.

In an alternative approach, peptides can be fragmented by collision activated dissociation (CAD). This type of fragmentation is less susceptible to the dipole induced by the sulfoxide and is therefore an important tool in generating sequence information from Met-SO peptides (example 18).

Another method to obtain further information is based on partial $NH_2$-terminal degradation either using chemically induced ladders with isothiocyanate (Chait et al., 1993) or by aminopeptidases (Caprioli and Fan, 1986). This method provides sufficient information at the $NH_2$-terminus of every peptide leading to full identification. Such aminopeptidase digestion or ladder sequencing is particularly beneficial in a high-throughput system, but is only practicable to less complex peptide mixtures.

Thus a combination of the accurately measured peptide mass, the assignment of one or more methionine residues combined with partial sequence information from the $NH_2$-termini of the peptides is sufficiently restrictive in order to unambiguously identify most, if not all, peptides from total lysates.

At this stage reference is also made to additional methods described for peptide and parent protein identification based on accurately measured masses and which are described in example 10.

Example 16

A Determination of Quantitative Relative Amounts of Proteins in Two Samples

In order to compare in a relative quantitative manner the protein expression levels in two sets of cells or more generally in two different samples, protein lysates of each preparation are digested with trypsin. In one sample, trypsin digestion is carried out in $H_2^{16}O$, while the digestion of the second sample is proceeding in $H_2^{18}O$. Trypsin has the possibility of incorporating two oxygens of water molecules at the COOH-termini of newly generated sites (Rose et al., 1983 and Schnölzer et al., 1996). Thus, sample one, which has been trypsinized in $H_2^{16}O$ has all peptides with normal masses, while sample two contains peptides (except for most of the COOH-terminal peptides) with mass increases of 2 and 4 amu's corresponding with the incorporation of one and two $^{18}O$-isotopes. The relative ratio of the two $^{18}O$-forms of a peptide depends upon several factors, including the nature of the peptide, the activity of the enzyme and the purity of the $^{18}O$-water, and, therefore, when $^{18}O$-incorporation will be used for relative quantitative measurements, the extent of incorporation of two $^{18}O$-isotopes in peptides must be considered in the overall calculations (Stewart et al., 2001).

Figure 16A:
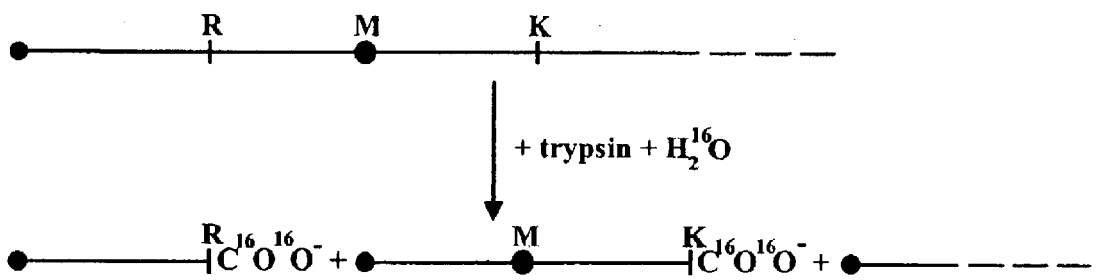
FIG. 16: Schematic of the quantitative differential proteome approach sorting for methionine peptides. MSO refers to methionine sulfoxide.
Figure 16A:
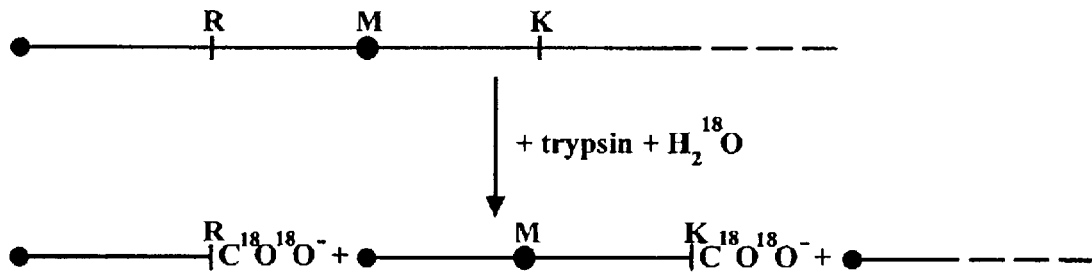
Figure 16A:
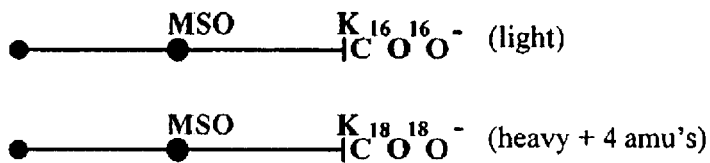

While the digestions are carried out separately, all further processes including the sorting of the methionine-peptides can proceed on the mixture of the two digests, without noticeable back-exchange of oxygen atoms. The $^{16}O$- and $^{18}O$-digests are mixed and subjected to the isolation of flagged peptides altered on methionine (Met-SO peptides). The methionine flagged peptides can for instance be identified as described in example 15. The light ($^{16}O$) and heavy ($^{18}O$) peptides are chemically very similar and each couple will separate in the same manner. They will also ionize in the same way. Only during mass spectrometry they segregate into the light peptide and the heavy peptides (the latter have higher masses of 2 and 4 amu's because of the incorporation of one and two $^{18}O$-atoms). The ion separation induced by $^{18}O$-incorporation is sufficient to accurately measure the ratios of the light versus the heavy peptides and thus determine the ratio of a protein in the two samples (e.g., Mirgorodskaya et al., 2000). A schematic presentation of the entire procedure is given in FIG. 16A.

In order to test the $^{18}O$-incorporation for relative quantitative analysis, we have digested a platelet cytosolic and membrane skeleton fraction (prepared as in examples 20 and 21) once in 'normal' $^{16}O$-water and once in $^{18}O$-water (95% pure, ARC Laboratories, Amsterdam, The Netherlands) using trypsin for 16 h at 37° C. Prior to the primary run, one part of the $^{16}O$-digest was mixed with two parts of the $^{18}O$-digest, the sample was acidified to 1% TFA and methionine flagged peptides were sorted out of the peptide mixture as described in example 1 using a single-column peptide sorting system (example 11).

Figure 16B:
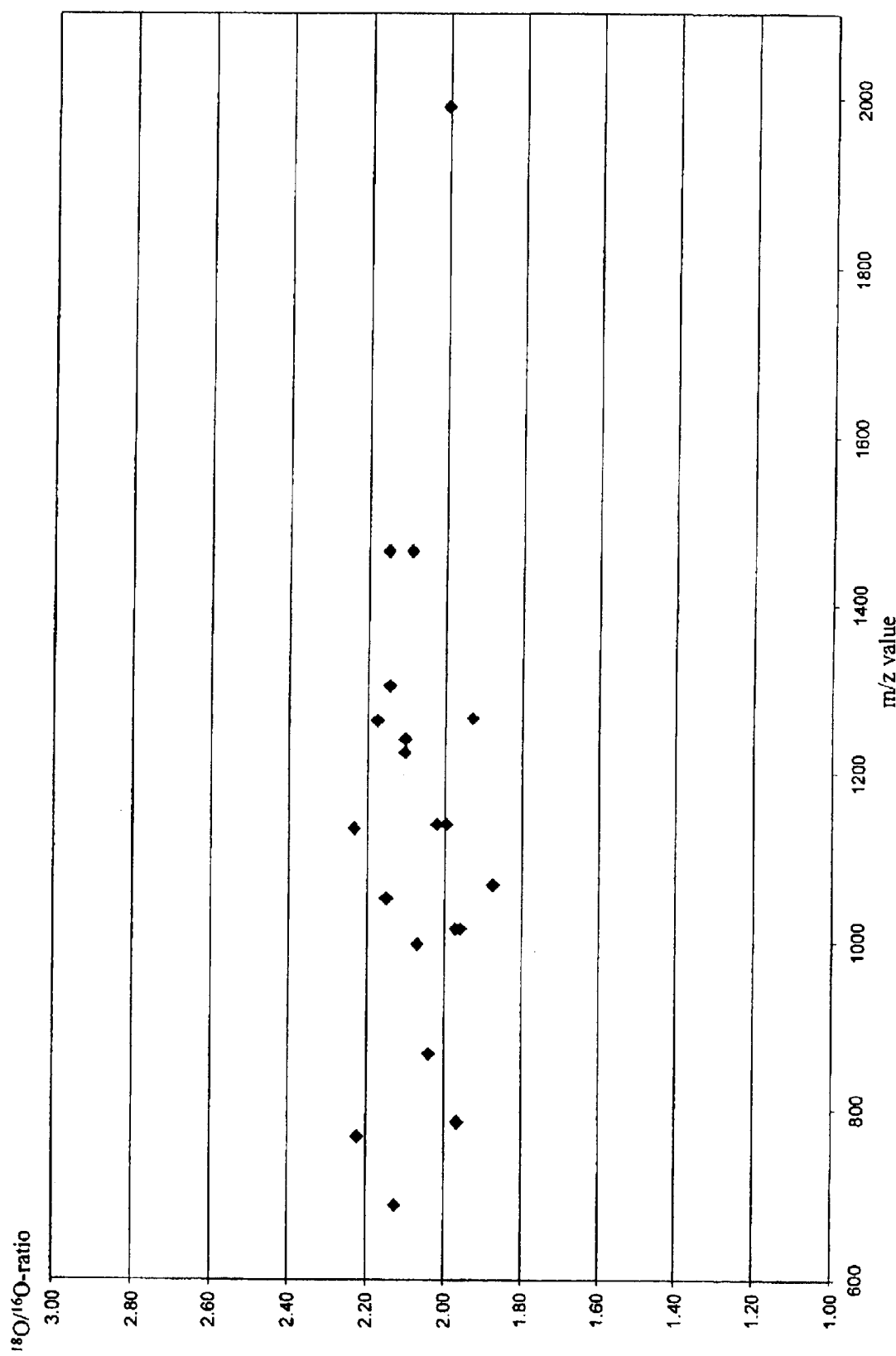

In LC-MS analysis the $^{18}O/^{16}O$-ratios of the observed peptide ions were calculated as described above. The results of this analysis are depicted in FIG. 16BB and confirms that peptide ratios generally vary around 2, indicating that this type of isotope labeling technology is suited for quantitative proteome analysis.

Figure 17:
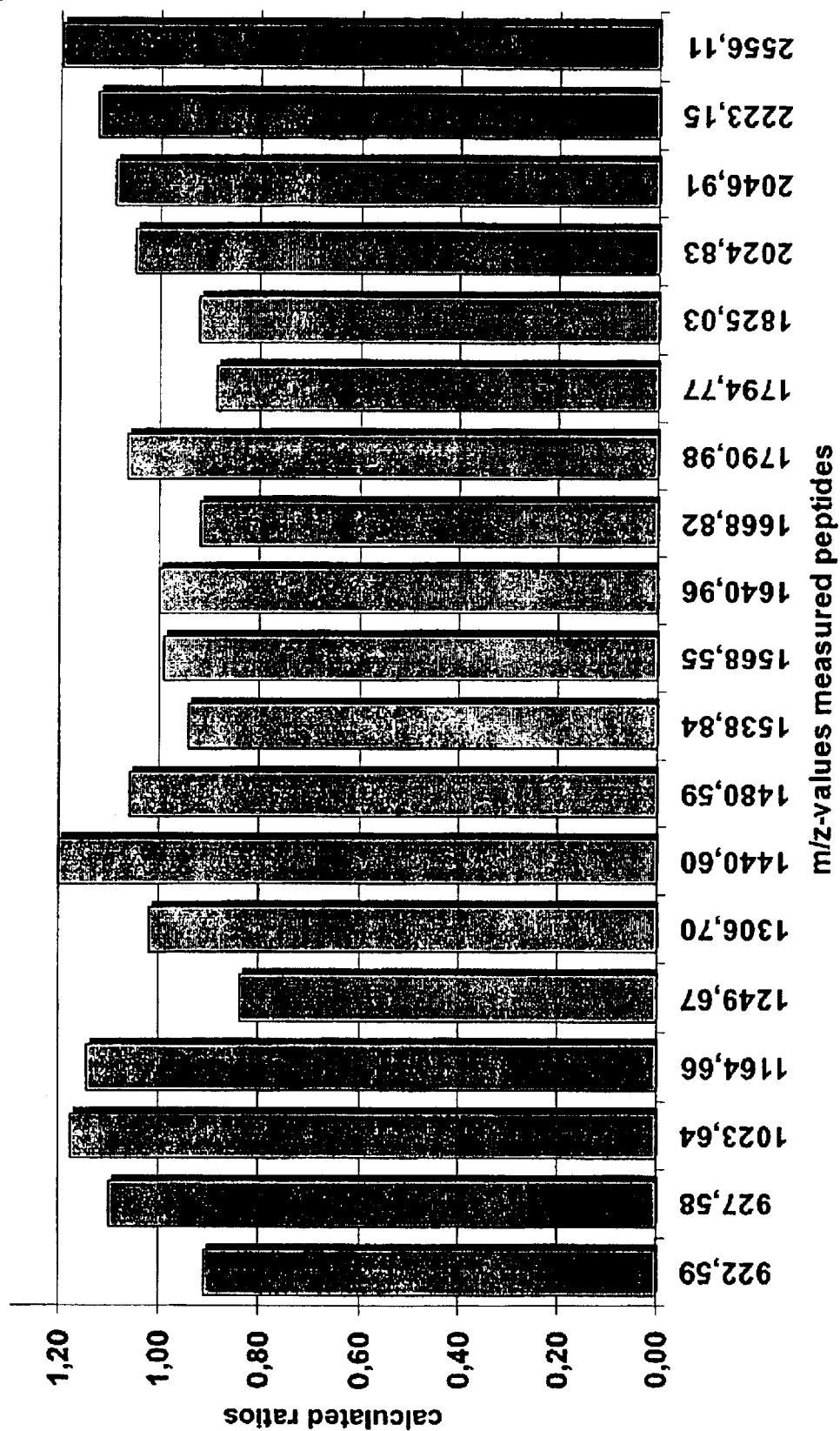
FIG. 17: MALDI-RETOF-MS measured isotopic ratios (Y-axis values) of 19 peptides (peptide masses on X-axis) obtained from a total of 5 pmol of a 1/1 mixture of $^{16}O$- and $^{18}O$-labeled tryptic digests of BSA. An average value of 1.03 was obtained for the measured ration of the BSA-mix.

We have furthermore verified the use of $^{18}O$-labeling by digesting two equal amounts of bovine serum albumin with trypsin, one in normal $H_2O$ and the second in $H_2^{18}O$ (95% $^{18}O$). After 18 h of digestion, both peptide mixtures were mixed, separated by HPLC and analyzed by MALDI-TOF-MS. For 19 peptides we compared the peak heights of the isotopes that were not affected by the labeling procedure (e.g., the $^{13}C$-isotopes). The values were further corrected for the presence of 95% $H_2^{18}O$ and combined in FIG. 17. We measured an average ratio of 1.03 for the nineteen peptides, corresponding very well with the molar ratio at which the protein digests were mixed at the start of the experiment. Most values agree very well with the expected value, with extreme values of 0.84 and 1.20 (Table IX). This experiment illustrates that stable isotope labeling during trypsin digestion forms the basis for a quantitative differential proteome study and is used with the current invention.

The differential isotopic labeling can also be done by alternative ways, some of which are briefly mentioned below. Labeling procedures are based on known chemical reactions and can be carried out either at the protein or at the peptide level. Below we describe a number of reactions, which are used for differential labeling. Peptides can for instance be changed with the reagent couples: methylisocyanate/trideuteromethylisocyanate (v); ethylisocyanate/pentadeutero-ethylisocyanate (vi); phenylisocyanate/pentadeutero-phenylisocyanate (vii); acetyl-N-hydroxysuccinimide/trideutero acetyl-N-hydroxysuccinimide (viii). All these compounds are known to react specifically and quantitatively with α—$NH_2$ and ε—$NH_2$ groups. The final choice of alteration reagent will depend on the availability of the deuterated form, price, chemical stability and laboratory comfort of the reagent. Another important aspect is the stability of the adduct during the ionization step in the mass spectrometer. The reaction equations for each of these reagents in their deuterated form are given below.

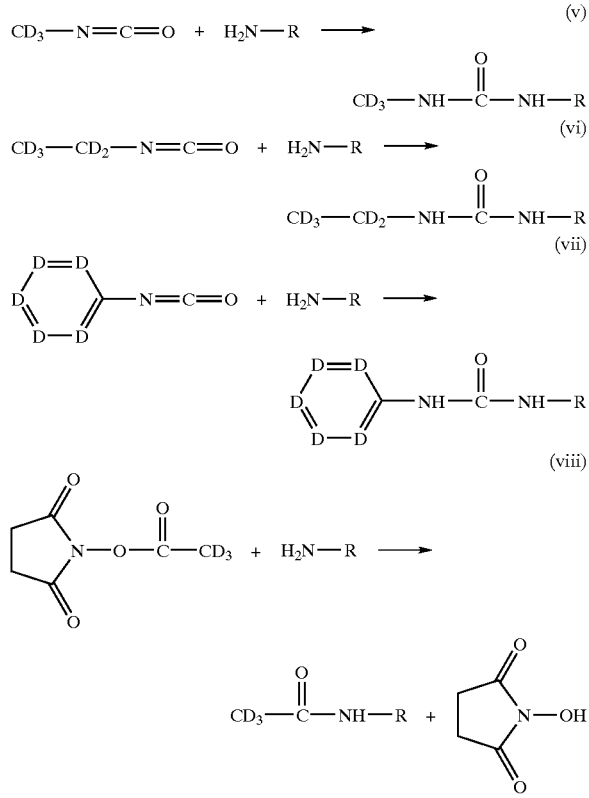

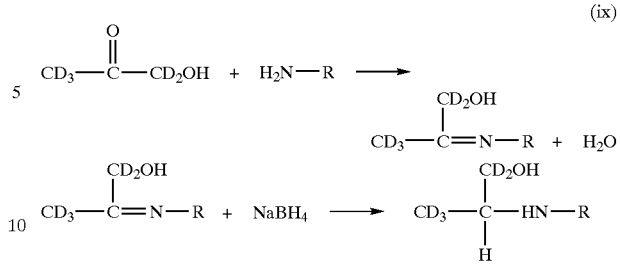

In case larger mass differences between the 'light' and 'heavy' peptides are required, then larger deuterated groups or groups in which $^{13}C$, $^{15}N$ and deuterium are combined could be used. For instance, the use of a hydroxybutyryl group (HO—$CD_2$—$CD_2$—$CD_2$—CO—) to specifically label the $NH_2$-terminus would allow us to create a difference of 6 amu's. Alternatively, the use of $^{13}CD_3$-$^{13}CD_2$-CO-propionyl group to label the $NH_2$-terminus would allow us to create a difference of 7 amu's. Even more explicitly, the use of $^{13}C$-labelled and deuterated nicotinoyl derivative ($N^{13}C_5D_4CO$—) would allow us to use a mass difference of 9 amu's. It should be known to those skilled in the art that from of all these groups N-hydroxysuccimide or sulfo-N-hydroxysuccinimide esters can be synthesized.

It is also clear that D represents deuterium $^2H$ in the formula described in this invention.

Peptides can also be altered via Shiff base formation with deuterated acetol followed by reduction with sodium borohydride (Geoghegan et al., 1979). This reaction has been described to proceed in mild conditions and leads to the addition of only one molecule acetol per amino group, creating a secondary amine (ix). The deuterated amine will now contain five non-exchangeable deuterium atoms and segregate by 5 amu's from its non-deuterated counterpart. Peptides are altered both at the α—$NH_2$-group, and ε—$NH_2$ groups of lysine, leading to a mass increase of five (for arginine peptides) or ten amu's (for lysine peptides). The underlying reactions are shown below.

The examples cited here represent only a few illustrations of a broader spectrum of alteration reactions that can be used for differential isotope tagging.

Example 17

A Quantitative Differential Proteome Display to Measure Molar Ratios of Proteins in One Sample The procedure for protein identification via their representative peptides using mass spectrometry is qualitative but not quantitative. Indeed, peptides show differential losses following their purification and peptides may ionize in a very variable and unpredictable manner depending on their chemical nature and on the other peptides that are present in the mixture. This phenomenon is well known in the MS-field as suppression of ionization (Krause et al., 1999). However, as demonstrated in example 16, mass spectrometry becomes quantitative when one of the two samples can be labeled with an isotope tag which does not differentiate the peptides chemically, but which can be distinguished and measured in the mass spectrometer. We now use the same principle of differential isotopic labeling in order to measure the relative ratios of proteins in one single sample. This can be done by adding to the sample known amounts of reference peptides. These are peptides that are derived from proteins present in the sample, and of which the sequence is sufficient to unambiguously identify its parent protein. Reference peptides are by preference also selected as easily isolated peptides that in addition ionize well in mass spectrometry. In the protocol selecting for methionine flagged peptides (Met-SO peptides), reference peptides are methionine-containing peptides preferably also containing an arginine residue or being treated for efficient ionization. Every protein to be quantified should be represented by at least one and preferably two or more reference peptides. Reference peptides should differ from their synthetic counterparts by a differential isotopic labeling which is sufficiently large to distinguish both forms in conventional mass spectrometers. As already pointed out herein, a difference of 4 amu's is sufficient. Such isotopic differentiation can be obtained in various ways and here we provide a few examples. Most conveniently, isotopically labeled reference peptides are generated by trypsin digestion of the protein mixture in $H_2^{18}O$. The corresponding synthetic counterparts of the reference peptides are synthesized with their natural isotopes. Such chemical synthesis is carried out at large scale using the Multiple Peptide Synthesizer (Zuckermann et al., 1992).

An example of a protocol to determine the quantity of a target protein in a particular sample containing proteins is summarized as follows: (i) a reference peptide is selected from the target protein, (ii) the corresponding synthetic counterpart is synthesized, (iii) the protein sample is digested with trypsin in the presence of $H_2^{18}O$, (iv) a known amount of the synthetic reference peptide is added to the protein peptide mixture (by preference, the amount of synthetic reference peptide is comparable to the expected amount of reference peptide), (v) the mixture is subjected to the invention to separate the flagged peptides, (vi) the flagged peptides are, for instance, analyzed by MALDI-TOF-MS, (vii) the reference peptide and the synthetic reference peptide will co-elute in the process and will appear as twin peaks in the mass spectrum, (viii) the peak surface of each of the twin peaks is calculated, (ix) the ratio between both peaks allow to calculate the amount of reference peptide and, correspondingly, the amount of target protein in the particular sample. This protocol can obviously also be used for identification peptides and can be adapted in several ways. It can for instance easily be expanded to determine the quantity of multiple (even more than 100) target proteins in a sample and thus measure the expression levels of many target proteins in a given sample. Obviously this approach can also be used to measure and compare the amount of target proteins in a large number of samples. Such results can for instance be used to prognose, monitor or diagnose diseases or the effect and side-effect of drugs.

In an alternative approach the synthetic peptides carry the uncommon isotopes, while the reference peptides generated from the proteins are natural isotopes. For instance, if we select methionine-containing peptides, it is possible to incorporate in the synthetic reference peptides the commercially available deuterated methionine ($CH_3SCD_2CD_2CH(NH_2)COOH$), adding 4 amu's to the total peptide mass. Alternatively, synthetic reference peptides also contain deuterated arginine which now adds 7 amu's to the total peptide mass. It should be clear that every amino acid from which deuterated, $^{15}N$ or $^{13}C$ forms exists can be considered in this protocol. Yet another alternative approach is to design the synthetic reference peptides with a colored, fluorescent or otherwise measurable group attached. By introducing a universal colored tag, displaying the same molecular extinction coefficient for all reference peptides, it will be easy to quantify the amount of every reference peptide. The quantifiable group should be attached to the peptide with an anchor or linker that is sufficiently stable during normal conservation, but which is released from the reference peptides by controlled chemical or enzymatic processes. For instance, a colored dye such as a 2,4,6-trinitrobenzenesulfonate group (maximal molecular absorption coefficient of 557 mm) can be linked via an Ala-Lys linker sequence to the reference peptide (Freedman and Radda, 1968). Trypsin digestion which is normally carried out to generate the peptide mixture from the total lysine, would now also cleave the reference peptides at the COOH-terminal bound of the lysine residue and thus release the dye and the linker from the rest of the peptide (x).

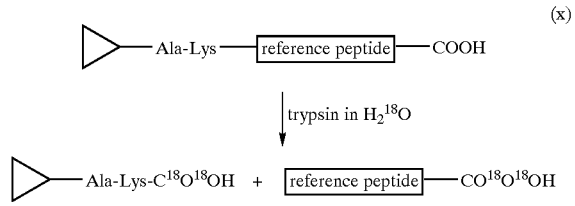

(x)

When the protein digestion is carried out in $H_2^{18}O$, in the presence of the colored reference peptides, then the liberated reference peptides also become isotopically labeled at their free COOH-terminus. Therefore the trypsin digestion of the colored peptides is done separately in $H_2^{16}O$ and only added to the total peptide mixture at the end of the digestion. The linker between the dye and the reference peptide can also be cleaved chemically in conditions where the rest of the peptide is not affected.

Example 18

Analysis of the Proteome of *Escherichia coli* (Strain K12)

Figure 18:
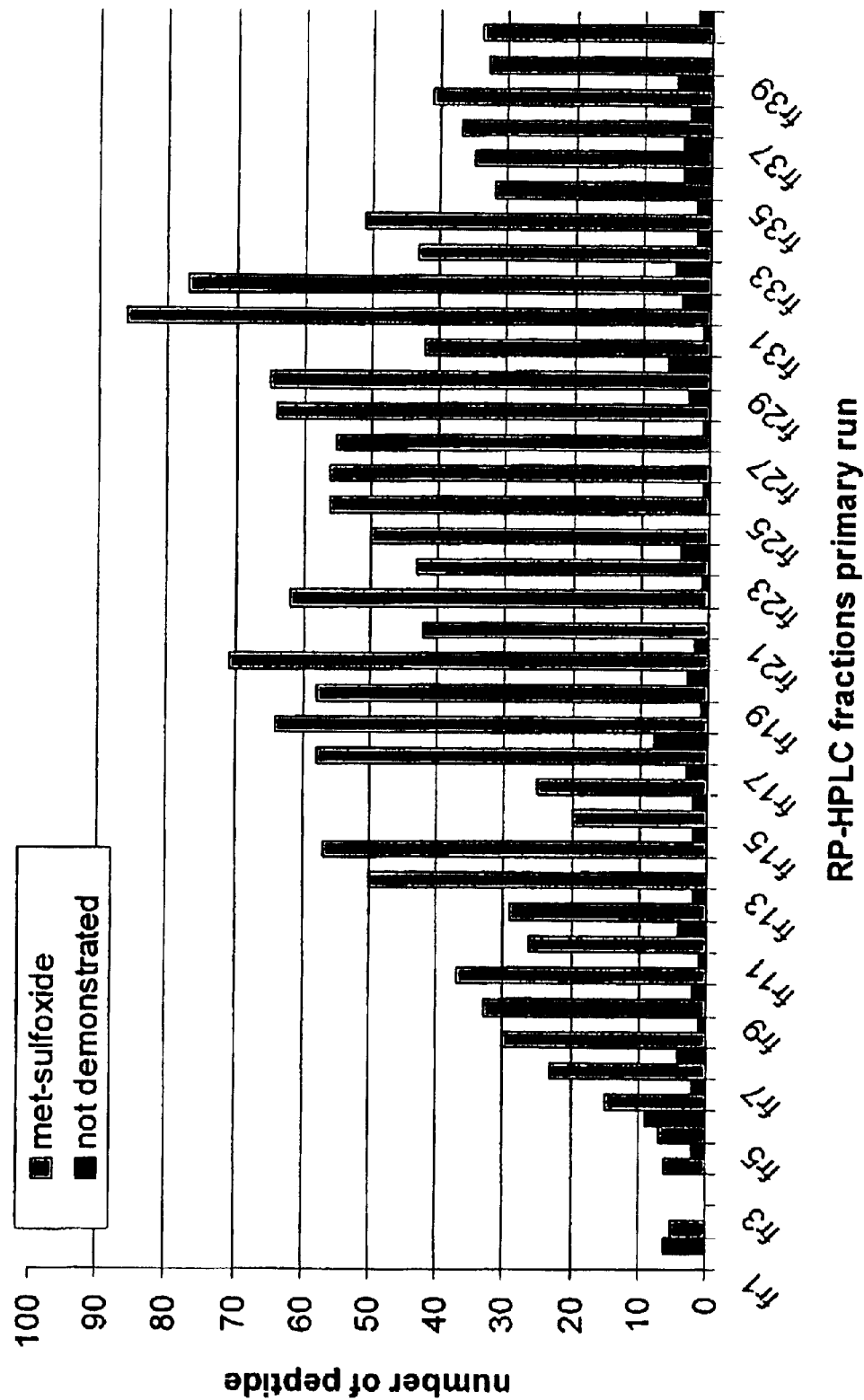
FIG. 18: Chart depicting the number of Met-SO peptides (shown in blue) using MALDI-RETOF-MS in the primary fractions of a tryptic digest of the protein material from $50.10^6$ E. coli cells versus the peptides from which it could not be demonstrated that they contained methionine (shown in red).

$10^9$ *E. coli* K12 cells were removed from a cultured stationary growth phase, pelleted by gentle centrifugation, washed four times with 1 ml of 100 mM NaCl in 20 mM phosphate buffer pH 7.2 and lysed by sonication in 1 ml of 4 M urea in 100 mM phosphate buffer pH 8.0. The lysate was cleared by centrifugation at 100,000×g in an airfuge after which the urea concentration was decreased to 1 M using 100 mM phosphate buffer at pH 8.0. 10 μg trypsin was added to 0.1 ml of the protein mixture (corresponding to $250.10^6$ *E. coli* cells) and the digestion was allowed to proceed overnight at 37° C. and stopped by acidification with TFA. One fifth of the obtained protein peptide mixture (corresponding to $50.10^6$ *E. coli* cells) was loaded onto a 2.1 mm i.d.×25 cm C18 reversed-phase HPLC column equilibrated in 0.1% TFA (solvent A). The column was first washed for 10 min with 5% of solvent B (70% acetonitrile in 0.09% TFA), after which a linear gradient of increasing concentrations of solvent B was used to elute the peptides from the stationary column phase. The flow rate was kept at 80 μl/min and a gradient of 1% solvent B/min was set. Fractions of 1 min (i.e. 80 μl) were collected. The first fraction was collected 18 min after the start of the gradient and was numbered 10. This fraction was followed by 39 additional 80 μl fractions and at the last fraction (fraction 49), the concentration of solvent B reached 63% corresponding to approximately 44% acetonitrile. The gradient was continued for 37 min without fraction collection and terminated 105 min after the start of the HPLC-run. The UV-absorbance profile (at 214 nm) of this run (here referred to as the primary run) is shown in FIG. 10. All collected fractions were vacuum-dried and stored at -20° C. until further use. Fractions that were pooled for the secondary runs were re-dissolved in 59 μl of 1% TFA and made 0.5% in $H_2O_2$ by adding 1 μl of a 30% stock solution of $H_2O_2$. The oxidation reaction was allowed to proceed for 30 min at 30° C. after which the sample was not dried, but immediately used for chromatography. Using a single column peptide sorter (see example 11), we combined fractions 10, 22, 34 and 46 for the first secondary run (run 2A) and collected the oxidized methionine-peptides in the time intervals 4–7, 16–19, 28–31 and 40–43. For the pooling of the other fractions of the primary run, we used the combinations and collection times as summarized in Table IVA. The UV-absorbance profile of a typical secondary run (run 2A in which fractions 10, 22, 34 and 46 were combined) is shown in FIG. 11. The time intervals during which these peptides were collected are shown between bars in FIG. 11. During this 4 minute period, peptides were collected in eight consecutive fractions of 30 seconds each (i.e. 40 μl fractions). In total we obtained 32 fractions of run 2A. Eleven additional secondary runs were executed consecutively in order to cover the full peptide set (Table IVA). A suspension of hydrophobic Poros® 50 R2 beads was added to the collected fractions (Gevaert et al., 1997) and the fractions were vacuum dried. Peptides concentrated on the added beads were desorbed in 0.7 μl of MALDI-matrix solution (containing 4% α-cyanocinnamic acid and 1%–2,5-dihydroxybenzoic acid) in 0.1% TFA acetonitrile (1/1) and transferred to the MALDI-target for peptide mass analysis in the reflectron mode (which allows easy monitoring and verification of the methionine-sulfoxide containing peptides). FIG. 15 shows the MALDI-RETOF-MS spectra of two fractions from the secondary run 2A in which as expected only methionine-sulfoxide peptides were observed. Following analysis of all peptides present in the collected 320 secondary fractions, we were able to measure 1720 different peptides of which 1618 contained at least one methionine residue. The measured masses of these 1618 peptides are listed in Table IX. FIG. 18 shows for every fraction of the primary run, the number of Met-SO-peptides (blue) versus peptides of which we could not demonstrate they contained an oxidised Met (red). This is either due to the fact that the typical neutral loss of methane sulfenic acid was not clearly observed, or that some non-methionine containing peptides slipped in during the sorting process. In this experiment, we verified that the sorted peptides consisted for 94% of peptides of which the presence of Met was verifiable. This illustrates the specificity of our sorting system, even when total cell lysates were used.

In a second step we now identified the sorted peptides and their corresponding parent proteins. Therefore we again digested 1 ml of the protein mixture prepared from $250.10^6$ E. coli K12 cells in 1M urea and 0.1M phosphate buffer pH 8.0. 10 µg of trypsin was added and the digestion was allowed to proceed overnight at 37° C. At the end of the digestion the resulting protein peptide mixture was reduced with tributylphosphine for 5 min, and acidified with formic acid (final concentration 1%). One fifth of the obtained protein peptide mixture (corresponding to $50.10^6$ E. coli cells) was loaded onto a C18 reversed phase HPLC column (ID 2.1 mm×250 mm; Vydac 218MS52). This column was equilibrated with 0.05% HCOOH as solvent A. The column was first washed for 10 min with 100% of solvent A. A linear gradient of 1% solvent B/min (solvent B is 0.05% HCOOH in 70% acetonitrile) was used to elute the peptides at a flow rate of 80 µl/min. The peptide UV absorbancy profiles were recorded at 214 nm using a UV detector (Applied Biosystems Inc., 759A Absorbance Detector). Fractions of 1 min were collected. The first fraction was collected 30 min after the start of the gradient and was numbered 30. 50 fractions were further collected until number 80. All collected fractions were vacuum-dried and stored at −20° C. until further use. Fractions that were pooled for the secondary runs were re-dissolved in 59 µl of 1% TFA and made 0.5% in $H_2O_2$ by adding 1 µl of a stock solution of 30% $H_2O_2$. The oxidation reaction (the alteration step for methionine as a specific amino acid, according to the present invention) is allowed to proceed for 30 min at 30° C., after which the sample is not dried but immediately loaded on the RP-column for the secondary run. Using a single column peptide sorter described in example 11, we combined the following fractions from the primary run: 41, 54, 67, 80 and collected the oxidised peptides (the flagged peptides) in the respectively time intervals 31–39, 44–52, 57–65 and 70–78. Pooled fractions of the primary run and collected fractions from the secondary run are indicated in Table X. In contrast to our previous example where the flagged peptides were collected in 4 min time intervals, we now collected the flagged peptides in a time interval of 8 min (8 fractions of each 80 µl) and 1 min before the elution of the unaltered peptides. Thus $\delta_{max}=10$ min, $\delta_{min}=1$ min and $w_2=8$ min with $w_1=1$ min. Since each secondary run contained four combined windows ($w_2$), the Met-SO peptides (thus methionine altered flagged peptides) were collected over 32 fractions of each 80 µl. Then all unevenly numbered secondary fractions were combined, dried and re-dissolved in 45 µl of solvent A (=0.05% HCOOH); half of this mixture was loaded on a 0.075 mm ID (15 cm long) nano-column (C18 Pepmap, LC Packings) connected to a trapping column and an Applied Biosystems Inc. 120A Analyzer HPLC. A gradient, from 0% B to 100% B in 220 minutes, was formed with 0.05% HCOOH as solvent A and 0.05% HCOOH in 70% acetonitrile as solvent B. The pre-splitter solvent flow rate of 60 µl/min was reduced to approximately 200 nl/min using a flow splitter (Acurate, LC Packings). The eluting peptides were introduced via a metal-coated fused silica needle (FS360-20-10-D-5-C7, New Objective) into the Z-spray ion source of a Q-TOF mass spectrometer (Micromass UK Limited, Altincham, UK). Data were analysed in the data dependent acquisition mode using Masslynx NT (version 3.4). Only doubly charged ions were automatically selected for MS/MS-analysis. The threshold was set at 40 counts/s and selected ions were fragmented for 4 s by collision with argon atoms. All MS/MS spectra were accumulated and analysed by MASCOT (Matrix Science Ltd, London) using a protein database containing only E. coli proteins. Unambiguous identification relied on MASCOT's 'probability-based Mowse score' (Perkins et al., 1999). The remaining half of each of the fractions was again subjected to nanoLC-MS/MS using an exclusion list containing all the doubly charged ions detected in the previous run. The threshold was now set to 25 counts/s and the selected ions were fragmented for 5 s. The same procedures were repeated for the evenly numbered fractions. All protein identification data were finally combined. From all the nano LC-MS/MS runs, a total of 6437 CID-spectra were generated (Table XI). These CID-spectra resulted in 2543 annotated spectra after submission to the MASCOT-server.

An identification of the sorted Met-SO peptides of all the fractions led to the identification of about 767 different E. Coli peptides (Table XII). Every protein was covered by an average of 2.2 methionine containing peptides per protein.

We identified all detectable ribosomal proteins, representing about 10% of the total protein mass of E. coli, next to families of minor proteins such as the aminoacyl t-RNA synthetases and next to very minor proteins such as the lac-repressor (confirmed by three independently isolated Met-peptides) and at least 19 other repressors. These results illustrate the extent of dynamic range reached by the invention, allowing the detection of low abundancy proteins in the presence of major proteins. In addition we also identified an important number of known membrane proteins and proteins with a high hydrophobic profile, suggesting a better access to the vast array of biologically important membrane proteins.

When the double amount of E. coli cells ($100.10^6$ cells) was analysed by conventional 2D-gel analysis, followed by MALDI-based protein identification, 86 proteins were identified. Compared to the 767 proteins in the gel-free study, there is a sensitivity that is at least ten times and most likely even much higher for the latter. It is also important to stress that contamination by human skin keratins, which is often noticed as "the classical contaminant" when 2D-gels are run, is drastically reduced and even completely absent when the methods of the invention are used. These analyses were carried out with an equivalent of $50.10^6$ E-coli bacteria. This corresponds to protein quantities that are present in ±50.000 to 100.000 animal cells, illustrating the high sensitivity of the technique. The invention allows to determine the proteome starting from small numbers of cells. This allows to analyze differential protein expression in situations which are out of the reach of conventional applications. The current invention allows to analyse protein expression in small tumor biopsies, in small sub-regions of the brain, in cells that have been selected by cell sorting, in small sub-regions of the heart, in plaque-forming loci in blood vessels, etc. The methods of the present invention efficiently sorts the methionine-peptides from highly complex mixtures. Moreover, the flagged peptides are not obtained at once but are gradually sorted over many fractions and thus fed into the mass spectrometer in a continuous manner guaranteeing much more efficient detection. This is best illustrated by the detection of 1618 different Met-peptides from an E. coli proteome using MALDI-TOF-MS detection of eluates of the secondary runs.

It should be noted that if desired, the methods of the present invention can be accomplished without the use of toxic or corrosive chemicals. For instance, acetonitrile can be replaced by ethanol and TFA by $NH_4Ac$ buffer without affecting the overall sorting quality.

Example 19

Partial Proteome Analysis of Human Plasma

As starting material, 1 ml of lyophilised human plasma (containing approximately 60 mg of protein material and essentially free of contaminating cells), was used. The dried sample was re-dissolved in 1 ml of freshly prepared 8 M urea containing 2% of tributyl phosphine and 50 mM of Tris-HCl at pH 8.7. Prior to digestion, the concentration of urea was diluted 4 times by adding 3 ml of 50 mM of Tris-HCl buffer (pH 8.7). A fraction of this sample, 200 µl (corresponding to about 3 mg of protein material) was used for protein digestion with 20 µg of trypsin (sequencing-grade modified trypsin form Promega, Madison, Wiss., USA). Digestion proceeded overnight at a constant temperature of 37° C. and was stopped by acidification. Half of this digestion mixture was preconditioned by passing the peptides over a Sample Cleanup RP-Column (Agilent Technologies) (2.1 I.D. mm×20 mm, packed with Vydac $C_{18}$ RP-beads), using a steep gradient of acetonitrile in 0.1% TFA. A lineair gradient form 0% solvent B (70% acetonitrile in 0.1% TFA in water) to 100% solvent B was generated during 14 min at a flowrate of 0.2 ml/min. The total eluate was collected, dried in vacuo and redissolved in 100 µl of solvent A (0.1% TFA in water).

The protein peptide mixture was then subjected to the sorting process. After loading the peptide mixture, the column was rinsed with 0.1% of TFA in water (Baker HPLC analysed, Mallinckrodt Baker B. V., Deventer, The Netherlands) (solvent A) for 20 min at a constant flow of 1 ml/min using a Waters ACTION Analyzer (Waters Corporate, Milford, Mass., USA). Subsequently, a linear gradient to 70% of acetonitrile (Baker HPLC analysed) in 0.1% of TFA in water (100% solvent B) over 70 min (thus an increase of 1% of solvent B per min) was used to elute the peptides from the RP column. In a last phase, the column was rinsed with solvent B and re-equilibrated with solvent A prior to the next sample injection. In run 1 peptides eluting in a time frame between 28 min (corresponding to 11.4% of solvent B or 8% of acetonitrile) and 70 min (71.4% of solvent B or 50% of acetonitrile) were collected in 1 min (or 1 ml) fractions using a Gilson 221XL Liquid Handler (Gilson SAS, Villers Le Bel, France). A total of 42 primary fractions were thus collected.

Each primary fraction was dried to complete dryness before oxidation of methionine residues. Primary fractions that could be pooled for the secondary runs (in an analogous set-up as described in Table IVA) were re-dissolved in 100 µl of 1% of TFA to which 2 µl of 30% of $H_2O_2$ was added. The oxidation reaction of methionine residues proceeded for 30 min at 30° C., after which the primary fractions were pooled and loaded on the same RP—HPLC column that was used for the primary separation and peptides were fractionated in this secondary run under the exact same chromatographic conditions as during the primary run. Here, flagged peptides were collected in a time interval of 8 min (8 sub-fractions of each 1 ml), between 9 and 1 min prior to the elution of the unaltered peptides. LC-MS/MS analyses were performed on the peptides sorted out of two primary fractions. Therefore, the collected sorted peptides from primary fraction 25 were all combined, dried and re-dissolved in 200 µl of solvent A (0.05% formic acid in water), and one twentieth of this mixture was loaded on a 0.075 mm I.D. (15 cm long) nano-column (C 18 Pepmap, LC Packings) connected to a trapping column and an Applied Biosystems Inc. 120A Analyzer HPLC. The same was done for all sorted peptides from primary fraction 26.

A gradient, from 0% B to 100% B in 220 minutes, was formed with 0.05% HCOOH as solvent A and 0.05% HCOOH in 70% acetonitrile as solvent B. The pre-splitter solvent flow rate of 60 µl/min was reduced to approximately 200 nl/min using a flow splitter (Acurate, LC Packings). Eluting peptides were introduced via a metal-coated fused silica needle (FS360-20-10-D-5-C7, New Objective) into the Z-spray ion source of a Q-TOF mass spectrometer (Micromass UK Limited, Altincham, UK). Data were analysed in the data dependent acquisition mode using Masslynx NT (version 3.4) and doubly charged ions were automatically selected for MS/MS-analysis. The threshold was set at 40 counts/s and selected ions were fragmented for 4 s by collision with argon atoms.

All MS/MS spectra were accumulated and analysed by MASCOT (Matrix Science Ltd, London) using the SWISS-PROT protein database (Release 40.10) and restricting the search to human proteins. Protein identification relied on MASCOT's 'probability-based Mowse score' (Perkins et al., 1999). Following the first LC-MS/MS runs, ion exclusion lists were made and used for subsequent LC-MS/MS runs, so as to increase the number of peptides that were analysed. Now, the threshold was now set to 25 counts/s and the selected ions were fragmented for 5 s.

The resulting protein identification data from these four LC-MS/MS runs is combined and shown in Table XIII. As can be noticed, highly to moderate abundant plasma proteins, such as serum albumin (concentration of about 3 to 4 g per 100 ml), alpha-microglobulin, apolipoprotein B-100 and fibrinogen beta-chain, are present, next to unexpected (nuclear) proteins such as the splicing factor U2AF 35 kDa subunit and a zinc finger protein. This limited analysis of the human plasma proteome already clearly demonstrates the high dynamic range of the technique: highly abundant proteins are identified next to very scarce proteins. In addition it is important to indicate that minor proteins could be identified without prior removal of major components such as serum albumin and the antibodies. Furthermore, the corresponding volume of plasma that was used for these LC-MS/MS studies is in the range of 1 microliter, illustrating the ultimate sensitivity of this technique.

Example 20

Partial Proteome Analysis of Human Thrombocytes

The buffy coat cell material of an equivalent of one human blood withdrawal, containing approximately $500 \times 10^9$ platelets was divided into two equal fractions and centrifuged for 10 min at 1,000×g. The pelleted platelets were washed 3 times with 10 ml of Tyrode I buffer from which BSA was omitted, each time followed by a centrifugation step for 10 min at 1,000×g, and were finally suspended in a total of 10 ml of BSA-free Tyrode I buffer (Ardlie et al., 1970). The platelet suspension was lysed by adding 10 ml of 0.5% Triton X-100 in 25 mM of sodium phosphate buffer at pH 7.5 containing a protease inhibitor cocktail (Complete™, Roche Diagnostics GmbH, Mannheim, Germany). The lysed platelets suspension was centrifuged for 10 min at 10,000×g to remove the cytoskeleton fraction (Fox et al., 1993), after which 2.5 ml of the protein mixture (i.e. an equivalent of $62.5 \times 10^9$ platelets) was desalted in 3.5 ml 10 mM sodium phosphate buffer at pH 9.0 on a Sephadex® G-25 M column (PD-10 column, Pharmacia Biotech AB, Uppsala, Sweden). The desalted protein mixture was concentrated to 1 ml in a centrifugal vacuum concentrator, boiled for 5 min in a water bath and put on ice for 15 min. A protein peptide mixture was generated by overnight digestion of the proteins with 20 μg trypsin (sequencing-grade modified trypsin form Promega, Madison, Wiss., USA) at 37° C.

A fraction of the protein digest, 50 μl, corresponding to the protein material extracted from about $3 \times 10^9$ platelets, was injected onto a narrow-bore reverse-phase ZORBAX® 300SB-C18 column (2.1 I.D.×150 mm, Agilent Technologies, Waldbronn, Germany) coupled to an Agilent 1100 Series capillary LC-system under the control of the Agilent ChemStation software modules. Following injection of the sample, a solvent gradient was developed at a constant flow of 80 μl/min. First, the column was rinsed with 0.1% TFA in water (Baker HPLC analysed, Mallinckrodt Baker B. V., Deventer, The Netherlands) (solvent A) for 10 min, followed by a linear gradient to 70% acetonitrile (Baker HPLC analysed) in 0.1% TFA (solvent B) over 100 min (thus an increase of 1% of solvent B/min) (primary run). Peptides were collected in a total of 48 fractions of 1 min (or 80 μl) each, in a microtiterplate using the Agilent 1100 Series fraction collector, starting from 40 min (corresponding to a concentration of 30% of solvent B). Fractions that were separated by 12 min (see Table XIV) were pooled and dried to complete dryness in a centrifugal vacuum concentrator.

The dried fractions were re-dissolved in 70 μl 1% TFA in water and placed in the Agilent 1100 Series Well-plate sampler. The methionine oxidation reaction proceeded automatically in this compartment by transferring 14 μl of a fresh aqueous 3% $H_2O_2$ solution to the vial containing the peptide mixture. This reaction proceeded for 30 min at a constant temperature of 30° C., after which the sample was immediately injected onto the RP—HPLC column. Under the given experimental conditions methionine-sulfoxide containing peptides elute generally in a time frame 7 min to 1 min prior to the equivalent time of the corresponding primary fraction (see Table XIV), and were collected in 8 subfractions. Following collection of Met-SO-peptides, all identically numbered subfractions were pooled, e.g., for run 2A (Table XIV) fractions 12.1, 24.1, 36.1 and 48.1 were pooled, and dried to complete dryness before LC-MS/MS analysis.

Peptides present in the pooled and dried subfractions of one secondary run were dissolved in 20 μl of 0.1% formic acid in a mixture of acetonitrile/water (2/98, by volume) (solvent A), of which 10 μl was automatically injected on a 0.3 mm I.D.×5 mm trapping column (PepMap, LC Packings, Amsterdam, The Netherlands) at a flow rate of 20 μl/min solvent A (total loading time of 5 min) with a CapLC system (Micromass UK Limited, Cheshire, UK). By switching the stream valve, the trapping column is back-flushed with a binary solvent gradient, which is started simultaneously with the injection cycle, and the sample is thereby loaded on a nano-scale reverse-phase C18 column (0.75 I.D.×150 mm PepMap™ column, LC Packings). The solvent delivery system was run at a constant flow of 5 μl/min and by the use of a ⅟25 flow splitter, 200 nl/min of solvent was directed through the nano-column. Peptides were eluted from the stationary phase using a gradient from 0% to 100% solvent B applied in 25 min. The outlet of the nano-column was on-line connected to a distal metal-coated fused silica PicoTip™ needle (PicoTip™ FS360-20-10-D-C7, New Objective, Inc., Woburn, Mass., USA), placed in front of the inlet of a Q-TOF mass spectrometer (Micromass UK Limited, Cheshire, UK). Automated data-dependent acquisition with the Q-TOF mass spectrometer was initiated 15 min after the stream valve was switched. The acquisition parameters were chosen such that only doubly and triply charged ions were selected for fragmentation. The stream valve was switched back 51 min after the start of the injection cycle.

The obtained CID-spectra in each LC-MS/MS run were automatically converted to a Mascot acceptable format (pkl-format) using Proteinlynx available from the Micromass' Masslynx software (version 3.4). The CID-peaklists were used for protein identification in a locally stored database only containing the SWISSPROT (Release 40.10) human sequences using the Mascot algorithm. The following search parameters were used: enzyme: trypsin, maximum number of missed cleavages: 2, fixed modifications: none, variable modifications: oxidation (M), pyro-Glu (N-terminal E and Q), peptide tolerance: 0.3 Da, MS/MS tolerance: 0.25 Da and peptide charge: 2+ or 3+. A batch processing of the result sets from Mascot was performed to obtain a final list of identified peptides. Only the peptides ranked first by Mascot were kept and the peptides for which the score was lower than the identity or the homology thresholds were discarded.

In Table XV, the results are presented that were obtained by analysing the methionine-sulfoxide containing peptides sorted out of 8 primary fractions in two secondary runs (2A and 2E, Table XIV). A total of 16 LC-MS/MS analyses were performed to sequence the flagged peptides. Using the MASCOT database search algorithm, 201 peptides were identified that contained at least one Met-SO-residue. Some flagged peptides—especially those from highly abundant platelet proteins such as actin and myosin—, were present in consecutive sub-fractions, explaining the fact that upon data 'cleaning', 98 unique MetSO-peptides could be withheld. These MetSO-peptides corresponded to 74 different proteins (see Table XV). Some of the known abundant platelet proteins such as myosin, alfa-actinin, talin, vinculin and actin were identified by multiple peptides, however, a majority of the proteins could be identified using only one peptide sequence. It is important to emphasize that some of these proteins, due to their large size (for instance talin (MW of 270 kDa) and the heavy chain of myosin (MW of 226 kDa)), are hardly detected on 2-D gels.

The dynamic range of our peptide sorting technology for proteome analysis is already obvious in this limited set of data. For instance, low abundant proteins, such as the ras-related proteins, that are hard to detect on 2-D gels, are identified next to highly abundant proteins such as actin, tubulin, the tropomyosins, talin and myosin, which are probably at least a thousand fold more abundant in these cells. Importantly, 5 different isoforms of these proteins (RACI_HUMAN, RALA_HUMAN, RAPB_HUMAN, RB5A_HUMAN and RB5B_HUMAN) were identified (Table XV), of which one, RB5A_HUMAN, was even identified with two different flagged peptides.

One of the classes of proteins that are hard to detect on 2-D gels are hydrophobic proteins. In our limited platelet proteome, we have identified very hydrophobic proteins such as the LIM and SH3 domain protein 1 (GRAVY value of −1,02), the calumenin precursor (GRAVY value of −1,01) and moesin (GRAVY value of −0,98), which, due to their hydrophobic nature, are normally hardly detected on 2-D gels.

Example 21

Acetylated Amino Terminal Arginine-Ending Peptides of the Proteome of Human Thrombocytes As starting material, a cytosolic and membrane skeleton preparation as prepared in example 20 was used. 1.5 ml of the desalted protein mixture (estimated amount of about 9 mg or 300 nmol of total protein material) was dried in a centrifugal vacuum concentrator to about 1 ml. To this protein mixture, solid guanidinium-hydrochloride was added to a final concentration of 4 M. The proteins were reduced by adding 40 µl of 0.5% tributylphosphine in n-propanol to this mixture and incubation for 30 min at ambient temperature. 188 µl of a freshly prepared 40 nmol/µl solution of iodoacetamide was added to the reduced protein mixture, and the proteins were alkylated for 90 min at 37° C. in the dark. The protein solution was diluted with water to a total volume of 1.5 ml, after which 500 µl of this mixture was desalted on a NAP™-5 column (Amersham Pharmacia Biotech) and collected in 1 ml of 250 mM Tris.HCl pH 7.9 containing 250 mM guanidinium-hydrochloride. This desalted protein mixture was concentrated to half its volume by vacuum drying, boiled for 5 min in a water bath, put on ice for 10 min, after which 10 µg of trypsin (sequencing-grade modified trypsin from Promega) was added. Proteolytic digestion proceeded overnight at a constant temperature of 37° C. and was stopped by acidification by TFA.

Following centrifugation to remove any insoluble material, the obtained peptide mixture was separated on a reverse-phase HPLC column (4.6 I.D.×250 mm RP-HPLC C18 column, Vydac Separations Group). Following injection of the sample onto the column, a gradient of increasing concentration of acetonitrile was used to fractionate the peptide mixture. First, the column was rinsed with 0.1% of TFA in water (Baker HPLC analysed) (solvent A) for 5 min at a constant flow of 1 ml/min using a Waters Gradient Controller and two Waters Model 510 solvent pumps. Subsequently, a linear gradient to 70% of acetonitrile (Baker HPLC analysed) in 0.1% of TFA in water (100% solvent B) over 70 min (thus an increase of 1% of acetonitrile per min) was used to elute the peptides from the RP column. In a last phase, the column was thoroughly rinsed with solvent B and re-equilibrated with solvent A prior to the next sample injection. Peptides eluting between 2 min (corresponding to 0% of solvent B) and 66 min (87.1% of solvent B or 61% of acetonitrile) were collected in 16 primary fractions of 4 ml each.

All primary fractions were dried to complete dryness in a centrifugal vacuum concentrator and re-dissolved in 1 ml of 50 mM sodium borate at pH 9.0. For each primary fraction, half of the peptide mixture was used to block peptides at their free amino groups by adding 3 µl of 0.1 M aqueous 2,4,6-trinitrobenzenesulfonic acid solution (TNBS) (Sigma), while the remaining half was used as control. The reaction proceeded for 60 min at 37° C., after which an additional 3 µl of 0.1 M TNBS was added and again incubated for 60 min at 37° C. The majority of TNB-peptides as well as the reaction byproducts of TNBS (e.g. picrate) are extracted with 500 µl of ethylacetate (equilibrated with water). This extraction procedure was repeated twice. The water phase, containing the N-terminally blocked (acetylated), lysine-free and arginine ending peptides is dried in vacuo. The TNBS-modification reaction, as described above, is repeated a second time so as to allow remaining traces of peptides with a free amino group to react. The dried product is dissolved in solvent A and subjected to the secondary run in which peptides were collected in total window of 7.5 min (starting 2 min before the onset of collection of the original primary fraction) in a total of 15 sub-fractions of 500 µl each. Each subfraction was dried, re-dissolved in 20 µl of 0.1% formic acid in a mixture of acetonitrile in water (2/98, by volume), of which 10 µl was used for LC-MS/MS analysis and used for protein identification as described in examples 19 and 20.

As for MASCOT-based database searching, the following search parameters were used: enzyme: trypsin, maximum number of missed cleavages: 2, fixed modifications: none, variable modifications: acetylation (N-terminus), oxidation (M), pyro-Glu (N-terminal E and Q), peptide mass tolerance: 0.3 Da, MS/MS tolerance: 0.25 Da and peptide charge: 2+ or 3+. A batch processing of the result sets from Mascot was performed to obtain a final list of identified peptides. Only the peptides that are ranked first by MASCOT and met its identity and/or homology thresholds were withheld and are combined in Table XVI together with their corresponding precursor proteins. As expected, next to naturally blocked (acetylated) N-terminal peptides ending on an arginine residue, peptides starting with a pyroglutamic acid and beginning with a proline residue, are also sorted. The former is due to the formation of a cyclic blocking residue, while N-terminal proline forms a secondary amine, which does not react with TNBS.

In addition to the identified peptides, we present a list of 183 de novo derived peptide sequence tags from MS/MS-spectra that did not lead to an unambiguous identification in the SWISSPROT database using the MASCOT database search algorithm (Table XVII). Most of the derived tags are homology-based searching tools such as BLAST and FASTA. Most likely they represent acetylated N-terminal peptides of proteins whose corresponding sequences are yet not listed in the available sequence database.

Example 22

A Limited Proteome Analysis Based on the Isolation of $NH_2$-Terminal Peptides of the Proteins Present in Human Thrombocyte Extracts In contrast to the previous example, we here modified the alteration chemistry such that now the $NH_2$-terminal identification peptides of the proteins present in the sample, including those with blocked and those with a free amino-terminus, can be isolated and used for protein identification.

As starting material we used a cytosolic and membrane skeleton preparation of human thrombocytes as prepared for examples 20 and 21. Five hundred µl of the desalted protein mixture (estimated amount of about 3 mg) was concentrated in a centrifugal vacuum concentrator to about 400 µl. To this protein mixture, solid guanidinium hydrochloride was added to a final concentration of 4 M. Proteins were reduced by addition of tributylphosphine (14 µl of a fresh 0.5% solution in n-propanol) for 30 min at ambient temperature. 62.5 µl of a freshly prepared 40 nmol/µl solution of iodoacetamide in H$_2$O was added to the reduced protein mixture, and the proteins were alkylated for 90 min at 37° C. in the dark. Subsequently, this mixture was desalted on a NAP™-5 column (Amersham Pharmacia Biotech) and collected in 1 ml of 250 mM sodium phosphate buffered at pH 8.0 containing 1 M guanidine hydrochloride. This volume was concentrated to half of its volume in a centrifugal vacuum concentrator. Both the α- and ε-amines were acetylated by adding 50-fold molar excess of solid sulfo-N-hydroxysuccinimide acetate, and incubating this mixture for 90 min at room temperature. Possible acetylation of hydroxyl and COOH-groups was reverted by adding 1 µl of hydroxylamine to the protein-reaction mixture. Prior to proteolysis, the protein mixture was desalted on a NAP™-5 column and collected in a total volume of 1 ml of 50 mM Tris.HCl at pH 7.9 containing 250 mM of guanidine hydrochloride. This desalted protein mixture was concentrated to half its volume by vacuum drying, boiled for 5 min in a water bath, put on ice for 10 min, after which 10 µg of trypsin (sequencing-grade modified trypsin from Promega) was added. Proteolytic digestion proceeded overnight at a constant temperature of 37° C. and was stopped by acidification by TFA.

The sorting process for the acetylated amino terminal peptides was conducted under identical conditions and on the same RP-HPLC column as described in example 21. Shown in Table XVIII are the results obtained following LC-MS/MS analysis of the amino terminal peptides sorted from two primary fractions (9 and 10). This represents $\frac{1}{8}^{th}$ of the total number of fraction. The MASCOT algorithm was again used to identify the fragmented peptides and the parameters here were set as described in example 21, except that acetylation of lysine residues was an additional variable modification.

This partial proteome analysis (only 12.5% of the total analysable material was used) yielded 26 different proteins which could be identified (see Table XVIII). Interestingly, major proteins, such as actin, are identified next to low abundant ones, such as kinases and phosphatases, and hydrophobic proteins, such as the DAD-1 protein, which is predicted to be a integral membrane protein. Furthermore, as in example 21, we have analysed a number of peptide ions that did not lead to any identification using the MASCOT algorithm, but gave interpretable fragmentation spectra. These spectra were de novo interpreted, however, the obtained 48 peptide sequence tags (shown in Table XIX) did not lead to any unambiguous identification using sequence homology based database searching tools such as FASTA and BLAST. We assume that these sequences represent novel proteins whose sequences are not yet available in the databases.

Example 23

Specific Isolation of the COOH-Terminal Peptides of Proteins in Complex Mixtures The procedure starts with the conversion of the protein cysteines with iodoacetamide or similar SH-specific reagents known in the field. Then the protein mixture is digested with trypsin, generating a protein-peptide mixture. This total mixture of peptides is then treated with a diazo-derivative forming ethers with tyrosine and esters with all COOH-groups, including the COOH-groups of Arg and Lys at the end of the peptides and the COOH-termini of the peptides derived from the COOH-terminal part of the proteins.

These pretreated peptides are then separated by normal— or reversed phase chromatography and eluting peptides are collected in such number of fractions that allow, in each of the collected fractions, the separation of altered peptides from non-altered peptides during the secondary run. In each fraction trypsin is added, back-hydrolysing the esters at the Arg and Lys residues, while the other COOH-esters, including the ester at the COOH-termini of proteins—which generally do not consist of an Arg or Lys residue—are not back-hydrolysed by trypsin. Thus all trypsin peptides, except for the COOH-terminal peptides, are altered and shift during the secondary run. The COOH-terminal peptides are thus recovered in the secondary run as non-altered peptides in the same time interval as they elute during the primary run.

Candidate diazo-derivatives could be the very reactive and toxic diazomethane or phenyldiazomethane or more ideally a non-volatile, more stable and water soluble diazo-derivative. All these compounds react with COOH-groups to their corresponding esters or with phenolic groups to the corresponding ethers.

The esters of Arg and Lys COOH-groups are substrates of trypsin and are hydrolysed similarly as the corresponding peptide bonds.

The hydrolysis reaction of the benzoylester of COOH-terminal Lys is depicted in the schema (xi)

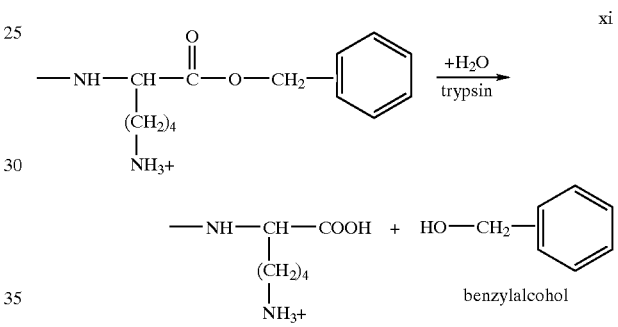

Abbreviations

2D: two-dimensional
CAD: collision activated dissociation
DTT: dithiothreitol
ESI: electrospray ionisation
EST: expressed sequence tag
FTMS: Fourier transform mass spectrometry
ICAT: isotope coded affinity tag
ID-peptide: identification peptide
IPG: immobilized pH gradient
ITC: isothiocyanate
LC: liquid chromatography
LC-MS/MS: liquid chromatography and tandem MS
MALDI-RETOF-MS: MALDI-reflectron TOF-MS
MALDI-TOF-MS: matrix-assisted laser desorption ionisation—time-of-flight—mass spectrometry
Met-SO: methionine-sulfoxide
MS/MS: tandem MS
MS: mass spectrometry
MW: molecular weight
pI: isoelectric point
PITC: phenylisothiocyanate
PMF: peptide mass fingerprint
PSD: post-source decay
PTC: phenylthiocarbamyl
RP—HPLC: reversed-phase high performance liquid chromatography
SDS: sodium dodecyl sulfate
TFA: trifluoroacetic acid Tables

TABLE I

Percentage of predicted proteins lacking rare amino acids. All species protein sequences were extracted from SwissProt, version 39. Met (−initiator) refers to the number obtained after the initiator methionine was removed.

|  | Trp | His | Cys | Met | Met (−initiator) |
|---|---|---|---|---|---|
| E. coli | 11.34 | 4.12 | 14.55 | 0.32 | 3.49 |
| Yeast | 10.32 | 2.55 | 8.68 | 0.89 | 4.18 |
| Rat | 10.43 | 3.66 | 5.80 | 1.91 | 3.92 |
| Human | 8.74 | 3.79 | 4.42 | 2.01 | 3.66 |

TABLE II

The principle of the peptide sorter is illustratively worked out for flagged peptides. Fractions are isolated in run 1 with an elution window $w_1$ equalling $x/2$. If the total run 1 elution window of all peptides originating from the protein peptide mixture equals $20x$, than 40 fractions with an $x/2$ window (first fraction: 0 to $x/2$; second fraction: $x/2$ to $x$; third fraction: $x$ to $3x/2$, . . . ) are collected. If the alteration of the specific amino acid in the flagged peptides induces a forward shift on a hydrophobic separation column, with the shift varying in value between $x$ and $2x$ then this implies that the values for $\delta min = x/2$, $\delta max = 5x/2$, $w1 = x/2$ and $w3 = 7x/2$). The general principle of a parallel sorter can be explained by example whereby 12 pools of peptide fractions are generated. Thus, after the primary chromatographic run, the following fractions can be pooled: fraction 1 (0 to $x/2$), with fractions 13 ($6x$ to $13x/2$), 25 ($12x$ to $25x/2$,) and 37 ($18x$ to $37x/2$). Similarly, fraction 2 is pooled with fractions 14, 26 and 38; fraction 3 is pooled with fractions 15, 27 and 39; fraction 4 is pooled with fractions 16, 28 and 40; fraction 5 is pooled with fractions 17 and 29; fraction 6 is pooled with fractions 18 and 30; fraction 7 is pooled with fractions 19 and 31; fraction 8 is pooled with fractions 20 and 32; fraction 9 is pooled with fractions 21 and 33; fraction 10 is pooled with fractions 22 and 34; fraction 11 is pooled with fractions 23 and 35; and fraction 12 is pooled with fractions 24 and 36. The 12 pools are then chemically and/or enzymatically altered on at least one selected amino acid. Table II, contains calculations of the theoretical shifts of the 12 flagged peptide pools.

| Pool | | | | |
|---|---|---|---|---|
| Pool 1 (1, 13, 25, 37) | $-2x$ to $-x/2$ | $4x$ to $11x/2$ | $10x$ to $23x/2$ | $16x$ to $35x/2$ |
| Pool 2 (2, 14, 26, 38) | $-3x/2$ to 0 | $9x/2$ to $6x$ | $21x/2$ to $12x$ | $33x/2$ to $18x$ |
| Pool 3 (3, 15, 27, 39) | $-x$ to $x/2$ | $5x$ to $13x/2$ | $11x$ to $25x/2$ | $17x$ to $37x/2$ |
| Pool 4 (4, 16, 28, 40) | $-x/2$ to $x$ | $11x/2$ to $7x$ | $23x/2$ to $13x$ | $35x/2$ to $19x$ |
| Pool 5 (5, 17, 29) | 0 to $3x/2$ | $6x$ to $15x/2$ | $12x$ to $27x/2$ | |
| Pool 6 (6, 18, 30) | $x/2$ to $2x$ | $13x/2$ to $8x$ | $25x/2$ to $14x$ | |
| Pool 7 (7, 19, 31) | $x$ to $5x/2$ | $7x$ to $17x/2$ | $13x$ to $29x/2$ | |
| Pool 8 (8, 20, 32) | $3x/2$ to $3x$ | $15x/2$ to $9x$ | $27x/2$ to $15x$ | |
| Pool 9 (9, 21, 33) | $2x$ to $7x/2$ | $8x$ to $19x/2$ | $14x$ to $31x/2$ | |
| Pool 10 (10, 22, 34) | $5x/2$ to $4x$ | $17x/2$ to $10x$ | $29x/2$ to $16x$ | |
| Pool 11 (11, 23, 35) | $3x$ to $9x/2$ | $9x$ to $21x/2$ | $15x$ to $33x/2$ | |
| Pool 12 (12, 24, 36) | $7x/2$ to $5x$ | $19x/2$ to $11x$ | $31x/2$ to $17x$ | |

TABLE III

Hydrophylic shifts of the peptide NH2-YSFVMTAEK-COOH, due to oxidation to the sulfoxide form. Elutions were carried out with different organic solvents using linear gradients of 1% per min. Buffer compositions were either trifluoroacetic acid, ammonium acetate at pH 5.7 or formic acid. The column was each time a C18 reversed-phase column (4.6 i.d. × 2500 mm). Retention times of the oxidized peptide forms are indicated in min. (Rt MET-OX$_{(min)}$) and shifts are expressed in min between the non-oxidized and the sulfoxide peptides (Rt$_{(min)}$). The absolute elution times (Rt MET-OX$_{(min)}$) are strongly dependent on the nature of the ions used in the system, while the extent of shifts (Rt$_{(min)}$) is largely determined by the nature of the organic modifier. The strongest shifts were observed when methanol was used as organic modifier. In practice this was however not used because there was an important peak broadening effect, which was not observed for ethanol or acetonitrile as modifiers.

| BUFFER | ORGANIC MODIFIER | Rt MET-OX$_{(min)}$ | $\Delta$Rt$_{(min)}$ |
|---|---|---|---|
| 0.1% TFA | ACETONITRILE 70% | 28.0 | 3.0 |
| | METHANOL 70% | 45.5 | 5.0 |

TABLE III-continued

Hydrophylic shifts of the peptide NH2-YSFVMTAEK-COOH, due to oxidation to the sulfoxide form. Elutions were carried out with different organic solvents using linear gradients of 1% per min. Buffer compositions were either trifluoroacetic acid, ammonium acetate at pH 5.7 or formic acid. The column was each time a C18 reversed-phase column (4.6 i.d. × 2500 mm). Retention times of the oxidized peptide forms are indicated in min. (Rt MET-OX$_{(min)}$) and shifts are expressed in min between the non-oxidized and the sulfoxide peptides (Rt$_{(min)}$). The absolute elution times (Rt MET-OX$_{(min)}$) are strongly dependent on the nature of the ions used in the system, while the extent of shifts (Rt$_{(min)}$) is largely determined by the nature of the organic modifier. The strongest shifts were observed when methanol was used as organic modifier. In practice this was however not used because there was an important peak broadening effect, which was not observed for ethanol or acetonitrile as modifiers.

| BUFFER | ORGANIC MODIFIER | Rt MET-OX$_{(min)}$ | ΔRt$_{(min)}$ |
|---|---|---|---|
|  | ETHANOL 70% | 31.6 | 4.5 |
| 10 Mm NH4Ac | ACETONITRILE 70% | 24.2 | 3.4 |
|  | METHANOL 70% | 41.5 | 7.3 |
|  | ETHANOL 70% | 27.5 | 5.3 |
| 0.1% HCOOH | ACETONITRILE 70% | 22.6 | 3.1 |
|  | METHANOL 70% | 32.9 | 5.1 |
|  | ETHANOL 70% | 24.0 | 4.0 |

TABLE IVA

Modes of combining fractions derived from the primary runs and collecting fractions during the secondary runs. Run numbers (2A–2L) refer to the numbers given to the secondary runs. For convenience we call the first collected fraction n° 10 (see text). This fraction elutes between 18 and 19 min after the start of the acetonitrile gradient during the primary run. Consecutive fractions are numbered up to 49 and represent 1 min fractions.

| RUN NUMBER | COMBINED FRACTIONS | COLLECTED FRACTIONS |
|---|---|---|
| 2A | 10, 22, 34, 46 | 4–7, 16–19, 28–31, 40–43 |
| 2B | 11, 23, 35, 47 | 5–8, 17–20, 29–32, 41–44 |
| 2C | 12, 24, 36, 48 | 6–9, 18–21, 30–33, 42–45 |
| 2D | 13, 25, 37, 49 | 7–10, 19–22, 31–34, 43–46 |
| 2E | 14, 26, 38 | 8–11, 20–23, 32–35 |
| 2F | 15, 27, 39 | 9–12, 21–24, 33–36 |
| 2G | 16, 28, 40 | 10–13, 22–25, 34–37 |
| 2H | 17, 29, 41 | 11–14, 23–26, 35–38 |
| 2I | 18, 30, 42 | 12–15, 24–27, 36–39 |
| 2J | 19, 31, 43 | 13–16, 25–28, 37–40 |
| 2K | 20, 32, 44 | 14–17, 26–29, 38–41 |
| 2L | 21, 33, 45 | 15–18, 27–30, 38–42 |

TABLE IVB

Modes of combining fractions derived from the secondary runs for separation in the ternary runs. 3A–3D refer to the number given to the ternary runs. Colors refer to those used in Table IVA.

| RUN NUMBER | POOLED FRACTIONS OF METOX-PEPTIDES |
|---|---|
| 3A | 4–7, 8–11, 12–15, 16–19, 20–23, 24–27, 28–31, 32–35, 36–39, 40–43 |
| 3B | 5–8, 9–12, 13–16, 17–20, 21–24, 25–28, 29–32, 33–36, 37–40, 41–44 |
| 3C | 6–9, 10–13, 14–17, 18–21, 22–25, 26–29, 30–33, 34–37, 38–41, 42–45 |
| 3D | 7–10, 11–14, 15–18, 19–22, 23–26, 27–30, 31–34, 35–38, 39–42, 43–46 |

TABLE IVC

Modes of combining fractions derived from the secondary runs for separation in the ternary runs. Here we give an alternative way of combining fractions when formic acid is used as buffer system (3'A–3'H). Color codes used in the fraction numbers are identical to those used in Tables IVA and IVB.

| RUN NUMBER | POOLED FRACTIONS OF METOX-PEPTIDES |
|---|---|
| 3'A | 4–7, 12–15, 20–23, 28–31, 36–39, |
| 3'B | 8–11, 16–19, 24–27, 32–35, 40–43 |
| 3'C | 5–8, 13–16, 21–24, 29–32, 37–40, |
| 3'D | 9–12, 17–20, 25–28, 33–36, 41–44 |
| 3'E | 6–9, 14–17, 22–25, 30–33, 38–41, |
| 3'F | 10–13, 18–21, 26–29, 34–37, 42–45 |
| 3'G | 7–10, 15–18, 23–26, 31–34, 39–42, |
| 3'H | 11–14, 19–22, 27–30, 35–38, 43–46 |

TABLE V

Modes of combining fractions derived from the primary runs for separation in the secondary runs using a 3-column peptide sorter (FIG. 12). 2A–2D refer to the secondary runs and eluting fractions can be either on-line connected to an ESI-based mass spectrometer or can be collected for further analysis by MALDI-TOF-MS.

| | Primary run fractions | Collected fractions |
|---|---|---|
| Run 2A Column I | 10, 22, 34, 46 | 4–7, 16–19, 28–31, 40–43 |
| Column II | 14, 26, 38 | 8–11, 20–23, 32–35 |
| Column III | 18, 30, 42 | 12–15, 24–27, 36–39 |
| Run 2B Column I | 11, 23, 35, 47 | 5–8, 17–20, 29–32, 41–44 |
| Column II | 15, 27, 39 | 9–12, 21–24, 33–36 |
| Column III | 19, 31, 43 | 13–16, 25–28, 37–40 |
| Run 2C Column I | 12, 24, 36, 48 | 6–9, 18–21, 30–33, 42–45 |
| Column II | 16, 28, 40 | 10–13, 22–25, 34–37 |
| Column III | 20, 32, 44 | 14–17, 26–29, 38–41 |
| Run 2D Column I | 13, 25, 37, 49 | 7–10, 19–22, 31–34, 43–46 |
| Column II | 17, 29, 41 | 11–14, 23–26, 35–38 |
| Column III | 21, 33, 45 | 15–18, 27–30, 38–42 |

TABLE VII

Modes of combining fractions derived from the primary runs for separation in the secondary runs using a 9-column peptide sorter (FIG. 13). 2A–2E refer to the secondary runs and eluting fractions can be either on-line connected to an ESI-based mass spectrometer or can be collected for further analysis by MALDI-TOF-MS.

| | SYSTEM A | | | SYSTEM B | | | SYSTEM C | | |
|---|---|---|---|---|---|---|---|---|---|
| | I | II | III | I' | II' | III' | I" | II" | III" |
| Run 2A | 12 | 24 | 36 | 13 | 25 | 37 | 14 | 26 | 38 |
| Run 2B | 15 | 27 | 39 | 16 | 28 | 40 | 17 | 29 | 41 |
| Run 2C | 18 | 30 | 42 | 19 | 31 | 43 | 20 | 32 | 44 |
| Run 2D | 21 | 33 | 45 | 22 | 34 | 46 | 23 | 35 | 48 |
| Run 2E | 10 | 22 | | 11 | | | 49 | | |

TABLE VI

| | load 10, 2 2 34, 4 6(I) 1 min | Load 14, 26 38 (II) 1 min | load 18, 30 42 (III) 1 min | wash 10 min | 2–3 | 4–7 | 8–11 | 12–15 | 16–19 | 20–23 | 24–27 | 28–31 | 32–35 | 36–39 | 40–43 | acetonitrile 44–70 | Regeneration reg 20 m |
|---|---|---|---|---|---|---|---|---|---|---|---|---|---|---|---|---|---|
| | | | | | | | | B. Linear gradient | | | | | | | | Wash at high | |
| a | − | − | − | + | + | + | + | + | + | + | + | + | + | + | + | + | + |
| b | + | − | − | − | − | − | − | − | − | − | − | − | − | − | − | − | − |
| c | − | − | − | + | + | + | + | + | + | + | + | + | + | + | + | + | + |
| d | − | + | − | − | − | − | − | − | − | − | − | − | − | − | − | − | − |
| e | − | − | − | + | + | + | + | + | + | + | + | + | + | + | + | + | + |
| f | − | − | + | − | − | − | − | − | − | − | − | − | − | − | − | − | − |
| g | + | − | − | − | − | − | − | − | − | − | − | − | − | − | − | − | − |
| h | − | + | − | − | − | − | − | − | − | − | − | − | − | − | − | − | − |
| i | − | − | + | − | − | − | − | − | − | − | − | − | − | − | − | − | − |
| j | − | − | − | − | − | + | − | − | + | − | − | + | − | − | + | − | − |
| k | − | − | − | − | − | − | + | − | − | + | − | − | + | − | − | − | − |
| l | − | − | − | − | − | − | − | + | − | − | + | − | − | + | − | − | − |
| m | + | − | − | + | + | − | + | + | − | + | + | − | + | + | − | + | + |
| n | − | + | − | + | + | + | − | + | + | − | + | + | − | + | + | + | + |
| o | − | − | + | + | + | + | + | − | + | + | − | + | + | − | + | + | + |

Valve Operations During a Complete run of the Three-Column Peptide Sorter.

Fractions 10, 22, 34 and 46 of the primary run are loaded as mixture on column I, fractions 14, 26, 38 and 50 on column II and fractions 18, 30 and 42 on column III. Each loading is expected to take 1 min. Then the three columns are washed simultaneously for 10 min. with 2% solvent B. Then a linear gradient is started from 2% solvent B to 55% solvent B with solvent B being 70% acetonitrile in water to which 0.1% TFA was added. The gradient is identical to this used in the primary run. Open valves (+); closed valves (−). The valves are numbered a–i (high-pressure valves) and j–o (low-pressure dead volume valves) and are indicated in FIG. 12. A total run including loading, washing, Example of Valve Settings in the Nine-Column Peptide Sorter.

A description of the operation of the valve settings of system A is given. +: open valve; −: closed valve. Fraction 12 of the primary run is loaded on column I, fraction 24 on column II and fraction 36 on column III. A linear gradient is formed increasing by 1% per min of solvent B. This gradient increases to 55% of solvent B. Altered peptides are collected between 6 min and 9 min (6–9), 18–21 and 30–33 and indicated by solid bars. Valves are indicated; a–g are high-pressure valves; h–o and p–r are dead-volume low-pressure valves. Lines represent the connecting tubing.

TABLE VIII

| | load fr12 (I) 1 min | wash (I) 5 min | load fr24 (II) 1 min | wash (II) 5 min | load fr36 III 1 min | wash III 5 min | 0–5 | 6–9 | 10–16 | 17 | 18–21 | 22–28 | 29 | 30–33 | 34–55 |
|---|---|---|---|---|---|---|---|---|---|---|---|---|---|---|---|
| a | + | − | + | − | + | − | − | − | − | − | − | − | − | − | − |
| b | − | + | − | + | − | + | + | + | + | + | + | + | + | + | + |
| c | − | − | + | + | + | + | − | − | − | + | + | + | + | + | + |
| d | + | + | − | − | − | − | + | + | + | − | − | − | − | − | − |
| e | − | − | − | − | + | + | − | − | − | − | − | − | + | + | + |
| f | − | − | + | + | − | − | − | − | − | + | + | + | − | − | − |
| g | − | − | − | − | + | + | − | − | − | − | − | − | + | + | + |
| h | − | − | − | − | − | − | − | + | − | − | − | − | − | − | − |
| i | + | + | − | − | − | − | + | − | + | − | − | − | − | − | − |
| j | − | − | − | − | − | − | − | − | − | − | − | + | − | + | − |
| k | − | − | − | − | − | − | − | − | − | − | + | − | − | − | − |
| l | − | − | + | + | − | − | − | − | − | + | − | + | − | − | − |
| m | − | − | − | − | − | − | − | − | − | − | − | − | − | + | − |
| n | − | − | − | − | − | − | − | − | − | − | − | − | − | + | − |
| o | − | − | − | − | + | + | − | − | − | − | − | − | + | − | + |
| p | − | − | − | − | − | − | − | + | − | − | + | − | − | + | − |
| q | − | − | − | − | − | − | − | − | − | − | − | − | − | − | − |
| r | − | − | − | − | − | − | − | − | − | − | − | − | − | − | − |

TABLE IX

| fr1 | fr2 | fr3 | fr4 | fr5 | fr6 | fr7 | fr8 | fr9 | fr10 | fr11 | fr12 |
|---|---|---|---|---|---|---|---|---|---|---|---|
| | 957.59 | | 922.46 | 1102.44 | 881.37 | 880.53 | 878.59 | 870.42 | 825.58 1649.72 | 919.56 | 996.50 |
| | 1002.62 | | 1203.47 | 1112.36 | 1007.40 | 950.49 | 969.54 | 886.54 | 856.51 1687.66 | 960.59 | 1067.43 |
| | 1012.40 | | 1218.40 | 1115.57 | 1082.45 | 1051.47 | 1021.42 | 898.39 | 906.58 1690.65 | 961.54 | 1119.65 |
| | 1110.44 | | 1237.42 | 1173.35 | 1100.32 | 1094.50 | 1053.33 | 916.55 | 945.51 | 993.50 | 1142.44 |
| | 1265.47 | | 1307.33 | 1196.39 | 1114.37 | 1133.42 | 1070.56 | 951.42 | 988.51 | 994.66 | 1185.33 |
| | | | 1499.22 | 1205.45 | 1186.27 | 1158.47 | 1078.54 | 971.33 | 991.46 | 1015.53 | 1187.41 |
| | | | | 1528.59 | 1241.40 | 1265.51 | 1099.53 | 984.44 | 998.52 | 1098.54 | 1197.56 |
| | | | | | 1262.46 | 1269.49 | 1185.50 | 992.59 | 1000.35 | 1112.38 | 1213.39 |
| | | | | | 1283.54 | 1276.50 | 1191.38 | 1022.47 | 1011.56 | 1254.57 | 1215.48 |
| | | | | | 1360.32 | 1278.46 | 1199.51 | 1066.38 | 1028.51 | 1279.39 | 1229.63 |
| | | | | | 1398.36 | 1281.51 | 1210.31 | 1158.46 | 1036.48 | 1289.35 | 1246.50 |
| | | | | | 1600.49 | 1297.50 | 1223.58 | 1167.58 | 1125.51 | 1338.59 | 1324.52 |
| | | | | | 1669.74 | 1352.44 | 1244.49 | 1176.40 | 1129.41 | 1384.33 | 1333.53 |
| | | | | | 1925.73 | 1355.44 | 1250.51 | 1177.42 | 1149.43 | 1444.65 | 1335.50 |
| | | | | | 2031.02 | 1406.52 | 1266.37 | 1184.34 | 1186.45 | 1473.51 | 1360.43 |
| | | | | | | 1414.46 | 1268.49 | 1218.43 | 1190.44 | 1484.38 | 1372.62 |
| | | | | | | 1446.78 | 1315.40 | 1261.45 | 1228.46 | 1558.43 | 1409.53 |
| | | | | | | 1565.57 | 1351.38 | 1263.55 | 1267.43 | 1681.83 | 1537.56 |
| | | | | | | 1704.69 | 1364.55 | 1270.46 | 1274.36 | 1718.58 | 1562.59 |
| | | | | | | 1725.63 | 1401.49 | 1271.45 | 1281.55 | 1740.51 | 1564.55 |
| | | | | | | 1736.77 | 1468.47 | 1306.25 | 1331.47 | 1741.41 | 1594.62 |
| | | | | | | 1747.59 | 1535.40 | 1354.40 | 1353.45 | 1808.49 | 1625.67 |
| | | | | | | 2374.97 | 1663.50 | 1355.47 | 1364.38 | 1918.71 | 1690.58 |
| | | | | | | | 1664.48 | 1358.34 | 1378.45 | 2069.79 | 1703.54 |
| | | | | | | | 1746.59 | 1405.38 | 1381.44 | 2640.30 | 1754.64 |
| | | | | | | | 1747.73 | 1459.33 | 1421.57 | 2699.44 | 1858.74 |
| | | | | | | | 1761.50 | 1584.64 | 1424.53 | | 1946.70 |
| | | | | | | | 1778.53 | 1586.41 | 1464.50 | | 1964.91 |
| | | | | | | | 1855.82 | 1592.53 | 1481.49 | | 2708.24 |
| | | | | | | | 2043.76 | 1759.61 | 1514.62 | | |
| | | | | | | | | 2070.94 | 1523.52 | | |
| | | | | | | | | 2241.02 | 1553.55 | | |
| | | | | | | | | 3015.64 | 1574.43 | | |
| | | | | | | | | | 1629.67 | | |

| fr13 | | fr14 | | fr15 | | fr16 | | fr17 | | fr18 | | fr19 | |
|---|---|---|---|---|---|---|---|---|---|---|---|---|---|
| 896.63 | 1615.73 | 881.51 | 1342.59 | 889.56 | | 811.52 | 945.64 | 1553.45 | 890.62 | 1449.58 | 871.64 | 1718.97 | |
| 937.51 | 1645.85 | 939.49 | 1363.53 | 1048.54 | | 844.58 | 974.62 | 1578.54 | 932.59 | 1476.59 | 1021.64 | 1733.68 | |
| 938.38 | 1647.50 | 941.47 | 1377.51 | 1138.44 | | 1010.55 | 981.61 | 1587.89 | 940.62 | 1512.59 | 1024.45 | 1742.87 | |
| 965.52 | 1652.73 | 942.51 | 1421.60 | 1239.52 | | 1019.63 | 987.67 | 1592.78 | 954.41 | 1530.64 | 1057.64 | 1763.80 | |
| 995.40 | 1708.66 | 945.47 | 1450.53 | 1284.58 | | 1027.58 | 989.43 | 1597.75 | 1073.36 | 1540.55 | 1067.60 | 1783.71 | |
| 1003.41 | 1711.72 | 957.47 | 1505.60 | 1395.56 | | 1124.58 | 1034.59 | 1623.65 | 1088.49 | 1598.70 | 1074.66 | 1803.86 | |
| 1017.44 | 1730.83 | 959.55 | 1511.63 | 1396.70 | | 1130.58 | 1074.65 | 1676.85 | 1091.54 | 1614.71 | 1097.63 | 1815.70 | |
| 1028.37 | 1746.52 | 967.42 | 1519.58 | 1444.59 | | 1146.50 | 1093.49 | 1697.83 | 1101.51 | 1624.70 | 1119.64 | 1863.98 | |
| 1037.56 | 1758.66 | 973.45 | 1576.58 | 1452.58 | | 1154.38 | 1102.56 | 1707.77 | 1112.43 | 1649.81 | 1120.53 | 1897.84 | |
| 1104.39 | 1781.72 | 978.40 | 1579.57 | 1462.60 | | 1172.47 | 1103.57 | 1753.68 | 1141.51 | 1667.66 | 1133.61 | 1907.91 | |
| 1123.42 | 1914.81 | 985.47 | 1593.58 | 1496.64 | | 1262.61 | 1117.51 | 1761.86 | 1144.49 | 1672.52 | 1137.58 | 1922.81 | |
| 1132.54 | 1989.72 | 1012.51 | 1601.50 | 1535.60 | | 1271.54 | 1123.63 | 1771.77 | 1146.41 | 1673.80 | 1206.71 | 1989.97 | |
| 1135.52 | 2113.06 | 1027.47 | 1608.59 | 1548.98 | | 1313.56 | 1125.46 | 1795.92 | 1148.53 | 1687.76 | 1249.48 | 2003.96 | |
| 1211.50 | 2168.85 | 1042.63 | 1624.62 | 1617.75 | | 1356.56 | 1128.56 | 1822.76 | 1185.59 | 1739.99 | 1292.57 | 2019.03 | |
| 1219.39 | 2324.93 | 1043.55 | 1639.75 | 1697.70 | | 1382.43 | 1152.61 | 1901.83 | 1203.49 | 1756.94 | 1308.47 | 2029.81 | |
| 1232.43 | 2751.30 | 1050.55 | 1786.79 | 1751.70 | | 1427.73 | 1173.61 | 1908.65 | 1213.40 | 1760.96 | 1326.45 | 2030.01 | |
| 1252.40 | | 1072.43 | 1789.88 | 1985.68 | | 1432.64 | 1215.53 | 1910.92 | 1223.55 | 1873.85 | 1341.49 | 2113.93 | |
| 1269.47 | | 1117.52 | 1822.88 | 2017.76 | | 1479.54 | 1233.63 | 1989.88 | 1226.43 | 1885.61 | 1426.66 | 2116.06 | |
| 1280.49 | | 1133.37 | 1943.89 | 2041.84 | | 1520.62 | 1258.62 | 2064.65 | 1238.41 | 1909.80 | 1448.56 | 2131.95 | |
| 1289.36 | | 1137.38 | 1947.76 | 2047.99 | | 1538.78 | 1279.54 | 2235.05 | 1239.44 | 1928.79 | 1453.70 | 2137.28 | |
| 1313.47 | | 1150.40 | 2049.94 | | | 1740.77 | 1304.42 | 2264.69 | 1242.49 | 2013.99 | 1498.58 | 2267.18 | |
| 1317.41 | | 1164.52 | 2092.86 | | | 1836.92 | 1318.54 | 2440.13 | 1253.57 | 2016.98 | 1518.52 | 2475.23 | |
| 1336.58 | | 1165.37 | 2185.93 | | | 1973.96 | 1359.52 | 2771.21 | 1254.44 | 2028.82 | 1524.64 | 2680.38 | |
| 1338.35 | | 1167.51 | | | | 2096.16 | 1394.46 | 2854.93 | 1277.49 | 2119.97 | 1531.56 | 3105.72 | |
| 1344.41 | | 1197.46 | | | | 2169.11 | 1399.54 | | 1280.59 | 2211.85 | 1567.58 | | |
| 1387.46 | | 1206.49 | | | | | 1438.33 | | 1291.47 | 2275.96 | 1580.68 | | |
| 1407.63 | | 1210.52 | | | | | 1439.27 | | 1350.39 | 2287.13 | 1583.72 | | |
| 1443.39 | | 1228.50 | | | | | 1451.59 | | 1384.66 | 2737.18 | 1595.63 | | |
| 1461.52 | | 1234.44 | | | | | 1461.41 | | 1409.66 | 2768.47 | 1607.78 | | |
| 1469.44 | | 1283.40 | | | | | 1463.75 | | 1412.55 | 2812.98 | 1615.56 | | |
| 1476.62 | | 1297.56 | | | | | 1478.65 | | 1413.57 | | 1622.79 | | |
| 1503.53 | | 1299.40 | | | | | 1494.60 | | 1427.48 | | 1668.74 | | |
| 1541.57 | | 1325.51 | | | | | 1500.59 | | 1435.66 | | 1669.67 | | |
| 1583.50 | | 1331.43 | | | | | 1532.59 | | 1443.62 | | 1715.72 | | |

| fr20 | | | fr21 | | | fr22 | | fr23 | | fr24 | | fr25 | |
|---|---|---|---|---|---|---|---|---|---|---|---|---|---|
| 863.65 | 1519.09 | 2388.08 | 1015.61 | 2103.88 | | 865.62 | 1647.75 | 952.76 | 2277.20 | 1027.70 | 1966.02 | 944.52 | 1911.71 |
| 934.66 | 1533.75 | 2513.10 | 1090.45 | 2151.00 | | 939.51 | 1703.62 | 960.62 | 2305.84 | 1031.58 | 1972.81 | 983.41 | 1935.93 |
| 945.67 | 1562.63 | 2570.33 | 1111.46 | 2180.20 | | 960.51 | 1744.94 | 1044.65 | 2307.58 | 1038.58 | 2002.05 | 1072.42 | 1946.06 |

TABLE IX-continued

| | | | | | | | | | | | |
|---|---|---|---|---|---|---|---|---|---|---|---|
| 1000.66 | 1568.64 | 1116.44 | 2388.15 | 975.69 | 1760.74 | 1052.69 | 2424.24 | 1082.42 | 2013.68 | 1089.78 | 1954.73 |
| 1005.55 | 1596.60 | 1182.40 | 2634.16 | 989.43 | 1796.68 | 1105.79 | 2432.92 | 1152.53 | 2028.72 | 1139.52 | 1961.05 |
| 1062.55 | 1671.85 | 1211.55 | 2819.38 | 1009.50 | 1806.66 | 1157.56 | 2468.52 | 1217.55 | 2042.92 | 1146.49 | 1987.75 |
| 1065.55 | 1686.18 | 1213.44 | 3180.76 | 1043.45 | 1878.76 | 1160.61 | 2469.74 | 1222.71 | 2045.88 | 1167.51 | 2111.03 |
| 1071.93 | 1735.92 | 1217.43 | 3501.74 | 1059.40 | 1879.95 | 1254.71 | 2510.04 | 1242.63 | 2087.11 | 1321.53 | 2175.10 |
| 1096.51 | 1738.90 | 1229.76 | | 1061.54 | 1883.72 | 1266.70 | 2569.28 | 1245.61 | 2301.96 | 1342.58 | 2180.10 |
| 1102.60 | 1739.95 | 1284.46 | | 1139.44 | 1891.92 | 1308.51 | | 1285.42 | 2356.25 | 1358.53 | 2201.94 |
| 1107.60 | 1751.83 | 1304.71 | | 1178.49 | 1922.76 | 1332.81 | | 1305.48 | 2388.87 | 1382.64 | 2210.11 |
| 1131.68 | 1768.84 | 1313.41 | | 1194.50 | 1924.83 | 1348.83 | | 1311.27 | 2450.12 | 1407.53 | 2217.02 |
| 1136.65 | 1771.11 | 1338.50 | | 1197.41 | 2053.01 | 1402.58 | | 1313.35 | 2489.84 | 1409.44 | 2253.11 |
| 1154.57 | 1783.00 | 1356.41 | | 1202.40 | 2098.89 | 1424.66 | | 1335.59 | 2521.01 | 1447.61 | 2260.32 |
| 1198.69 | 1802.74 | 1388.54 | | 1219.66 | 2195.08 | 1501.86 | | 1363.65 | 2822.36 | 1451.60 | 2286.32 |
| 1223.60 | 1818.82 | 1394.77 | | 1261.43 | 2255.30 | 1598.66 | | 1373.58 | 2900.35 | 1481.61 | 2314.10 |
| 1242.53 | 1864.79 | 1404.58 | | 1267.49 | 2288.75 | 1612.88 | | 1440.51 | | 1500.89 | 2342.19 |
| 1270.54 | 1910.97 | 1499.50 | | 1282.43 | 2362.85 | 1630.67 | | 1466.56 | | 1521.55 | 2392.94 |
| 1299.57 | 1987.88 | 1537.63 | | 1284.52 | 2379.18 | 1636.84 | | 1472.61 | | 1602.61 | 2490.53 |
| 1335.88 | 2002.46 | 1573.97 | | 1311.43 | 2431.32 | 1637.13 | | 1478.58 | | 1605.68 | 2587.20 |
| 1348.66 | 2004.03 | 1575.75 | | 1320.54 | 2528.96 | 1665.69 | | 1507.40 | | 1611.66 | 2725.67 |
| 1354.61 | 2011.93 | 1580.62 | | 1345.49 | 2573.78 | 1695.82 | | 1523.68 | | 1617.01 | 2917.46 |
| 1369.59 | 2036.62 | 1590.51 | | 1378.46 | 2614.94 | 1758.74 | | 1551.69 | | 1626.00 | |
| 1395.74 | 2073.85 | 1598.88 | | 1381.66 | 2830.08 | 1769.02 | | 1571.69 | | 1641.71 | |
| 1399.60 | 2086.98 | 1673.66 | | 1429.60 | 3180.12 | 1842.69 | | 1596.54 | | 1662.84 | |
| 1400.67 | 2130.30 | 1674.71 | | 1431.60 | 3415.61 | 1861.85 | | 1614.44 | | 1690.62 | |
| 1428.00 | 2203.04 | 1720.58 | | 1432.46 | 3501.48 | 1907.39 | | 1721.88 | | 1732.78 | |
| 1432.57 | 2217.08 | 1753.10 | | 1481.47 | 3620.11 | 1909.95 | | 1762.82 | | 1766.90 | |
| 1441.48 | 2333.02 | 1813.87 | | 1514.57 | | 1975.69 | | 1779.82 | | 1803.99 | |
| 1455.95 | 2344.18 | 1830.88 | | 1569.48 | | 2010.04 | | 1793.55 | | 1814.81 | |
| 1463.51 | 2349.63 | 1864.11 | | 1571.51 | | 2055.07 | | 1833.98 | | 1860.66 | |
| 1494.73 | 2358.79 | 2001.87 | | 1574.60 | | 2132.09 | | 1843.79 | | 1867.13 | |
| 1513.85 | 2363.97 | 2004.18 | | 1576.49 | | 2139.23 | | 1872.90 | | 1878.16 | |
| 1517.77 | 2381.08 | 2035.03 | | 1587.77 | | 2235.54 | | 1889.76 | | 1895.15 | |

| fr26 | | fr27 | | fr28 | | fr29 | | fr30 | | fr31 | |
|---|---|---|---|---|---|---|---|---|---|---|---|
| 968.60 | 1998.82 | 1030.57 | 2065.90 | 855.49 | 1895.86 | 1073.46 | 2057.26 | 907.60 | 2478.23 | 1001.68 | 1714.78 | 2379.41 |
| 991.54 | 2003.83 | 1074.47 | 2127.12 | 1010.51 | 1904.94 | 1076.58 | 2106.20 | 1080.48 | 2556.35 | 1027.66 | 1716.87 | 2400.33 |
| 1061.56 | 2005.29 | 1125.44 | 2142.00 | 1063.58 | 1906.00 | 1215.67 | 2116.26 | 1101.57 | 2619.24 | 1116.51 | 1731.64 | 2425.36 |
| 1109.63 | 2031.08 | 1151.60 | 2167.19 | 1077.69 | 1923.04 | 1271.54 | 2126.03 | 1174.54 | 2622.24 | 1119.58 | 1743.91 | 2426.23 |
| 1204.65 | 2055.05 | 1160.58 | 2181.08 | 1100.60 | 1944.95 | 1294.59 | 2127.39 | 1223.53 | 2683.42 | 1128.52 | 1754.74 | 2465.18 |
| 1280.69 | 2094.04 | 1207.48 | 2195.10 | 1132.43 | 1952.92 | 1378.67 | 2194.46 | 1243.59 | 2688.28 | 1242.59 | 1755.82 | 2505.45 |
| 1311.55 | 2149.97 | 1299.63 | 2207.90 | 1136.58 | 1978.15 | 1416.62 | 2299.13 | 1301.51 | 2840.53 | 1321.52 | 1767.65 | 2601.39 |
| 1316.62 | 2194.12 | 1372.47 | 2298.92 | 1200.46 | 2038.14 | 1425.84 | 2301.58 | 1358.70 | 3380.56 | 1337.50 | 1829.67 | 2618.32 |
| 1327.56 | 2280.00 | 1391.59 | 2309.96 | 1216.59 | 2039.89 | 1439.55 | 2323.18 | 1457.68 | | 1356.65 | 1832.92 | 2640.36 |
| 1330.57 | 2340.07 | 1396.63 | 2338.18 | 1247.34 | 2158.13 | 1440.65 | 2358.18 | 1526.65 | | 1361.47 | 1837.75 | 2644.23 |
| 1349.61 | 2405.96 | 1446.69 | 2384.71 | 1270.48 | 2221.98 | 1450.82 | 2365.12 | 1592.65 | | 1373.40 | 1875.75 | 2850.61 |
| 1356.65 | 2419.11 | 1483.61 | 2444.00 | 1272.57 | 2230.04 | 1473.79 | 2436.04 | 1623.68 | | 1377.54 | 1914.00 | 2859.50 |
| 1391.56 | 2422.11 | 1495.64 | 2499.22 | 1325.34 | 2233.95 | 1535.74 | 2472.64 | 1623.68 | | 1389.53 | 1923.55 | 3052.68 |
| 1430.69 | 2440.27 | 1500.75 | 2532.38 | 1360.57 | 2270.13 | 1550.92 | 2528.37 | 1661.89 | | 1409.50 | 1937.92 | 3271.87 |
| 1486.59 | 2459.09 | 1531.76 | 2641.09 | 1373.46 | 2322.98 | 1566.75 | 2528.45 | 1702.76 | | 1417.64 | 1940.09 | 3465.06 |
| 1503.61 | 2674.34 | 1567.66 | 2653.54 | 1401.80 | 2413.15 | 1588.97 | 2550.22 | 1749.83 | | 1438.70 | 1958.13 | 3566.10 |
| 1519.59 | 2796.80 | 1590.68 | 2657.06 | 1409.51 | 2419.20 | 1614.78 | 2569.25 | 1752.04 | | 1453.56 | 1972.03 | 3781.80 |
| 1661.63 | 2808.41 | 1622.60 | 2673.14 | 1452.60 | 2494.38 | 1634.90 | 2623.60 | 1812.97 | | 1483.50 | 1992.90 | 4214.15 |
| 1667.73 | 2901.53 | 1636.68 | 2847.29 | 1455.74 | 2501.19 | 1680.02 | 2675.29 | 1817.68 | | 1531.49 | 2029.15 | |
| 1714.75 | 2975.44 | 1676.76 | 2872.64 | 1457.67 | 2555.35 | 1699.04 | 2731.64 | 1852.95 | | 1547.80 | 2056.14 | |
| 1727.93 | 2986.44 | 1684.63 | 2987.25 | 1496.63 | 2578.10 | 1702.07 | 2869.34 | 1886.08 | | 1549.54 | 2058.15 | |
| 1733.78 | 3003.67 | 1730.68 | | 1498.65 | 2631.26 | 1706.74 | 2875.39 | 1895.86 | | 1552.61 | 2113.12 | |
| 1760.03 | | 1740.85 | | 1544.72 | 2641.20 | 1728.75 | 2885.53 | 1896.81 | | 1562.68 | 2143.89 | |
| 1779.77 | | 1797.96 | | 1549.71 | 2716.32 | 1766.95 | 2930.45 | 1898.83 | | 1570.64 | 2189.89 | |
| 1804.92 | | 1862.93 | | 1573.79 | 2777.48 | 1785.87 | 2998.39 | 1939.93 | | 1577.81 | 2190.10 | |
| 1809.03 | | 1872.79 | | 1615.68 | 2885.24 | 1791.73 | 3002.73 | 1952.02 | | 1584.87 | 2199.17 | |
| 1811.71 | | 1876.93 | | 1627.55 | 2922.14 | 1861.03 | 3057.88 | 2069.18 | | 1586.80 | 2221.09 | |
| 1812.85 | | 1892.74 | | 1638.51 | 2989.56 | 1881.27 | 3276.57 | 2098.95 | | 1594.81 | 2260.91 | |
| 1814.85 | | 1907.87 | | 1650.85 | 3077.37 | 1891.89 | 3295.31 | 2289.17 | | 1598.82 | 2275.35 | |
| 1817.84 | | 1968.04 | | 1678.81 | 3224.49 | 1913.98 | 3653.25 | 2307.96 | | 1600.79 | 2294.29 | |
| 1845.85 | | 2004.05 | | 1693.75 | | 1970.96 | 3657.95 | 2318.30 | | 1662.78 | 2299.19 | |
| 1849.90 | | 2005.90 | | 1694.85 | | 2023.15 | | 2386.19 | | 1668.87 | 2308.93 | |
| 1889.01 | | 2024.98 | | 1727.82 | | 2043.38 | | 2401.06 | | 1679.77 | 2337.20 | |
| 1971.01 | | 2063.90 | | 1875.76 | | 2054.10 | | 2469.18 | | 1692.87 | 2364.22 | |

| fr32 | | fr33 | | fr34 | | fr35 | | fr36 | | fr37 | |
|---|---|---|---|---|---|---|---|---|---|---|---|
| 937.70 | 1896.96 | 2777.33 | 1061.56 | 2339.97 | 1063.44 | 2525.10 | 1315.53 | 1286.58 | 3146.72 | 1240.47 | 3252.67 |
| 1047.68 | 1921.04 | 2867.16 | 1065.53 | 2389.14 | 1086.71 | 2587.11 | 1447.65 | 1378.61 | | 1270.49 | 3369.00 |
| 1060.54 | 1925.05 | 2931.64 | 1093.54 | 2478.17 | 1087.54 | 2632.21 | 1487.63 | 1427.70 | | 1286.53 | 3821.04 |
| 1221.58 | 1941.09 | 3053.64 | 1197.60 | 2503.07 | 1126.35 | 2693.40 | 1598.65 | 1446.65 | | 1512.79 | |
| 1264.65 | 1947.07 | 3124.89 | 1203.62 | 2545.26 | 1156.57 | 2697.18 | 1757.78 | 1508.58 | | 1539.71 | |
| 1275.57 | 1957.11 | 3186.62 | 1243.59 | 2598.04 | 1451.41 | 2701.19 | 1780.85 | 1549.64 | | 1653.86 | |
| 1299.56 | 1961.98 | 3347.56 | 1251.51 | 2684.34 | 1555.74 | 2717.13 | 1795.87 | 1641.73 | | 1794.90 | |
| 1315.62 | 1964.95 | 3500.84 | 1378.58 | 2849.05 | 1579.61 | 2725.55 | 1801.87 | 1643.77 | | 1905.90 | |

TABLE IX-continued

| | | | | | | | | | |
|---|---|---|---|---|---|---|---|---|---|
| 1343.66 | 2003.19 | 3799.33 | 1384.61 | 3000.48 | 1597.78 | 2800.49 | 1841.93 | 1644.79 | 1955.82 |
| 1350.71 | 2048.05 | | 1386.58 | | 1637.67 | 2849.49 | 1857.05 | 1668.75 | 1964.88 |
| 1384.56 | 2066.02 | | 1404.69 | | 1653.83 | 2867.53 | 1858.96 | 1746.82 | 1986.07 |
| 1394.65 | 2068.23 | | 1465.70 | | 1669.90 | 2965.74 | 1860.81 | 1760.91 | 2051.10 |
| 1395.73 | 2117.11 | | 1541.60 | | 1688.70 | 3000.60 | 1880.83 | 1833.90 | 2087.96 |
| 1444.55 | 2150.23 | | 1543.71 | | 1696.67 | 3045.42 | 1892.81 | 1906.99 | 2108.13 |
| 1474.72 | 2165.01 | | 1568.82 | | 1764.69 | 3106.57 | 1970.96 | 1920.78 | 2143.15 |
| 1475.70 | 2207.99 | | 1633.66 | | 1807.87 | 3195.86 | 2009.75 | 1968.07 | 2146.06 |
| 1495.65 | 2232.10 | | 1635.64 | | 1824.93 | 3489.99 | 2012.95 | 1972.95 | 2243.31 |
| 1506.77 | 2246.98 | | 1639.79 | | 1878.78 | | 2036.96 | 1980.92 | 2285.18 |
| 1507.73 | 2345.39 | | 1758.86 | | 1910.77 | | 2058.06 | 2070.01 | 2302.15 |
| 1525.87 | 2353.16 | | 1839.76 | | 1912.78 | | 2065.02 | 2085.10 | 2359.38 |
| 1556.82 | 2379.30 | | 1869.75 | | 1976.10 | | 2208.17 | 2114.10 | 2405.49 |
| 1572.69 | 2404.02 | | 1911.99 | | 2109.15 | | 2218.02 | 2188.23 | 2490.18 |
| 1630.69 | 2410.02 | | 1918.92 | | 2123.92 | | 2360.32 | 2206.01 | 2497.16 |
| 1644.89 | 2421.27 | | 1920.02 | | 2124.89 | | 2379.20 | 2277.16 | 2590.18 |
| 1681.87 | 2463.25 | | 1957.04 | | 2146.02 | | 2441.30 | 2362.21 | 2623.09 |
| 1689.80 | 2486.38 | | 1970.96 | | 2179.12 | | 2515.14 | 2402.28 | 2643.34 |
| 1693.76 | 2544.02 | | 2071.00 | | 2233.01 | | 2572.39 | 2489.24 | 2662.32 |
| 1728.72 | 2549.10 | | 2076.06 | | 2308.92 | | 2618.15 | 2558.27 | 2704.40 |
| 1764.87 | 2576.43 | | 2077.95 | | 2363.17 | | 2771.47 | 2617.14 | 2717.29 |
| 1814.01 | 2608.42 | | 2187.80 | | 2373.16 | | 2929.33 | 2698.37 | 2729.30 |
| 1824.78 | 2619.26 | | 2235.19 | | 2393.28 | | 3162.59 | 2867.35 | 2782.52 |
| 1853.98 | 2641.35 | | 2236.12 | | 2421.12 | | 3420.73 | 2881.51 | 2803.22 |
| 1875.01 | 2666.25 | | 2317.40 | | 2422.31 | | | 2894.57 | 2809.60 |
| 1878.91 | 2673.38 | | 2329.84 | | 2512.25 | | | 2928.43 | 2831.55 |

| fr38 | fr39 | fr40 |
|---|---|---|
| 1294.58 | 2962.63 | 1115.58 | 1169.58 |
| 1338.56 | 3054.87 | 1470.66 | 1327.69 |
| 1343.60 | 3076.72 | 1511.55 | 1604.81 |
| 1366.67 | 3177.64 | 1555.84 | 1656.70 |
| 1404.67 | 3243.01 | 1652.84 | 1672.91 |
| 1487.69 | 3255.79 | 1654.77 | 1991.97 |
| 1582.80 | 3464.69 | 1659.92 | 2049.12 |
| 1597.69 | | 1769.94 | 2074.04 |
| 1792.74 | | 1776.95 | 2105.21 |
| 1885.00 | | 1804.00 | 2224.14 |
| 1898.78 | | 1860.92 | 2242.21 |
| 2009.11 | | 1874.92 | 2283.34 |
| 2016.97 | | 1895.02 | 2310.17 |
| 2030.08 | | 1898.87 | 2383.10 |
| 2109.02 | | 1987.09 | 2473.14 |
| 2163.06 | | 2052.08 | 2504.22 |
| 2167.07 | | 2104.99 | 2544.42 |
| 2172.17 | | 2122.15 | 2573.24 |
| 2181.17 | | 2184.07 | 2575.29 |
| 2248.29 | | 2187.19 | 2640.22 |
| 2250.14 | | 2198.75 | 2657.47 |
| 2345.31 | | 2204.14 | 2681.26 |
| 2362.19 | | 2402.37 | 2744.49 |
| 2444.29 | | 2443.37 | 2780.35 |
| 2494.31 | | 2445.26 | 2839.46 |
| 2498.37 | | 2620.47 | 2857.32 |
| 2504.19 | | 2829.38 | 2871.68 |
| 2532.20 | | 3005.19 | 3081.53 |
| 2547.00 | | 3054.72 | 3107.67 |
| 2628.16 | | 3207.55 | 3255.76 |
| 2699.16 | | 3235.61 | 3270.69 |
| 2719.42 | | 3237.34 | 3294.89 |
| 2789.30 | | 3503.58 | 3540.03 |
| 2811.35 | | | 3874.18 |

TABLE X

Modes of combining fractions derived from the secondary runs for separation in the ternary runs combined with automated MS/MS analysis. The results from run 3L are further depicted in Tables 11 and 12 and in the text.

| RUN NUMBER | POOLED FRACTIONS OF MET-OX PEPTIDES |
|---|---|
| 3A | 30–43–56–69 |
| 3B | 31–44–57–70 |
| 3C | 32–45–58–71 |
| 3D | 33–46–59–72 |

TABLE X-continued

Modes of combining fractions derived from the secondary runs for separation in the ternary runs combined with automated MS/MS analysis. The results from run 3L are further depicted in Tables 11 and 12 and in the text.

| RUN NUMBER | POOLED FRACTIONS OF MET-OX PEPTIDES |
|---|---|
| 3E | 34–47–60–73 |
| 3F | 35–48–61–44 |
| 3G | 36–49–62–75 |
| 3H | 37–50–63–76 |
| 3I | 38–51–64–77 |
| 3J | 39–52–65–78 |
| 3K | 40–53–66–79 |
| 3L | 41–54–67–80 |
| 3M | 42–55–68 |

TABLE XI

Table indicating the number of obtained MS/MS-spectra that were obtained and lead to the identification of *E. coil* proteins.

| | | |
|---|---|---|
| total number of CID-spectra | 6437 | |
| total number of identified peptides | 2543 | 39.5% success rate |
| number of unique peptides | 1688 | |
| number of unique proteins | 767 | |

TABLE XII

List of proteins that were identified by LC-MS/MS analysis on MetSO-sorted peptides. The proteins are sorted according to their SwissProt entry name.

| | | |
|---|---|---|
| 1 | 1A1D_ECOLI | (P76316) PUTATIVE 1-AMINOCYCLOPROPANE-1-CARBOXYLATE DEAMINA |
| 2 | 60IM_ECOLI | (P25714) 60 KDA INNER-MEMBRANE PROTEIN. |
| 3 | 6PG9_ECOLI | (P37754) 6-PHOSPHOGLUCONATE DEHYDROGENASE, DECARBOXYLATING |
| 4 | 6PGD_ECOLI | (P00350) 6-PHOSPHOGLUCONATE DEHYDROGENASE, DECARBOXYLATING |
| 5 | AAS_ECOLI | (P31119) AAS BIFUNCTIONAL PROTEIN [INCLUDES: 2-ACYLGLYCEROP |
| 6 | AAT_ECOLI | (P00509) ASPARTATE AMINOTRANSFERASE (EC 2.6.1.1) (TRANSAMIN |
| 7 | ACCA_ECOLI | (P30867) ACETYL-COENZYME A CARBOXYLASE CARBOXYL TRANSFERASE |
| 8 | ACCC_ECOLI | (P24182) BIOTIN CARBOXYLASE (EC 6.3.4.14) (A SUBUNIT OF ACE |
| 9 | ACCD_ECOLI | (P08193) ACETYL-COENZYME A CARBOXYLASE CARBOXYL TRANSFERASE |
| 10 | ACEA_ECOLI | (P05313) ISOCITRATE LYASE (EC 4.1.3.1) (ISOCITRASE) (ISOCIT |
| 11 | ACKA_ECOLI | (P15046) ACETATE KINASE (EC 2.7.2.1) (ACETOKINASE). |
| 12 | ACO1_ECOLI | (P25516) ACONITATE HYDRATASE 1 (EC 4.2.1.3) (CITRATE HYDRO- |
| 13 | ACO2_ECOLI | (P36683) ACONITATE HYDRATASE 2 (EC 4.2.1.3) (CITRATE HYDRO- |
| 14 | ACP_ECOLI | (P02901) ACYL CARRIER PROTEIN (ACP) (CYTOSOLIC ACTIVATING F |
| 15 | ACRB_ECOLI | (P31224) ACRIFLAVINE RESISTANCE PROTEIN B. |
| 16 | ADH3_ECOLI | (P25437) ALCOHOL DEHYDROGENASE CLASS III (EC 1.1.1.1) (GLUT |
| 17 | ADHE_ECOLI | (P17547) ALDEHYDE-ALCOHOL DEHYDROGENASE [INCLUDES: ALCOHOL |
| 18 | AGAL_ECOLI | (P06720) ALPHA-GALACTOSIDASE (EC 3.2.1.22) (MELIBIASE). |
| 19 | AGP_ECOLI | (P19926) GLUCOSE-1-PHOSPHATASE PRECURSOR (EC 3.1.3.10) (G1P |
| 20 | AHPC_ECOLI | (P26427) ALKYL HYDROPEROXIDE REDUCTASE C22 PROTEIN (EC 1.6. |
| 21 | AIDB_ECOLI | (P33224) AIDB PROTEIN. |
| 22 | AK1H_ECOLI | (P00561) BIFUNCTIONAL ASPARTOKINASE/HOMOSERINE DEHYDROGENAS |
| 23 | AK3_ECOLI | (P08660) LYSINE-SENSITIVE ASPARTOKINASE III (EC 2.7.2.4) (A |
| 24 | ALDA_ECOLI | (P25553) ALDEHYDE DEHYDROGENASE A (EC 1.2.1.22) (LACTALDEHY |
| 25 | ALF_ECOLI | (P11604) FRUCTOSE-BISPHOSPHATE ALDOLASE CLASS II (EC 4.1.2. |
| 26 | ALF1_ECOLI | (P71295) FRUCTOSE-BISPHOSPHATE ALDOLASE CLASS I (EC 4.1.2.1 |
| 27 | ALR1_ECOLI | (P29743) ALANINE RACEMASE, BIOSYNTHETIC (EC 5.1.1.1). |
| 28 | ALSB_ECOLI | (P39265) D-ALLOSE-BINDING PERIPLASMIC PROTEIN PRECURSOR (AL |
| 29 | AMPP_ECOLI | (P15034) XAA-PRO AMINOPEPTIDASE (EC 3.4.11.9) (X-PRO AMINOP |
| 30 | AMY2_ECOLI | (P26612) CYTOPLASMIC ALPHA-AMYLASE (EC 3.2.1.1) (1,4-ALPHA- |
| 31 | APPC_ECOLI | (P26459) CYTOCHROME BD-II OXIDASE SUBUNIT I (EC 1.10.3.-). |
| 32 | ARAF_ECOLI | (P02924) L-ARABINOSE-BINDING PERIPLASMIC PROTEIN PRECURSOR |
| 33 | ARCA_ECOLI | (P03026) AEROBIC RESPIRATION CONTROL PROTEIN ARCA (DYE RESI |
| 34 | ARCB_ECOLI | (P22763) AEROBIC RESPIRATION CONTROL SENSOR PROTEIN ARCB (E |
| 35 | ARGA_ECOLI | (P08205) AMINO-ACID ACETYLTRANSFERASE (EC 2.3.1.1) (N-ACETY |
| 36 | AROB_ECOLI | (P07639) 3-DEHYDROQUINATE SYNTHASE (EC 4.6.1.3). |
| 37 | AROK_ECOLI | (P24167) SHIKIMATE KINASE I (EC 2.7.1.71) (SKI). |
| 38 | ARTI_ECOLI | (P30859) ARGININE-BINDIING PERIPLASMIC PROTEIN 1 PRECURSOR. |
| 39 | ASG2_ECOLI | (P00805) L-ASPARAGINASE II PRECURSOR (EC 3.5.1.1) (L-ASPARA |
| 40 | ASMA_ECOLI | (P28249) ASMA PROTEIN PRECURSOR |
| 41 | ASNA_ECOLI | (P00963) ASPARTATE--AMMONIA LIGASE (EC 6.3.1.1) (ASPARAGINE |
| 42 | ASPA_ECOLI | (P04422) ASPARTATE AMMONIA-LYASE (EC 4.3.1.1) (ASPARTASE). |
| 43 | ASSY_ECOLI | (P22767) ARGININOSUCCINATE SYNTHASE (PC 6.3.4.5) (CITRULLIN |
| 44 | ATCU_ECOLI | (Q59385) PROBABLE COPPER-TRANSPORTING ATPASE (EC 3.6.3.4). |
| 45 | ATDA_ECOLI | (P37354) SPERMIDINE N1-ACETYLTRANSFERASE (EC 2.3.1.57)(DIA |
| 46 | ATMA_ECOLI | (P39168) MG(2+) TRANSPORT ATPASE, P-TYPE 1 (PC 3.6.3.2). |

TABLE XII-continued

List of proteins that were identified by LC-MS/MS analysis on MetSO-sorted peptides. The proteins are sorted according to their SwissProt entry name.

| | | |
|---|---|---|
| 47 | ATPA_ECOLI | (P00822) ATP SYNTHASE ALPHA CHAIN (EC 3.6.1.34). |
| 48 | ATPB_ECOLI | (P00824) ATP SYNTHASE BETA CHAIN (EC 3.6.1.34). |
| 49 | ATPD_ECOLI | (P00831) ATP SYNTHASE DELTA CHAIN (EC 3.6.1.34). |
| 50 | ATPF_ECOLI | (P00859) ATP SYNTHASE B CHAIN (EC 3.6.1.34). |
| 51 | ATPG_ECOLI | (P00837) ATP SYNTHASE GAMMA CHAIN (EC 3.6.1.34). |
| 52 | BARA_ECOLI | (P26607) SENSOR PROTEIN BARA (EC 2.7.3.-). |
| 53 | BGAL_ECOLI | (P00722) BETA-GALACTOSIDASE (EC 3.2.1.23) (LACTASE). |
| 54 | BGLA_ECOLI | (Q46829) 6-PHOSPHO-BETA-GLUCOSIDASE BGLA (EC 3.2.1.86). |
| 55 | BGLX_ECOLI | (P33363) PERIPLASMIC BETA-GLUCOSIDASE PRECURSOR (EC 3.2.1.2 |
| 56 | BTUB_ECOLI | (P06129) VITAMIN B12 RECEPTOR PRECURSOR. |
| 57 | BTUE_ECOLI | (P06610) VITAMIN B12 TRANSPORT PERIPLASMIC PROTEIN BTUE. |
| 58 | CAID_ECOLI | (P31551) CARNITINE RACEMASE (EC 5.-.-.-). |
| 59 | CAPP_ECOLI | (P00864) PHOSPHOENOLPYRUVATE CARBOXYLASE (EC 4.1.1.31) (PEP |
| 60 | CARB_ECOLI | (P00968) CARBAMOYL-PHOSPHATE SYNTHASE LARGE CHAIN (EC 6.3.5 |
| 61 | CATA_ECOLI | (P13029) PEROXIDASE/CATALASE HPI (EC 1.11.1.6) (CATALASE-PE |
| 62 | CBPA_ECOLI | (P36659) CURVED DNA-BINDING PROTEIN. |
| 63 | CDD_ECOLI | (P13652) CYTIDINE DEAMINASE (EC 3.5.4.5) (CYTIDINE AMINOHYD |
| 64 | CH10_ECOLI | (P05380) 10 KDA CHAPERONIN (PROTEIN CPN10) (PROTEIN GROES). |
| 65 | CH60_ECOLI | (P06139) 60 KDA CHAPERONIN (PROTEIN CPN60) (GROEL PROTEIN) |
| 66 | CISY_ECOLI | (P00891) CITRATE SYNTHASE (EC 4.1.3.7). |
| 67 | CISZ_ECOLI | (P31660) METHYLCITRATE SYNTHASE (EC 4.1.3.-) (CITRATE SYNTH |
| 68 | CLPA_ECOLI | (P15716) ATP-DEPENDENT CLP PROTEASE ATP-BINDING SUBUNIT CLP |
| 69 | CLPB_ECOLI | (P03815) CLPB PROTEIN (HEAT SHOCK PROTEIN F84.1). |
| 70 | CLPP_ECOLI | (P19245) ATP-DEPENDENT CLP PROTEASE PROTEOLYTIC SUBUNIT (EC |
| 71 | CLPX_ECOLI | (P33138) ATP-DEPENDENT CLP PROTEASE ATP-BINDING SUBUNIT CLP |
| 72 | CLS_ECOLI | (P31071) CARDIOLIPIN SYNTHETASE (EC 2.7.8.-) (CARDIOLIPIN S |
| 73 | CORC_ECOLI | (P77392) MAGNESIUM AND COBALT EFFLUX PROTEIN CORC. |
| 74 | CPPM_ECOLI | (P77541) PUTATIVE CARBOXYVINYL-CARBOXYPHOSPHONATE PHOSPHORY |
| 75 | CPXA_ECOLI | (P08336) SENSOR PROTEIN CPXA (EC 2.7.3.-). |
| 76 | CRP_ECOLI | (P03020) CATABOLITE GENE ACTIVATOR (CAMP RECEPTOR PROTEIN) |
| 77 | CSPA_ECOLI | (P15277) COLD SHOCK PROTEIN CSPA (CSP-A) (7.4 KDA COLD SHOC |
| 78 | CSPC_ECOLI | (P36996) COLD SHOCK-LIKE PROTEIN CSPC (CSP-C). |
| 79 | CSPE_ECOLI | (P36997) COLD SHOCK-LIKE PROTEIN CSPE (CSP-E). |
| 80 | CYDA_ECOLI | (P11026) CYTOCHROME D UBIQUINOL OXIDASE SUBUNIT I (EC 1.10. |
| 81 | CYOA_ECOLI | (P18400) UBIQUINOL OXIDASE POLYPEPTIDE II PRECURSOR (EC 1.1 |
| 82 | CYSE_ECOLI | (P05796) SERINE ACETYLTRANSFERASE (EC 2.3.1.30) (SAT). |
| 83 | CYSG_ECOLI | (P11098) SIROHEME SYNTHASE [INCLUDES: UROPORPHYRIN-III C-ME |
| 84 | CYSK_ECOLI | (P11096) CYSTEINE SYNTHASE A (EC 4.2.99.8) (O-ACETYLSERINE |
| 85 | CYSM_ECOLI | (P16703) CYSTEINE SYNTHASE B (EC 4.2.99.8) (O-ACETYLSERINE |
| 86 | DACA_ECOLI | (P04287) PENICILLIN-BINDING PROTEIN 5 PRECURSOR (D-ALANYL-D |
| 87 | DACC_ECOLI | (P08506) PENICILLIN-BINDING PROTEIN 6 PRECURSOR (D-ALANYL-D |
| 88 | DAPA_ECOLI | (P05640) DIHYDRODIPICOLINATE SYNTHASE (EC 4.2.1.52) (DHDPS) |
| 89 | DAPB_ECOLI | (P04036) DIHYDRODIPICOLINATE REDUCTASE (EC 1.3.1.26) (DHPR) |
| 90 | DBHA_ECOLI | (P02342) DNA-BINDING PROTEIN HU-ALPHA (NS2) (HU-2). |
| 91 | DBHB_ECOLI | (P02341) DNA-BINDING PROTEIN HU-BETA (NS1) (HU-1). |
| 92 | DCEA_ECOLI | (P80063) GLUTAMATE DECARBOXYLASE ALPHA (EC 4.1.1.15) (GAD-A |
| 93 | DCEB_ECOLI | (P28302) GLUTAMATE DECARBOXYLASE BETA (EC 4.1.1.15) (GAD-BE |
| 94 | DCLY_ECOLI | (P23892) LYSINE DECARBOXYLASE, INDUCIBLE (EC 4.1.1.18) (LDC |
| 95 | DCP_ECOLI | (P24171) PEPTIDYL-DIPEPTIDASE DCP (EC 3.4.15.5) (DIPEPTIDYL |
| 96 | DCRB_ECOLI | (P37620) DCRB PROTEIN PRECURSOR. |
| 97 | DCUP_ECOLI | (P29680) UROPORPHYRINOGEN DECARBOXYLASE (EC 4.1.1.37) (URO- |
| 98 | DEAD_ECOLI | (P23304) COLD-SHOCK DEAD-BOX PROTEIN A (ATP-DEPENDENT RNA H |
| 99 | DEGP_ECOLI | (P09376) PROTEASE DO PRECURSOR (EC 3.4.21.-). |
| 100 | DEOB_ECOLI | (P07651) PHOSPHOPENTOMUTASE (EC 5.4.2.7) (PHOSPHODEOXYRIBOM |
| 101 | DEOC_ECOLI | (P00882) DEOXYRIBOSE-PHOSPHATE ALDOLASE (EC 4.1.2.4) (PHOSP |
| 102 | DEOD_ECOLI | (P09743) PURINE NUCLEOSIDE PHOSPHORYLASE (EC 2.4.2.1) (INOS |
| 103 | DEOR_ECOLI | (P06217) DEOXYRIBOSE OPERON REPRESSOR. |
| 104 | DGAL_ECOLI | (P02927) D-GALACTOSE-BINDING PERIPLASMIC PROTEIN PRECURSOR |
| 105 | DHAB_ECOLI | (P17445) BETAINE ALDEHYDE DEHYDROGENASE (EC 1.2.1.8) (BADH) |
| 106 | DHAS_ECOLI | (P00353) ASPARTATE-SEMIALDEHYDE DEHYDROGENASE (EC 1.2.1.11) |
| 107 | DHPS_ECOLI | (P26282) DIHYDROPTEROATE SYNTHASE (EC 2.5.1.15) (DHPS) (DIH |
| 108 | DHSA_ECOLI | (P10444) SUCCINATE DEHYDROGENASE FLAVOPROTEIN SUBUNIT (EC 1 |
| 109 | DHSB_ECOLI | (P07014) SUCCINATE DEHYDROGENASE IRON-SULFUR PROTEIN (EC 1. |
| 110 | DINF_ECOLI | (P28303) DNA-DAMAGE-INDUCIBLE PROTEIN F. |
| 111 | DLD_ECOLI | (P06149) D-LACTATE DEHYDROGENASE (EC 1.1.1.28). |
| 112 | DLDH_ECOLI | (P00391) DIHYDROLIPOAMIDE DEHYDROGENASE (EC 1.8.1.4) (E3 CO |
| 113 | DMSA_ECOLI | (P18775) ANAEROBIC DIMETHYL SULFOXIDE REDUCTASE CHAIN A PRE |
| 114 | DNAB_ECOLI | (P03005) REPLICATIVE DNA HELICASE (EC 3.6.1.-). |
| 115 | DNAJ_ECOLI | (P08622) CHAPERONE PROTEIN DNAJ (HEAT SHOCK PROTEIN J) (HSP |
| 116 | DNAK_ECOLI | (P04475) CHAPERONE PROTEIN DNAK (HEAT SHOCK PROTEIN 70) (HE |
| 117 | DP3B_ECOLI | (P00583) DNA POLYMERASE III, BETA CHAIN (EC 2.7.7.7). |
| 118 | DP3X_ECOLI | (P06710) DNA POLYMERASE III SUBUNIT TAU (EC 2.7.7.7) [CONTA |
| 119 | DPO1_ECOLI | (P00582) DNA POLYMERASE I (EC 2.7.7.7) (POL I). |
| 120 | DPPA_ECOLI | (P23847) PERIPLASMIC DIPEPTIDE TRANSPORT PROTEIN PRECURSOR |
| 121 | DPS_ECOLI | (P27430) DNA PROTECTION DURING STARVATION PROTEIN. |
| 122 | DSBA_ECOLI | (P24991) THIOL:DISULFIDE INTERCHANGE PROTEIN DSBA PRECURSOR |

TABLE XII-continued

List of proteins that were identified by LC-MS/MS analysis on MetSO-sorted peptides. The proteins are sorted according to their SwissProt entry name.

| | | |
|---|---|---|
| 123 | DSBC_ECOLI | (P21892) THIOL:DISULFIDE INTERCHANGE PROTEIN DSBC PRECURSOR |
| 124 | DSBG_ECOLI | (P77202) THIOL:DISULFIDE INTERCHANGE PROTEIN DSBG PRECURSOR |
| 125 | DXS_ECOLI | (P77488) 1-DEOXY-D-XYLULOSE 5-PHOSPHATE SYNTHASE (EC 2.2.-. |
| 126 | E4PD_ECOLI | (P11603) D-ERYTHROSE 4-PHOSPHATE DEHYDROGENASE (EC 1.2.1.-) |
| 127 | EFG_ECOLI | (P02996) ELONGATION FACTOR G (EF-G). |
| 128 | EFTS_ECOLI | (P02997) ELONGATION FACTOR TS (EF-TS). |
| 129 | EFTU_ECOLI | (P02990) ELONGATION FACTOR TU (EF-TU) (P-43). |
| 130 | EMRA_ECOLI | (P27303) MULTIDRUG RESISTANCE PROTEIN A. |
| 131 | ENGA_ECOLI | (P77254) PROBABLE GTP-BINDING PROTEIN ENGA. |
| 132 | ENGB_ECOLI | (P24253) PROBABLE GTP-BINDING PROTEIN ENGB. |
| 133 | ENO_ECOLI | (P08324) ENOLASE (EC 4.2.1.11) (2-PHOSPHOGLYCERATE DEHYDRAT |
| 134 | ENTB_ECOLI | (P15048) ISOCHORISMATASE (EC 3.3.2.1) (2,3 DIHYDRO-2,3 DIHY |
| 135 | ERFK_ECOLI | (P39176) PROTEIN ERFK/SRFK PRECURSOR. |
| 136 | EUTQ_ECOLI | (P76555) ETHANOLAMINE UTILIZATION PROTEIN EUTQ. |
| 137 | EVGA_ECOLI | (P30854) PUTATIVE POSITIVE TRANSCRIPTION REGULATOR EVGA. |
| 138 | EX1_ECOLI | (P04995) EXODEOXYRIBONUCLEASE I (EC 3.1.11.1) (EXONUCLEASE |
| 139 | EX3_ECOLI | (P09030) EXODEOXYRIBONUCLEASE III (EC 3.1.11.2) (EXONUCLEAS |
| 140 | FABA_ECOLI | (P18391) 3-HYDROXYDECANOYL-[ACYL-CARRIER-PROTEIN] DEHYDRATA |
| 141 | FABB_ECOLI | (P14926) 3-OXOACYL-[ACYL-CARRIER-PROTEIN] SYNTHASE I (EC 2. |
| 142 | FABD_ECOLI | (P25715) MALONYL COA-ACYL CARRIER PROTEIN TRANSACYLASE (EC |
| 143 | FABF_ECOLI | (P39435) 3-OXOACYL-[ACYL-CARRIER-PROTEIN] SYNTHASE II (EC 2 |
| 144 | FABG_ECOLI | (P25716) 3-OXOACYL-[ACYL-CARRIER PROTEIN] REDUCTASE (EC 1.1 |
| 145 | FABH_ECOLI | (P24249) 3-OXOACYL-[ACYL-CARRIER-PROTEIN] SYNTHASE III (EC |
| 146 | FABI_ECOLI | (P29132) ENOYL-[ACYL-CARRIER-PROTEIN] REDUCTASE [NADH] (EC |
| 147 | FADB_ECOLI | (P21177) FATTY OXIDATION COMPLEX ALPHA SUBUNIT [INCLUDES: E |
| 148 | FARR_ECOLI | (P13669) FATTY ACYL RESPONSIVE REGULATOR (P30 PROTEIN). |
| 149 | FDNH_ECOLI | (P24184) FORMATE DEHYDROGENASE, NITRATE-INDUCIBLE, IRON-SUL |
| 150 | FENR_ECOLI | (P28861) FERREDOXIN--NADP REDUCTASE (EC 1.18.1.2) (FNR) (FL |
| 151 | FIC_ECOLI | (P20605) CELL FILAMENTATION PROTEIN FIC. |
| 152 | FIMC_ECOLI | (P31697) CHAPERONE PROTEIN FIMC PRECURSOR. |
| 153 | FIMD_ECOLI | (P30130) OUTER MEMBRANE USHER PROTEIN FIMD PRECURSOR. |
| 154 | FIS_ECOLI | (P11028) DNA-BINDING PROTEIN FIS (FACTOR-FOR-INVERSION STIM |
| 155 | FKBB_ECOLI | (P39311) FKBP-TYPE 22 KDA PEPTIDYL-PROLYL CIS-TRANS ISOMERA |
| 156 | FLGH_ECOLI | (P75940) FLAGELLAR L-RING PROTEIN PRECURSOR (BASAL BODY L-R |
| 157 | FLIY_ECOLI | (P39174) CYSTINE-BINDING PERIPLASMIC PROTEIN PRECURSOR (CBP |
| 158 | FM1A_ECOLI | (P04128) TYPE-1 FIMBRIAL PROTEIN, A CHAIN PRECURSOR (TYPE-1 |
| 159 | FMT_ECOLI | (P23882) METHIONYL-TRNA FORMYLTRANSFERASE (EC 2.1.2.9). |
| 160 | FNR_ECOLI | (P03019) FUMARATE AND NITRATE REDUCTION REGULATORY PROTEIN. |
| 161 | FOLX_ECOLI | (P80449) D-ERYTHRO-7,8-DIHYDRONEOPTERIN TRIPHOSPHATE EPIMER |
| 162 | FRDA_ECOLI | (P00363) FUMARATE REDUCTASE FLAVOPROTEIN SUBUNIT (EC 1.3.99 |
| 163 | FRDB_ECOLI | (P00364) FUMARATE REDUCTASE IRON-SULFUR PROTEIN (EC 1.3.99. |
| 164 | FRE_ECOLI | (P23486) NAD(P)H-FLAVIN REDUCTASE (EC 1.6.8.-) (NAD(P)H:FLA |
| 165 | FRVR_ECOLI | (P32152) PUTATIVE FRV OPERON REGULATORY PROTEIN. |
| 166 | FTSH_ECOLI | (P28691) CELL DIVISION PROTEIN FTSH (EC 3.4.24.-). |
| 167 | FTSY_ECOLI | (P10121) CELL DIVISION PROTEIN FTSY. |
| 168 | FTSZ_ECOLI | (P06138) CELL DIVISION PROTEIN FTSZ. |
| 169 | FUCI_ECOLI | (P11552) L-FUCOSE ISOMERASE (EC 5.3.1.25). |
| 170 | FUCO_ECOLI | (P11549) LACTALDEHYDE REDUCTASE (EC 1.1.1.77) (PROPANEDIOL |
| 171 | FUMA_ECOLI | (P00923) FUMARATE HYDRATASE CLASS I, AEROBIC (EC 4.2.1.2) ( |
| 172 | FUMB_ECOLI | (P14407) FUMARATE HYDRATASE CLASS I, ANAEROBIC (EC 4.2.1.2) |
| 173 | FUMC_ECOLI | (P05042) FUMARATE HYDRATASE CLASS II (EC 4.2.1.2) (FUMARASE |
| 174 | FUR_ECOLI | (P06975) FERRIC UPTAKE REGULATION PROTEIN (FERRIC UPTAKE RE |
| 175 | G3P1_ECOLI | (P06977) GLYCERALDEHYDE 3-PHOSPHATE DEHYDROGENASE A (EC 1.2 |
| 176 | G6PD_ECOLI | (P22992) GLUCOSE-6-PHQSPHATE 1-DEHYDROGENASE (EC 1.1.1.49) |
| 177 | G6PI_ECOLI | (P11537) GLUCOSE-6-PHOSPHATE ISOMERASE (GPI) (EC 5.3.1.9) ( |
| 178 | GABT_ECOLI | (P22256) 4-AMINOBUTYRATE AMINOTRANSFERASE (EC 2.6.1.19) (GA |
| 179 | GALE_ECOLI | (P09147) UDP-GLUCOSE 4-EPIMERASE (EC 5.1.3.2) (GALACTOWALDE |
| 180 | GALF_ECOLI | (P78083) UTP--GLUCOSE-1-PHOSPHATE URIDYLYLTRANSFERASE (EC 2 |
| 181 | GALU_ECOLI | (P25520) UTP--GLUCOSE-1-PHOSPHATE URIDYLYLTRANSFERASE (EC 2 |
| 182 | GARD_ECOLI | (P39829) D-GALACTARATE DEHYDRATASE (EC 4.2.1.42) (GALCD). |
| 183 | GARL_ECOLI | (P23522) 5-KETO-4-DEOXY-D-GLUCARATE ALDOLASE (EC 4.1.2.-) ( |
| 184 | GARR_ECOLI | (P23523) 2-HYDROXY-3-OXOPROPIONATE REDUCTASE (EC 1.1.1.60) |
| 185 | GCPE_ECOLI | (P27433) GCPE PROTEIN (PROTEIN E). |
| 186 | GCST_ECOLI | (P27248) AMINOMETHYLTRANSFERASE (EC 2.1.2.10) (GLYCINE CLEA |
| 187 | GENK_ECOLI | (P02988) PROTEIN K. |
| 188 | GIDA_ECOLI | (P17112) GLUCOSE INHIBITED DIVISION PROTEIN A. |
| 189 | GLCF_ECOLI | (P52074) GLYCOLATE OXIDASE IRON-SULFUR SUBUNIT. |
| 190 | GLDA_ECOLI | (P32665) GLYCEROL DEHYDROGENASE (EC 1.1.1.6) (GLDH) |
| 191 | GLF_ECOLI | (P37747) UDP-GALACTOPYRANOSE MUTASE (EC 5.4.99.9). |
| 192 | GLGA_ECOLI | (P08323) GLYCOGEN SYNTHASE (EC 2.4.1.21) (STARCH [BACTERIAL |
| 193 | GLGB_ECOLI | (P07762) 1,4-ALPHA-GLUCAN BRANCHING ENZYME (EC 2.4.1.18) (G |
| 194 | GLGX_ECOLI | (P15067) GLYCOGEN OPERON PROTEIN GLGX (EC 3.2.1.-). |
| 195 | GLMS_ECOLI | (P17169) GLUCOSAMINE--FRUCTOSE-6-PHOSPHATE AMINOTRANSFERASE |
| 196 | GLMU_ECOLI | (P17114) UDP-N-ACETYLGLUCOSAMINE PYROPHOSPHORYLASE (EC 2.7. |
| 197 | GLNA_ECOLI | (P06711) GLUTAMINE SYNTHETASE (EC 6.3.1.2) (GLUTAMATE--AMMO |
| 198 | GLNB_ECOLI | (P05826) NITROGEN REGULATORY PROTEIN P-II 1. |

TABLE XII-continued

List of proteins that were identified by LC-MS/MS analysis on MetSO-sorted peptides. The proteins are sorted according to their SwissProt entry name.

| | | |
|---|---|---|
| 199 | GLNQ_ECOLI | (P10346) GLUTAMINE TRANSPORT ATP-BINDING PROTEIN GLNQ. |
| 200 | GLO2_ECOLI | (Q47677) PROBABLE HYDROXYACYLGLUTATHIONE HYDROLASE (EC 3.1. |
| 201 | GLPA_ECOLI | (P13032) ANAEROBIC GLYCEROL-3-PHOSPHATE DEHYDROGENASE SUBUN |
| 202 | GLPB_ECOLI | (P13033) ANAEROBIC GLYCEROL-3-PHOSPHATE DEHYDROGENASE SUBUN |
| 203 | GLPC_ECOLI | (P13034) ANAEROBIC GLYCEROL-3-PHOSPHATE DEHYDROGENASE SUBUN |
| 204 | GLPD_ECOLI | (P13035) AEROBIC GLYCEROL-3-PHOSPHATE DEHYDROGENASE (EC 1.1 |
| 205 | GLPK_ECOLI | (P08859) GLYCEROL KINASE (EC 2.7.1.30) (ATP:GLYCEROL 3-PHOS |
| 206 | GLPQ_ECOLI | (P09394) GLYCEROPHOSPHORYL DIESTER PHOSPHODIESTERASE, PERIP |
| 207 | GLPT_ECOLI | (P08194) GLYCEROL-3-PHOSPHATE TRANSPORTER (G-3-P TRANSPORTE |
| 208 | GLPX_ECOLI | (P28860) GLPX PROTEIN. |
| 209 | GLR2_ECOLI | (P39811) GLUTAREDOXIN 2 (GRX2). |
| 210 | GLTB_ECOLI | (P09831) GLUTAMATE SYNTHASE [NADPH] LARGE CHAIN PRECURSOR ( |
| 211 | GLTL_ECOLI | (P41076) GLUTAMATE/ASPARTATE TRANSPORT ATP-BINDING PROTEIN |
| 212 | GLYA_ECOLI | (P00477) SERINE HYDROXYMETHYLTRANSFERASE (EC 2.1.2.1) (SERI |
| 213 | GNTR_ECOLI | (P46860) GLUCONATE UTILIZATION SYSTEM GNT-I TRANSCRIPTIONAL |
| 214 | GPH_ECOLI | (P32662) PHOSPHOGLYCOLATE PHOSPHATASE (EC 3.1.3.18) (PGP). |
| 215 | GREA_ECOLI | (P21346) TRANSCRIPTION ELONGATION FACTOR GREA (TRANSCRIPT C |
| 216 | GRPE_ECOLI | (P09372) GRPE PROTEIN (HSP-70 COFACTOR) (HEAT SHOCK PROTEIN |
| 217 | GSA_ECOLI | (P23893) GLUTAMATE-1-SEMIALDEHYDE 2,1-AMINOMUTASE (EC 5.4.3 |
| 218 | GSH1_ECOLI | (P06980) GLUTAMATE--CYSTEINE LIGASE (EC 6.3.2.2) (GAMMA-GLU |
| 219 | GSHB_ECOLI | (P04425) GLUTATHIONE SYNTHETASE (BC 6.3.2.3) (GLUTATHIONE S |
| 220 | GSHR_ECOLI | (P06715) GLUTATHIONE REDUCTASE (EC 1.6.4.2) (GR) (GRASE). |
| 221 | GT_ECOLI | (P39100) GLUTATHIONE S-TRANSFERASE (EC 2.5.1.18). |
| 222 | GUAA_ECOLI | (P04079) GMP SYNTHASE [GLUTAMTIME-HYDROLYZING] (EC 6.3.5.2) |
| 223 | GUDH_ECOLI | (P76637) GLUCARATE DEHYDRATASE (EC 4.2.1.40) (GDH) (GLUCD). |
| 224 | GUDX_ECOLI | (Q46915) GLUCARATE DEHYDRATASE RELATED PROTEIN (EC 4.2.1.-) |
| 225 | GYRA_ECOLI | (P09097) DNA GYRASE SUBUNIT A (EC 5.99.1.3). |
| 226 | GYRB_ECOLI | (P06982) DNA GYRASE SUBUNIT B (EC 5.99.1.3). |
| 227 | HDEB_ECOLI | (P26605) PROTEIN HDEB PRECURSOR (10K-L PROTEIN). |
| 228 | HDHA_ECOLI | (P25529) 7-ALPHA-HYDROXYSTEROID DEHYDROGENASE (EC 1.1 .1.159 |
| 229 | HEM2_ECOLI | (P15002) DELTA-AMINOLEVULINIC ACID DEHYDRATASE (EC 4.2.1.24 |
| 230 | HEM6_ECOLI | (P36553) COPROPORPHYRINOGEN III OXIDASE, AEROBIC (EC 1.3.3. |
| 231 | HEMX_ECOLI | (P09127) PUTATIVE UROPORPHYRIN-III C-METHYLTRANSFERASE (EC |
| 232 | HEPA_ECOLI | (P23852) RNA POLYMERASE ASSOCIATED PROTEIN (ATP-DEPENDENT H |
| 233 | HFLC_ECOLI | (P25661) HFLC PROTEIN (EC 3.4.-.-). |
| 234 | HFLK_ECOLI | (P25662) HFLK PROTEIN. |
| 235 | HHA_ECOLI | (P23870) HAEMOLYSIN EXPRESSION MODULATING PROTEIN. |
| 236 | HISI_ECOLI | (P10366) ATP PHOSPHORIBOSYLTRANSFERASE (EC 2.4.2.17). |
| 237 | HISJ_ECOLI | (P39182) HISTIDINE-BINDING PERIPLASMIC PROTEIN PRECURSOR (H |
| 238 | HLPA_ECOLI | (P11457) HISTONE-LIKE PROTEIN HLP-1 PRECURSOR (DNA-BINDING |
| 239 | HMPA_ECOLI | (P24232) FLAVOHEMOPROTEIN (HEMOGLOBIN-LIKE PROTEIN) (FLAVOH |
| 240 | HNR_ECOLI | (P37055) HNR PROTEIN. |
| 241 | HNS_ECOLI | (P08936) DNA-BINDING PROTEIN H-NS (HISTONE-LIKE PROTEIN HLP |
| 242 | HOLA_ECOLI | (P28630) DNA POLYMERASE III, DELTA SUBUNIT (EC 2.7.7.7). |
| 243 | HOLE_ECOLI | (P28689) DNA POLYMERASE III, THETA SUBUNIT (EC 2.7.7.7). |
| 244 | HRPA_ECOLI | (P43329) ATP-DEPENDENT HELICASE HRPA. |
| 245 | HSLU_ECOLI | (P32168) ATP-DEPENDENT HSL PROTEASE ATP-BINDING SUBUNIT HSL |
| 246 | HTPG_ECOLI | (P10413) HEAT SHOCK PROTEIN HTPG (HIGH TEMPERATURE PROTEIN |
| 247 | HTRL_ECOLI | (P25666) HTRL PROTEIN. |
| 248 | HYPE_ECOLI | (P24193) HYDROGENASE ISOENZYMES FORMATION PROTEIN HYPE. |
| 249 | ICLR_ECOLI | (P16528) ACETATE OPERON REPRESSOR. |
| 250 | IDH_ECOLI | (P08200) ISOCITRATE DEHYDROGENASE [NADP] (EC 1.1.1.42) (OXA |
| 251 | IF2_ECOLI | (P02995) TRANSLATION INITIATION FACTOR IF-2. |
| 252 | IF3_ECOLI | (P02999) TRANSLATION INITIATION FACTOR IF-3. |
| 253 | IHFA_ECOLI | (P06984) INTEGRATION HOST FACTOR ALPHA-SUBUNIT (IHF-ALPHA). |
| 254 | IHFB_ECOLI | (P08756) INTEGRATION HOST FACTOR BETA-SUBUNIT (IHF-BETA). |
| 255 | IMDH_ECOLI | (P06981) INOSINE-5'-MONOPHOSPHATE DEHYDROGENASE (EC 1.1.1.2 |
| 256 | INGK_ECOLI | (P22937) INOSINE-GUANOSINE KINASE (EC 2.7.1.73). |
| 257 | INH5_ECOLI | (P76071) TRANSPOSASE INSH FOR INSERTION SEQUENCE ELEMENT IS |
| 258 | INSE_ECOLI | (P77681) TRANSPOSASE INSE FOR INSERTION SEQUENCE IS3A/B/C/D |
| 259 | IPYR_ECOLI | (P17288) INORGANIC PYROPHOSPHATASE (EC 3.6.1.1) (PYROPHOSPH |
| 260 | ISCS_ECOLI | (P39171) CYSTEINE DESULFURASE (EC 4.4.1.-) (THII TRANSPERSU |
| 261 | ISPB_ECOLI | (P19641) OCTAPRENYL-DIPHOSPHATE SYNTHASE (EC 2.5.1.-) (OCTA |
| 262 | K6P1_ECOLI | (P06998) 6-PHOSPHOFRUCTOKINASE ISOZYME 1 (EC 2.7.1.11) (PHO |
| 263 | K6P2_ECOLI | (P06999) 6-PHOSPHOFRUCTOKINASE ISOZYME 2 (EC 2.7.1.11) (PHO |
| 264 | KAD_ECOLI | (P05082) ADENYLATE KINASE (EC 2.7.4.3) (ATP-AMP TRANSPHOSPH |
| 265 | KBL_ECOLI | (P07912) 2-AMINO-3-KETOBUTYRATE COENZYME A LIGASE (EC 2.3.1 |
| 266 | KCY_ECOLI | (P23863) CYTIDYLATE KINASE (EC 2.7.4.14) (CK) (CYTIDINE MON |
| 267 | KDSA_ECOLI | (P17579) 2-DEHYDRO-3-DEOXYPHOSPHOOCTONATE ALDOLASE (EC 4.1. |
| 268 | KEA1_ECOLI | (Q52278) KLEA PROTEIN (KCRA1 PROTEIN). |
| 269 | KPRS_ECOLI | (P08330) RIBOSE-PHOSPHATE PYROPHOSPHOKINASE (EC 2.7.6.1) (P |
| 270 | KPY1_ECOLI | (P14178) PYRUVATE KINASE I (EC 2.7.1.40) (PK-1). |
| 271 | KPY2_ECOLI | (P21599) PYRUVATE KINASE II (EC 2.7.1.40) (PK-2). |
| 272 | KSGA_ECOLI | (P06992) DIMETHYLADENOSINE TRANSFERASE (EC 2.1.1.-) (S-ADEN |
| 273 | LACI_ECOLI | (P03023) LACTOSE OPERON REPRESSOR. |
| 274 | LCFA_ECOLI | (P29212) LONG-CHAIN-FATTY-ACID--COA LIGASE (EC 6.2.1.3) (LO |

TABLE XII-continued

List of proteins that were identified by LC-MS/MS analysis on MetSO-sorted peptides. The proteins are sorted according to their SwissProt entry name.

| | | |
|---|---|---|
| 275 | LDHD_ECOLI | (P52643) D-LACTATE DEHYDROGENASE (EC 1.1.1.28) (D-LDH). |
| 276 | LEPA_ECOLI | (P07682) GTP-BINDING PROTEIN LEPA. |
| 277 | LEXA_ECOLI | (P03033) LEXA REPRESSOR (EC 3.4.21.88). |
| 278 | LIPA_ECOLI | (P25845) LIPOIC ACID SYNTHETASE (LIP-SYN) (LIPOATE SYNTHASE |
| 279 | LLDD_ECOLI | (P33232) L-LACTATE DEHYDROGENASE (CYTOCHROME) (EC 1.1.2.3). |
| 280 | LOLA_ECOLI | (P39178) OUTER-MEMBRANE LIPOPROTEINS CARRIER PROTEIN PRECUR |
| 281 | LOLB_ECOLI | (P24208) OUTER-MEMBRANE LIPOPROTEIN LOLB PRECURSOR. |
| 282 | LON_ECOLI | (P08177) ATP-DEPENDENT PROTEASE LA (EC 3.4.21.53). |
| 283 | LPCA_ECOLI | (P51001) PHOSPHOHEPTOSE ISOMERASE (EC 5.-.-.-). |
| 284 | LPXB_ECOLI | (P10441) LIPID-A-DISACCHARIDE SYNTHASE (EC 2.4.1.182). |
| 285 | LPXD_ECOLI | (P21645) UDP-3-O-[3-HYDROXYMYRISTOYL] GLUCOSAMINE N-ACYLTRA |
| 286 | LRHA_ECOLI | (P36771) PROBABLE TRANSCRIPTIONAL REGULATOR LRHA. |
| 287 | LUXS_ECOLI | (P45578) AUTOINDUCER-2 PRODUCTION PROTEIN LUXS (AI-2 SYNTHE |
| 288 | MALE_ECOLI | (P02928) MALTOSE-BINDING PERIPLASMIC PROTEIN PRECURSOR (MAL |
| 289 | MALQ_ECOLI | (P15977) 4-ALPHA-GLUCANOTRANSFERASE (EC 2.4.1.25) (AMYLOMAL |
| 290 | MALY_ECOLI | (P23256) MALY PROTEIN (EC 2.6.1.-). |
| 291 | MANA_ECOLI | (P00946) MANNOSE-6-PHOSPHATE ISOMERASE (EC 5.3.1.8) (PHOSPH |
| 292 | MAO1_ECOLI | (P26616) NAD-DEPENDENT MALIC ENZYME (EC 1.1.1.38) (NAD-ME). |
| 293 | MAO2_ECOLI | (P76558) NADP-DEPENDENT MALIC ENZYME (EC 1.1.1.40) (NADP-ME |
| 294 | MASY_ECOLI | (P08997) MALATE SYNTHASE A (EC 4.1.3.2) (MSA). |
| 295 | MASZ_ECOLI | (P37330) MALATE SYNTHASE G (EC 4.1.3.2) (MSG). |
| 296 | MBHL_ECOLI | (P19927) HYDROGENASE-1 LARGE CHAIN (EC 1.18.99.1) (NIFE HYD |
| 297 | MBHM_ECOLI | (P37181) HYDROGENASE-2 LARGE CHAIN PRECURSOR (EC 1.18.99.1) |
| 298 | MDH_ECOLI | (P06994) MALATE DEHYDROGENASE (EC 1.1.1.37). |
| 299 | MENB_ECOLI | (P27290) NAPHTHOATE SYNTHASE (EC 4.1.3.36) (DIHYDROXYNAPHTH |
| 300 | MEND_ECOLI | (P17109) MENAQUINONE BIOSYNTHESIS PROTEIN MEND [INCLUDES: 2 |
| 301 | MENG_ECOLI | (P32165) S-ADENOSYLMETHIONINE:2-DEMETHYLMENAQUINONE METHYLT |
| 302 | METJ_ECOLI | (P08338) MET REPRESSOR (MET REGULON REGULATORY PROTEIN METJ |
| 303 | METK_ECOLI | (P04384) S-ADENOSYLMETHIONINE SYNTHETASE (PC 2.5.1.6) (METH |
| 304 | MFD_ECOLI | (P30958) TRANSCRIPTION-REPAIR COUPLING FACTOR (TRCF). |
| 305 | MGLA_ECOLI | (P23199) GALACTOSIDE TRANSPORT ATP-BINDING PROTEIN MGLA. |
| 306 | MGSA_ECOLI | (P37066) METHYLGLYOXAL SYNTHASE (EC 4.2.99.11) (MGS). |
| 307 | MHPC_ECOLI | (P77044) 2-HYDROXY-6-KETONONA-2,4-DIENEDIOIC ACID HYDROLASE |
| 308 | MHPF_ECOLI | (P77580) ACETALDEHYDE DEHYDROGENASE (EC 1.2.1.10) (ACETALDE |
| 309 | MIAA_ECOLI | (P16384) TRNA DELTA(2)-ISOPENTENYLPYROPHOSPHATE TRANSFERASE |
| 310 | MIND_ECOLI | (P18197) SEPTUM SITE-DETERMINING PROTEIN MIND (CELL DIVISIO |
| 311 | MINE_ECOLI | (P18198) CELL DIVISION TOPOLOGICAL SPECIFICITY FACTOR. |
| 312 | MIPA_ECOLI | (P77486) MLTA-INTERACTING PROTEIN PRECURSOR. |
| 313 | MOAB_ECOLI | (P30746) MOLYBDENUM COFACTOR BIOSYNTHESIS PROTEIN B. |
| 314 | MOAC_ECOLI | (P30747) MOLYBDENUM COFACTOR BIOSYNTHESIS PROTEIN C. |
| 315 | MOAE_ECOLI | (P30749) MOLYBDOPTERIN [MPT] CONVERTING FACTOR, SUBUNIT 2 ( |
| 316 | MOG_ECOLI | (P28694) MOLYBDOPTERIN BIOSYNTHESIS MOG PROTEIN. |
| 317 | MOLR_ECOLI | (P33345) MOLYBDATE METABOLISM REGULATOR. |
| 318 | MPPA_ECOLI | (P77348) PERIPLASMIC MUREIN PEPTIDE-BINDING PROTEIN PRECURS |
| 319 | MPRA_ECOLI | (P24201) TRANSCRIPTIONAL REPRESSOR MPRA (EMRR PROTEIN). |
| 320 | MREB_ECOLI | (P13519) ROD SHAPE-DETERMINING PROTEIN MREB. |
| 321 | MRSA_ECOLI | (P31120) MRSA PROTEIN. |
| 322 | MSBA_ECOLI | (P27299) PROBABLE TRANSPORT ATP-BINDING PROTEIN MSBA. |
| 323 | MSYB_ECOLI | (P25738) ACIDIC PROTEIN MSYB. |
| 324 | MTLD_ECOLI | (P09424) MANNITOL-1-PHOSPHATE 5-DEHYDROGENASE (EC 1.1.1.17) |
| 325 | MUKB_ECOLI | (P22523) CELL DIVISION PROTEIN MUKB. |
| 326 | MUKE_ECOLI | (P22524) MUKE PROTEIN (KICA PROTEIN). |
| 327 | MUKF_ECOLI | (P36567) MUKF PROTEIN (KILLING FACTOR KICB). |
| 328 | MUL1_ECOLI | (P02937) MAJOR OUTER MEMBRANE LIPOPROTEIN PRECURSOR (MUREIN |
| 329 | MURA_ECOLI | (P28909) UDP-N-ACETYLGLUCOSAMINE 1-CARBOXYVINYLTRANSFERASE |
| 330 | MURE_ECOLI | (P22188) UDP-N-ACETYLMURAMOYLALANYL-D-GLUTAMATE--2,6-DIAMIN |
| 331 | MUTS_ECOLI | (P23909) DNA MISMATCH REPAIR PROTEIN MUTS. |
| 332 | NADR_ECOLI | (P27278) TRANSCRIPTIONAL REGULATOR NADR. |
| 333 | NAGA_ECOLI | (P15300) N-ACETYLGLUCOSAMINE-6-PHOSPHATE DEACETYLASE (EC 3. |
| 334 | NAGB_ECOLI | (P09375) GLUCOSAMINE-6-PHOSPHATE ISOMERASE (EC 3.5.99.6) (G |
| 335 | NAPA_ECOLI | (P33937) PERIPLASMIC NITRATE REDUCTASE PRECURSOR (EC 1.7.99 |
| 336 | NARH_ECOLI | (P11349) RESPIRATORY NITRATE REDUCTASE 1 BETA CHAIN (EC 1.7 |
| 337 | NFNB_ECOLI | (P38489) OXYGEN-INSENSITIVE NAD(P)H NITROREDUCTASE (EC 1.-. |
| 338 | NLPB_ECOLI | (P21167) LIPOPROTEIN-34 PRECURSOR. |
| 339 | NPL_ECOLI | (P06995) N-ACETYLNEURAMINATE LYASE SUBUNIT (EC 4.1.3.3) (N- |
| 340 | NUCD_ECOLI | (P33599) NADH DEHYDROGENASE I CHAIN C/D (EC 1.6.5.3) (NADH- |
| 341 | NUOG_ECOLI | (P33602) NADH DEHYDROGENASE I CHAIN G (EC 1.6.5.3) (NADH-UB |
| 342 | NUSA_ECOLI | (P03003) N UTILIZATION SUBSTANCE PROTEIN A (NUSA PROTEIN) ( |
| 343 | ODO1_ECOLI | (P07015) 2-OXOGLUTARATE DEHYDROGENASE E1 COMPONENT (EC 1.2. |
| 344 | ODO2_ECOLI | (P07016) DIHYDROLIPOAMIDE SUCCINYLTRANSFERASE COMPONENT OF |
| 345 | ODP1_ECOLI | (P06958) PYRUVATE DEHYDROGENASE E1 COMPONENT (EC 1.2.4.1). |
| 346 | ODP2_ECOLI | (P06959) DIHYDROLIPOAMIDE ACETYLTRANSFERASE COMPONENT OF PY |
| 347 | OMPA_ECOLI | (P02934) OUTER MEMBRANE PROTEIN A PRECURSOR (OUTER MEMBRANE |
| 348 | OMPF_ECOLI | (P02931) OUTER MEMBRANE PROTEIN F PRECURSOR (PORIN OMPF) (O |
| 349 | OMPP_ECOLI | (P34210) OUTER MEMBRANE PROTEASE OMPP PRECURSOR (EC 3.4.21. |
| 350 | OMPR_ECOLI | (P03025) TRANSCRIPTIONAL REGULATORY PROTEIN OMPR. |

TABLE XII-continued

List of proteins that were identified by LC-MS/MS analysis on MetSO-sorted peptides. The proteins are sorted according to their SwissProt entry name.

| | | |
|---|---|---|
| 351 | OMPT_ECOLI | (P09169) PROTEASE VII PRECURSOR (EC 3.4.21.87) (OMPTIN) (OU |
| 352 | OPDA_ECOLI | (P27298) OLIGOPEPTIDASE A (EC 3.4.24.70). |
| 353 | OPPA_ECOLI | (P23843) PERIPLASMIC OLIGOPEPTIDE-BINDING PROTEIN PRECURSOR |
| 354 | OPPB_ECOLI | (P31132) OLIGOPEPTIDE TRANSPORT SYSTEM PERMEASE PROTEIN OPP |
| 355 | OPPD_ECOLI | (P76027) OLIGOPEPTIDE TRANSPORT ATP-BINDING PROTEIN OPPD. |
| 356 | OPPF_ECOLI | (P77737) OLIGOPEPTIDE TRANSPORT ATP-BINDING PROTEIN OPPF. |
| 357 | OSMC_ECOLI | (P23929) OSMOTICALLY INDUCIBLE PROTEIN C. |
| 358 | OSMY_ECOLI | (P27291) OSMOTICALLY INDUCIBLE PROTEIN Y PRECURSOR |
| 359 | OSTA_ECOLI | (P31554) ORGANIC SOLVENT TOLERANCE PROTEIN PRECURSOR. |
| 360 | PAL_ECOLI | (P07176) PEPTIDOGLYCAN-ASSOCIATED LIPOPROTEIN PRECURSOR. |
| 361 | PANC_ECOLI | (P31663) PANTOATE--BETA-ALANINE LIGASE (EC 6.3.2.1) (PANTOT |
| 362 | PARC_ECOLI | (P20082) TOPOISOMERASE IV SUBUNIT A (EC 5.99.1.-). |
| 363 | PARE_ECOLI | (P20083) TOPOISOMERASE IV SUBUNIT B (EC 5.99.1.-). |
| 364 | PBPA_ECOLI | (P02918) PENICILLIN-BINDING PROTEIN 1A (PBP-1A) (PBP1A) [IN |
| 365 | PBPB_ECOLI | (P02919) PENICILLIN-BINDING PROTEIN 1B (PBP-1B) (PBP1B) (MU |
| 366 | PCNB_ECOLI | (P13685) POLY(A) POLYMERASE (EC 2.7.7.19) (PAP) (PLASMID CO |
| 367 | PDXA_ECOLI | (P19624) PYRIDOXAL PHOSPHATE BIOSYNTHETIC PROTEIN PDXA. |
| 368 | PDXB_ECOLI | (P05459) ERYTHRONATE-4-PHOSPHATE DEHYDROGENASE (EC 1.1.1.-) |
| 369 | PDXH_ECOLI | (P28225) PYRIDOXAMINE 5'-PHOSPHATE OXIDASE (EC 1.4.3.5) (PN |
| 370 | PDXK_ECOLI | (P40191) PYRIDOXINE KINASE (EC 2.7.1.35) (PYRIDOXAL KINASE) |
| 371 | PEPD_ECOLI | (P15288) AMINOACYL-HISTIDINE DIPEPTIDASE (EC 3.4.13.3) (XAA |
| 372 | PEPE_ECOLI | (P32666) PEPTIDASE E (EC 3.4.-.-) (ALPHA-ASPARTYL DIPEPTIDA |
| 373 | PEPQ_ECOLI | (P21165) XAA-PRO DIPEPTIDASE (EC 3.4.13.9) (X-PRO DIPEPTIDA |
| 374 | PEPT_ECOLI | (P29745) PEPTIDASE T (EC 3.4.11.-) (AMINOTRIPEPTIDASE) (TRI |
| 375 | PFLA_ECOLI | (P09374) PYRUVATE FORMATE-LYASE 1 ACTIVATING ENZYME (EC 1.9 |
| 376 | PFLB_ECOLI | (P09373) FORMATE ACETYLTRANSFERASE 1 (EC 2.3.1.54) (PYRUVAT |
| 377 | PGK_ECOLI | (P11665) PHOSPHOGLYCERATE KINASE (EC 2.7.2.3). |
| 378 | PGMU_ECOLI | (P36938) PHOSPHOGLUCOMUTASE (EC 5.4.2.2) (GLUCOSE PHOSPHOMU |
| 379 | PHEA_ECOLI | (P07022) P-PROTEIN [INCLUDES: CHORISMATE MUTASE (EC 5.4.99. |
| 380 | PHNQ_ECOLI | (P16693) VERY HYPOTHETICAL PHNQ PROTEIN. |
| 381 | PHOB_ECOLI | (P08402) PHOSPHATE REGULON TRANSCRIPTIONAL REGULATORY PROTE |
| 382 | PHOL_ECOLI | (P77349) PHOH-LIKE PROTEIN. |
| 383 | PHOU_ECOLI | (P07656) PHOSPHATE TRANSPORT SYSTEM PROTEIN PHOU. |
| 384 | PHSM_ECOLI | (P00490) MALTODEXTRIN PHOSPHORYLASE (EC 2.4.1.1). |
| 385 | PIFA_ECOLI | (P96329) PHAGE T7 EXCLUSION PROTEIN. |
| 386 | PIFC_ECOLI | (P10030) TRANSCRITPIONAL REPRESSOR PIFC (PROTEIN C). |
| 387 | PITA_ECOLI | (P37308) LOW-AFFINITY INORGANIC PHOSPHATE TRANSPORTER 1. |
| 388 | PLSB_ECOLI | (P00482) GLYCEROL-3-PHOSPHATE ACYLTRANSFERASE (EC 2.3.1.15) |
| 389 | PMBA_ECOLI | (P24231) PMBA PROTEIN (TLDE PROTEIN). |
| 390 | PMG1_ECOLI | (P31217) PHOSPHOGLYCERATE MUTASE 1 (EC 5.4.2.1)(PHOSPHOGLY |
| 391 | PMG2_ECOLI | (P36942) PROBABLE PHOSPHOGLYCERATE MUTASE 2 (EC 5.4.2.1) (P |
| 392 | PMGI_ECOLI | (P37689) 2,3-BISPHOSPHOGLYCERATE-INDEPENDENT PHOSPHOGLYCERA |
| 393 | PNP_ECOLI | (P05055) POLYRIBONUCLEOTIDE NUCLEOTIDYLTRANSFERASE (EC 2.7. |
| 394 | PNTA_ECOLI | (P07001) NAD(P) TRANSHYDROGENASE SUBUNIT ALPHA (EC 1.6.1.2) |
| 395 | POTD_ECOLI | (P23861) SPERMIDINE/PUTRESCINE-BINDING PERIPLASMIC PROTEIN |
| 396 | POXB_ECOLI | (P07003) PYRUVATE DEHYDROGENASE [CYTOCHROME] (EC 1.2.2.2) ( |
| 397 | PPCK_ECOLI | (P22259) PHOSPHOENOLPYRUVATE CARBOXYKINASE [ATP] (EC 4.1.1. |
| 398 | PPIB_ECOLI | (P23869) PEPTIDYL-PROLYL CIS-TRANS ISOMERASE B (EC 5.2.1.8) |
| 399 | PPID_ECOLI | (P77241) PEPTIDYL-PROLYL CIS-TRANS ISOMERASE D (EC 5.2.1.8) |
| 400 | PPSA_ECOLI | (P23538) PHOSPHOENOLPYRUVATE SYNTHASE (EC 2.7.9.2) (PYRUVAT |
| 401 | PPX_ECOLI | (P29014) EXOPOLYPHOSPHATASE (EC 3.6.1.11) (EXOPOLYPASE) (ME |
| 402 | PQIB_ECOLI | (P43671) PARAQUAT-INDUCIBLE PROTEIN B. |
| 403 | PROA_ECOLI | (P07004) GAMMA-GLUTAMYL PHOSPHATE REDUCTASE (GPR) (EC 1.2.1 |
| 404 | PROB_ECOLI | (P07005) GLUTAMATE 5-KINASE (EC 2.7.2.11) (GAMMA-GLUTAMYL K |
| 405 | PROC_ECOLI | (P00373) PYRROLINE-5-CARBOXYLATE REDUCTASE (EC 1.5.1.2) (P5 |
| 406 | PROQ_ECOLI | (P45577) PROP EFFECTOR. |
| 407 | PRPD_ECOLI | (P77243) PRPD PROTEIN. |
| 408 | PSPE_ECOLI | (P23857) PHAGE SHOCK PROTEIN E PRECURSOR. |
| 409 | PT1_ECOLI | (P08839) PHOSPHOENOLPYRUVATE-PROTEIN PHOSPHOTRANSFERASE (EC |
| 410 | PTA_ECOLI | (P39184) PHOSPHATE ACETYLTRANSFERASE (EC 2.3.1.8) (PHOSPHOT |
| 411 | PTAA_ECOLI | (P09323) PTS SYSTEM, N-ACETYLGLUCOSAMINE-SPECIFIC IIABC COM |
| 412 | PTGA_ECOLI | (P08837) PTS SYSTEM, GLUCOSE-SPECIFIC IIA COMPONENT (EIIA-G |
| 413 | PTH_ECOLI | (P23932) PEPTIDYL-TRNA HYDROLASE (EC 3.1.1.29) (PTH). |
| 414 | PTMA_ECOLI | (P00550) PTS SYSTEM, MANNITOL-SPECIFIC IIABC COMPONENT (EII |
| 415 | PTNA_ECOLI | (P08186) PTS SYSTEM, MANNOSE-SPECIFIC IIAB COMPONENT (EIIAB |
| 416 | PTRA_ECOLI | (P05458) PROTEASE III PRECURSOR (EC 3.4.24.55) (PITRILYSIN) |
| 417 | PUR1_ECOLI | (P00496) AMIDOPHOSPHORIBOSYLTRANSFERASE (EC 2.4.2.14) (GLUT |
| 418 | PUR4_ECOLI | (P15254) PHOSPHORIBOSYLFORMYLGLYCINAMIDINE SYNTHASE (EC 6.3 |
| 419 | PUR8_ECOLI | (P25739) ADENYLOSUCCINATE LYASE (EC 4.3.2.2) (ADENYLOSUCCIN |
| 420 | PUR9_ECOLI | (P15639) BIFUNCTIONAL PURINE BIOSYNTHESIS PROTEIN PURH [INC |
| 421 | PURA_ECOLI | (P12283) ADENYLOSUCCINATE SYNTHETASE (EC 6.3.4.4) (IMP--ASP |
| 422 | PUTA_ECOLI | (P09546) BIFUNCTIONAL PUTA PROTEIN [INCLUDES: PROLINE DEHYD |
| 423 | PYRB_ECOLI | (P00479) ASPARTATE CARBAMOYLTRANSFERASE CATALYTIC CHAIN (EC |
| 424 | PYRC_ECOLI | (P05020) DIHYDROOROTASE (EC 3.5.2.3) (DHOASE). |
| 425 | PYRD_ECOLI | (P05021) DIHYDROOROTATE DEHYDROGENASE (EC 1.3.3.1) (DIHYDRO |
| 426 | PYRG_ECOLI | (P08398) CTP SYNTHASE (EC 6.3.4.2) (UTP--AMMONIA LIGASE) (C |

TABLE XII-continued

List of proteins that were identified by LC-MS/MS analysis on MetSO-sorted peptides. The proteins are sorted according to their SwissProt entry name.

| | | |
|---|---|---|
| 427 | PYRH_ECOLI | (P29464) URIDYLATE KINASE (EC 2.7.4.-) (UK) (URIDINE MONOPH |
| 428 | RBA2_ECOLI | (P55253) GLUCOSE-1-PHOSPHATE THYMIDYLYLTRANSFERASE (EC 2.7. |
| 429 | RBFA_ECOLI | (P09170) RIBOSOME-BINDING FACTOR A (P15B PROTEIN). |
| 430 | RBSA_ECOLI | (P04983) RIBOSE TRANSPORT ATP-BINDING PROTEIN RBSA. |
| 431 | RBSB_ECOLI | (P02925) D-RIBOSE-BINDING PERIPLASMIC PROTEIN PRECURSOR. |
| 432 | RDGC_ECOLI | (P36767) RECOMBINATION ASSOCIATED PROTEIN RDGC. |
| 433 | RECA_ECOLI | (P03017) RECA PROTEIN (RECOMBINASE A). |
| 434 | RF2_ECOLI | (P07012) PEPTIDE CHAIN RELEASE FACTOR 2 (RF-2). |
| 435 | RF3_ECOLI | (P33998) PEPTIDE CHAIN RELEASE FACTOR 3 (RF-.3). |
| 436 | RFAE_ECOLI | (P76658) ADP-HEPTOSE SYNTHASE (EC 2.7.-.-). |
| 437 | RFFG_ECOLI | (P27830) DTDP-GLUCOSE 4,6-DEHYDRATASE (EC 4.2.1.46). |
| 438 | RFFH_ECOLI | (P27831) GLUCOSE-1-PHOSPHATE THYMIDYLYLTRANSFERASE (EC 2.7. |
| 439 | RHLB_ECOLI | (P24229) PUTATIVE ATP-DEPENDENT RNA HELICASE RHLB. |
| 440 | RHO_ECOLI | (P03002) TRANSCRIPTION TERMINATION FACTOR RHO. |
| 441 | RIBD_ECOLI | (P25539) RIBOFLAVIN BIOSYNTHESIS PROTEIN RIBD [INCLUDES: DI |
| 442 | RIMM_ECOLI | (P21504) 16S RRNA PROCESSING PROTEIN RIMM (21K). |
| 443 | RIR1_ECOLI | (P00452) RIBONUCLEOSIDE-DIPHOSPHATE REDUCTASE 1 ALPHA CHAIN |
| 444 | RIR2_ECOLI | (P00453) RIBONUCLEOSIDE-DIPHOSPHATE REDUCTASE 1 BETA CHAIN |
| 445 | RISA_ECOLI | (P29015) RIBOFLAVIN SYNTHASE ALPHA CHAIN (EC 2.5.1.9). |
| 446 | RL1_ECOLI | (P02384) 50S RIBOSOMAL PROTEIN L1. |
| 447 | RL10_ECOLI | (P02408) 50S RIBOSOMAL PROTEIN L10 (L8). |
| 448 | RL11_ECOLI | (P02409) 50S RIBOSOMAL PROTEIN L11. |
| 449 | RL13_ECOLI | (P02410) 50S RIBOSOMAL PROTEIN L13. |
| 450 | RL14_ECOLI | (P02411) 50S RIBOSOMAL PROTEIN L14. |
| 451 | RL15_ECOLI | (P02413) 50S RIBOSOMAL PROTEIN L15. |
| 452 | RL16_ECOLI | (P02414) 50S RIBOSOMAL PROTEIN L16. |
| 453 | RL17_ECOLI | (P02416) 50S RIBOSOMAL PROTEIN L17. |
| 454 | RL2_ECOLI | (P02387) 50S RIBOSOMAL PROTEIN L2. |
| 455 | RL20_ECOLI | (P02421) 50S RIBOSOMAL PROTEIN L20. |
| 456 | RL21_ECOLI | (P02422) 50S RIBOSOMAL PROTEIN L21. |
| 457 | RL22_ECOLI | (P02423) 50S RIBOSOMAL PROTEIN L22. |
| 458 | RL24_ECOLI | (P02425) 50S RIBOSOMAL PROTEIN L24. |
| 459 | RL25_ECOLI | (P02426) 50S RIBOSOMAL PROTEIN L25. |
| 460 | RL27_ECOLI | (P02427) 50S RIBOSOMAL PROTEIN L27. |
| 461 | RL3_ECOLI | (P02386) 50S RIBOSOMAL PROTEIN L3. |
| 462 | RL30_ECOLI | (P02430) 50S RIBOSOMAL PROTEIN L30. |
| 463 | RL31_ECOLI | (P02432) 50S RIBOSOMAL PROTEIN L31. |
| 464 | RL32_ECOLI | (P02435) 50S RIBOSOMAL PROTEIN L32. |
| 465 | RL33_ECOLI | (P02436) 50S RIBOSOMAL PROTEIN L33. |
| 466 | RL4_ECOLI | (P02388) 50S RIBOSOMAL PROTEIN L4. |
| 467 | RL5_ECOLI | (P02389) 50S RIBOSOMAL PROTEIN L5. |
| 468 | RL6_ECOLI | (P02390) 50S RIBOSOMAL PROTEIN L6. |
| 469 | RL7_ECOLI | (P02392) 50S RIBOSOMAL PROTEIN L7/L12 (L8). |
| 470 | RL9_ECOLI | (P02418) 50S RIBOSOMAL PROTEIN L9. |
| 471 | RNB_ECOLI | (P30850) EXORIBONUCLEASE II (EC 3.1.13.1) (RIBONUCLEASE II) |
| 472 | RNE_ECOLI | (P21513) RIBONUCLEASE E (EC 3.1.4.-) (RNASE E). |
| 473 | RNG_ECOLI | (P25537) RIBONUCLEASE G (EC 3.1.4.-) (RNASE G) (CYTOPLASMIC |
| 474 | RNK_ECOLI | (P40679) REGULATOR OF NUCLEOSIDE DIPHOSPHATE KINASE. |
| 475 | RNR_ECOLI | (P21499) RIBONUCLEASE R (EC 3.1.-.-) (RNASE R) (VACB PROTEI |
| 476 | ROB_ECOLI | (P27292) RIGHT ORIGIN-BINDING PROTEIN. |
| 477 | RP32_ECOLI | (P00580) RNA POLYMERASE SIGMA-32 FACTOR (HEAT SHOCK REGULAT |
| 478 | RPIA_ECOLI | (P27252) RIBOSE 5-PHOSPHATE ISOMERASE A (EC 5.3.1.6) (PHOSP |
| 479 | RPOA_ECOLI | (P00574) DNA-DIRECTED RNA POLYMERASE ALPHA CHAIN (EC 2.7.7. |
| 480 | RPOB_ECOLI | (P00575) DNA-DIRECTED RNA POLYMERASE BETA CHAIN (EC 2.7.7.6 |
| 481 | RPOC_ECOLI | (P00577) DNA-DIRECTED RNA POLYMERASE BETA CHAIN (EC 2.7.7. |
| 482 | RPOE_ECOLI | (P34086) RNA POLYMERASE SIGMA-E FACTOR (SIGMA-24). |
| 483 | RPSD_ECOLI | (P00579) RNA POLYMERASE SIGMA FACTOR RPOD (SIGMA-70). |
| 484 | RRF_ECOLI | (P16174) RIBOSOME RECYCLING FACTOR (RIBOSOME RELEASING FACT |
| 485 | RRMJ_ECOLI | (P28692) RIBOSOMAL RNA LARGE SUBUNIT METHYLTRANSFERASE J (E |
| 486 | RS1_ECOLI | (P02349) 30S RIBOSOMAL PROTEIN S1. |
| 487 | RS10_ECOLI | (P02364) 30S RIBOSOMAL PROTEIN S10. |
| 488 | RS13_ECOLI | (P02369) 30S RIBOSOMAL PROTEIN S13. |
| 489 | RS15_ECOLI | (P02371) 30S RIBOSOMAL PROTEIN S15. |
| 490 | RS17_ECOLI | (P02373) 30S RIBOSOMAL PROTEIN S17. |
| 491 | RS18_ECOLI | (P02374) 30S RIBOSOMAL PROTEIN S18. |
| 492 | RS19_ECOLI | (P02375) 30S RIBOSOMAL PROTEIN S19. |
| 493 | RS2_ECOLI | (P02351) 30S RIBOSOMAL PROTEIN S2. |
| 494 | RS20_ECOLI | (P02378) 30S RIBOSOMAL PROTEIN S20. |
| 495 | RS21_ECOLI | (P02379) 30S RIBOSOMAL PROTEIN S21. |
| 496 | RS3_ECOLI | (P02352) 30S RIBOSOMAL PROTEIN S3. |
| 497 | RS4_ECOLI | (P02354) 30S RIBOSOMAL PROTEIN S4. |
| 498 | RS5_ECOLI | (P02356) 30S RIBOSOMAL PROTEIN S5. |
| 499 | RS6_ECOLI | (P02358) 30S RIBOSOMAL PROTEIN S6. |
| 500 | RS8_ECOLI | (P02361) 30S RIBOSOMAL PROTEIN S8. |
| 501 | RS9_ECOLI | (P02363) 30S RIBOSOMAL PROTEIN S9. |
| 502 | RSEA_ECOLI | (P38106) SIGMA-E FACTOR NEGATIVE REGULATORY PROTEIN. |

TABLE XII-continued

List of proteins that were identified by LC-MS/MS analysis on MetSO-sorted peptides. The proteins are sorted according to their SwissProt entry name.

| | | |
|---|---|---|
| 503 | RSEB_ECOLI | (P46186) SIGMA-E FACTOR REGULATORY PROTEIN RSEB PRECURSOR. |
| 504 | RSMC_ECOLI | (P39406) RIBOSOMAL RNA SMALL SUBUNIT METHYLTRANSFERASE C (E |
| 505 | SDHL_ECOLI | (P16095) L-SERINE DEHYDRATASE 1 (EC 4.2.1.13) (L-SERINE DEA |
| 506 | SECA_ECOLI | (P10408) PREPROTEIN TRANSLOCASE SECA SUBUNIT. |
| 507 | SECD_ECOLI | (P19673) PROTEIN-EXPORT MEMBRANE PROTEIN SECD. |
| 508 | SELA_ECOLI | (P23328) L-SERYL-TRNA(SEC) SELENIUM TRANSFERASE (EC 2.9.1.1 |
| 509 | SELD_ECOLI | (P16456) SELENIDE, WATER DIKINASE (EC 2.7.9.3) (SELENOPHOSPH |
| 510 | SERC_ECOLI | (P23721) PHOSPHOSERINE AMINOTRANSFERASE (EC 2.6.1.52) (PSAT |
| 511 | SGAH_ECOLI | (P39304) PROBABLE HEXULOSE-6-PHOSPHATE SYNTHASE (EC 4.1.2.- |
| 512 | SIXA_ECOLI | (P76502) PHOSPHOHISTIDINE PHOSPHATASE SIXA (EC 3.1.3.-) (RX |
| 513 | SLT_ECOLI | (P03810) SOLUBLE LYTIC MUREIN TRANSGLYCOSYLASE PRECURSOR (E |
| 514 | SLYD_ECOLI | (P30856) FKBP-TYPE PEPTIDYL-PROLYL CIS-TRANS ISOMERASE SLYD |
| 515 | SODF_ECOLI | (P09157) SUPEROXIDE DISMUTASE [FE] (EC 1.15.1.1). |
| 516 | SPEA_ECOLI | (P21170) BIOSYNTHETIC ARGININE DECARBOXYLASE (EC 4.1.1.19) |
| 517 | SPPA_ECOLI | (P08395) PROTEASE IV (EC 3.4.21.-) (ENDOPEPTIDASE IV) (SIGN |
| 518 | SR54_ECOLI | (P07019) SIGNAL RECOGNITION PARTICLE PROTEIN (FIFTY-FOUR HO |
| 519 | SRLR_ECOLI | (P15082) GLUCITOL OPERON REPRESSOR. |
| 520 | SSNA_ECOLI | (Q46812) SSNA PROTEIN. |
| 521 | SSPA_ECOLI | (P05838) STRINGENT STARVATION PROTEIN A. |
| 522 | STHA_ECOLI | (P27306) SOLUBLE PYRIDINE NUCLEOTIDE TRANSHYDROGENASE (EC 1 |
| 523 | STPA_ECOLI | (P30017) DNA-BINDING PROTEIN STPA (H-NS HOMOLOG STPA). |
| 524 | SUCC_ECOLI | (P07460) SUCCINYL-COA SYNTHETASE BETA CHAIN (EC 6.2.1.5) (S |
| 525 | SUCD_ECOLI | (P07459) SUCCINYL-COA SYNTHETASE ALPHA CHAIN (EC 6.2.1.5) ( |
| 526 | SUFD_ECOLI | (P77689) SUFD PROTEIN. |
| 527 | SUFI_ECOLI | (P26648) SUFI PROTEIN PRECURSOR. |
| 528 | SURA_ECOLI | (P21202) SURVIVAL PROTEIN SURA PRECURSOR (PEPTIDYL-PROLYL C |
| 529 | SYA_ECOLI | (P00957) ALANYL-TRNA SYNTHETASE (EC 6.1.1.7) (ALANINE--TRNA |
| 530 | SYC_ECOLI | (P21888) CYSTEINYL-TRNA SYNTHETASE (EC 6.1.1.16) (CYSTEINE- |
| 531 | SYD_ECOLI | (P21889) ASPARTYL-TRNA SYNTHETASE (EC 6.1.1.12) (ASPARTATE- |
| 532 | SYE_ECOLI | (P04805) GLUTAMYL-TRNA SYNTHETASE (EC 6.1.1.17) (GLUTAMATE- |
| 533 | SYFA_ECOLI | (P08312) PHENYLALANYL-TRNA SYNTHETASE ALPHA CHAIN (EC 6.1.1 |
| 534 | SYFB_ECOLI | (P07395) PHENYLALANYL-TRNA SYNTHETASE BETA CHAIN (EC 6.1.1. |
| 535 | SYGA_ECOLI | (P00960) GLYCYL-TRNA SYNTHETASE ALPHA CHAIN (EC 6.1.1.14) ( |
| 536 | SYGB_ECOLI | (P00961) GLYCYL-TRNA SYNTHETASE BETA CHAIN (EC 6.1.1.14) (G |
| 537 | SYH_ECOLI | (P04804) HISTIDYL-TRNA SYNTHETASE (EC 6.1.1.21) (HISTIDINE. |
| 538 | SYI_ECOLI | (P00956) ISOLEUCYL-TRNA SYNTHETASE (EC 6.1.1.5) (ISOLEUCINE |
| 539 | SYK1_ECOLI | (P13030) LYSYL-TRNA SYNTHETASE (EC 6.1.1.6) (LYSINE--TRNA L |
| 540 | SYK2_ECOLI | (P14825) LYSYL-TRNA SYNTHETASE, HEAT INDUCIBLE (EC 6.1.1.6) |
| 541 | SYK3_ECOLI | (P03812) PUTATIVE LYSYL-TRNA SYNTHETASE (EC 6.1.1.6) (LYSIN |
| 542 | SYL_ECOLI | (P07813) LEUCYL-TRNA SYNTHETASE (EC 6.1.1.4) (LEUCINE--TRNA |
| 543 | SYM_ECOLI | (P00959) METHIONYL-TRNA SYNTHETASE (EC 6.1.1.10) (METHIONIN |
| 544 | SYN_ECOLI | (P17242) ASPARAGINYL-TRNA SYNTHETASE (EC 6.1.L22) (ASPARAG |
| 545 | SYP_ECOLI | (P16659) PROLYL-TRNA SYNTHETASE (EC 6.1.1.15) (PROLINE--TRN |
| 546 | SYQ_ECOLI | (P00962) GLUTAMINYL-TRNA SYNTHETASE (EC 6.1.1.18) (GLUTAMIN |
| 547 | SYR_ECOLI | (P11875) ARGINYL-TRNA SYNTHETASE (EC 6.1.1.19) (ARGININE--T |
| 548 | SYS_ECOLI | (P09156) SERYL-TRNA SYNTHETASE (EC 6.1.1.11) (SERINE--TRNA |
| 549 | SYT_ECOLI | (P00955) THREONYL-TRNA SYNTHETASE (EC 6.1.1.3) (THREONINE-- |
| 550 | SYV_ECOLI | (P07118) VALYL-TRNA SYNTHETASE (BC 6.1.1.9) (VALINE--TRNA L |
| 551 | SYW_ECOLI | (P00954) TRYPTOPHANYL-TRNA SYNTHETASE (EC 6.1.1.2) (TRYPTOP |
| 552 | SYY_ECOLI | (P00951) TYROSYL-TRNA SYNTHETASE (EC 6.1.1.1) (TYROSINE--TR |
| 553 | T1MK_ECOLI | (P08957) TYPE 1 RESTRICTION ENZYME ECOKI M PROTEIN (EC 2.1. |
| 554 | TALB_ECOLI | (P30148) TRANSALDOLASE B (EC 2.2.1.2). |
| 555 | TDCE_ECOLI | (P42632) KETO-ACID FORMATE ACETYLTRANSFERASE (EC 2.3.1.-) ( |
| 556 | TDCF_ECOLI | (P42631) TDCF PROTEIN. |
| 557 | TDH_ECOLI | (P07913) THREONINE 3-DEHYDROGENASE (EC 1.1.1.103). |
| 558 | TEHB_ECOLI | (P25397) TELLURITE RESISTANCE PROTEIN TEHB. |
| 559 | THD2_ECOLI | (P05792) THREONINE DEHYDRATASE CATABOLIC (EC 4.2.1.16) (THR |
| 560 | THIC_ECOLI | (P30136) THIAMINE BIOSYNTHESIS PROTEIN THIC. |
| 561 | THII_ECOLI | (P77718) THIAMINE BIOSYNTHESIS PROTEIN THIII. |
| 562 | TIG_ECOLI | (P22257) TRIGGER FACTOR (TF). |
| 563 | TKRA_ECOLI | (P37666) 2-KETOGLUCONATE REDUCTASE (EC 1.1.1.215) (2KR) (2- |
| 564 | TKT1_ECOLI | (P27302) TRANSKETOLASE 1 (EC 2.2.1.1) (TK 1). |
| 565 | TKT2_ECOLI | (P33570) TRANSKETOLASE 2 (EC 2.2.1.1) (TK 2). |
| 566 | TOLB_ECOLI | (P19935) TOLB PROTEIN PRECURSOR. |
| 567 | TOLC_ECOLI | (P02930) OUTER MEMBRANE PROTEIN TOLC PRECURSOR. |
| 568 | TOP1_ECOLI | (P06612) DNA TOPOISOMERASE I (EC 5.99.1.2) (OMEGA-PROTEIN) |
| 569 | TPIS_ECOLI | (P04790) TRIOSEPHOSPHATE ISOMERASE (EC 5.3.1.1) (TIM). |
| 570 | TRAC_ECOLI | (P18004) TRAC PROTEIN. |
| 571 | TRAN_ECOLI | (P24082) TRAN PROTEIN PRECURSOR. |
| 572 | TRAU_ECOLI | (P18471) TRAU PROTEIN PRECURSOR. |
| 573 | TRAW_ECOLI | (P18472) TRAW PROTEIN PRECURSOR. |
| 574 | TRB1_ECOLI | (P41067) TRAB PROTEIN. |
| 575 | TRB1_ECOLI | (P18006) TRB1 PROTEIN. |
| 576 | TRD1_ECOLI | (P09130) TRAD PROTEIN. |
| 577 | TRD2_ECOLI | (P22708) TRAD PROTEIN. |
| 578 | TREA_ECOLI | (P13482) PERIPLASMIC TREHALASE PRECURSOR (EC 3.2.1.28) (ALP |

TABLE XII-continued

List of proteins that were identified by LC-MS/MS analysis on MetSO-sorted peptides. The proteins are sorted according to their SwissProt entry name.

| | | |
|---|---|---|
| 579 | TREC_ECOLI | (P28904) TREHALOSE-6-PHOSPHATE HYDROLASE (EC 3.2.1.93) (ALP |
| 580 | TRG1_ECOLI | (P33790) TRAG PROTEIN. |
| 581 | TRI1_ECOLI | (P14565) TRAI PROTEIN (DNA HELICASE I) (EC 3.6.1.-) [CONTAI |
| 582 | TRI2_ECOLI | (P22706) TRAI PROTEIN (DNA HELICASE I) (EC 3.6.1.-). |
| 583 | TRKA_ECOLI | (P23868) TRK SYSTEM POTASSIUM UPTAKE PROTEIN TRKA. |
| 584 | TRMA_ECOLI | (P23003) TRNA (URACIL-5-)-METHYLTRANSFERASE (EC 2.1.1.35) ( |
| 585 | TRT4_ECOLI | (P15177) TRAT COMPLEMENT RESISTANCE PROTEIN PRECURSOR. |
| 586 | TRUB_ECOLI | (P09171) TRNA PSEUDOURIDINE SYNTHASE B (EC 4.2.130) (TRNA |
| 587 | TRXB_ECOLI | (P09625) THIOREDOXIN REDUCTASE (EC 1.6.4.5) (TRXR). |
| 588 | TTDT_ECOLI | (P39414) PUTATIVE TARTRATE CARRIER (TARTRATE TRANSPORTER) ( |
| 589 | TYPH_ECOLI | (P07650) THYMIDINE PHOSPHORYLASE (EC 2.4.2.4) (TDRPASE). |
| 590 | TYRB_ECOLI | (P04693) AROMATIC-AMINO-ACID AMINOTRANSFERASE (EC 2.6.1.57) |
| 591 | TYRR_ECOLI | (P07604) TRANSCRIPTIONAL REGULATORY PROTEIN TYRR. |
| 592 | UBIE_ECOLI | (P27851) UBIQUINONE/MENAQUINONE BIOSYNTHESIS METHYLTRANSFER |
| 593 | UBIG_ECOLI | (P17993) 3-DEMETHYLUBIQUINONE-9 3-METHYLTRANSFERASE (EC 2.1 |
| 594 | UBIH_ECOLI | (P25534) 2-OCTAPRENYL-6-METHOXYPHENOL HYDROXYLASE (EC 1.14. |
| 595 | UCPA_ECOLI | (P37440) OXIDOREDUCTASE UCPA (EC 1 .-.-.-). |
| 596 | UDP_ECOLI | (P12758) URIDINE PHOSPHORYLASE (EC 2.4.2.3) (UDRPASE). |
| 597 | UGPB_ECOLI | (P10904) GLYCEROL-3-PHOSPHATE-BINDING PERIPLASMIC PROTEIN P |
| 598 | UIDR_ECOLI | (Q59431) UID OPERON REPRESSOR (GUS OPERON REPRESSOR). |
| 599 | UNG_ECOLI | (P12295) URACIL-DNA GLYCOSYLASE (EC 3.2.2.-) (UDG). |
| 600 | UP05_ECOLI | (P39170) UNKNOWN PROTEIN FROM 2D-PAGE SPOTS M62/M63/O3/o9/T |
| 601 | UP12_ECOLI | (P39177) UNKNOWN PROTEIN FROM 2D-PAGE (SPOTS PR25/LM16/2D_0 |
| 602 | UP14_ECOLI | (P39179) UNKNOWN PROTEIN FROM 2D-PAGE (SPOT PR51). |
| 603 | UP18_ECOLI | (P45502) UNKNOWN PROTEIN 2D_000LSD FROM 2D-PAGE PRECURSOR. |
| 604 | UPP_ECOLI | (P25532) URACIL PHOSPHORIBOSYLTRANSFERASE (EC 2.4.2.9) (UMP |
| 605 | URK_ECOLI | (P31218) URIDINE KINASE (EC2.7.1.48) (URIDINE MONOPHOSPHOK |
| 606 | USG_ECOLI | (P08390) USG-1 PROTEIN. |
| 607 | USHA_ECOLI | (P07024) PROTEIN USHA PRECURSOR [INCLUDES: UDP-SUGAR HYDROL |
| 608 | USPA_ECOLI | (P28242) UNIVERSAL STRESS PROTEIN A. |
| 609 | UUP_ECOLI | (P43672) ABC TRANSPORTER ATP-BINDING PROTEIN UUP. |
| 610 | UVRB_ECOLI | (P07025) EXCINUCLEASE ABC SUBUNIT B. |
| 611 | UXAC_ECOLI | (P42607) URONATE ISOMERASE (EC 5.3.1.12) (GLUCURONATE ISOME |
| 612 | UXUB_ECOLI | (P39160) D-MANNONATE OXIDOREDUCTASE (EC 1.1.1.57) (FRUCTURO |
| 613 | UXUR_ECOLI | (P39161) UXU OPERON TRANSCRIPTIONAL REGULATOR. |
| 614 | WECC_ECOLI | (P27829) UDP-N-ACETYL-D-MANNOSAMINURONIC ACID DEHYDROGENASE |
| 615 | WRBA_ECOLI | (P30849) TRP REPRESSOR BINDING PROTEIN. |
| 616 | WZB3_ECOLI | (P35272) CHAIN LENGTH DETERMINANT PROTEIN (POLYSACCHARIDE A |
| 617 | YAAF_ECOLI | (P22564) HYPOTHETICAL 32.6 KDA PROTEIN IN LYTB-DAPB INTERGE |
| 618 | YABC_ECOLI | (P18595) PROTEIN YABC. |
| 619 | YACL_ECOLI | (P45567) HYPOTHETICAL 13.9 KDA PROTEIN IN ACNB-SPED INTERGE |
| 620 | YADF_ECOLI | (P36857) 25.1 KDA PROTEIN IN HPT-PAND INTERGENIC REGION. |
| 621 | YAEB_ECOLI | (P28634) HYPOTHETICAL 26.4 KDA PROTEIN IN PROS-RCSF INTERGE |
| 622 | YAFA_ECOLI | (P04335) HYPOTHETICAL 49.1 KDA PROTEIN IN GPT-CRL INTERGENI |
| 623 | YAFH_ECOLI | (Q47146) HYPOTHETICAL 87.0 KDA PROTEIN IN DNAQ-GMHA INTERGE |
| 624 | YAHK_ECOLI | (P75691) HYPOTHETICAL ZINC-TYPE ALCOHOL DEHYDROGENASE-LIKE |
| 625 | YAHL_ECOLI | (P77393) HYPOTHETICAL 31.8 KDA PROTEIN IN BETT-PRPR INTERGE |
| 626 | YAHO_ECOLI | (P75694) HYPOTHETICAL 9.9 KDA PROTEIN IN BETT-PRPR INTERGEN |
| 627 | YAIL_ECOLI | (P52088) HYPOTHETICAL 17.0 KDA PROTEIN IN PROC-AROL INTERGE |
| 628 | YAJI_ECOLI | (P46122) HYPOTHETICAL LIPOPROTEIN YAJI PRECURSOR. |
| 629 | YBAB_ECOLI | (P17577) HYPOTHETICAL 12.0 KDA PROTEIN IN DNAX-RECR INTERGE |
| 630 | YBAD_ECOLI | (P25538) HYPOTHETICAL 17.2 KDA PROTEIN IN TSX-RIBG INTERGEN |
| 631 | YBBK_ECOLI | (P77367) HYPOTHETICAL 33.7 KDA PROTEIN IN USHA-TESA INTERGE |
| 632 | YBBP_ECOLI | (P77504) HYPOTHETICAL 89.3 KDA PROTEIN IN TESA-RHSD INTERGE |
| 633 | YBDG_ECOLI | (P39455) HYPOTHETICAL 46.6 KDA PROTEIN IN PHEP-NFNB INTERGE |
| 634 | YBDK_ECOLI | (P77213) HYPOTHETICAL 41.7 KDA PROTEIN IN NFNB-ENTD INTERGE |
| 635 | YBEJ_ECOLI | (P37902) AMINO-ACID ABC TRANSPORTER BINDING PROTEIN YBEJ PR |
| 636 | YBFF_ECOLI | (P75736) PUTATIVE ESTERASE/LIPASE YBFF (EC 3.1.-.-). |
| 637 | YBHB_ECOLI | (P12994) HYPOTHETICAL 17.1 KDA PROTEIN IN MODC-BIOA INTERGE |
| 638 | YBHE_ECOLI | (P52697) HYPOTHETICAL 36.3 KDA PROTEIN IN MODC-BIOA INTERGE |
| 639 | YBIT_ECOLI | (P75790) HYPOTHETICAL ABC TRANSPORTER ATP-BINDING PROTEIN Y |
| 640 | YBJD_ECOLI | (P75828) HYPOTHETICAL 63.6 KDA PROTEIN IN AQPZ-CSPD INTERGE |
| 641 | YCAJ_ECOLI | (P45526) HYPOTHETICAL 49.6 KDA PROTEIN IN LOLA-SERS INTERGE |
| 642 | YCBL_ECOLI | (P75849) HYPOTHETICAL 23.8 KDA PROTEIN IN MUKB-ASPC INTERGE |
| 643 | YCBY_ECOLI | (P75864) HYPOTHETICAL 78.9 KDA PROTEIN IN PYRD-PQIA INTERGE |
| 644 | YCCJ_ECOLI | (P46131) HYPOTHETICAL 8.5 KDA PROTEIN IN AGP-WRBA INTERGENI |
| 645 | YCCK_ECOLI | (P45572) HYPOTHETICAL 12.4 KDA PROTEIN IN HELD-SERT INTERGE |
| 646 | YCDX_ECOLI | (P75914) HYPOTHETICAL 26.9 KDA PROTEIN IN PHOH-CSGG INTERGE |
| 647 | YCEH_ECOLI | (P29217) HYPOTHETICAL 24.2 KDA PROTEIN IN RIMJ-MVIM INTERGE |
| 648 | YCFD_ECOLI | (P27431) HYPOTHETICAL 42.6 KDA PROTEIN IN PEPT-PHOQ INTERGE |
| 649 | YCFH_ECOLI | (P37346) PUTATIVE DEOXYRIBONUCLEASE YCFH (EC 3.1.21.-). |
| 650 | YCFX_ECOLI | (P75959) HYPOTHETICAL 33.0 KDA PROTEIN IN MFD-COBB INTERGEN |
| 651 | YCGF_ECOLI | (P75990) HYPOTHETICAL 45.3 KDA PROTEIN IN ELBA-MINE INTERGE |
| 652 | YCGL_ECOLI | (P76003) PROTEIN YCGL. |
| 653 | YCGM_ECOLI | (P76004) PROTEIN YCGM. |
| 654 | YCHN_ECOLI | (P39164) HYPOTHETICAL 12.7 KDA PROTEIN IN CHAC-NARL INTERGE |

TABLE XII-continued

List of proteins that were identified by LC-MS/MS analysis on MetSO-sorted peptides. The proteins are sorted according to their SwissProt entry name.

| | | |
|---|---|---|
| 655 | YCIE_ECOLI | (P21363) PROTEIN YCIE. |
| 656 | YCIK_ECOLI | (P31808) HYPOTHETICAL OXIDOREDUCTASE IN BTUR-SOHB INTERGENI |
| 657 | YCIN_ECOLI | (P46132) HYPOTHETICAL 9.4 KDA PROTEIN IN SOHB-TOPA INTERGEN |
| 658 | YCJP_ECOLI | (P77716) HYPOTHETICAL ABC TRANSPORTER PERMEASE PROTEIN YCJP |
| 659 | YCJX_ECOLI | (P76046) HYPOTHETICAL 52.6 KDA PROTEIN IN OMPG-TYRR INTERGE |
| 660 | YDAO_ECOLI | (P76055) HYPOTHETICAL 35.6 KDA PROTEIN IN DBPA-INTR INTERGE |
| 661 | YDCH_ECOLI | (P46135) HYPOTHETICAL 6.5 KDA PROTEIN IN TRG-RIML INTERGENI |
| 662 | YDCL_ECOLI | (P76101) HYPOTHETICAL 24.4 KDA LIPOPROTEIN IN TEHB-ANSB INT |
| 663 | YDCS_ECOLI | (P76108) HYPOTHETICAL ABC TRANSPORTER PERIPLASMIC BINDING P |
| 664 | YDEN_ECOLI | (P77318) PUTATIVE SULFATASE YDEN PRECURSOR (EC 3.1.6.-). |
| 665 | YDES_ECOLI | (P77789) HYPOTHETICAL FIMBRIAL-LIKE PROTEIN YDES PRECURSOR. |
| 666 | YDFG_ECOLI | (P39831) PROBABLE OXIDOREDUCTASE IN DCP-PINQ INTERGENIC REG |
| 667 | YDFY_ECOLI | (P77695) HYPOTHETICAL 6.5 KDA PROTEIN IN NOHA-CSPI INTERGEN |
| 668 | YDGA_ECOLI | (P77804) HYPOTHETICAL 54.7 KDA PROTEIN IM MANA-GUSC INTERGE |
| 669 | YDGH_ECOLI | (P76177) PROTEIN YDGH PRECURSOR. |
| 670 | YDGT_ECOLI | (P76179) HYPOTHETICAL 8.4 KDA PROTEIN IN ADD-NTH INTERGENIC |
| 671 | YDHD_ECOLI | (P37010) PROTEIN YDHD. |
| 672 | YDIA_ECOLI | (P03822) HYPOTHETICAL 31.2 KDA PROTEIN IN PPSA-AROH INTERGE |
| 673 | YDIB_ECOLI | (P28244) HYPOTHETICAL 31.2 KDA PROTEIN IN LPP-AROD INTERGEN |
| 674 | YDJF_ECOLI | (P77721) HYPOTHETICAL TRANSCRIPTIONAL REGULATOR IN PNCA-GAP |
| 675 | YEAG_ECOLI | (P77391) HYPOTHETICAL 74.5 KDA PROTEIN IN GAPA-RND INTERGEN |
| 676 | YEAH_ECOLI | (P76235) HYPOTHETICAL 49.4 KDA PROTEIN IN GAPA-RND INTERGEN |
| 677 | YEAN_ECOLI | (P76242) HYPOTHETICAL 41.2 KDA PROTEIN IN GAPA-RND INTERGEN |
| 678 | YEAZ_ECOLI | (P76256) HYPOTHETICAL 25.2 KDA PROTEIN IN FADD-PABB INTERGE |
| 679 | YEBC_ECOLI | (P24237) PROTEIN YEBC. |
| 680 | YEBY_ECOLI | (P76277) HYPOTHETICAL 12.4 KDA PROTEIN IN PPHA-HOLE INTERGE |
| 681 | YECA_ECOLI | (P06979) HYPOTHETICAL 25.0 KDA PROTEIN IN TYRP-LEUZ INTERGE |
| 682 | YECO_ECOLI | (P76290) PROTEIN YECO. |
| 683 | YEDD_ECOLI | (P31063) HYPOTHETICAL 15.0 KDA PROTEIN IN AMYA-FLIE INTERGE |
| 684 | YEDS_ECOLI | (P76335) POTENTIAL OUTER MEMBRANE PROTEIN YEDS PRECURSOR. |
| 685 | YEDU_ECOLI | (P31658) PROTEIN YEDU. |
| 686 | YEEZ_ECOLI | (P76370) PROTEIN YEEZ PRECURSOR. |
| 687 | YEFG_ECOLI | (P37749) HYPOTHETICAL 37.8 KDA PROTEIN IN GND-RFC INTERGENI |
| 688 | YEGJ_ECOLI | (P76394) HYPOTHETICAL 17.4 KDA PROTEIN IN ALKA-BAES INTERGE |
| 689 | YEGP_ECOLI | (P76402) HYPOTHETICAL 12.0 KDA PROTEIN IN BAER-OGRK INTERGE |
| 690 | YEGQ_ECOLI | (P76403) PUTATIVE PROTEASE YEGQ (EC 3.4.-.-). |
| 691 | YEIA_ECOLI | (P25889) HYPOTHETICAL 45.1 KDA PROTEIN IN CDD-MGLC INTERGEN |
| 692 | YFBQ_ECOLI | (P77727) PROBABLE AM1NOTRANSFERASE YFBQ (EC 2.6.1.-). |
| 693 | YFCG_ECOLI | (P77526) HYPOTHETICAL 24.5 KDA PROTEIN IN PTA-FOLX INTERGEN |
| 694 | YFCH_ECOLI | (P77775) HYPOTHETICAL 32.7 KDA PROTEIN IN FOLX-HISP INTERGE |
| 695 | YFEY_ECOLI | (P76537) HYPOTHETICAL 20.9 KDA PROTEIN IN UCPA-AMIA INTERGE |
| 696 | YFGB_ECOLI | (P36979) HYPOTHETICAL 43.1 KDA PROTEIN IN NDK-GCPE INTERGEN |
| 697 | YFIA_ECOLI | (P11285) PROTEIN YFIA. |
| 698 | YFID_ECOLI | (P33633) 14.3 KDA PROTEIN IN SRMB-UNG INTERGENIC REGION. |
| 699 | YFIF_ECOLI | (P33635) HYPOTHETICAL TRNA/RRNA METHYLTRANSFERASE YFIF (EC |
| 700 | YFIO_ECOLI | (P77146) HYPOTHETICAL 27.8 KDA LIPOPROTEIN IN RLUD-PHEL INT |
| 701 | YFIQ_ECOLI | (P76594) HYPOTHETICAL 98.0 KDA PROTEIN IN UNG-PSSA INTERGEN |
| 702 | YGAD_ECOLI | (P41053) PROTEIN YGAD. |
| 703 | YGAT_ECOLI | (P76621) HYPOTHETICAL 37.4 KDA PROTEIN IN ILEY-GABD INTERGE |
| 704 | YGCA_ECOLI | (P55135) HYPOTHETICAL RNA METHYLTRANSFERASE IN RELA-BARA IN |
| 705 | YGDE_ECOLI | (P32066) HYPOTHETICAL 41.9 KDA PROTEIN IN FUCR-GCVA INTERGE |
| 706 | YGEV_ECOLI | (Q46802) HYPOTHETICAL SIGMA-54-DEPENDENT TRANSCRIPTIONAL RE |
| 707 | YGEW_ECOLI | (Q46803) HYPOTHETICAL 40.2 KDA PROTEIN IN KDUI-LYSS INTERGE |
| 708 | YGEY_ECOLI | (Q46805) HYPOTHETICAL 44.8 KDA PROTEIN IN KDUI-LYSS INTERGE |
| 709 | YGIN_ECOLI | (P40718) PROTEIN YGIN. |
| 710 | YHBC_ECOLI | (P03843) HYPOTHETICAL 15.5 KDA PROTEIN N NUSA-METY INTERGE |
| 711 | YHBJ_ECOLI | (P33995) HYPOTHETICAL 32.5 KDA PROTEIN IN PTSN-PTSO INTERGE |
| 712 | YHBZ_ECOLI | (P42641) HYPOTHETICAL 43.3 KDA GTP-BINDNG PROTEIN IN DACB- |
| 713 | YHCB_ECOLI | (P39436) HYPOTHETICAL 15.2 KDA PROTEIN IN RPLM-HHOA INTERGE |
| 714 | YHCS_ECOLI | (P45691) HYPOTHETICAL TRANSCRIPTIONAL REGULATOR IN ARGR-CAF |
| 715 | YHDH_ECOLI | (P26646) PROTEIN YHDH. |
| 716 | YHFZ_ECOLI | (P45552) HYPOTHETICAL 30.3 KDA PROTEIN IN CYSG-TRPS INTERGE |
| 717 | YHGF_ECOLI | (P46837) PROTEIN YHGF. |
| 718 | YHHA_ECOLI | (P23850) HYPOTHETICAL 16.6 KDA PROTEIN IN GGT-UGPQ INTERGEN |
| 719 | YHHW_ECOLI | (P46852) PROTEIN YHHW. |
| 720 | YHIL_ECOLI | (P37629) HYPOTHETICAL 61.6 KDA PROTEIN IN RHSB-PIT INTERGEN |
| 721 | YHIR_ECOLI | (P37634) HYPOTHETICAL 31.9 KDA PROTEIN IN PRLC-GOR INTERGEN |
| 722 | YHIV_ECOLI | (P37637) HYPOTHETICAL 111.5 KDA PROTEIN IN HDED-GADA INTERG |
| 723 | YHJA_ECOLI | (P37197) PROBABLE CYTOCHROME C PEROXIDASE (EC 1.11.1.5). |
| 724 | YHJJ_ECOLI | (P37648) PROTEIN YHJJ PRECURSOR. |
| 725 | YI9A_ECOLI | (Q47309) INSERTION ELEMENT IS1397 HYPOTHETICAL 20.1 KDA PRO |
| 726 | YIAF_ECOLI | (P37667) HYPOTHETICAL 30.2 KDA PROTEIN IN BISC-CSPA INTERGE |
| 727 | YIAJ_ECOLI | (P37671) HYPOTHETICAL TRANSCRIPTIONAL REGULATOR IN AVTA-SEL |
| 728 | YIBL_ECOLI | (P36564) HYPOTHETICAL 13.7 KDA PROTEIN IN MTLR-LCTP INTERGE |
| 729 | YIBP_ECOLI | (P37690) HYPOTHETICAL 46.6 KDA PROTEIN IN SECB-TDH INTERGEN |
| 730 | YICC_ECOLI | (P23839) PROTEIN YICC. |

TABLE XII-continued

List of proteins that were identified by LC-MS/MS analysis on MetSO-sorted peptides. The proteins are sorted according to their SwissProt entry name.

| | | |
|---|---|---|
| 731 YIGA_ECOLI | (P23305) | HYPOTHETICAL 26.7 KDA PROTEIN IN DAPF-XERC INTERGE |
| 732 YIHL_ECOLI | (P32133) | HYPOTHETICAL TRANSCRIPTIONAL REGULATOR IN GLNA-RBN |
| 733 YIHO_ECOLI | (P32136) | HYPOTHETICAL SYMPORTER IN GLNA-RBN INTERGENIC REGI |
| 734 YIIM_ECOLI | (P32157) | HYPOTHETICAL 26.6 KDA PROTEIN IN KDGT-CPXA INTERGE |
| 735 YIIT_ECOLI | (P32163) | HYPOTHETICAL 16.3 KDA PROTEIN IN TPIA-FPR INTERGEN |
| 736 YJBB_ECOLI | (P32683) | HYPOTHETICAL 59.5 KDA PROTEIN IN METH-PEPE INTERGE |
| 737 YJBJ_ECOLI | (P32691) | PROTEIN YJBJ. |
| 738 YJBQ_ECOLI | (P32698) | HYPOTHETICAL 15.7 KDA PROTEIN IN APHA-UVRA INTERGE |
| 739 YJBR_ECOLI | (P32699) | HYPOTHETICAL 13.5 KDA PROTEIN IN APHA-UVRA INTERGE |
| 740 YJDK_ECOLI | (P39275) | HYPOTHETICAL 11.5 KDA PROTEIN IN DCUB-LYSU INTERGE |
| 741 YJEQ_ECOLI | (P39286) | HYPOTHETICAL 39.2 KDA PROTEIN IN PSD-AMIB INTERGEN |
| 742 YJFH_ECOLI | (P39290) | HYPOTHETICAL TRNA/RRNA METHYLTRANSFERASE YJFH (EC |
| 743 YJGB_ECOLI | (P27250) | HYPOTHETICAL ZINC-TYPE ALCOHOL DEHYDROGENASE-LIKE |
| 744 YJGF_ECOLI | (P39330) | 13.5 KDA PROTEIN IN MGTA-PYRI INTERGENIC REGION. |
| 745 YJGR_ECOLI | (P39342) | HYPOTHETICAL 54.3 KDA PROTEIN IN PEPA-GNTV INTERGE |
| 746 YJHU_ECOLI | (P39356) | HYPOTHETICAL TRANSCRIPTIONAL REGULATOR IN FECI-FIM |
| 747 YJIA_ECOLI | (P24203) | HYPOTHETICAL 35.7 KDA PROTEIN IN MRR-TSR INTERGENI |
| 748 YJIM_ECOLI | (P39384) | HYPOTHETICAL 42.7 KDA PROTEIN IN IADA-MCRD INTERGE |
| 749 YJJK_ECOLI | (P37797) | ABC TRANSPORTER ATP-BINDING PROTEIN YJJK. |
| 750 YKGE_ECOLI | (P77252) | HYPOTHETICAL 26.0 KDA PROTEIN IN EAEH-BETA INTERGE |
| 751 YKGF_ECOLI | (P77536) | HYPOTHETICAL 53.1 KDA PROTEIN IN EAEH-BETA INTERGE |
| 752 YLEA_ECOLI | (P77645) | HYPOTHETICAL 53.7 KDA PROTEIN N CUTE-GLNX INTERGE |
| 753 YLIB_ECOLI | (P75797) | PUTATIVE BINDING PROTEIN YLIB PRECURSOR. |
| 754 YLIG_ECOLI | (P75802) | HYPOTHETICAL 49.6 KDA PROTEIN IN MOEA-DACC INTERGE |
| 755 YLIJ_ECOLI | (P75805) | HYPOTHETICAL 23.7 KDA PROTEIN IN MOEA-DACC INTERGE |
| 756 YMBA_ECOLI | (P75866) | HYPOTHETICAL 20.0 KDA PROTEIN IN PQIB-RMF INTERGEN |
| 757 YNEB_ECOLI | (P76143) | PUTATIVE ALDOLASE YNEB (EC 4.2.1.-). |
| 758 YNFF_ECOLI | (P77783) | PUTATIVE DIMETHYL SULFOXIDE REDUCTASE CHAIN YNFF P |
| 759 YNIC_ECOLI | (P77247) | HYPOTHETICAL 24.3 KDA PROTEIN IN PFKB-CEDA INTERGE |
| 760 YNJE_ECOLI | (P78067) | PUTATIVE THIOSULFATE SULFURTRANSFERASE YNJE PRECUR |
| 761 YOJN_ECOLI | (P39838) | PROBABLE SENSOR PROTEIN YOJN (EC 2.7.3.-). |
| 762 YPFH_ECOLI | (P76561) | HYPOTHETICAL 24.9 KDA PROTEIN IN DAPE-PURC INTERGE |
| 763 YQGE_ECOLI | (P52049) | PROTEIN YQGE. |
| 764 YQHD_ECOLI | (Q46856) | HYPOTHETICAL OXIDOREDUCTASE IN METC-SUFI INTERGENI |
| 765 YRAP_ECOLI | (P45467) | HYPOTHETICAL 20.0 KDA PROTEIN IN AGAI-MTR INTERGEN |
| 766 YRBF_ECOLI | (P45393) | HYPOTHETICAL ABC TRANSPORTER ATP-BINDING PROTEIN I |
| 767 YTFQ_ECOLI | (P39325) | ABC TRANSPORTER PERIPLASMIC BINDING PROTEIN YTFQ P |

TABLE XIII

A complex protein peptide mixture was generated by trypsin digestion on total unfractionated human plasma. The equivalent of one microliter plasma was used to sort Met-peptides by oxidation. Only two out of . . . fractions of the primary run were further analysed. The identified peptides and corresponding proteins in these fractions are listed. (DB Entry: entry in the SWISSPROT database, available via http://www.expasy.ch/sprot)

| DB Entry | Protein Description | Identified Peptide |
|---|---|---|
| A2MG_HUMAN | (P01023) ALPHA-2-MACROGLOBULIN PRECURSOR | SSSNEEVMFLTVQVK |
| ALBU_HUMAN | (P02768) SERUM ALBUMIN PRECURSOR | AVMDDFAAFVEK |
| AMBP_HUMAN | (P02760) ALPHAE-1-MICROGLOBULIN | VVAQGVGIPEDSIFTMADR |
| ANT3_HUMAN | (P01008) ANTITHROMBIN-III PRECURSOR | GDDITMVLILPKPEK |
| APB_HUMAN | (P04114) APOLIPOPROTEIN B-100 PRECURSOR | AVSMPSFSILGSDVR |
| | | LIDVISMYR |
| | | TEHGSEMLFFGNAIEGK |
| CO3_HUMAN | (P01024) COMPLEMENT C3 PRECURSOR | ILLQGTPVAQMTEDAVDAER |
| | | LMNIFLK |
| FIBB_HUMAN | (P02675) FIBRINOGEN BETA CHAIN PRECURSOR | HGTDDGWWMNWK |
| | | YYWGGQYTWDMAK |
| GSHP_HUMAN | (P22352) PLASMA GLUTATHIONE PEROXIDASE PRECURSOR | FLVGPDGIPIMR |
| HBA_HUMAN | (P01922) HEMOGLOBIN ALPHA CHAIN | MFLSFPTTK |
| HBB_HUMAN | (P02023) HEMOGLOBIN BETA CHAIN | FFESFGDLSTPDAVMGNPK |
| IC1_HUMAN | (P05155) PLASMA PROTEASE C1 INHIBITOR PRECURSOR | LEDMEQALSPSVFK |
| ITH4_HUMAN | (Q14624) INTER-ALPHA-TRYPSIN INHIBITOR HEAVY CHAIN | ETLFSVMPGLK |
| TRFE_HUMAN | (P02787) SEROTRANSFERRIN PRECURSOR | IMNGEADAMSLDGGFVYIAGK |
| U2AG_HUMAN | (Q01081) SPLICING FACTOR U2AF 35 KDA SUBUNIT | MAEYLASIFGTEK |
| Z298_HUMAN | (P57071) ZINC FINGER PROTEIN 298 | KMDKPMLK |

TABLE XIV

| RUN | Primary Fractions | | | | Elution time intervals primary fractions | | | | Elution time intervals MetSO-peptides | | | |
|---|---|---|---|---|---|---|---|---|---|---|---|---|
| 2A | 12 | 24 | 36 | 48 | 51–52 | 63–64 | 75–76 | 87–88 | 44–50 | 56–62 | 68–74 | 80–86 |
| 2B | 11 | 23 | 35 | 47 | 50–51 | 62–63 | 74–75 | 86–87 | 43–49 | 55–61 | 67–73 | 79–85 |
| 2C | 10 | 22 | 34 | 46 | 49–50 | 61–62 | 73–74 | 85–86 | 42–48 | 54–60 | 66–72 | 78–84 |
| 2D | 9 | 21 | 33 | 45 | 48–49 | 60–61 | 72–73 | 84–85 | 41–47 | 53–59 | 65–71 | 77–83 |
| 2E | 8 | 20 | 32 | 44 | 47–48 | 59–60 | 71–72 | 83–84 | 40–46 | 52–58 | 64–70 | 76–82 |
| 2F | 7 | 19 | 31 | 43 | 46–47 | 58–59 | 70–71 | 82–83 | 39–45 | 51–57 | 63–69 | 75–81 |
| 2G | 6 | 18 | 30 | 42 | 45–46 | 57–58 | 69–70 | 81–82 | 38–44 | 50–56 | 62–68 | 74–80 |
| 2H | 5 | 17 | 29 | 41 | 44–45 | 56–57 | 68–69 | 80–81 | 37–43 | 49–55 | 61–67 | 73–79 |
| 2I | 4 | 16 | 28 | 40 | 43–44 | 55–56 | 67–68 | 79–80 | 36–42 | 48–54 | 60–66 | 72–78 |
| 2K | 3 | 15 | 27 | 39 | 42–43 | 54–55 | 66–67 | 78–79 | 35–41 | 47–53 | 59–65 | 71–77 |
| 2L | 2 | 14 | 26 | 38 | 41–42 | 53–54 | 65–66 | 77–78 | 34–40 | 46–52 | 58–64 | 70–76 |
| 2M | 1 | 13 | 25 | 37 | 40–41 | 52–53 | 64–65 | 76–77 | 33–39 | 45–51 | 57–63 | 69–75 |

Schematic overview showing which primary fractions (of which the collection times depicted are given in the third column) can be pooled for the sorting of methionine-containing peptides during the secondary runs (second column) under the given chromatographic conditions. The elution intervals for the collection of the MetSO-peptides are given in the last column. The Met-SO peptides that were obtained in runs 2A and 2F were further one used for protein identification (see Table XV).

TABLE XV

List of proteins and peptides identified by analysing the Met-SO peptides sorted in two secondary runs from a total of 8 primary fractions. The results presented in this table were obtained following 16 LC-MS/MS runs on the sorted Met-SO peptides. Proteins were obtained from a Triton-soluble fraction of human thrombocytes.

| | SWISSPROT entry | Protein Description | Identified Peptide(s) |
|---|---|---|---|
| 1 | 143G_HUMAN | 14-3-3 PROTEIN (different isoforms) | DSTLIMQLLR EMQPTHPIR |
| 2 | 2AAA_HUMAN | SERINE/THREONINE PROTEIN PHOSPHATASE 2A | MAGDPVANVR TDLVPAFQNLMK |
| 3 | 5NTD_HUMAN | 5'-NUCLEOTIDASE RECURSOR | MKVIYPAVEGRIK |
| 4 | AAC1/2/4_HUMAN | ALPHA-ACTININ 1/2/4 | HTNYTMEHIR |
| 5 | AAC1/4_HUMAN | ALPHA-ACTININ 1/4 | AIMTYVSSFYHAFSGAQK |
| 6 | AAC1_HUMAN | ALPHA-ACTININ 1 | ILAGDKNYITMDELR |
| 7 | AAC4_HUMAN | ALPHA-ACTININ 4 | VLAVNQENEHLMEDYEK |
| 8 | ACTB/G_HUMAN | ACTIN, CYTOPLASMIC 1 (BETA/GAMMA-ACTIN) | DLTDYLMK EITALAPSTMK HQGVMVGMGQK TTGIVMDSGDGVTHTV PIYEGYALPHAILR |
| 9 | AR21_HUMAN | ARP2/3 COMPLEX 21 KDA SUBUNIT (P21-ARC) | LIGNMALLPIR |
| 10 | AR34_HUMAN | ARP2/3 COMPLEX 34 KDA SUBUNIT (P34-ARC) | MILLEVNNR |
| 11 | ARFI_HUMAN | ADP-RIBOSYLATION FACTOR (different isoforms) | ILMVGLDAAGK |
| 12 | ARP2_HUMAN | ACTIN-LIKE PROTEIN 2 | DLMVGDEASELR |
| 13 | ARP3_HUMAN | ACTIN-LIKE PROTEIN 3 | NIVLSGGSTMFR |
| 14 | CALU_HUMAN | CALUMENIN PRECURSOR | MADKDGDLIATK |
| 15 | CAN1_HUMAN | CALPAIN 1, LARGE [CATALYTIC] SUBUNIT | MEDGEFWMSFR SMVNLMDR |
| 16 | CAP1_HUMAN | ADENYLYL CYCLASE-ASSOCIATED PROTEIN 1 | EMNDAAMFYTNR LEAVSHTSDMHR |
| 17 | CAZ1_HUMAN | F-ACTIN CAPPING PROTEIN ALPHA-1 SUBUNIT | EGAAHAFAQYNMDQFTPVK |
| 18 | CBP2_HUMAN | COLLAGEN-BINDING PROTEIN 2 PRECURSOR | LQIVEMPLAHK |
| 19 | CD63_HUMAN | CD63 ANTIGEN | QQMENYPK |
| 20 | CLI4_HUMAN | CHLORIDE INTRACELLULAR CHANNEL PROTEIN | EMTGIWR |
| 21 | CLP2_HUMAN | CALPONIN H2, SMOOTH MUSCLE | SMQNWHQLENLSNFIK |
| 22 | CO3_HUMAN | COMPLEMENT C3 PRECURSOR | YYTYLIMNK |

TABLE XV-continued

List of proteins and peptides identified by analysing the Met-SO peptides sorted in two secondary runs from a total of 8 primary fractions. The results presented in this table were obtained following 16 LC-MS/MS runs on the sorted Met-SO peptides. Proteins were obtained from a Triton-soluble fraction of human thrombocytes.

| | SWISSPROT entry | Protein Description | Identified Peptide(s) |
|---|---|---|---|
| 23 | CYPB_HUMAN | PEPTIDYL-PROLYL CIS-TRANS ISOMERASE B | HYGPGWVSMANAGK |
| 24 | CYPH_HUMAN | PEPTIDYL-PROLYL CIS-TRANS ISOMERASE A | VKEGMNIVEAMER |
| 25 | DEMA_HUMAN | DEMATIN | VFAMSPEEFGK |
| 26 | DYNC_HUMAN | DYNACTIN COMPLEX 50 KDA SUBUNIT | DNTTLLTQVQTTMR |
| 27 | EHD1_HUMAN | EH-DOMAIN CONTAINING PROTEIN 1 | MQELLQTQDFSK |
| 28 | F13A_HUMAN | COAGULATION FACTOR XIII A CHAIN PRECURSOR | KPLNTEGVMK |
| 29 | FIBA_HUMAN | FIBRINOGEN ALPHA/ALPHA-E CHAIN PRECURSOR | MKPVPDLVPGNFK |
| 30 | FIBB_HUMAN | FIBRINOGEN BETA CHAIN PRECURSOR | TMTIHNGMFFSTYDR |
| 31 | GDIA_HUMAN | RAB GDP DISSOCIATION INHIBITOR ALPHA | MAGTAFDFENMK |
| 32 | GR78_HUMAN | 78 KDA GLUCOSE-REGULATED PROTEIN PRECUROR | FEELNMDLFR<br>TFAPEEISAMVLTK |
| 33 | GTO1_HUMAN | GLUTATHIONE TRANSFERASE OMEGA 1 | MILELFSK |
| 34 | HS47_HUMAN | 47 KDA HEAT SHOCK PROTEIN PRECURSOR | LQLVEMPLAHK |
| 35 | HS71_HUMAN | HEAT SHOCK 70 KDA PROTEIN 1 | NALESYAFNMK |
| 36 | HS7C_HUMAN | HEAT SHOCK COGNATE 71 KDA PROTEIN | MVNHFIAEFK |
| 37 | HS9A/B_HUMAN | HEAT SHOCK PROTEIN HSP 90-ALPHA/BETA | TLTIVDTGIGMTK |
| 38 | IDHC_HUMAN | ISOCITRATE DEHYDROGENASE | LIDDMVAQAMK |
| 39 | ILK1/2_HUMAN | INTEGRIN-LINKED PROTEIN KINASE 1/2 | GMAFLHTLEPLIPR<br>SAVVEMLIMR |
| 40 | ITA2_HUMAN | INTEGRIN ALPHA-2 PRECURSOR | VMVVVTDGESHDGSMLK |
| 41 | K6PP_HUMAN | 6-PHOSPHOFRUCTOKINASE, TYPE C | IIEVVDAIMTTAQSHQR<br>MLAIYDGFDGFAK |
| 42 | KAP0_HUMAN | CAMP-DEPENDENT PROTEIN KINASE | MYEEFLSK |
| 43 | KPY1_HUMAN | PYRUVATE KINASE, M1 ISOZYME | MQHLIAR |
| 44 | LAS1_HUMAN | LIM AND SH3 DOMAIN PROTEIN 1 | QSFTMVADTPENLR |
| 45 | LOXP_HUMAN | ARACHIDONATE 12-LIPOXYGENASE, 12S-TYPE | AGALEMALK |
| 46 | MIF_HUMAN | MACROPHAGE MIGRATION INHIBITORY FACTOR | PMFIVNTNVPR |
| 47 | MOES_HUMAN | MOESIN | AQMVQEDLEK<br>IAQDLEMYGVNYFSIK<br>KPDTIEVQQMK |
| 48 | MYH9_HUMAN | MYOSIN HEAVY CHAIN, NONMUSCLE TYPE A | ELEDATETADAMNR<br>EMEAELEDER<br>IIGLDQVAGMSETALPGAFK<br>LEVNLQAMK<br>QQQLTAMK |
| 49 | MYHA_HUMAN | MYOSIN HEAVY CHAIN, NONMUSCLE TYPE B | ADEWLMK |
| 50 | PA1F_HUMAN | RED CELL ACID PHOSPHATASE 1, ISOZYME F | HGIPMSHVAR |
| 51 | PDA3_HUMAN | PROTEIN DISULFIDE ISOMERASE A3 PRECURSOR | FVMQEEFSR |
| 52 | PDI_HUMAN | PROTEIN DISULFIDE ISOMERASE PRECURSOR | LITLEEEMTK |
| 53 | PDL1_HUMAN | PDZ AND LIM DOMAIN PROTEIN 1 | MNLASEPQEVLHIGSAHNR |
| 54 | PHS3_HUMAN | GLYCOGEN PHOSPHORYLASE, BRAIN FORM | VAIQLNDTHPALSIPELMR |

TABLE XV-continued

List of proteins and peptides identified by analysing the Met-SO peptides sorted in two secondary runs from a total of 8 primary fractions. The results presented in this table were obtained following 16 LC-MS/MS runs on the sorted Met-SO peptides. Proteins were obtained from a Triton-soluble fraction of human thrombocytes.

| | SWISSPROT entry | Protein Description | Identified Peptide(s) |
|---|---|---|---|
| 55 | PIMT_HUMAN | PROTEIN-L-ISOASPARTATE(D-ASPARTATE) | MKPLMGVIYVPLTDK |
| 56 | PLEK_HUMAN | PLECKSTRIN (PLATELET P47 PROTEIN) | LPETIDLGALYLSMK |
| 57 | PNPH_HUMAN | PURINE NUCLEOSIDE PHOSPHORYLASE | VIMDYESLEK |
| 58 | PSE1_HUMAN | PROTEASOME ACTIVATOR COMPLEX SUBUNIT 1 | LMVMEIR |
| 59 | R23B_HUMAN | UV EXCISION REPAIR PROTEIN RAD23 HOMOLOGUE | NFVVVMVTKPK |
| 60 | RAC1_HUMAN | RAS-RELATED C3 BOTULINUM TOXIN SUBSTRATE | LTPITYPQGLAMAK |
| 61 | RALA/B_HUMAN | RAS-RELATED PROTEIN RAL-A/B | VFFDLMR |
| 62 | RAPB_HUMAN | RAS-RELATED PROTEIN RAP-1B | VKDTDDVPMILVGNK |
| 63 | RB5A/B/C_HUMAN | RAS-RELATED PROTEIN RAB-5/A/B/C | YHSLAPMYYR |
| 64 | RB5A_HUMAN | RAS-RELATED PROTEIN RAB-5A | TSMNVNEIFMAIAK |
| 65 | RB5B_HUMAN | RAS-RELATED PROTEIN RAB-5B | TAMNVNDLFLAIAK |
| 66 | RSG3_HUMAN | RAS GTPASE-ACTIVATING PROTEIN 3 | NMFQVIQPER |
| 67 | TALI_HUMAN | TALIN | ALDYYMLR<br>DHFGLEGDEESTMLEDSVSPK<br>MATNAAAQNAIK<br>TLSHPQQMALLDQTK<br>VEHGSVALPAIMR<br>VSQMAQYFEPLTLAAVGAASK |
| 68 | TBB1_HUMAN | TUBULIN BETA-CHAIN (different isoforms) | IMNTFSVVPSPK<br>LHFFMPGFAPLTSR |
| 69 | TCPG_HUMAN | T-COMPLEX PROTEIN 1, GAMMA SUBUNIT | ALDDMISTLK |
| 70 | TPM2_HUMAN | TROPOMYOSIN BETA CHAIN | MELQEMQLK |
| 71 | TPMN_HUMAN | TROPOMYOSIN, CYTOSKELETAL TYPE | MLDQTLLDLNEM |
| 72 | UBIQ_HUMAN | UBIQUITIN | MQIFVK |
| 73 | VINC_HUMAN | VINCULIN (METAVINCULIN) | ELLPVLISAMK<br>MTGLVDEAIDTK<br>VMLVNSMNTVK |
| 74 | WDR1_HUMAN | WD-REPEAT PROTEIN 1 | YTSLMLR |

TABLE XVI

Proteins identified following selection of their acetylated N-terminal, lysine-free and arginine-ending peptides out of a tryptic digest of a human thrombocyte cytosolic and membrane skeleton extract. The identified peptides are divided in three parts: (1) the naturally N-terminal blocked peptides, (2) peptides starting with a proline (that also cover the N-terminus of the protein) and (3) internal peptides beginning with a pyroglutamic acid (which is a side-effect of the preparation of the protein peptide mixture).

| SWISSPROT entry name | Accession number and protein Description | Identified peptide | Position |
|---|---|---|---|
| | | N-terminal peptides | |
| 143F_HUMAN | Q04917, 14-3-3 PROTEIN ETA PROTEIN AS1 | GDREQLLQR | 1_9 |
| APT_HUMAN | P07741, ADENINE PHOSPHORIBOSYLTRANSFERASE | ADSELQLVEQR | 1_11 |

TABLE XVI-continued

Proteins identified following selection of their acetylated N-terminal, lysine-free and arginine-ending peptides out of a tryptic digest of a human thrombocyte cytosolic and membrane skeleton extract. The identified peptides are divided in three parts: (1) the naturally N-terminal blocked peptides, (2) peptides starting with a proline (that also cover the N-terminus of the protein) and (3) internal peptides beginning with a pyroglutamic acid (which is a side-effect of the preparation of the protein peptide mixture).

| SWISSPROT entry name | Accession number and protein Description | Identified peptide | Position |
|---|---|---|---|
| AR72_HUMAN | O43488, AFLATOXIN B1 ALDEHYDE REDUCTASE 1 | SRPPPPR | 2_8 |
| ATA3_HUMAN | Q93084, SARCOPLASMIC/ENDOPLASMIC RETICULUM CALCIUM ATPASE 3 | MEAAHLLPAADVLR | 1_14 |
| CAP1_HUMAN | Q01518, ADENYLYL CYCLASE-ASSOCIATED PROTEIN 1 | ADMQNLVER | 2_9 |
| CAPB_HUMAN | P47756, F-ACTIN CAPPING PROTEIN BETA SUBUNIT | SDQQLDCALDLMR | 2_14 |
| CDN7_HUMAN | P55273, CYCLIN-DEPENDENT KINASE 4 INHIBITOR D | MLLEEVR | 1_7 |
| DEST_HUMAN | P18282, DESTRIN ACTIN DEPOLYMERIZING FACTOR | ASGVQVADEVCR | 2_13 |
| DREB_HUMAN | Q16643, DREBRIN E | AGVSFSGHR | 2_10 |
| EHD3_HUMAN | Q9NZN3, EH-DOMAIN CONTAINING PROTEIN 3 | MFSWLGTDDR | 1_10 |
| ERF1_HUMAN | P46055, EUKARYOTIC PEPTIDE CHAIN RELEASE FACTOR | ADDPSAADR | 2_10 |
| FABE_HUMAN | Q01469, FATTY ACID-BINDING PROTEIN, EPIDERMAL | ATVQQLEGR | 2_10 |
| FLIH_HUMAN | Q13045, FLIGHTLESS-I PROTEIN HOMOLOG | MEATGVLPFVR | 1_11 |
| FN3K_HUMAN | Q9H479, FRUCTOSAMINE-3-KINASE | MEQLLR | 1_6 |
| G6PD_HUMAN | P11413, GLUCOSE-6-PHOSPHATE 1 DEHYDROGENASE | AEQVALSR | 1_8 |
| IF4H_HUMAN | Q15056, EUKARYOTIC TRANSLATION INITIATION FACTOR | ADFDTYDDR | 2_10 |
| ILEU_HUMAN | P30740, LEUKOCYTE ELASTASE INHIBITOR | MEQLSSANTR | 1_10 |
| ILK2_HUMAN | P57043, INTEGRIN-LINKED PROTEIN KINASE 2 | MDDIFTQCR | 1_9 |
| KAP0_HUMAN | P10644, CAMP-DEPENDENT PROTEIN KINASE TYPE I-ALPHA REGULATORY CHAIN | MESGSTAASEEAR | 1_13 |
| KPC1_HUMAN | P05771, PROTEIN KINASE C, BETA-I TYPE | ADPAAGPPPSEGEESTVR | 2_19 |
| LAS1_HUMAN | Q14847, LIM AND SH3 DOMAIN PROTEIN 1 LASP-1 | MNPNCAR | 1_7 |
| MK01_HUMAN | P28482, MITOGEN-ACTIVATED PROTEIN KINASE 1 | AAAAAAGAGPEMVR | 2_15 |
| PINC_HUMAN | P48059, PINCH PROTEIN PARTICULARLY INTERESTING NEW CYS-HIS PROTEIN | ANALASATCER | 2_12 |
| PP1B_HUMAN | P37140, SERINE/THREONINE PROTEIN PHOSPHATASE | ADGELNVDSLITR | 2_14 |
| PSD5_HUMAN | Q16401, 26S PROTEASOME SUBUNIT S5B 26S PROTEASE | AAQALALLR | 2_10 |
| PTNC_HUMAN | Q05209, PROTEIN-TYROSINE PHOSPHATASE, NON-RECEPTOR, TYPE 12 | MEQVEILR | 1_8 |
| PYR1_HUMAN | P27708, CAD PROTEIN | AALVLEDGSVLR | 2_13 |
| SMP1_HUMAN | O95807, SMALL MEMBRANE PROTEIN 1 | SGFLEGLR | 2_9 |
| SN23_HUMAN | O00161, SYNAPTOSOMAL-ASSOCIATED PROTEIN 23 SNAP-23 | MDNLSSEEIQQR | 1_12 |
| SNX3_HUMAN | O60493, SORTING NEXIN 3 SDP3 PROTEIN | AETVADTR | 2_9 |
|  |  | AETVADTRR | 2_10 |
| SYFA_HUMAN | Q9Y285, PHENYLALANYL-TRNA SYNTHETASE ALPHA CHAIN | ADGQVAELLLR | 2_12 |
| SYG_HUMAN | P41250, GLYCYL-TRNA SYNTHETASE | MDGAGAEEVLAPLR | 1_14 |
| TCPA_HUMAN | P17987, T-COMPLEX PROTEIN 1, ALPHA SUBUNIT | MEGPLSVFGDR | 1_11 |
| UBCG_HUMAN | Q99462, UBIQUITIN-CONJUGATING ENZYME E2 G1 | TELQSALLLR | 2_11 |
| VAM3_HUMAN | Q15836, VESICLE-ASSOCIATED MEMBRANE PROTEIN 3 | STGPTAATGSNRR | 2_14 |
| VASP_HUMAN | P50552, VASODILATOR-STIMULATED PHOSPHOPROTEIN | SETVICSSR | 2_10 |

TABLE XVI-continued

Proteins identified following selection of their acetylated N-terminal, lysine-free and arginine-ending peptides out of a tryptic digest of a human thrombocyte cytosolic and membrane skeleton extract. The identified peptides are divided in three parts: (1) the naturally N-terminal blocked peptides, (2) peptides starting with a proline (that also cover the N-terminus of the protein) and (3) internal peptides beginning with a pyroglutamic acid (which is a side-effect of the preparation of the protein peptide mixture).

| SWISSPROT entry name | Accession number and protein Description | Identified peptide | Position |
|---|---|---|---|
| *N-terminal proline peptides* | | | |
| AOP2_HUMAN | P30041, ANTIOXIDANT PROTEIN 2 1-CYS PEROXIREDO | PGGLLLGDVAPNFEANTTVGR | 1_21 |
| GTP_HUMAN | P09211, GLUTATHIONE S-TRANSFERASE P | PPYTVVYFPVR | 1_11 |
| MIF_HUMAN | P14174, MACROPHAGE MIGRATION INHIBITORY FACTOR | PMFIVNTNVPR | 1_11 |
| *Pyroglutamic acid containing peptides* | | | |
| ACTB_HUMAN | P02570, ACTIN, CYTOPLASMIC 1 BETA-ACTIN, | QEYDESGPSIVHR | 360_372 |
| ALFA_HUMAN | P04075 FRUCTOSE-BISPHOSPHATE ALDOLASE A | QLLLTADDR | 60_68 |
| FIBA_HUMAN | P02671, FIBRINOGEN ALPHA/ALPHA-E CHAIN PRECURSOR | QFTSSTSYNR | 582_591 |
| FIBB_HUMAN | P02675, FIBRINOGEN BETA CHAIN PRECURSOR | QDGSVDFGR | 286_294 |
| GPV_HUMAN | P40197, PLATELET GLYCOPROTEIN V PRECURSOR GPV | QHLGLVGGEEPPR | 438_450 |
| HS27_HUMAN | P04792, HEAT SHOCK 27 KDA PROTEIN HSP 27, | QDEHGYISR | 128_136 |
| ITAB_HUMAN | P08514, INTEGRIN ALPHA-IIB PRECURSOR PLATELET | QIFLPEPEQPSR | 891_902 |
| MYH9_HUMAN | P35579, MYOSIN HEAVY CHAIN, NONMUSCLE TYPE A | QLAAENR QLEEAEEEAQR | 861_867 1878_1888 |
| PSE1_HUMAN | Q06323, PROTEASOME ACTIVATOR COMPLEX SUBUNIT 1 | QLVHELDEAEYR | 199_210 |
| SORC_HUMAN | P30626, SORCIN 22 KDA PROTEIN | QHFISFDTDR | 107_116 |
| TALI_HUMAN | Q9Y490, TALIN | QEDVIATANLSR | 2198_2209 |
| UVRG_HUMAN | Q9P2Y5, UV RADIATION RESISTANCE-ASSOCIATED GENE | EIEEKLR | 219_225 |
| VASP_HUMAN | P50552, VASODILATOR-STIMULATED PHOSPHOPROTEIN | QQPGPSEHIER | 144_154 |
| VINC_HUMAN | P18206, VINCULIN METAVINCULIN | QLHDEAR QQELTHQEHR | 903_909 178_187 |
| ZYX_HUMAN | Q15942, ZYXIN | QHPVPPPAQNQNQVR | 329_343 |

TABLE XVII

De novo derived peptide sequence tags from MS/MS spectra from sorted acetylated arginine-containing lysine-free amino terminal peptides (example 21) that did not lead to an unambiguous identification of proteins using MS/MS-based database searching tools such as MASCOT. The primary fraction from which the peptides are sorted is indicated, the mass of the peptide and the derived sequence tag from N –> C (m = methionine-sulfoxide. x = unassigned amino acid).

| fr5 | | fr6 | | fr7 | |
|---|---|---|---|---|---|
| 882.36 | PAPGGAEQR | 851.30 | AEDGA | 761.34 | SNSPSN |
| 899.34 | YmPR | 851.32 | AQCEA | 848.39 | mAGDD |
| 911.31 | ESPQA | 858.34 | PEDIA | 855.36 | IAIDG |
| 920.36 | TGAGPAG | 858.34 | PQDIA | 863.36 | EGSSVQT |
| 964.38 | ATGAG(Q/E)P | 899.39 | CHVNPR | 874.37 | GPGIER |
| 964.39 | PGGAGQP | 899.39 | PRCPPR | 911.30 | (D/N)PYC |
| 966.34 | ATGAG | 899.45 | CNAPIAR | 955.42 | VTINA |
| 986.39 | ASSTTA | 904.37 | NPNGC | 1011.32 | PSSPAm |
| 996.32 | AANPDG | 967.40 | HPSANNR | 1018.33 | GSSSIEAV |
| 1073.39 | SSGGSI | 973.43 | TSQDAR | 1048.45 | EVQA |
| 1466.53 | QEAGSTS | 984.37 | SSANNR | 1076.46 | YVDMS |
| 1466.54 | QEESD | 1008.39 | GSSVQTR | 1092.46 | EVDFSDR |
| 1522.41 | AHPDSEEQ | 1028.40 | RTWMG | 1098.46 | VEPQIEA |
| 1649.63 | GSGGSI | 1103.57 | PPPPPG | 1099.39 | PDSSTH |
| | | 1168.48 | ITSGQMH | 1099.48 | EPQIEA |

TABLE XVII-continued

De novo derived peptide sequence tags from MS/MS spectra from sorted acetylated arginine-containing lysine-free amino terminal peptides (example 21) that did not lead to an unambiguous identification of proteins using MS/MS-based database searching tools such as MASCOT. The primary fraction from which the peptides are sorted is indicated, the mass of the peptide and the derived sequence tag from N -> C (m = methionine-sulfoxide. x = unassigned amino acid).

| | | | | | |
|---|---|---|---|---|---|
| | | 1180.46 | DEEQYA | 1113.38 | ETTTAE |
| | | 1285.42 | HDENGD | 1121.48 | WEAGAY |
| | | 1303.49 | HDGNmDAN | 1145.57 | GGGGIGSG |
| | | 1345.54 | HDENTA | 1147.54 | RSNQISVR |
| | | 1475.69 | SQVTQVSPQ | 1213.51 | AGAGIQ |
| | | 1571.61 | GTGSET | 1213.52 | (Q/E)AEIQE |
| | | 1571.63 | SETESGTCESP | 1215.43 | (Q/E)AQTASEN |
| | | 1589.57 | SYGTGSETESP | 1231.42 | (Q/E)AQGGQEm |
| | | 1653.61 | SETESPR | 1231.43 | QTRIE |
| | | | | 1257.46 | EAQSIGAS |
| | | | | 1282.67 | PATPT |
| | | | | 1295.40 | AQGIQ |
| | | | | 1375.52 | SFTTTA |
| | | | | 1432.51 | STGTWSSATA |
| | | | | 1483.50 | TSVESNSDG |
| | | | | 1483.51 | VTSVE(TT/SN) |
| | | | | 1483.52 | VTSVESNSDG |
| | | | | 1640.61 | EQADEAP |
| | | | | 1809.52 | DESGPSIVH |

| fr8 | | fr9 | | fr10 | | fr11 | |
|---|---|---|---|---|---|---|---|
| 856.52 | IATVISPR | 591.21 | EmASHI | 693.34 | FLEER | 740.72 | EQFIR |
| 923.38 | MFDEAI | 1075.50 | EQVEI | 709.36 | MFLTR | 767.50 | LLNELR |
| 974.46 | PAANFD | 1149.44 | EMASHI | 848.42 | FEELLR | 900.54 | VDIINAQK |
| 1002.42 | PEDFIR | 1187.56 | IISTVSI | 920.52 | SGFLEGLR | 954.46 | MASMDDR |
| 1004.41 | PAAFSSP | 1208.57 | GPAAmSA | 988.55 | ISISDR | 954.46 | MASEExxxR |
| 1004.44 | TPAAFSA | 1290.65 | GITAI | 1016.48 | PYPFVVPR | 971.52 | QSASSFFR |
| 1011.33 | MNNSHG | 1298.72 | YPSIVVP | 1018.50 | PEAFR | 1027.48 | FSQE |
| 1021.45 | TPEDFIR | 1396.54 | GEETH | 1027.46 | FSQE | 1028.63 | LAGAVSEIIR |
| 1027.52 | TMLAD | 1432.55 | GAQIV | 1064.50 | QSGTLFR | 1105.60 | VFIGQG |
| 1035.44 | FSEVERAR | 1478.71 | ESAGGIIQTA | 1080.67 | QVLLDSL | 1110.56 | PEEQFIR |
| 1035.44 | GSSVGVEAR | 1537.59 | DEVNQDmT | 1103.84 | PLVELTFER | 1126.62 | IVNI |
| 1039.45 | DPENFR | 1596.67 | IYTII | 1168.70 | NLGGLAVAR | 1177.61 | AAHY |
| 1048.31 | FASHI | 1615.67 | QRIQNV | 1171.67 | MNLNLAVAR | 1190.48 | VNREEQFLR |
| 1077.39 | IGAHC | | | 1202.66 | QVTTLQDSLR | 1284.77 | NVLEDGDVLR |
| 1077.44 | WPAAVWR | | | 1204.56 | NLVLNAAR | 1308.78 | AVVYPW |
| 1095.45 | IGAGVG | | | 1219.61 | TTLQDSLR | 1353.72 | VFVTA |
| 1095.50 | IGHAG | | | 1299.62 | QVWTQLLR | 1420.72 | QWIIPEIR |
| 1096.44 | GLDFNR | | | 1416.69 | MTDFLFTLCAR | 1449.80 | WHPxPP |
| 1113.49 | ETTTAER | | | 1519.83 | LVFLGQSEAR | 1500.80 | VDSVV |
| 1131.33 | FTTAER | | | | | 1519.89 | VFIGQSEGLR |
| 1137.41 | SGVSEIR | | | | | 1645.96 | TGTNIVVVSHT |
| 1149.35 | EIGTT | | | | | 1965.98 | SEESPAIEAIH |
| 1151.46 | PAAPD | | | | | 1998.06 | ADLDFDF |
| 1177.41 | AFTEE | | | | | 2021.10 | PSIIITGTQLY |
| 1181.51 | QGHNES | | | | | 2021.11 | ANTGTQIYGR |
| 1199.54 | QGHIESSR | | | | | 2021.11 | VNTGTQIYGR |
| 1200.53 | PGISWVV | | | | | | |
| 1211.51 | TDPEDVI | | | | | | |
| 1216.36 | GNSVG | | | | | | |
| 1216.37 | GIS(V/Y)G | | | | | | |
| 1252.50 | PAAPPVA | | | | | | |
| 1257.59 | TT(I/N)EAV | | | | | | |
| 1258.40 | AVNEI | | | | | | |
| 1275.50 | DGWI | | | | | | |
| 1284.49 | DIFII | | | | | | |
| 1299.59 | IATA | | | | | | |
| 1319.53 | NITNTVAR | | | | | | |
| 1333.51 | GQTGFFPR | | | | | | |
| 1337.58 | QMNE | | | | | | |
| 1353.51 | EMNEFR | | | | | | |
| 1353.53 | IQDTGASDTR | | | | | | |
| 1360.53 | DTDIESTR | | | | | | |
| 1370.98 | NDPNWVVR | | | | | | |
| 1376.56 | PSIAAHG | | | | | | |

TABLE XVIIIA

Proteins identified following selection of their N-terminal peptides. Two primary fractions were analysed in a tryptic digest of a human thrombocyte cytosolic and membrane skeleton extract. A, Identified proteins; B, list of sequences derived from the MS/MS spectra, which could not be identified in the available data bases.

| SWISSPROT entry number | Protein name | Identified peptide | Location |
|---|---|---|---|
| Q9H4M9 | EH-DOMAIN CONTAINING PROTEIN 1 | MFSWVSKDAR | 1–10 |
| Q13045 | FLIGHTLESS-I PROTEIN HOMOLOG | MEATGVLPFVR | 1–11 |
| P17987 | T-COMPLEX PROTEIN 1, ALPHA SUBUNIT | MEGPLSVFGDR | 1–11 |
| P14174 | MACROPHAGE MIGRATION INHIBITORY FACTOR | PMFIVNTNVPR | 1–11 |
| P09211 | GLUTATHIONE S-TRANSFERASE P | PPYTVVYFPVR | 1–11 |
| P00354 | GLYCERALDEHYDE 3-PHOSPHATE DEHYDROGENASE | GKVKVGVDGFGR | 1–12 |
| P07108 | ACYL-COA-BINDING PROTEIN (ACBP) (DIAZEP | SQAEFEKAAEEVR | 1–13 |
| Q93084 | SARCOPLASMIC/ENDOPLASMIC RETICULUM CALCIUM ATPase 3 | MEAAHLLPAADVLR | 1–14 |
| P55273 | CYCLIN-DEPENDENT KINASE 4 INHIBITOR D | MLLEEVR | 1–7 |
| P48739 | PHOSPHATIDYLINOSITOL TRANSFER PROTEIN B | VLIKEFR | 1–7 |
| Q05209 | PROTEIN-TYROSINE PHOSPHATASE | MEQVEILR | 1–8 |
| P06733 | ALPHA ENOLASE (EC 4.2.1.11) (2-PHOSPHO- | SILKIHAR | 1–8 |
| P18669 | PHOSPHOGLYCERATE MUTASE, BRAIN FORM | AAYKLVLIR | 1–9 |
| Q13418 | INTEGRIN-LINKED PROTEIN KINASE 1 | MDDIFTQCR | 1–9 |
| P17858 | 6-PHOSPHOFRUCTOKINASE, LIVER TYPE | AAVDLEKLR | 2–10 |
| Q05940 | SYNAPTIC VESICLE AMINE TRANSPORTER | ALSELALVR | 2–10 |
| P46966 | DEFENDER AGAINST CELL DEATH 1 (DAD-1) | SASVVSVISR | 2–11 |
| P12324 | TROPOMYOSIN, CYTOSKELETAL TYPE | AGITTIEAVKR | 2–12 |
| P07226 | TROPOMYOSIN, FIBROBLAST NON-MUSCLE TYPE | AGLNSLEAVK | 2–12 |
| P27708 | CAD PROTEIN | AALVLEDGSVLR | 2–13 |
| P47756 | F-ACTIN CAPPING PROTEIN BETA SUBUNIT | SDQQLDCALDLMR | 2–14 |
| O00151 | PDZ AND LIM DOMAIN PROTEIN 1 | TTQQIDLQGPGPWGFR | 2–17 |
| O60234 | GLIA MATURATION FACTOR GAMMA | SDSLVVCEVDPELTEKLR | 2–19 |
| P02570 | ACTIN, CYTOPLASMIC 1 (BETA-ACTIN) | DDDIAALVVDNGSGMCKAGFAGDDAPR | 2–28 |
| P02775 | LOW AFFINITY PLATELET FACTOR IV (LA-PF4) | NLAKGKEESLDSDLYAELR | 44–62 |
| Q12768 | HYPOTHETICAL PROTEIN KIAA0196 | MLVSYYR | 165–171 |

TABLE XVIIIB k represents acetylated lysine

| FR9 | | FR10 | |
|---|---|---|---|
| SNDkR | 999.46 | PEAFR | 1017.48 |
| PFVVPR | 1049.46 | PLVETL | 1102.56 |
| DVNLA | 1085.42 | PLGkkAR | 1187.56 |
| PkDVLVR | 1140.44 | WTQLLR | 1298.7 |
| ELSAEYLR | 1152.46 | TVFDE | 1306.72 |
| ASHR | 1157.48 | LGEFVSE | 1441.64 |
| DLLSTV | 1186.48 | LVFLG | 1518.8 |
| TNFVQVLR | 1224.4 | VQkAkLAEAQAER | 1523.36 |
| LLkGLLANR | 1245.54 | EALEETEQP | 1546.06 |
| DDLF | 1258.4 | EAAHLL | 1564.76 |
| TWFV | 1294.46 | kSLkkLVEESR | 1570.7 |
| AAQEEPYR | 1299.48 | EPELWFVSE | 1609.6 |
| NSHLR | 1347.48 | AFLLDDLSE | 1624.68 |
| kLGTkLVSVER | 1354.6 | EVLFDEVVk | 1703.84 |
| LTAXMVL | 1372.66 | EDLMLEVVk | 1705.9 |
| EVEPQLLTR | 1383.54 | PASLVVIAAEEGER | 1730.7 |
| VEXXVHTR | 1401.6 | VEWLAEEAAEkATSR | 2044.88 |
| SAGkLWNR | 1435.76 | | |
| EVENQLLTR | 1442.54 | | |
| QYVYNVDQR | 1480.38 | | |
| DTFTVkYTPR | 1497.58 | | |
| DNEEGFFSAR | 1551.62 | | |
| APEEEDHVLVLR | 1562.48 | | |
| YVTLAQAEQAER | 1575.86 | | |
| EFEkAAEEVR | 1576.72 | | |
| EWPLNA | 1585.96 | | |
| LTDAATVSQER | 1628.68 | | |
| VXEAQSkR | 1646.72 | | |
| LELTDDNFESR | 1680.52 | | |
| QTGTAEFSSLLEER | 1719.6 | | |
| VTSkXVLXXLR | 1770.84 | | |

TABLE XIX

De novo derived peptide sequence from MS/MS spectra from sorted amino terminal peptides (example 22) that did not lead to an unambiguous identification using searching tools such as MASCOT (k = acetylated lysine, x = unassigned amino acid).

| Peptide Mass | Derived Sequence Tag |
|---|---|
| 999.46 | SNDkR |
| 1017.48 | PEAFR |
| 1049.46 | PFVVPR |
| 1085.42 | DVNLA |
| 1102.56 | PLVETL |
| 1140.44 | PkDVLVR |
| 1152.46 | ELSAEYLR |
| 1157.48 | ASHR |
| 1186.48 | DLLSTV |
| 1187.56 | PLGkkAR |
| 1224.40 | TNFVQVLR |
| 1245.54 | LLkGLLANR |
| 1258.40 | DDLF |
| 1294.46 | TWFV |
| 1298.70 | WTQLLR |
| 1299.48 | AAQEEPYR |
| 1306.72 | TVFDE |
| 1347.48 | NSHLR |
| 1354.60 | kLGTkLVSVER |
| 1372.66 | LTAXMVL |
| 1383.54 | EVEPQLLTR |
| 1401.60 | VEXXVHTR |
| 1435.76 | SAGkLWNR |
| 1441.64 | LGEFVSE |
| 1442.54 | EVENQLLTR |
| 1480.38 | QYVYNVDQR |
| 1497.58 | DTFTVkYTPR |
| 1518.80 | LVFLG |

TABLE XIX-continued

De novo derived peptide sequence from MS/MS spectra from sorted amino terminal peptides (example 22) that did not lead to an unambiguous identification using searching tools such as MASCOT (k = acetylated lysine, x = unassigned amino acid).

| Peptide Mass | Derived Sequence Tag |
|---|---|
| 1523.36 | VQkAkLAEAQAER |
| 1546.06 | EALEETEQP |
| 1551.62 | DNEEGFFSAR |
| 1562.48 | APEEEDHVLVLR |
| 1564.76 | EAAHLL |
| 1570.70 | kSLkkLVEESR |
| 1575.86 | YVTLAQAEQAER |
| 1576.72 | EFEkAAEEVR |
| 1585.96 | EWPLNA |
| 1609.60 | EPELWFVSE |
| 1624.68 | AFLLDDLSE |
| 1628.68 | LTDAATVSQER |
| 1646.72 | VXEAQSkR |
| 1680.52 | LELTDDNFESR |
| 1703.84 | EVLFDEVVk |
| 1705.90 | EDLMLEVVk |
| 1719.60 | QTGTAEFSSLLEER |
| 1730.70 | PASLVVAAEEGER |
| 1770.84 | VTSkXVLXXLR |
| 2044.88 | VEWLAEEAAEkATSR |

References

Ahmed, A. I., Yeh, Y., Osuga, Y. Y., Feeney, R. E. (1976), 'Antifreeze glycoproteins from Antarctic fish. Inactivation, by borate.', *J. Biol. Chem.* 251, 3033–3036.

Ardlie, N. G., Packham, M. A., Mustard, J. F. (1970), 'Adenosine diphosphate induced platelet aggregation in suspensions of washed rabbit platelets.', *Br. J. Haematol.* 19, 7–17.

Biemann, K. (1990), 'Sequencing of peptides by tandem mass spectrometry and high-energy collision-induced dissociation.', *Meth. Enzymol.* 193, 455–480.

Bjellqvist, B., Ek, K., Righetti, P. G., Gianazza, E., Gorg, A., Westermeier, R., Postel, W. (1982), 'Isoelectric focusing in immobilized pH gradients: principle, methodology and some applications.', *J. Biochem. Biophys. Methods* 6, 317–339.

Brancia, F. L., Butt, A., Beynon, R. J., Hubbard, S. J., Gaskell, S. J., Oliver, S. G. (2001), 'A combination of chemical derivatisation and improved bioinformatic tools optimises protein identification for proteomics.', *Electrophoresis* 22, 552–559.

Brown, J. R., Hartley, B. S. (1966), 'Location of disulphide bridges by diagonal paper electrophoresis. The disulphide bridges of bovine chymotrypsin A.', *Biochem. J.* 101, 214–228.

Caprioli, R. M., Fan, T. (1986), 'Peptide sequence analysis using exopeptidases with molecular analysis of the truncated polypeptides by mass spectrometry.', *Anal. Biochem.* 154, 596–603.

Chait, B. T., Wang, R., Beavis, R. C. and Kent, S. B. (1993), 'Protein ladder sequencing.', *Science* 262, 89–92.

Cruickshank, W. H., Radhakrishnan, T. M., Kaplan, H. (1971), 'A diagonal paper electrophoretic method for the selective isolation of histidyl peptides.', *Can. J. Biochem.* 49, 1225–1232.

Davis, M. T., Stahl, D.C., Hefta, S. A., Lee, T. D. (1995), 'A microscale electrospray interface for on-line, capillary liquid chromatography/tandem mass spectrometry of complex peptide mixtures.', *Anal. Chem.* 67, 4549–4556.

Degen, J., Kyte, J. (1978), 'The purification of peptides which contain methionine residues.', *Anal. Biochem.* 89, 529–539.

Edman, P. (1950), *Acta Chem. Scand.* 4, 283–293.

Ellman, G. L. (1959), *Arch. Biochem. Biophys.* 82, 70.

Freedman, R. B., Radda, G. K. (1968), 'The reaction of 2,4,6-trinitrobenzenesulphonic acid with amino acids, Peptides and proteins.', *Biochem. J.* 108, 383–391.

Fox, J. E., Lipfert, L., Clark, E. A., Reynolds, C. C., Austin, C. D., Brugge, J. S. (1993) 'On the role of the platelet membrane skeleton in mediating signal transduction. Association of GP IIb IIIa, pp60c-src, pp62c-yes, and the p21ras GTPase-activating protein with the membrane skeleton.', *J. Biol. Chem.* 268, 25973–25984.

Furumai, R., Komatsu, Y., Nishino, N., Khochin, S., Yoshida, M., Horinouchi, S. (2001) *Proc. Natl. Acad. Sci. USA* 98, 87–92.

Geng, M., Ji, J., Regnier, F. E. (2000), 'Signature-peptide approach to detecting proteins in complex mixtures.', *J. Chromatogr. A* 870, 295–313.

Geoghegan, K. F., Ybarra, D. M., Feeney, R. E. (1979), 'Reversible reductive alkylation of amino groups in proteins.', *Biochemistry* 18, 5392–5399.

Gevaert, K., Verschelde, J. L., Puype, M., Van Damme, J., Goethals, M., De Boeck, S., Vandekerckhove, J. (1996), 'Structural analysis and identification of gel-purified proteins, available in the femtomole range, using a novel computer program for peptide sequence assignment, by matrix-assisted laser desorption ionization-reflectron time-of-flight-mass spectrometry.', *Electrophoresis* 17, 918–924.

Gevaert, K., Demol, H., Puype, M., Broekaert, D., De Boeck, S., Houthaeve, T. and Vandekerckhove, J. (1997), 'Peptides adsorbed on reverse-phase chromatographic beads as targets for femtomole sequencing by post-source decay matrix assisted laser desorption ionization-reflectron time of flight mass spectrometry (MALDI-RETOF-MS).', *Electrophoresis* 18, 2950–2960.

Gevaert, K., Demol, H., Sklyarova, T., Vandekerckhove, J., Houthaeve, T. (1998), 'A peptide concentration and purification method for protein characterization in the subpicomole range using matrix assisted laser desorption/ionization-postsource decay (MALDI—PSD) sequencing.', *Electrophoresis* 19, 909–917.

Glazer, A. N., DeLange, R. J., Sigman, D. S. (1975), in Work, T. S., Work, E. (Eds.) 'Chemical alteration of proteins, selected methods and analytical procedures.', North-Holland Publishing Company, Amsterdam, The Netherlands.

Griffin, P. R., MacCoss, M. J., Eng, J. K., Blevins, R. A., Aaronson, J. S. and Yates, J. R. 3rd (1995), 'Direct database searching with MALDI-PSD spectra of peptides.', *Rapid Commun. Mass Spectrom.* 9, 1546–1551.

Gygi, S. P., Rist, B., Gerber, S. A., Turecek, F., Gelb, M. H., Aebersold R. (1999), 'Quantitative analysis of complex protein mixtures using isotope-coded affinity tags.', *Nat. Biotechnol.* 17, 994–999.

Hansen, P., Andersson, L., Lindeberg, G. (1996), 'Purification of cysteine-containing synthetic peptides via selective binding of the alpha-amino group to immobilised Cu2+ and Ni2+ ions.', *J. Chromatogr. A.* 723, 51–59.

Henzel, W. J., Billeci, T. M., Stults, J. T., Wong, S. C., Grimley, C. and Watanabe, C. (1993), 'Identifying proteins from two-dimensional gels by molecular mass searching of peptide fragments in protein sequence databases.', *Proc. Natl. Acad. Sci. USA* 90, 5011–5015.

Hirs, C. H. W. (1956), *J. Biol. Chem.* 219, 611.

Houghten, R. A., Li, C. H. (1981), 'Reduction of sulfoxides in peptides and proteins.', *Meth. Enzymol.* 91, 549–559.

Hunt, D. F., Buko, A. M., Ballard, J. M., Shabanowitz, J., Giordani, A. B. (1981), 'Sequence analysis of polypeptides by collision activated dissociation on a triple quadrupole mass spectrometer.', *Biomed. Mass Spectrom.* 8, 397–408.

James, P., Quadroni, M., Carafoli, E. and Gonnet, G. (1993), 'Protein identification by mass profile fingerprinting.', *Biochem. Biophys. Res. Commun.* 195, 58–64.

Ji, J., Chakraborty, A., Geng, M., Zhang, X., Amini, A., Bina, M., Regnier, F. (2000), 'Strategy for qualitative and quantitative analysis in proteomics based on signature peptides.', *J. Chromatogr. B Biomed. Sci. Appl.* 745, 197–210.

Jiang, X., Smith J. B., Abraham, E. C. (1996), 'Identification of a MS/MS fragment diagnostic for methionine sulfoxide.', *J. Mass Spectrom.* 31, 1309–1310.

Keough, T. et al. (1999) *Proc. Natl. Acad Sci.* 96, 7131.

Krause, E., Wenschuh, H., Jungblut, P. R. (1999), 'The dominance of arginine-containing peptides in MALDI-derived tryptic mass fingerprints of proteins.', *Anal. Chem.* 71, 4160–4165.

Link, A. J., Eng, J., Schieltz, D. M., Carmack, E., Mize, G. J., Morris, D. R., Garvik, B. M., Yates J R 3rd. (1999), 'Direct analysis of protein complexes using mass spectrometry.', *Nat. Biotechnol.* 17, 676–82.

Lundblad, R. I. and Noyes, C. M., eds., Chemical Reagents for Protein Alteration, Vol. 1, p. 99, CRC Press (1984).

Mann, M., Højrup, P., Roepstorff, P. (1993), 'Use of mass spectrometric molecular weight information to identify proteins in sequence databases.', *Biol. Mass Spectrom.* 22, 338–345.

Mann, M., Wilm, M. (1994), 'Error-tolerant identification of peptides in sequence databases by peptide sequence tags.', *Anal. Chem.* 66, 4390–4399.

McCloskey, J. A. (1990), 'Calculation of isotopic abundance distributions.', *Meth. Enzymol.* 193, 882–886.

Merrifield, R. B. (1963), J. Am. Chem. Soc. 85, 2149–2154

Mirgorodskaya, O. A., Kozmin, Y. P., Titov, M. I., Komer, R., Sonksen, C. P., Roepstorff, P. (2000), 'Quantitation of peptides and proteins by matrix-assisted laser desorption/ionization mass spectrometry using (18)O-labeled internal standards.', *Rapid Commun. Mass Spectrom.* 14, 1226–1232.

Mirza, U. A., Chait, B. T. (1994), 'Effects of anions on the positive ion electrospray ionisation mass spectra of peptides and proteins.', *Anal. Chem.* 66, 2898–2904.

Munchbach, M., Quadroni, M., Miotto, G., James, P. (2000) *Anal. Chem.* 72, 4047–4057.

O'Connor, P. B., Costello, C. E. (2000), 'Internal calibration on adjacent samples (InCAS) with Fourier transform mass spectrometry.', *Anal. Chem.* 72, 5881–5885.

O'Farrell, P. H. (1975), 'High resolution two-dimensional electrophoresis of proteins.', *J. Biol. Chem.* 250, 4007–4021.

Opiteck, G. J., Ramirez, S. M., Jorgenson, J. W., Moseley, M. A. (1998), 'Comprehensive two-dimensional high-performance liquid chromatography for the isolation of overexpressed proteins and proteome mapping.', *Anal. Biochem.* 258, 349–361.

Pappin, D., Højrup, P. and Bleasby, A. (1993), 'Rapid identification of proteins by peptide-mass fingerprinting.' *Curr. Biol.* 3, 338–345.

Patterson, S. D., Thomas, D., Bradshaw, R. A. (1996), 'Application of combined mass spectrometry and partial amino acid sequence to the identification of gel-separated proteins.', *Electrophoresis* 17, 877–891.

Penn, R. E., Block, E., Revelle, L. K. (1978), 'Flash vacuum pyrolysis studies. 5. Methanesulfenic acid.', *J. Am. Chem. Soc.* 100, 3622–3623.

Perham, R. N. (1967), 'A diagonal paper electrophoretic technique for studying amino acid sequences around the cysteine and cystine residues of proteins.', *Biochem. J.* 105, 1203–1207.

Perkins, D. N., Pappin, D. J., Creasy, D. M., Cottrell, J. S. 'Probability-based protein identification by searching sequence databases using mass spectrometry.', *Electrophoresis* 20 (18), 3551–3567.

Plapp, B. V., Moore, S., Stein, W. H. (1971), 'Activity of bovine pancreatic deoxyribonuclease A with altered amino groups.', *J. Biol. Chem.* 246, 939–945.

Redman, K. L., Rubenstein, P. A. (1984), 'Actin amino-terminal acetylation and processing in a rabbit reticulocyte lysate.', *Meth. Enzymol.* 106, 179–192.

Rose, K., Simona, M. G., Offord, R. E., Prior, C. P., Otto, B., Thatcher, D. R. (1983), 'A new mass-spectrometric C-terminal sequencing technique finds a similarity between gamma-interferon and alpha 2-interferon and identifies a proteolytically clipped gamma-interferon that retains full antiviral activity.', *Biochem. J.* 215, 273–277.

Rothgeb, T. M., Jones, B. N., Hayes, D. F., Gurd, R. S. (1977), 'Methylation of glucagons, chracaterization of the sulfonium derivative, and regeneration of the native covalent structure.', *Biochemistry* 16, 5813–5818.

Sakaguchi, H., Watanabe, M., Ueoka, C., Sugiyama, E., Taketomi, T., Yamada, S., Sugahara, K. (2001) *J. Biochem* (Tokyo) 129, 107–118.

Sanger, F. (1949), *Biochem. J.* 44, 126.

Schena, M., Shalon, D., Davis, R. W., Brown, P. O. (1995), 'Quantitative monitoring of gene expression patterns with a complementary DNA microarray.', *Science* 270, 467–470.

Schölzer, M., Jedrzejewski, P., Lehmann, W. D. (1996), 'Protease-catalyzed incorporation of 18O into peptide fragments and its application for protein sequencing by electrospray and matrix-assisted laser desorption/ionization mass spectrometry.', *Electrophoresis* 17, 945–953.

Sechi, S., Chait, B. T. (1998), 'Alteration of cysteine residues by alkylation. A tool in peptide mapping and protein identification.', *Anal. Chem.* 70, 5150–5158.

Spengler, B., Kirsch, D., Kaufinann, R., Jaeger, E. (1992), 'Peptide sequencing by matrix-assisted laser-desorption mass spectrometry.', *Rapid Commun. Mass Spectrom.* 6, 105–108.

Steen, H., Mann, M. (2001), 'Similarity between condensed phase and gas phase chemistry: fragmentation of peptides containing oxidized cysteine residues and its implications for proteomics.', *J. Am. Soc. Mass Spec.* 12, 228–232.

Stewart, I. I., Thomson, T., Figeys, D. (2001), '18O Labeling: a tool for proteomics.', *Rapid Commun. Mass Spectrom.* 15, 2456–2465.

Tang, J., Hartley B. S. (1967), 'A diagonal electrophoretic method for selective purification of methionine peptides.', *Biochem. J.* 102, 593–599.

Toennies, G., Homiller, R. P. (1942), 'The oxidation of amino acids by hydrogen peroxide in formic acid.', *Amer. Chem. Soc.* 64, 3054–3056.

Turecek, F., Drinkwater, D. E., McLafferty, F. W. (1989), 'Gas-phase chemistry of CH3SOH, —CH2+SHOH, CH3SO., and CH2SOH by neutralization reionization mass-spectrometry.', *J. Am. Chem. Soc.* 111, 7696–7701.

Vandekerckhove, J., Weber, K. (1981), 'Actin typing on total cellular extracts: a highly sensitive protein-chemical procedure able to distinguish different actins.', *Eur. J. Biochem.* 113, 593–603.

Vuong, G. L., Weiss, S. M., Kammer, W., Priemer, M., Vingron, M., Nordheim, A., Cahill, M. A. (2000), 'Improved sensitivity proteomics by postharvest alkylation and radioactive labeling of proteins.', *Electrophoresis* 21, 2594–2605.

Weckwerth, W., Willmitzer, L., Fiehn, O. (2000), 'Comparative quantification and identification of phosphoproteins using stable Isotope labeling and liquid chromatography/mass spectrometry.' *Rapid Commun. Mass Spectrom.* 14, 1677–1681.

Yates, J. R. 3d, Speicher, S., Griffin, P. R., Hunkapiller, T. (1993), 'Peptide mass maps: a highly informative approach to protein identification.', *Anal. Biochem.* 214, 397–408.

Zuckermann, R. N., Kerr, J. M., Siani, M. A., Banville, S. C. (1992), 'Design, construction and application of a fully automated equimolar peptide mixture synthesizer.', *Int. J. Pept. Protein Res.* 40, 497–506.

All patents, published patent applications, literature references and databases disclosed herein are expressly incorporated by reference.

What is claimed is:

1. A method for the isolation of a subset of peptides out of a protein peptide mixture, comprising the steps of: (a) separating the protein peptide mixture into fractions of peptides via chromatography; (b) chemically, or enzymatically, or chemically and enzymatically, altering at least one amino acid of at least one of the peptides in each fraction, thereby generating a subset of altered peptides; and (c) isolating said altered or flagged peptides out of each fraction via chromatography, wherein the chromatography of steps (a) and (c) is performed with the same type of chromatography.

2. A method to determine the relative amount of at least one protein in more than one sample comprising proteins, comprising the steps of: (a) labeling the peptides present in a first sample with a first isotope; (b) labeling the peptides present in a second sample with a second isotope; (c) combining the protein peptide mixture of the first sample with the protein peptide mixture of the second sample; (d) separating the combined protein peptide mixtures into fractions of peptides via chromatography; (e) chemically, or enzymatically, or chemically and enzymatically, altering at least one amino acid of at least one of the peptides in each fraction; (f) isolating the flagged peptides out of each fraction via chromatography, wherein the chromatography is performed with the same type of chromatography as in step (d); (g) performing mass spectrometric analysis of the isolated flagged peptides; (h) calculating the relative amounts of the flagged peptides in each sample by comparing the peak heights of the identical but differentially, isotopically labelled flagged peptides, and (i) determining the identity of said flagged peptides and their corresponding proteins.

3. A method for the isolation of a subset of peptides out of a protein peptide mixture, comprising the steps of: (a) separating the protein peptide mixture into fractions of peptides via chromatography; (b) chemically, or enzymatically, or chemically and enzymatically, altering at least one amino acid in the majority of the peptides in each fraction, thereby generating a subset of unaltered peptides; and (c) isolating said unaltered or so called identification peptides out of each fraction via chromatography, wherein the chromatography of steps (a) and (c) is performed with the same type of chromatography.

4. A system for sorting peptides comprising: a primary chromatographic column for separating a protein peptide mixture into a plurality of fractions under a defined set of conditions and whereby each fraction is subsequently subjected to an alteration of at least one amino acid to generate flagged peptides and wherein the altered fractions are pooled into a set of pooled fractions, each pooled fraction comprising at least two altered fractions and a set of secondary chromatographic columns comprising a first secondary chromatographic column for separating a first pooled fraction and at least a second secondary chromatographic column arranged in parallel with the first secondary chromatographic column for separating a second pooled fraction, wherein the set of secondary chromatography columns perform isolation of the flagged peptides under substantially identical conditions as the defined set of conditions, whereby there is no elution overlap between i) the flagged peptides from different fractions within one pool or between pools and ii) the flagged peptides and the unaltered peptides.

* * * * *

SEQUENCE LISTING

<160> NUMBER OF SEQ ID NOS: 473

<210> SEQ ID NO 1
<211> LENGTH: 9
<212> TYPE: PRT
<213> ORGANISM: Artificial Sequence
<220> FEATURE:
<223> OTHER INFORMATION: peptide used in Fig 3A

<400> SEQUENCE: 1

Tyr Ser Phe Val Met Thr Ala Glu Arg
1               5

<210> SEQ ID NO 2
<211> LENGTH: 9
<212> TYPE: PRT
<213> ORGANISM: Artificial Sequence
<220> FEATURE:
<223> OTHER INFORMATION: peptide used in Fig 3B

<400> SEQUENCE: 2

Tyr Ser Phe Val Cys Thr Ala Glu Arg
1               5

<210> SEQ ID NO 3
<211> LENGTH: 9
<212> TYPE: PRT
<213> ORGANISM: Artificial Sequence
<220> FEATURE:
<223> OTHER INFORMATION: peptide used in Fig 3C

<400> SEQUENCE: 3

Tyr Ser Phe Val Trp Thr Ala Glu Arg
1               5

<210> SEQ ID NO 4
<211> LENGTH: 15
<212> TYPE: PRT
<213> ORGANISM: Homo sapiens
<220> FEATURE:
<221> NAME/KEY: MISC_FEATURE
<223> OTHER INFORMATION: part of A2MG_HUMAN
      ((P01023)alpha-2-macroglobulin precursor)

<400> SEQUENCE: 4

Ser Ser Ser Asn Glu Glu Val Met Phe Leu Thr Val Gln Val Lys
1               5                   10                  15

<210> SEQ ID NO 5
<211> LENGTH: 12
<212> TYPE: PRT
<213> ORGANISM: Homo sapiens

```
<220> FEATURE:
<221> NAME/KEY: MISC_FEATURE
<223> OTHER INFORMATION: part of ALBU_HUMAN ((P02768)serum albumin
      precursor)

<400> SEQUENCE: 5

Ala Val Met Asp Asp Phe Ala Ala Phe Val Glu Lys
1               5                   10

<210> SEQ ID NO 6
<211> LENGTH: 19
<212> TYPE: PRT
<213> ORGANISM: Homo sapiens
<220> FEATURE:
<221> NAME/KEY: MISC_FEATURE
<223> OTHER INFORMATION: part of AMBP_HUMAN ((P02760)
      alphae-1-microglobulin)

<400> SEQUENCE: 6

Val Val Ala Gln Gly Val Gly Ile Pro Glu Asp Ser Ile Phe Thr Met
1               5                   10                  15

Ala Asp Arg

<210> SEQ ID NO 7
<211> LENGTH: 15
<212> TYPE: PRT
<213> ORGANISM: Homo sapiens
<220> FEATURE:
<221> NAME/KEY: MISC_FEATURE
<223> OTHER INFORMATION: part of ANT3_HUMAN ((P01008) antithrombin-III
      precursor)

<400> SEQUENCE: 7

Gly Asp Asp Ile Thr Met Val Leu Ile Leu Pro Lys Pro Glu Lys
1               5                   10                  15

<210> SEQ ID NO 8
<211> LENGTH: 15
<212> TYPE: PRT
<213> ORGANISM: Homo sapiens
<220> FEATURE:
<221> NAME/KEY: MISC_FEATURE
<223> OTHER INFORMATION: part of APB_HUMAN ((P04114) apolipoprotein
      B-100 precursor)

<400> SEQUENCE: 8

Ala Val Ser Met Pro Ser Phe Ser Ile Leu Gly Ser Asp Val Arg
1               5                   10                  15

<210> SEQ ID NO 9
<211> LENGTH: 9
<212> TYPE: PRT
<213> ORGANISM: Homo sapiens
<220> FEATURE:
<221> NAME/KEY: MISC_FEATURE
<223> OTHER INFORMATION: part of APB_HUMAN ((P04114) apolipoprotein
      B-100 precursor)

<400> SEQUENCE: 9

Leu Ile Asp Val Ile Ser Met Tyr Arg
1               5

<210> SEQ ID NO 10
<211> LENGTH: 17
<212> TYPE: PRT
<213> ORGANISM: Homo sapiens
<220> FEATURE:
<221> NAME/KEY: MISC_FEATURE
```

```
<223> OTHER INFORMATION: part of APB_HUMAN ((P04114) apolipoprotein
      B-100 precursor)

<400> SEQUENCE: 10

Thr Glu His Gly Ser Glu Met Leu Phe Phe Gly Asn Ala Ile Glu Gly
1               5                   10                  15

Lys

<210> SEQ ID NO 11
<211> LENGTH: 20
<212> TYPE: PRT
<213> ORGANISM: Homo sapiens
<220> FEATURE:
<221> NAME/KEY: MISC_FEATURE
<223> OTHER INFORMATION: part of CO3_HUMAN ((P01024) complement C3
      precursor)

<400> SEQUENCE: 11

Ile Leu Leu Gln Gly Thr Pro Val Ala Gln Met Thr Glu Asp Ala Val
1               5                   10                  15

Asp Ala Glu Arg
            20

<210> SEQ ID NO 12
<211> LENGTH: 7
<212> TYPE: PRT
<213> ORGANISM: Homo sapiens
<220> FEATURE:
<221> NAME/KEY: MISC_FEATURE
<223> OTHER INFORMATION: part of CO3_HUMAN ((P01024) complement C3
      precursor)

<400> SEQUENCE: 12

Leu Met Asn Ile Phe Leu Lys
1               5

<210> SEQ ID NO 13
<211> LENGTH: 13
<212> TYPE: PRT
<213> ORGANISM: Homo sapiens
<220> FEATURE:
<221> NAME/KEY: MISC_FEATURE
<223> OTHER INFORMATION: part of FIBB_HUMAN ((P02675) fibrinogen beta
      chain precursor)

<400> SEQUENCE: 13

His Gly Thr Asp Asp Gly Val Val Trp Met Asn Trp Lys
1               5                   10

<210> SEQ ID NO 14
<211> LENGTH: 13
<212> TYPE: PRT
<213> ORGANISM: Homo sapiens
<220> FEATURE:
<221> NAME/KEY: MISC_FEATURE
<223> OTHER INFORMATION: part of FIBB_HUMAN ((P02675) fibrinogen beta
      chain precursor)

<400> SEQUENCE: 14

Tyr Tyr Trp Gly Gly Gln Tyr Thr Trp Asp Met Ala Lys
1               5                   10

<210> SEQ ID NO 15
<211> LENGTH: 12
<212> TYPE: PRT
<213> ORGANISM: Homo sapiens
<220> FEATURE:
```

```
<221> NAME/KEY: MISC_FEATURE
<223> OTHER INFORMATION: part of GSHP_HUMAN ((P22352) plasma glutathione
      peroxidase precursor)

<400> SEQUENCE: 15

Phe Leu Val Gly Pro Asp Gly Ile Pro Ile Met Arg
1               5                   10

<210> SEQ ID NO 16
<211> LENGTH: 9
<212> TYPE: PRT
<213> ORGANISM: Homo sapiens
<220> FEATURE:
<221> NAME/KEY: MISC_FEATURE
<223> OTHER INFORMATION: part of HBA_HUMAN ((P01922) hemoglobin alpha
      chain)

<400> SEQUENCE: 16

Met Phe Leu Ser Phe Pro Thr Thr Lys
1               5

<210> SEQ ID NO 17
<211> LENGTH: 19
<212> TYPE: PRT
<213> ORGANISM: Homo sapiens
<220> FEATURE:
<221> NAME/KEY: MISC_FEATURE
<223> OTHER INFORMATION: part of HBB_HUMAN ((P02023) hemoglobin beta
      chain)

<400> SEQUENCE: 17

Phe Phe Glu Ser Phe Gly Asp Leu Ser Thr Pro Asp Ala Val Met Gly
1               5                   10                  15

Asn Pro Lys

<210> SEQ ID NO 18
<211> LENGTH: 14
<212> TYPE: PRT
<213> ORGANISM: Homo sapiens
<220> FEATURE:
<221> NAME/KEY: MISC_FEATURE
<223> OTHER INFORMATION: part of IC1_HUMAN ((P05155) plasma protease
      C1 inhibitor precursor)

<400> SEQUENCE: 18

Leu Glu Asp Met Glu Gln Ala Leu Ser Pro Ser Val Phe Lys
1               5                   10

<210> SEQ ID NO 19
<211> LENGTH: 11
<212> TYPE: PRT
<213> ORGANISM: Homo sapiens
<220> FEATURE:
<221> NAME/KEY: MISC_FEATURE
<223> OTHER INFORMATION: part of ITH4_HUMAN ((Q14624)
      inter-alpha-trypsin inhibitor heavy chain)

<400> SEQUENCE: 19

Glu Thr Leu Phe Ser Val Met Pro Gly Leu Lys
1               5                   10

<210> SEQ ID NO 20
<211> LENGTH: 21
<212> TYPE: PRT
<213> ORGANISM: Homo sapiens
<220> FEATURE:
<221> NAME/KEY: MISC_FEATURE
<223> OTHER INFORMATION: part of TRFE_HUMAN ((P02787) serotransferrin
```

-continued precursor)

<400> SEQUENCE: 20

Ile Met Asn Gly Glu Ala Asp Ala Met Ser Leu Asp Gly Gly Phe Val
1               5                   10                  15

Tyr Ile Ala Gly Lys
            20

<210> SEQ ID NO 21
<211> LENGTH: 13
<212> TYPE: PRT
<213> ORGANISM: Homo sapiens
<220> FEATURE:
<221> NAME/KEY: MISC_FEATURE
<223> OTHER INFORMATION: part of U2AG_HUMAN (Q01081) splicing factor
      U2AF 35KDA subunit)

<400> SEQUENCE: 21

Met Ala Glu Tyr Leu Ala Ser Ile Phe Gly Thr Glu Lys
1               5                   10

<210> SEQ ID NO 22
<211> LENGTH: 8
<212> TYPE: PRT
<213> ORGANISM: Homo sapiens
<220> FEATURE:
<221> NAME/KEY: MISC_FEATURE
<223> OTHER INFORMATION: part of Z298_HUMAN ((P57071) zinc finger
      protein 298)

<400> SEQUENCE: 22

Lys Met Asp Lys Pro Met Leu Lys
1               5

<210> SEQ ID NO 23
<211> LENGTH: 10
<212> TYPE: PRT
<213> ORGANISM: Homo sapiens
<220> FEATURE:
<221> NAME/KEY: MISC_FEATURE
<223> OTHER INFORMATION: part of 143G_HUMAN (14-3-3 protein (different
      isoforms))

<400> SEQUENCE: 23

Asp Ser Thr Leu Ile Met Gln Leu Leu Arg
1               5                   10

<210> SEQ ID NO 24
<211> LENGTH: 9
<212> TYPE: PRT
<213> ORGANISM: Homo sapiens
<220> FEATURE:
<221> NAME/KEY: MISC_FEATURE
<223> OTHER INFORMATION: part of 143G_HUMAN (14-3-3 protein (different
      isoforms))

<400> SEQUENCE: 24

Glu Met Gln Pro Thr His Pro Ile Arg
1               5

<210> SEQ ID NO 25
<211> LENGTH: 10
<212> TYPE: PRT
<213> ORGANISM: Homo sapiens
<220> FEATURE:
<221> NAME/KEY: MISC_FEATURE
<223> OTHER INFORMATION: part of 2AAA_HUMAN (serine/threonine protein
      phosphatase 2A)

```
<400> SEQUENCE: 25

Met Ala Gly Asp Pro Val Ala Asn Val Arg
1               5                   10

<210> SEQ ID NO 26
<211> LENGTH: 12
<212> TYPE: PRT
<213> ORGANISM: Homo sapiens
<220> FEATURE:
<221> NAME/KEY: MISC_FEATURE
<223> OTHER INFORMATION: part of 2AAA_HUMAN (serine/threonine protein
      phosphatase 2A)

<400> SEQUENCE: 26

Thr Asp Leu Val Pro Ala Phe Gln Asn Leu Met Lys
1               5                   10

<210> SEQ ID NO 27
<211> LENGTH: 13
<212> TYPE: PRT
<213> ORGANISM: Homo sapiens
<220> FEATURE:
<221> NAME/KEY: MISC_FEATURE
<223> OTHER INFORMATION: part of 5NTD_HUMAN (5'-nucleotidase precursor)

<400> SEQUENCE: 27

Met Lys Val Ile Tyr Pro Ala Val Glu Gly Arg Ile Lys
1               5                   10

<210> SEQ ID NO 28
<211> LENGTH: 10
<212> TYPE: PRT
<213> ORGANISM: Homo sapiens
<220> FEATURE:
<221> NAME/KEY: MISC_FEATURE
<223> OTHER INFORMATION: part of AAC1/2/4_HUMAN (alpha-actinin 1/2/4)

<400> SEQUENCE: 28

His Thr Asn Tyr Thr Met Glu His Ile Arg
1               5                   10

<210> SEQ ID NO 29
<211> LENGTH: 18
<212> TYPE: PRT
<213> ORGANISM: Homo sapiens
<220> FEATURE:
<221> NAME/KEY: MISC_FEATURE
<223> OTHER INFORMATION: part of AAC1/4_HUMAN (alpha-actinin 1/4)

<400> SEQUENCE: 29

Ala Ile Met Thr Tyr Val Ser Ser Phe Tyr His Ala Phe Ser Gly Ala
1               5                   10                  15

Gln Lys

<210> SEQ ID NO 30
<211> LENGTH: 15
<212> TYPE: PRT
<213> ORGANISM: Homo sapiens
<220> FEATURE:
<221> NAME/KEY: MISC_FEATURE
<223> OTHER INFORMATION: part of AAC1_HUMAN (alpha-actinin 1)

<400> SEQUENCE: 30

Ile Leu Ala Gly Asp Lys Asn Tyr Ile Thr Met Asp Glu Leu Arg
1               5                   10                  15
```

```
<210> SEQ ID NO 31
<211> LENGTH: 17
<212> TYPE: PRT
<213> ORGANISM: Homo sapiens
<220> FEATURE:
<221> NAME/KEY: MISC_FEATURE
<223> OTHER INFORMATION: part of AAC4_HUMAN (alpha-actinin 4)

<400> SEQUENCE: 31

Val Leu Ala Val Asn Gln Glu Asn Glu His Leu Met Glu Asp Tyr Glu
1               5                   10                  15
Lys

<210> SEQ ID NO 32
<211> LENGTH: 8
<212> TYPE: PRT
<213> ORGANISM: Homo sapiens
<220> FEATURE:
<221> NAME/KEY: MISC_FEATURE
<223> OTHER INFORMATION: part of ACTB/G_HUMAN (actin, cytoplasmic 1
      (beta/gamma-actin)

<400> SEQUENCE: 32

Asp Leu Thr Asp Tyr Leu Met Lys
1               5

<210> SEQ ID NO 33
<211> LENGTH: 11
<212> TYPE: PRT
<213> ORGANISM: Homo sapiens
<220> FEATURE:
<221> NAME/KEY: MISC_FEATURE
<223> OTHER INFORMATION: part of ACTB/G_HUMAN (actin, cytoplasmic 1
      (beta/gamma-actin)

<400> SEQUENCE: 33

Glu Ile Thr Ala Leu Ala Pro Ser Thr Met Lys
1               5                   10

<210> SEQ ID NO 34
<211> LENGTH: 11
<212> TYPE: PRT
<213> ORGANISM: Homo sapiens
<220> FEATURE:
<221> NAME/KEY: MISC_FEATURE
<223> OTHER INFORMATION: part of ACTB/G_HUMAN (actin, cytoplasmic 1
      (beta/gamma-actin)

<400> SEQUENCE: 34

His Gln Gly Val Met Val Gly Met Gly Gln Lys
1               5                   10

<210> SEQ ID NO 35
<211> LENGTH: 30
<212> TYPE: PRT
<213> ORGANISM: Homo sapiens
<220> FEATURE:
<221> NAME/KEY: MISC_FEATURE
<223> OTHER INFORMATION: part of ACTB/G_HUMAN (actin, cytoplasmic 1
      (beta/gamma-actin)

<400> SEQUENCE: 35

Thr Thr Gly Ile Val Met Asp Ser Gly Asp Gly Val Thr His Thr Val
1               5                   10                  15
Pro Ile Tyr Glu Gly Tyr Ala Leu Pro His Ala Ile Leu Arg
                20                  25                  30
```

-continued

```
<210> SEQ ID NO 36
<211> LENGTH: 11
<212> TYPE: PRT
<213> ORGANISM: Homo sapiens
<220> FEATURE:
<221> NAME/KEY: MISC_FEATURE
<223> OTHER INFORMATION: part of AR21_HUMAN (ARP2/3 complex 21 kDa
      subunit(P21-ARC))

<400> SEQUENCE: 36

Leu Ile Gly Asn Met Ala Leu Leu Pro Ile Arg
1               5                   10

<210> SEQ ID NO 37
<211> LENGTH: 9
<212> TYPE: PRT
<213> ORGANISM: Homo sapiens
<220> FEATURE:
<221> NAME/KEY: MISC_FEATURE
<223> OTHER INFORMATION: part of AR34_HUMAN (ARP2/3 complex 34 kDa
      subunit(P34-ARC))

<400> SEQUENCE: 37

Met Ile Leu Leu Glu Val Asn Asn Arg
1               5

<210> SEQ ID NO 38
<211> LENGTH: 11
<212> TYPE: PRT
<213> ORGANISM: Homo sapiens
<220> FEATURE:
<221> NAME/KEY: MISC_FEATURE
<223> OTHER INFORMATION: part of ARF1_HUMAN (ADP-ribosylation factor
      (different isoforms))

<400> SEQUENCE: 38

Ile Leu Met Val Gly Leu Asp Ala Ala Gly Lys
1               5                   10

<210> SEQ ID NO 39
<211> LENGTH: 12
<212> TYPE: PRT
<213> ORGANISM: Homo sapiens
<220> FEATURE:
<221> NAME/KEY: MISC_FEATURE
<223> OTHER INFORMATION: part of ARP2_HUMAN (actin-like protein 2)

<400> SEQUENCE: 39

Asp Leu Met Val Gly Asp Glu Ala Ser Glu Leu Arg
1               5                   10

<210> SEQ ID NO 40
<211> LENGTH: 12
<212> TYPE: PRT
<213> ORGANISM: Homo sapiens
<220> FEATURE:
<221> NAME/KEY: MISC_FEATURE
<223> OTHER INFORMATION: part of ARP3_HUMAN (actin-like protein 3)

<400> SEQUENCE: 40

Asn Ile Val Leu Ser Gly Gly Ser Thr Met Phe Arg
1               5                   10

<210> SEQ ID NO 41
<211> LENGTH: 12
<212> TYPE: PRT
<213> ORGANISM: Homo sapiens
<220> FEATURE:
```

-continued

<221> NAME/KEY: MISC_FEATURE
<223> OTHER INFORMATION: part of CALU_HUMAN (calumenin precursor)

<400> SEQUENCE: 41

Met Ala Asp Lys Asp Gly Asp Leu Ile Ala Thr Lys
1               5                   10

<210> SEQ ID NO 42
<211> LENGTH: 11
<212> TYPE: PRT
<213> ORGANISM: Homo sapiens
<220> FEATURE:
<221> NAME/KEY: MISC_FEATURE
<223> OTHER INFORMATION: part of CAN1_HUMAN (calpain 1,
      large [catalytic] subunit)

<400> SEQUENCE: 42

Met Glu Asp Gly Glu Phe Trp Met Ser Phe Arg
1               5                   10

<210> SEQ ID NO 43
<211> LENGTH: 8
<212> TYPE: PRT
<213> ORGANISM: Homo sapiens
<220> FEATURE:
<221> NAME/KEY: MISC_FEATURE
<223> OTHER INFORMATION: part of CAN1_HUMAN (calpain 1, large
      [catalytic] subunit)

<400> SEQUENCE: 43

Ser Met Val Asn Leu Met Asp Arg
1               5

<210> SEQ ID NO 44
<211> LENGTH: 12
<212> TYPE: PRT
<213> ORGANISM: Homo sapiens
<220> FEATURE:
<221> NAME/KEY: MISC_FEATURE
<223> OTHER INFORMATION: part of CAP1_HUMAN (adenylyl
      cyclase-associated protein 1)

<400> SEQUENCE: 44

Glu Met Asn Asp Ala Ala Met Phe Tyr Thr Asn Arg
1               5                   10

<210> SEQ ID NO 45
<211> LENGTH: 12
<212> TYPE: PRT
<213> ORGANISM: Homo sapiens
<220> FEATURE:
<221> NAME/KEY: MISC_FEATURE
<223> OTHER INFORMATION: part of CAP1_HUMAN (adenylyl
      cyclase-associated protein 1)

<400> SEQUENCE: 45

Leu Glu Ala Val Ser His Thr Ser Asp Met His Arg
1               5                   10

<210> SEQ ID NO 46
<211> LENGTH: 19
<212> TYPE: PRT
<213> ORGANISM: Homo sapiens
<220> FEATURE:
<221> NAME/KEY: MISC_FEATURE
<223> OTHER INFORMATION: part of CAZ1_HUMAN (F-actin capping protein
      alpha-1 subunit)

<400> SEQUENCE: 46

```
Glu Gly Ala Ala His Ala Phe Ala Gln Tyr Asn Met Asp Gln Phe Thr
1               5                   10                  15

Pro Val Lys

<210> SEQ ID NO 47
<211> LENGTH: 11
<212> TYPE: PRT
<213> ORGANISM: Homo sapiens
<220> FEATURE:
<221> NAME/KEY: MISC_FEATURE
<223> OTHER INFORMATION: part of CBP2_HUMAN (collagen-binding protein
      2 precursor)

<400> SEQUENCE: 47

Leu Gln Ile Val Glu Met Pro Leu Ala His Lys
1               5                   10

<210> SEQ ID NO 48
<211> LENGTH: 8
<212> TYPE: PRT
<213> ORGANISM: Homo sapiens
<220> FEATURE:
<221> NAME/KEY: MISC_FEATURE
<223> OTHER INFORMATION: part of CD63_HUMAN (CD63 antigen)

<400> SEQUENCE: 48

Gln Gln Met Glu Asn Tyr Pro Lys
1               5

<210> SEQ ID NO 49
<211> LENGTH: 7
<212> TYPE: PRT
<213> ORGANISM: Homo sapiens
<220> FEATURE:
<221> NAME/KEY: MISC_FEATURE
<223> OTHER INFORMATION: part of CLI4_HUMAN (chloride intracellular
      channel protein)

<400> SEQUENCE: 49

Glu Met Thr Gly Ile Trp Arg
1               5

<210> SEQ ID NO 50
<211> LENGTH: 16
<212> TYPE: PRT
<213> ORGANISM: Homo sapiens
<220> FEATURE:
<221> NAME/KEY: MISC_FEATURE
<223> OTHER INFORMATION: part of CLP2_HUMAN (calponin H2, smooth muscle)

<400> SEQUENCE: 50

Ser Met Gln Asn Trp His Gln Leu Glu Asn Leu Ser Asn Phe Ile Lys
1               5                   10                  15

<210> SEQ ID NO 51
<211> LENGTH: 9
<212> TYPE: PRT
<213> ORGANISM: Homo sapiens
<220> FEATURE:
<221> NAME/KEY: MISC_FEATURE
<223> OTHER INFORMATION: part of CO3_HUMAN (complement C3 precursor)

<400> SEQUENCE: 51

Tyr Tyr Thr Tyr Leu Ile Met Asn Lys
1               5
```

-continued

<210> SEQ ID NO 52
<211> LENGTH: 14
<212> TYPE: PRT
<213> ORGANISM: Homo sapiens
<220> FEATURE:
<221> NAME/KEY: MISC_FEATURE
<223> OTHER INFORMATION: part of CYPB_HUMAN (peptidyl-prolyl cis-trans
      isomerase B)

<400> SEQUENCE: 52

His Tyr Gly Pro Gly Trp Val Ser Met Ala Asn Ala Gly Lys
1               5                   10

<210> SEQ ID NO 53
<211> LENGTH: 13
<212> TYPE: PRT
<213> ORGANISM: Homo sapiens
<220> FEATURE:
<221> NAME/KEY: MISC_FEATURE
<223> OTHER INFORMATION: part of CYPH_HUMAN (peptidyl-prolyl cis-trans
      isomerase A)

<400> SEQUENCE: 53

Val Lys Glu Gly Met Asn Ile Val Glu Ala Met Glu Arg
1               5                   10

<210> SEQ ID NO 54
<211> LENGTH: 11
<212> TYPE: PRT
<213> ORGANISM: Homo sapiens
<220> FEATURE:
<221> NAME/KEY: MISC_FEATURE
<223> OTHER INFORMATION: part of DEMA_HUMAN (dematin)

<400> SEQUENCE: 54

Val Phe Ala Met Ser Pro Glu Glu Phe Gly Lys
1               5                   10

<210> SEQ ID NO 55
<211> LENGTH: 14
<212> TYPE: PRT
<213> ORGANISM: Homo sapiens
<220> FEATURE:
<221> NAME/KEY: MISC_FEATURE
<223> OTHER INFORMATION: part of DYNC_HUMAN (dynactin complex 50 kDa
      subunit)

<400> SEQUENCE: 55

Asp Asn Thr Thr Leu Leu Thr Gln Val Gln Thr Thr Met Arg
1               5                   10

<210> SEQ ID NO 56
<211> LENGTH: 12
<212> TYPE: PRT
<213> ORGANISM: Homo sapiens
<220> FEATURE:
<221> NAME/KEY: MISC_FEATURE
<223> OTHER INFORMATION: part of EHD1_HUMAN (EH-domain containing
      protein 1)

<400> SEQUENCE: 56

Met Gln Glu Leu Leu Gln Thr Gln Asp Phe Ser Lys
1               5                   10

<210> SEQ ID NO 57
<211> LENGTH: 10
<212> TYPE: PRT
<213> ORGANISM: Homo sapiens
<220> FEATURE:

```
<221> NAME/KEY: MISC_FEATURE
<223> OTHER INFORMATION: part of F13A_HUMAN (coagulation factor XIII a
      chain precursor)

<400> SEQUENCE: 57

Lys Pro Leu Asn Thr Glu Gly Val Met Lys
1               5                   10

<210> SEQ ID NO 58
<211> LENGTH: 13
<212> TYPE: PRT
<213> ORGANISM: Homo sapiens
<220> FEATURE:
<221> NAME/KEY: MISC_FEATURE
<223> OTHER INFORMATION: part of FIBA_HUMAN (fibrinogen alpha/alpha-E
      chain precursor)

<400> SEQUENCE: 58

Met Lys Pro Val Pro Asp Leu Val Pro Gly Asn Phe Lys
1               5                   10

<210> SEQ ID NO 59
<211> LENGTH: 15
<212> TYPE: PRT
<213> ORGANISM: Homo sapiens
<220> FEATURE:
<221> NAME/KEY: MISC_FEATURE
<223> OTHER INFORMATION: part of FIBB_HUMAN (fibrinogen beta chain
      precursor)

<400> SEQUENCE: 59

Thr Met Thr Ile His Asn Gly Met Phe Phe Ser Thr Tyr Asp Arg
1               5                   10                  15

<210> SEQ ID NO 60
<211> LENGTH: 12
<212> TYPE: PRT
<213> ORGANISM: Homo sapiens
<220> FEATURE:
<221> NAME/KEY: MISC_FEATURE
<223> OTHER INFORMATION: part of GDIA_HUMAN (RAP GDP dissociation
      inhibitor alpha)

<400> SEQUENCE: 60

Met Ala Gly Thr Ala Phe Asp Phe Glu Asn Met Lys
1               5                   10

<210> SEQ ID NO 61
<211> LENGTH: 10
<212> TYPE: PRT
<213> ORGANISM: Homo sapiens
<220> FEATURE:
<221> NAME/KEY: MISC_FEATURE
<223> OTHER INFORMATION: part of GR78_HUMAN (78 kDa glucose-regulated
      protein precursor)

<400> SEQUENCE: 61

Phe Glu Glu Leu Asn Met Asp Leu Phe Arg
1               5                   10

<210> SEQ ID NO 62
<211> LENGTH: 14
<212> TYPE: PRT
<213> ORGANISM: Homo sapiens
<220> FEATURE:
<221> NAME/KEY: MISC_FEATURE
<223> OTHER INFORMATION: part of GR78_HUMAN (78 kDa glucose-regulated
      protein precursor)
```

```
<400> SEQUENCE: 62

Thr Phe Ala Pro Glu Glu Ile Ser Ala Met Val Leu Thr Lys
1               5                   10

<210> SEQ ID NO 63
<211> LENGTH: 8
<212> TYPE: PRT
<213> ORGANISM: Homo sapiens
<220> FEATURE:
<221> NAME/KEY: MISC_FEATURE
<223> OTHER INFORMATION: part of GTO1_HUMAN (glutathione transferase
      omega 1)

<400> SEQUENCE: 63

Met Ile Leu Glu Leu Phe Ser Lys
1               5

<210> SEQ ID NO 64
<211> LENGTH: 11
<212> TYPE: PRT
<213> ORGANISM: Homo sapiens
<220> FEATURE:
<221> NAME/KEY: MISC_FEATURE
<223> OTHER INFORMATION: part of HS47_HUMAN (47 kDa heat shock protein
      precursor)

<400> SEQUENCE: 64

Leu Gln Leu Val Glu Met Pro Leu Ala His Lys
1               5                   10

<210> SEQ ID NO 65
<211> LENGTH: 11
<212> TYPE: PRT
<213> ORGANISM: Homo sapiens
<220> FEATURE:
<221> NAME/KEY: MISC_FEATURE
<223> OTHER INFORMATION: part of HS71_HUMAN (heat shock 70kDa protein 1)

<400> SEQUENCE: 65

Asn Ala Leu Glu Ser Tyr Ala Phe Asn Met Lys
1               5                   10

<210> SEQ ID NO 66
<211> LENGTH: 10
<212> TYPE: PRT
<213> ORGANISM: Homo sapiens
<220> FEATURE:
<221> NAME/KEY: MISC_FEATURE
<223> OTHER INFORMATION: part of HS7C_HUMAN (heat shock cognate 71kDa
      protein)

<400> SEQUENCE: 66

Met Val Asn His Phe Ile Ala Glu Phe Lys
1               5                   10

<210> SEQ ID NO 67
<211> LENGTH: 13
<212> TYPE: PRT
<213> ORGANISM: Homo sapiens
<220> FEATURE:
<221> NAME/KEY: MISC_FEATURE
<223> OTHER INFORMATION: part of HS9A/B_HUMAN (heat shock protein HSP
      90-alpha/beta)

<400> SEQUENCE: 67

Thr Leu Thr Ile Val Asp Thr Gly Ile Gly Met Thr Lys
1               5                   10
```

```
<210> SEQ ID NO 68
<211> LENGTH: 11
<212> TYPE: PRT
<213> ORGANISM: Homo sapiens
<220> FEATURE:
<221> NAME/KEY: MISC_FEATURE
<223> OTHER INFORMATION: part of IDHC_HUMAN (isocitrate dehydrogenase)

<400> SEQUENCE: 68

Leu Ile Asp Asp Met Val Ala Gln Ala Met Lys
1               5                   10

<210> SEQ ID NO 69
<211> LENGTH: 14
<212> TYPE: PRT
<213> ORGANISM: Homo sapiens
<220> FEATURE:
<221> NAME/KEY: MISC_FEATURE
<223> OTHER INFORMATION: part of ILK1/2_HUMAN (integrin-linked protein
      kinase 1/2)

<400> SEQUENCE: 69

Gly Met Ala Phe Leu His Thr Leu Glu Pro Leu Ile Pro Arg
1               5                   10

<210> SEQ ID NO 70
<211> LENGTH: 10
<212> TYPE: PRT
<213> ORGANISM: Homo sapiens
<220> FEATURE:
<221> NAME/KEY: MISC_FEATURE
<223> OTHER INFORMATION: part of ILK12b

<400> SEQUENCE: 70

Ser Ala Val Val Glu Met Leu Ile Met Arg
1               5                   10

<210> SEQ ID NO 71
<211> LENGTH: 17
<212> TYPE: PRT
<213> ORGANISM: Homo sapiens
<220> FEATURE:
<221> NAME/KEY: MISC_FEATURE
<223> OTHER INFORMATION: part of ITA2_HUMAN (integrin alpha-2 precursor)

<400> SEQUENCE: 71

Val Met Val Val Val Thr Asp Gly Glu Ser His Asp Gly Ser Met Leu
1               5                   10                  15

Lys

<210> SEQ ID NO 72
<211> LENGTH: 17
<212> TYPE: PRT
<213> ORGANISM: Homo sapiens
<220> FEATURE:
<221> NAME/KEY: MISC_FEATURE
<223> OTHER INFORMATION: part of K6PP_HUMAN (6-phosphofructokinase,
      type C)

<400> SEQUENCE: 72

Ile Ile Glu Val Val Asp Ala Ile Met Thr Thr Ala Gln Ser His Gln
1               5                   10                  15

Arg

<210> SEQ ID NO 73
<211> LENGTH: 13
```

-continued

```
<212> TYPE: PRT
<213> ORGANISM: Homo sapiens
<220> FEATURE:
<221> NAME/KEY: MISC_FEATURE
<223> OTHER INFORMATION: part of K6PP_HUMAN (6-phosphofructokinase,
      type C)

<400> SEQUENCE: 73

Met Leu Ala Ile Tyr Asp Gly Phe Asp Gly Phe Ala Lys
1               5                   10

<210> SEQ ID NO 74
<211> LENGTH: 8
<212> TYPE: PRT
<213> ORGANISM: Homo sapiens
<220> FEATURE:
<221> NAME/KEY: MISC_FEATURE
<223> OTHER INFORMATION: part of KAP0_HUMAN (cAMP-dependent protein
      kinase)

<400> SEQUENCE: 74

Met Tyr Glu Glu Phe Leu Ser Lys
1               5

<210> SEQ ID NO 75
<211> LENGTH: 13
<212> TYPE: PRT
<213> ORGANISM: Homo sapiens
<220> FEATURE:
<221> NAME/KEY: MISC_FEATURE
<223> OTHER INFORMATION: part of KAP0_HUMAN (P10644, cAMP-dependent
      protein kinase type I- alpha regulatory chain)

<400> SEQUENCE: 75

Met Glu Ser Gly Ser Thr Ala Ala Ser Glu Glu Ala Arg
1               5                   10

<210> SEQ ID NO 76
<211> LENGTH: 7
<212> TYPE: PRT
<213> ORGANISM: Homo sapiens
<220> FEATURE:
<221> NAME/KEY: MISC_FEATURE
<223> OTHER INFORMATION: part of KPY1_HUMAN (pyruvate kinase, M1
      isozyme)

<400> SEQUENCE: 76

Met Gln His Leu Ile Ala Arg
1               5

<210> SEQ ID NO 77
<211> LENGTH: 14
<212> TYPE: PRT
<213> ORGANISM: Homo sapiens
<220> FEATURE:
<221> NAME/KEY: MISC_FEATURE
<223> OTHER INFORMATION: part of LAS1_HUMAN (LIM and SH3 domain
      protein 1)

<400> SEQUENCE: 77

Gln Ser Phe Thr Met Val Ala Asp Thr Pro Glu Asn Leu Arg
1               5                   10

<210> SEQ ID NO 78
<211> LENGTH: 9
<212> TYPE: PRT
<213> ORGANISM: Homo sapiens
<220> FEATURE:
<221> NAME/KEY: MISC_FEATURE
```

-continued

```
<223> OTHER INFORMATION: part of LOXP_HUMAN (arachidonate
      12-lipoxygenase, 12S-type)

<400> SEQUENCE: 78

Ala Gly Ala Leu Glu Met Ala Leu Lys
1               5

<210> SEQ ID NO 79
<211> LENGTH: 11
<212> TYPE: PRT
<213> ORGANISM: Homo sapiens
<220> FEATURE:
<221> NAME/KEY: MISC_FEATURE
<223> OTHER INFORMATION: part of MIF_HUMAN (macrophage migration
      inhibitory factor)

<400> SEQUENCE: 79

Pro Met Phe Ile Val Asn Thr Asn Val Pro Arg
1               5                   10

<210> SEQ ID NO 80
<211> LENGTH: 10
<212> TYPE: PRT
<213> ORGANISM: Homo sapiens
<220> FEATURE:
<221> NAME/KEY: MISC_FEATURE
<223> OTHER INFORMATION: part of MOES_HUMAN (MOESIN)

<400> SEQUENCE: 80

Ala Gln Met Val Gln Glu Asp Leu Glu Lys
1               5                   10

<210> SEQ ID NO 81
<211> LENGTH: 16
<212> TYPE: PRT
<213> ORGANISM: Homo sapiens
<220> FEATURE:
<221> NAME/KEY: MISC_FEATURE
<223> OTHER INFORMATION: part of MOES_HUMAN (MOESIN)

<400> SEQUENCE: 81

Ile Ala Gln Asp Leu Glu Met Tyr Gly Val Asn Tyr Phe Ser Ile Lys
1               5                   10                  15

<210> SEQ ID NO 82
<211> LENGTH: 11
<212> TYPE: PRT
<213> ORGANISM: Homo sapiens
<220> FEATURE:
<221> NAME/KEY: MISC_FEATURE
<223> OTHER INFORMATION: part of MOES_HUMAN (MOESIN)

<400> SEQUENCE: 82

Lys Pro Asp Thr Ile Glu Val Gln Gln Met Lys
1               5                   10

<210> SEQ ID NO 83
<211> LENGTH: 14
<212> TYPE: PRT
<213> ORGANISM: Homo sapiens
<220> FEATURE:
<221> NAME/KEY: MISC_FEATURE
<223> OTHER INFORMATION: part of MYH9_HUMAN (myosin heavy chain,
      nonmuscle type A)

<400> SEQUENCE: 83

Glu Leu Glu Asp Ala Thr Glu Thr Ala Asp Ala Met Asn Arg
1               5                   10
```

```
<210> SEQ ID NO 84
<211> LENGTH: 10
<212> TYPE: PRT
<213> ORGANISM: Homo sapiens
<220> FEATURE:
<221> NAME/KEY: MISC_FEATURE
<223> OTHER INFORMATION: part of MYH9_HUMAN (myosin heavy chain,
      nonmuscle type A)

<400> SEQUENCE: 84

Glu Met Glu Ala Glu Leu Glu Asp Glu Arg
1               5                   10

<210> SEQ ID NO 85
<211> LENGTH: 20
<212> TYPE: PRT
<213> ORGANISM: Homo sapiens
<220> FEATURE:
<221> NAME/KEY: MISC_FEATURE
<223> OTHER INFORMATION: part of MYH9_HUMAN (myosin heavy chain,
      nonmuscle type A)

<400> SEQUENCE: 85

Ile Ile Gly Leu Asp Gln Val Ala Gly Met Ser Glu Thr Ala Leu Pro
1               5                   10                  15

Gly Ala Phe Lys
            20

<210> SEQ ID NO 86
<211> LENGTH: 9
<212> TYPE: PRT
<213> ORGANISM: Homo sapiens
<220> FEATURE:
<221> NAME/KEY: MISC_FEATURE
<223> OTHER INFORMATION: part of MYH9_HUMAN (myosin heavy chain,
      nonmuscle type A)

<400> SEQUENCE: 86

Leu Glu Val Asn Leu Gln Ala Met Lys
1               5

<210> SEQ ID NO 87
<211> LENGTH: 8
<212> TYPE: PRT
<213> ORGANISM: Homo sapiens
<220> FEATURE:
<221> NAME/KEY: MISC_FEATURE
<223> OTHER INFORMATION: part of MYH9_HUMAN (myosin heavy chain,
      nonmuscle type A)

<400> SEQUENCE: 87

Gln Gln Gln Leu Thr Ala Met Lys
1               5

<210> SEQ ID NO 88
<211> LENGTH: 7
<212> TYPE: PRT
<213> ORGANISM: Homo sapiens
<220> FEATURE:
<221> NAME/KEY: MISC_FEATURE
<223> OTHER INFORMATION: part of MYHA_HUMAN (myosin heavy chain,
      nonmuscle type B)

<400> SEQUENCE: 88

Ala Asp Glu Trp Leu Met Lys
1               5
```

-continued

```
<210> SEQ ID NO 89
<211> LENGTH: 10
<212> TYPE: PRT
<213> ORGANISM: Homo sapiens
<220> FEATURE:
<221> NAME/KEY: MISC_FEATURE
<223> OTHER INFORMATION: part of PA1F_HUMAN (red cell acid phosphatase
      1, isozyme F)

<400> SEQUENCE: 89

His Gly Ile Pro Met Ser His Val Ala Arg
1               5                   10

<210> SEQ ID NO 90
<211> LENGTH: 9
<212> TYPE: PRT
<213> ORGANISM: Homo sapiens
<220> FEATURE:
<221> NAME/KEY: MISC_FEATURE
<223> OTHER INFORMATION: part of PDA3_HUMAN (protein disulfide
      isomerase A3 precursor)

<400> SEQUENCE: 90

Phe Val Met Gln Glu Glu Phe Ser Arg
1               5

<210> SEQ ID NO 91
<211> LENGTH: 10
<212> TYPE: PRT
<213> ORGANISM: Homo sapiens
<220> FEATURE:
<221> NAME/KEY: MISC_FEATURE
<223> OTHER INFORMATION: part of PDI_HUMAN (protein disulfide isomerase
      precursor)

<400> SEQUENCE: 91

Leu Ile Thr Leu Glu Glu Glu Met Thr Lys
1               5                   10

<210> SEQ ID NO 92
<211> LENGTH: 19
<212> TYPE: PRT
<213> ORGANISM: Homo sapiens
<220> FEATURE:
<221> NAME/KEY: MISC_FEATURE
<223> OTHER INFORMATION: part of PDL1_HUMAN (PDZ and LIM domain
      protein 1)

<400> SEQUENCE: 92

Met Asn Leu Ala Ser Glu Pro Gln Glu Val Leu His Ile Gly Ser Ala
1               5                   10                  15

His Asn Arg

<210> SEQ ID NO 93
<211> LENGTH: 19
<212> TYPE: PRT
<213> ORGANISM: Homo sapiens
<220> FEATURE:
<221> NAME/KEY: MISC_FEATURE
<223> OTHER INFORMATION: part of PHS3_HUMAN (glycogen phosphorylase,
      brain form)

<400> SEQUENCE: 93

Val Ala Ile Gln Leu Asn Asp Thr His Pro Ala Leu Ser Ile Pro Glu
1               5                   10                  15

Leu Met Arg
```

```
<210> SEQ ID NO 94
<211> LENGTH: 15
<212> TYPE: PRT
<213> ORGANISM: Homo sapiens
<220> FEATURE:
<221> NAME/KEY: MISC_FEATURE
<223> OTHER INFORMATION: part of PIMT_HUMAN (protein-L-isoaspartate
      (D-aspartate))

<400> SEQUENCE: 94

Met Lys Pro Leu Met Gly Val Ile Tyr Val Pro Leu Thr Asp Lys
1               5                   10                  15

<210> SEQ ID NO 95
<211> LENGTH: 15
<212> TYPE: PRT
<213> ORGANISM: Homo sapiens
<220> FEATURE:
<221> NAME/KEY: MISC_FEATURE
<223> OTHER INFORMATION: part of PLEK_HUMAN (pleckstrin (platelet P47
      protein))

<400> SEQUENCE: 95

Leu Pro Glu Thr Ile Asp Leu Gly Ala Leu Tyr Leu Ser Met Lys
1               5                   10                  15

<210> SEQ ID NO 96
<211> LENGTH: 10
<212> TYPE: PRT
<213> ORGANISM: Homo sapiens
<220> FEATURE:
<221> NAME/KEY: MISC_FEATURE
<223> OTHER INFORMATION: part of PNPH_HUMAN (purine nucleoside
      phosphorylase)

<400> SEQUENCE: 96

Val Ile Met Asp Tyr Glu Ser Leu Glu Lys
1               5                   10

<210> SEQ ID NO 97
<211> LENGTH: 7
<212> TYPE: PRT
<213> ORGANISM: Homo sapiens
<220> FEATURE:
<221> NAME/KEY: MISC_FEATURE
<223> OTHER INFORMATION: part of PSE1_HUMAN (proteasome activator
      complex subunit 1)

<400> SEQUENCE: 97

Leu Met Val Met Glu Ile Arg
1               5

<210> SEQ ID NO 98
<211> LENGTH: 11
<212> TYPE: PRT
<213> ORGANISM: Homo sapiens
<220> FEATURE:
<221> NAME/KEY: MISC_FEATURE
<223> OTHER INFORMATION: part of R23B_HUMAN (UV excision repair
      protein RAD23 homologue)

<400> SEQUENCE: 98

Asn Phe Val Val Val Met Val Thr Lys Pro Lys
1               5                   10

<210> SEQ ID NO 99
<211> LENGTH: 14
<212> TYPE: PRT
```

-continued

```
<213> ORGANISM: Homo sapiens
<220> FEATURE:
<221> NAME/KEY: MISC_FEATURE
<223> OTHER INFORMATION: part of RAC1_HUMAN (RAS-related C3 botulinum
      toxin substrate)

<400> SEQUENCE: 99

Leu Thr Pro Ile Thr Tyr Pro Gln Gly Leu Ala Met Ala Lys
1               5                   10

<210> SEQ ID NO 100
<211> LENGTH: 7
<212> TYPE: PRT
<213> ORGANISM: Homo sapiens
<220> FEATURE:
<221> NAME/KEY: MISC_FEATURE
<223> OTHER INFORMATION: part of RALA/B_HUMAN (RAS-related protein
      RALA/B)

<400> SEQUENCE: 100

Val Phe Phe Asp Leu Met Arg
1               5

<210> SEQ ID NO 101
<211> LENGTH: 15
<212> TYPE: PRT
<213> ORGANISM: Homo sapiens
<220> FEATURE:
<221> NAME/KEY: MISC_FEATURE
<223> OTHER INFORMATION: part of RAPB_HUMAN (RAS-related protein RAP-1B)

<400> SEQUENCE: 101

Val Lys Asp Thr Asp Asp Val Pro Met Ile Leu Val Gly Asn Lys
1               5                   10                  15

<210> SEQ ID NO 102
<211> LENGTH: 10
<212> TYPE: PRT
<213> ORGANISM: Homo sapiens
<220> FEATURE:
<221> NAME/KEY: MISC_FEATURE
<223> OTHER INFORMATION: part of RB5A/B/C_HUMAN (RAS-related protein
      RAB-5A/B/C)

<400> SEQUENCE: 102

Tyr His Ser Leu Ala Pro Met Tyr Tyr Arg
1               5                   10

<210> SEQ ID NO 103
<211> LENGTH: 14
<212> TYPE: PRT
<213> ORGANISM: Homo sapiens
<220> FEATURE:
<221> NAME/KEY: MISC_FEATURE
<223> OTHER INFORMATION: part of RB5A_HUMAN (RAS-related protein RAB-5A)

<400> SEQUENCE: 103

Thr Ser Met Asn Val Asn Glu Ile Phe Met Ala Ile Ala Lys
1               5                   10

<210> SEQ ID NO 104
<211> LENGTH: 14
<212> TYPE: PRT
<213> ORGANISM: Homo sapiens
<220> FEATURE:
<221> NAME/KEY: MISC_FEATURE
<223> OTHER INFORMATION: part of RB5B_HUMAN (RAS-related protein RAB-5B)

<400> SEQUENCE: 104
```

Thr Ala Met Asn Val Asn Asp Leu Phe Leu Ala Ile Ala Lys
1               5                   10

<210> SEQ ID NO 105
<211> LENGTH: 10
<212> TYPE: PRT
<213> ORGANISM: Homo sapiens
<220> FEATURE:
<221> NAME/KEY: MISC_FEATURE
<223> OTHER INFORMATION: part of RSG3_HUMAN (RAS GTPase-activating
      protein 3)

<400> SEQUENCE: 105

Asn Met Phe Gln Val Ile Gln Pro Glu Arg
1               5                   10

<210> SEQ ID NO 106
<211> LENGTH: 8
<212> TYPE: PRT
<213> ORGANISM: Homo sapiens
<220> FEATURE:
<221> NAME/KEY: MISC_FEATURE
<223> OTHER INFORMATION: part of TALI_HUMAN (talin)

<400> SEQUENCE: 106

Ala Leu Asp Tyr Tyr Met Leu Arg
1               5

<210> SEQ ID NO 107
<211> LENGTH: 21
<212> TYPE: PRT
<213> ORGANISM: Homo sapiens
<220> FEATURE:
<221> NAME/KEY: MISC_FEATURE
<223> OTHER INFORMATION: part of TALI_HUMAN (talin)

<400> SEQUENCE: 107

Asp His Phe Gly Leu Glu Gly Asp Glu Glu Ser Thr Met Leu Glu Asp
1               5                   10                  15

Ser Val Ser Pro Lys
            20

<210> SEQ ID NO 108
<211> LENGTH: 12
<212> TYPE: PRT
<213> ORGANISM: Homo sapiens
<220> FEATURE:
<221> NAME/KEY: MISC_FEATURE
<223> OTHER INFORMATION: part of TALI_HUMAN (talin)

<400> SEQUENCE: 108

Met Ala Thr Asn Ala Ala Ala Gln Asn Ala Ile Lys
1               5                   10

<210> SEQ ID NO 109
<211> LENGTH: 15
<212> TYPE: PRT
<213> ORGANISM: Homo sapiens
<220> FEATURE:
<221> NAME/KEY: MISC_FEATURE
<223> OTHER INFORMATION: part of TALI_HUMAN (talin)

<400> SEQUENCE: 109

Thr Leu Ser His Pro Gln Gln Met Ala Leu Leu Asp Gln Thr Lys
1               5                   10                  15

```
<210> SEQ ID NO 110
<211> LENGTH: 13
<212> TYPE: PRT
<213> ORGANISM: Homo sapiens
<220> FEATURE:
<221> NAME/KEY: MISC_FEATURE
<223> OTHER INFORMATION: part of TALI_HUMAN (talin)

<400> SEQUENCE: 110

Val Glu His Gly Ser Val Ala Leu Pro Ala Ile Met Arg
1               5                   10

<210> SEQ ID NO 111
<211> LENGTH: 21
<212> TYPE: PRT
<213> ORGANISM: Homo sapiens
<220> FEATURE:
<221> NAME/KEY: MISC_FEATURE
<223> OTHER INFORMATION: part of TALI_HUMAN (talin)

<400> SEQUENCE: 111

Val Ser Gln Met Ala Gln Tyr Phe Glu Pro Leu Thr Leu Ala Ala Val
1               5                   10                  15

Gly Ala Ala Ser Lys
            20

<210> SEQ ID NO 112
<211> LENGTH: 12
<212> TYPE: PRT
<213> ORGANISM: Homo sapiens
<220> FEATURE:
<221> NAME/KEY: MISC_FEATURE
<223> OTHER INFORMATION: part of TBB1_HUMAN (tubulin beta-chain
      (different isoforms))

<400> SEQUENCE: 112

Ile Met Asn Thr Phe Ser Val Val Pro Ser Pro Lys
1               5                   10

<210> SEQ ID NO 113
<211> LENGTH: 14
<212> TYPE: PRT
<213> ORGANISM: Homo sapiens
<220> FEATURE:
<221> NAME/KEY: MISC_FEATURE
<223> OTHER INFORMATION: part of TBB1_HUMAN (tubulin beta-chain
      (different isoforms))

<400> SEQUENCE: 113

Leu His Phe Phe Met Pro Gly Phe Ala Pro Leu Thr Ser Arg
1               5                   10

<210> SEQ ID NO 114
<211> LENGTH: 10
<212> TYPE: PRT
<213> ORGANISM: Homo sapiens
<220> FEATURE:
<221> NAME/KEY: MISC_FEATURE
<223> OTHER INFORMATION: part of TCPG_HUMAN (T-complex protein 1,
      gamma subunit)

<400> SEQUENCE: 114

Ala Leu Asp Asp Met Ile Ser Thr Leu Lys
1               5                   10

<210> SEQ ID NO 115
<211> LENGTH: 9
<212> TYPE: PRT
```

```
<213> ORGANISM: Homo sapiens
<220> FEATURE:
<221> NAME/KEY: MISC_FEATURE
<223> OTHER INFORMATION: part of TPM2_HUMAN (tropomyosin beta chain)

<400> SEQUENCE: 115

Met Glu Leu Gln Glu Met Gln Leu Lys
1               5

<210> SEQ ID NO 116
<211> LENGTH: 12
<212> TYPE: PRT
<213> ORGANISM: Homo sapiens
<220> FEATURE:
<221> NAME/KEY: MISC_FEATURE
<223> OTHER INFORMATION: part of TPMN_HUMAN (tropomyosin, cytoskeletal
      type)

<400> SEQUENCE: 116

Met Leu Asp Gln Thr Leu Leu Asp Leu Asn Glu Met
1               5                   10

<210> SEQ ID NO 117
<211> LENGTH: 6
<212> TYPE: PRT
<213> ORGANISM: Homo sapiens
<220> FEATURE:
<221> NAME/KEY: MISC_FEATURE
<223> OTHER INFORMATION: part of UBIQ_HUMAN (ubiquitin)

<400> SEQUENCE: 117

Met Gln Ile Phe Val Lys
1               5

<210> SEQ ID NO 118
<211> LENGTH: 11
<212> TYPE: PRT
<213> ORGANISM: Homo sapiens
<220> FEATURE:
<221> NAME/KEY: MISC_FEATURE
<223> OTHER INFORMATION: part of VINC_HUMAN (vinculin (metavinculin))

<400> SEQUENCE: 118

Glu Leu Leu Pro Val Leu Ile Ser Ala Met Lys
1               5                   10

<210> SEQ ID NO 119
<211> LENGTH: 12
<212> TYPE: PRT
<213> ORGANISM: Homo sapiens
<220> FEATURE:
<221> NAME/KEY: MISC_FEATURE
<223> OTHER INFORMATION: part of VINC_HUMAN (vinculin (metavinculin))

<400> SEQUENCE: 119

Met Thr Gly Leu Val Asp Glu Ala Ile Asp Thr Lys
1               5                   10

<210> SEQ ID NO 120
<211> LENGTH: 11
<212> TYPE: PRT
<213> ORGANISM: Homo sapiens
<220> FEATURE:
<221> NAME/KEY: MISC_FEATURE
<223> OTHER INFORMATION: part of VINC_HUMAN (vinculin (metavinculin))

<400> SEQUENCE: 120

Val Met Leu Val Asn Ser Met Asn Thr Val Lys
```

```
1               5                    10
```

<210> SEQ ID NO 121
<211> LENGTH: 7
<212> TYPE: PRT
<213> ORGANISM: Homo sapiens
<220> FEATURE:
<221> NAME/KEY: MISC_FEATURE
<223> OTHER INFORMATION: part of WDR1_HUMAN (WD-repeat protein 1)

<400> SEQUENCE: 121

```
Tyr Thr Ser Leu Met Leu Arg
1               5
```

<210> SEQ ID NO 122
<211> LENGTH: 9
<212> TYPE: PRT
<213> ORGANISM: Homo sapiens
<220> FEATURE:
<221> NAME/KEY: MISC_FEATURE
<223> OTHER INFORMATION: part of 143F_HUMAN (Q04917, 14-3-3 protein ETA
      protein AS1)

<400> SEQUENCE: 122

```
Gly Asp Arg Glu Gln Leu Leu Gln Arg
1               5
```

<210> SEQ ID NO 123
<211> LENGTH: 11
<212> TYPE: PRT
<213> ORGANISM: Homo sapiens
<220> FEATURE:
<221> NAME/KEY: MISC_FEATURE
<223> OTHER INFORMATION: part of APT_HUMAN (P07741, adenine
      phosphoribosyltransferase)

<400> SEQUENCE: 123

```
Ala Asp Ser Glu Leu Gln Leu Val Glu Gln Arg
1               5                    10
```

<210> SEQ ID NO 124
<211> LENGTH: 7
<212> TYPE: PRT
<213> ORGANISM: Homo sapiens
<220> FEATURE:
<221> NAME/KEY: MISC_FEATURE
<223> OTHER INFORMATION: part of AR72_HUMAN (Q43488, afflatoxin B1
      aldehyde reductase 1)

<400> SEQUENCE: 124

```
Ser Arg Pro Pro Pro Pro Arg
1               5
```

<210> SEQ ID NO 125
<211> LENGTH: 14
<212> TYPE: PRT
<213> ORGANISM: Homo sapiens
<220> FEATURE:
<221> NAME/KEY: MISC_FEATURE
<223> OTHER INFORMATION: part of ATA3_HUMAN (Q93084, sarcoplasmic/
      endoplasmic reticulum calcium ATPase 3)

<400> SEQUENCE: 125

```
Met Glu Ala Ala His Leu Leu Pro Ala Ala Asp Val Leu Arg
1               5                    10
```

<210> SEQ ID NO 126
<211> LENGTH: 9

```
<212> TYPE: PRT
<213> ORGANISM: Homo sapiens
<220> FEATURE:
<221> NAME/KEY: MISC_FEATURE
<223> OTHER INFORMATION: part of CAP1_HUMAN (Q01518, adenylyl
      cyclase-associated protein 1)

<400> SEQUENCE: 126

Ala Asp Met Gln Asn Leu Val Glu Arg
1               5

<210> SEQ ID NO 127
<211> LENGTH: 13
<212> TYPE: PRT
<213> ORGANISM: Homo sapiens
<220> FEATURE:
<221> NAME/KEY: MISC_FEATURE
<223> OTHER INFORMATION: part of CAPB_HUMAN (P47756, F-actin capping
      protein beta subunit)

<400> SEQUENCE: 127

Ser Asp Gln Gln Leu Asp Cys Ala Leu Asp Leu Met Arg
1               5                   10

<210> SEQ ID NO 128
<211> LENGTH: 7
<212> TYPE: PRT
<213> ORGANISM: Homo sapiens
<220> FEATURE:
<221> NAME/KEY: MISC_FEATURE
<223> OTHER INFORMATION: part of CDN7_HUMAN (P55273, cyclin-dependent
      kinase 4 inhibitor D)

<400> SEQUENCE: 128

Met Leu Leu Glu Glu Val Arg
1               5

<210> SEQ ID NO 129
<211> LENGTH: 12
<212> TYPE: PRT
<213> ORGANISM: Homo sapiens
<220> FEATURE:
<221> NAME/KEY: MISC_FEATURE
<223> OTHER INFORMATION: part of DEST_HUMAN (P18282, destrin
      actin-depolymerizing factor)

<400> SEQUENCE: 129

Ala Ser Gly Val Gln Val Ala Asp Glu Val Cys Arg
1               5                   10

<210> SEQ ID NO 130
<211> LENGTH: 9
<212> TYPE: PRT
<213> ORGANISM: Homo sapiens
<220> FEATURE:
<221> NAME/KEY: MISC_FEATURE
<223> OTHER INFORMATION: part of DREB_HUMAN (Q16643, DREBIN E)

<400> SEQUENCE: 130

Ala Gly Val Ser Phe Ser Gly His Arg
1               5

<210> SEQ ID NO 131
<211> LENGTH: 10
<212> TYPE: PRT
<213> ORGANISM: Homo sapiens
<220> FEATURE:
<221> NAME/KEY: MISC_FEATURE
<223> OTHER INFORMATION: part of EHD3_HUMAN (Q9NZN3, EH-domain
```

```
                 containing protein 3)

<400> SEQUENCE: 131

Met Phe Ser Trp Leu Gly Thr Asp Asp Arg
1               5                   10

<210> SEQ ID NO 132
<211> LENGTH: 9
<212> TYPE: PRT
<213> ORGANISM: Homo sapiens
<220> FEATURE:
<221> NAME/KEY: MISC_FEATURE
<223> OTHER INFORMATION: part of ERF1_HUMAN (P46055, eukaryotic peptide
      chain release fact or)

<400> SEQUENCE: 132

Ala Asp Asp Pro Ser Ala Ala Asp Arg
1               5

<210> SEQ ID NO 133
<211> LENGTH: 9
<212> TYPE: PRT
<213> ORGANISM: Homo sapiens
<220> FEATURE:
<221> NAME/KEY: MISC_FEATURE
<223> OTHER INFORMATION: part of FABE_HUMAN (Q01469, fatty
      acid-binding protein, epidermal)

<400> SEQUENCE: 133

Ala Thr Val Gln Gln Leu Glu Gly Arg
1               5

<210> SEQ ID NO 134
<211> LENGTH: 11
<212> TYPE: PRT
<213> ORGANISM: Homo sapiens
<220> FEATURE:
<221> NAME/KEY: MISC_FEATURE
<223> OTHER INFORMATION: part of FLIH_HUMAN (Q13045, flightless-I
      protein homolog)

<400> SEQUENCE: 134

Met Glu Ala Thr Gly Val Leu Pro Phe Val Arg
1               5                   10

<210> SEQ ID NO 135
<211> LENGTH: 6
<212> TYPE: PRT
<213> ORGANISM: Homo sapiens
<220> FEATURE:
<221> NAME/KEY: MISC_FEATURE
<223> OTHER INFORMATION: part of FN3K_HUMAN (Q9H479,
      fructosamine-3-kinase)

<400> SEQUENCE: 135

Met Glu Gln Leu Leu Arg
1               5

<210> SEQ ID NO 136
<211> LENGTH: 8
<212> TYPE: PRT
<213> ORGANISM: Homo sapiens
<220> FEATURE:
<221> NAME/KEY: MISC_FEATURE
<223> OTHER INFORMATION: part of G6PD_HUMAN (P11413, glucose-6-phosphate
      1-dehydrogenase)

<400> SEQUENCE: 136
```

Ala Glu Gln Val Ala Leu Ser Arg
1               5

<210> SEQ ID NO 137
<211> LENGTH: 9
<212> TYPE: PRT
<213> ORGANISM: Homo sapiens
<220> FEATURE:
<221> NAME/KEY: MISC_FEATURE
<223> OTHER INFORMATION: part of IF4H_HUMAN (Q15056, eukaryotic
      translation initiation factor)

<400> SEQUENCE: 137

Ala Asp Phe Asp Thr Tyr Asp Asp Arg
1               5

<210> SEQ ID NO 138
<211> LENGTH: 10
<212> TYPE: PRT
<213> ORGANISM: Homo sapiens
<220> FEATURE:
<221> NAME/KEY: MISC_FEATURE
<223> OTHER INFORMATION: part of ILEU_HUMAN (P30740, leukocyte
      elastase inhibitor)

<400> SEQUENCE: 138

Met Glu Gln Leu Ser Ser Ala Asn Thr Arg
1               5                   10

<210> SEQ ID NO 139
<211> LENGTH: 9
<212> TYPE: PRT
<213> ORGANISM: Homo sapiens
<220> FEATURE:
<221> NAME/KEY: MISC_FEATURE
<223> OTHER INFORMATION: part of ILK2_HUMAN (P57043, integrin-linked
      protein kinase 2)

<400> SEQUENCE: 139

Met Asp Asp Ile Phe Thr Gln Cys Arg
1               5

<210> SEQ ID NO 140
<211> LENGTH: 18
<212> TYPE: PRT
<213> ORGANISM: Homo sapiens
<220> FEATURE:
<221> NAME/KEY: MISC_FEATURE
<223> OTHER INFORMATION: part of KPC1_HUMAN (P05771, protein kinase C,
      beta-I type)

<400> SEQUENCE: 140

Ala Asp Pro Ala Ala Gly Pro Pro Pro Ser Glu Gly Glu Glu Ser Thr
1               5                   10                  15

Val Arg

<210> SEQ ID NO 141
<211> LENGTH: 7
<212> TYPE: PRT
<213> ORGANISM: Homo sapiens
<220> FEATURE:
<221> NAME/KEY: MISC_FEATURE
<223> OTHER INFORMATION: part of LAS1_HUMAN (Q14847, LIM and SH3 domain
      protein 1 LASP-1)

<400> SEQUENCE: 141

Met Asn Pro Asn Cys Ala Arg
1               5

<210> SEQ ID NO 142
<211> LENGTH: 14
<212> TYPE: PRT
<213> ORGANISM: Homo sapiens
<220> FEATURE:
<221> NAME/KEY: MISC_FEATURE
<223> OTHER INFORMATION: part of MK01_HUMAN (P28482, mitogen-activated protein kinase 1)

<400> SEQUENCE: 142

Ala Ala Ala Ala Ala Ala Gly Ala Gly Pro Glu Met Val Arg
1               5                   10

<210> SEQ ID NO 143
<211> LENGTH: 11
<212> TYPE: PRT
<213> ORGANISM: Homo sapiens
<220> FEATURE:
<221> NAME/KEY: MISC_FEATURE
<223> OTHER INFORMATION: part of PINC_HUMAN (P48059, pinch protein particularly interesting new Cys-His protein)

<400> SEQUENCE: 143

Ala Asn Ala Leu Ala Ser Ala Thr Cys Glu Arg
1               5                   10

<210> SEQ ID NO 144
<211> LENGTH: 13
<212> TYPE: PRT
<213> ORGANISM: Homo sapiens
<220> FEATURE:
<221> NAME/KEY: MISC_FEATURE
<223> OTHER INFORMATION: part of PP1B_HUMAN (P37140, serine/threonine protein phosphatase)

<400> SEQUENCE: 144

Ala Asp Gly Glu Leu Asn Val Asp Ser Leu Ile Thr Arg
1               5                   10

<210> SEQ ID NO 145
<211> LENGTH: 9
<212> TYPE: PRT
<213> ORGANISM: Homo sapiens
<220> FEATURE:
<221> NAME/KEY: MISC_FEATURE
<223> OTHER INFORMATION: part of PSD5_HUMAN (Q16401, 26S proteasome subunit S5B 26S protease)

<400> SEQUENCE: 145

Ala Ala Gln Ala Leu Ala Leu Leu Arg
1               5

<210> SEQ ID NO 146
<211> LENGTH: 8
<212> TYPE: PRT
<213> ORGANISM: Homo sapiens
<220> FEATURE:
<221> NAME/KEY: MISC_FEATURE
<223> OTHER INFORMATION: part of PTNC_HUMAN (Q05209, protein-tyrosine phosphatase, non-receptor, type 12)

<400> SEQUENCE: 146

Met Glu Gln Val Glu Ile Leu Arg
1               5

<210> SEQ ID NO 147
<211> LENGTH: 12

-continued

```
<212> TYPE: PRT
<213> ORGANISM: Homo sapiens
<220> FEATURE:
<221> NAME/KEY: MISC_FEATURE
<223> OTHER INFORMATION: part of PYR1_HUMAN (P27708, CAD protein)

<400> SEQUENCE: 147

Ala Ala Leu Val Leu Glu Asp Gly Ser Val Leu Arg
1               5                   10

<210> SEQ ID NO 148
<211> LENGTH: 8
<212> TYPE: PRT
<213> ORGANISM: Homo sapiens
<220> FEATURE:
<221> NAME/KEY: MISC_FEATURE
<223> OTHER INFORMATION: part of SMP1_HUMAN (O95807, small membrane
      protein 1)

<400> SEQUENCE: 148

Ser Gly Phe Leu Glu Gly Leu Arg
1               5

<210> SEQ ID NO 149
<211> LENGTH: 12
<212> TYPE: PRT
<213> ORGANISM: Homo sapiens
<220> FEATURE:
<221> NAME/KEY: MISC_FEATURE
<223> OTHER INFORMATION: part of SN23_HUMAN (O00161,
      synaptosomal-associated protein 23 SN AP-23)

<400> SEQUENCE: 149

Met Asp Asn Leu Ser Ser Glu Glu Ile Gln Gln Arg
1               5                   10

<210> SEQ ID NO 150
<211> LENGTH: 8
<212> TYPE: PRT
<213> ORGANISM: Homo sapiens
<220> FEATURE:
<221> NAME/KEY: MISC_FEATURE
<223> OTHER INFORMATION: part of SNX3_HUMAN (O60493, sorting nexin 3
      SDP3 protein)

<400> SEQUENCE: 150

Ala Glu Thr Val Ala Asp Thr Arg
1               5

<210> SEQ ID NO 151
<211> LENGTH: 9
<212> TYPE: PRT
<213> ORGANISM: Homo sapiens
<220> FEATURE:
<221> NAME/KEY: MISC_FEATURE
<223> OTHER INFORMATION: part of SNX3_HUMAN (O60493, sorting nexin 3
      SDP3 protein)

<400> SEQUENCE: 151

Ala Glu Thr Val Ala Asp Thr Arg Arg
1               5

<210> SEQ ID NO 152
<211> LENGTH: 11
<212> TYPE: PRT
<213> ORGANISM: Homo sapiens
<220> FEATURE:
<221> NAME/KEY: MISC_FEATURE
<223> OTHER INFORMATION: part of SYFA_HUMAN (Q9Y285, phenylalanyl-tRNA
``` synthetase alpha chain)

<400> SEQUENCE: 152

Ala Asp Gly Gln Val Ala Glu Leu Leu Leu Arg
1               5                   10

<210> SEQ ID NO 153
<211> LENGTH: 14
<212> TYPE: PRT
<213> ORGANISM: Homo sapiens
<220> FEATURE:
<221> NAME/KEY: MISC_FEATURE
<223> OTHER INFORMATION: part of SYG_HUMAN (P41250, glycyl-tRNA
      synthetase

<400> SEQUENCE: 153

Met Asp Gly Ala Gly Ala Glu Glu Val Leu Ala Pro Leu Arg
1               5                   10

<210> SEQ ID NO 154
<211> LENGTH: 11
<212> TYPE: PRT
<213> ORGANISM: Homo sapiens
<220> FEATURE:
<221> NAME/KEY: MISC_FEATURE
<223> OTHER INFORMATION: part of TCPA_HUMAN (P17987, T-complex protein
      1, alpha subunit)

<400> SEQUENCE: 154

Met Glu Gly Pro Leu Ser Val Phe Gly Asp Arg
1               5                   10

<210> SEQ ID NO 155
<211> LENGTH: 10
<212> TYPE: PRT
<213> ORGANISM: Homo sapiens
<220> FEATURE:
<221> NAME/KEY: MISC_FEATURE
<223> OTHER INFORMATION: part of UBCG_HUMAN (Q99462,
      ubiquitin-conjugating enzyme E2 G1)

<400> SEQUENCE: 155

Thr Glu Leu Gln Ser Ala Leu Leu Leu Arg
1               5                   10

<210> SEQ ID NO 156
<211> LENGTH: 13
<212> TYPE: PRT
<213> ORGANISM: Homo sapiens
<220> FEATURE:
<221> NAME/KEY: MISC_FEATURE
<223> OTHER INFORMATION: part of VAM3_HUMAN (Q15836, vesicle-associated
      membrane protein3)

<400> SEQUENCE: 156

Ser Thr Gly Pro Thr Ala Ala Thr Gly Ser Asn Arg Arg
1               5                   10

<210> SEQ ID NO 157
<211> LENGTH: 9
<212> TYPE: PRT
<213> ORGANISM: Homo sapiens
<220> FEATURE:
<221> NAME/KEY: MISC_FEATURE
<223> OTHER INFORMATION: part of VASP_HUMAN (P50552,
      vasodilator-stimulated phosphoprotein)

<400> SEQUENCE: 157

-continued

Ser Glu Thr Val Ile Cys Ser Ser Arg
1               5

<210> SEQ ID NO 158
<211> LENGTH: 21
<212> TYPE: PRT
<213> ORGANISM: Homo sapiens
<220> FEATURE:
<221> NAME/KEY: MISC_FEATURE
<223> OTHER INFORMATION: part of AOP2_HUMAN (P30041, antioxidant
      protein 2 1-Cys peroxiredo)

<400> SEQUENCE: 158

Pro Gly Gly Leu Leu Leu Gly Asp Val Ala Pro Asn Phe Glu Ala Asn
1               5                   10                  15

Thr Thr Val Gly Arg
            20

<210> SEQ ID NO 159
<211> LENGTH: 11
<212> TYPE: PRT
<213> ORGANISM: Homo sapiens
<220> FEATURE:
<221> NAME/KEY: MISC_FEATURE
<223> OTHER INFORMATION: part of GTP_HUMAN (P09211, glutathione
      S-transferase P)

<400> SEQUENCE: 159

Pro Pro Tyr Thr Val Val Tyr Phe Pro Val Arg
1               5                   10

<210> SEQ ID NO 160
<211> LENGTH: 11
<212> TYPE: PRT
<213> ORGANISM: Homo sapiens
<220> FEATURE:
<221> NAME/KEY: MISC_FEATURE
<223> OTHER INFORMATION: part of MIF_HUMAN (P14174, macrophage migration
      inhibitory factor)

<400> SEQUENCE: 160

Pro Met Phe Ile Val Asn Thr Asn Val Pro Arg
1               5                   10

<210> SEQ ID NO 161
<211> LENGTH: 13
<212> TYPE: PRT
<213> ORGANISM: Homo sapiens
<220> FEATURE:
<221> NAME/KEY: MISC_FEATURE
<223> OTHER INFORMATION: part of ACTB_HUMAN (P02570, actin, cytoplasmic
      1 beta-actin)

<400> SEQUENCE: 161

Gln Glu Tyr Asp Glu Ser Gly Pro Ser Ile Val His Arg
1               5                   10

<210> SEQ ID NO 162
<211> LENGTH: 9
<212> TYPE: PRT
<213> ORGANISM: Homo sapiens
<220> FEATURE:
<221> NAME/KEY: MISC_FEATURE
<223> OTHER INFORMATION: part of ALFA_HUMAN (P04075,
      fructose-biphosphate aldolase A)

<400> SEQUENCE: 162

Gln Leu Leu Leu Thr Ala Asp Asp Arg

-continued

```
<210> SEQ ID NO 163
<211> LENGTH: 10
<212> TYPE: PRT
<213> ORGANISM: Homo sapiens
<220> FEATURE:
<221> NAME/KEY: MISC_FEATURE
<223> OTHER INFORMATION: part of FIBA_HUMAN (P02671, fibrinogen
      alpha/alpha-E chain precursor)

<400> SEQUENCE: 163

Gln Phe Thr Ser Ser Thr Ser Tyr Asn Arg
1               5                   10

<210> SEQ ID NO 164
<211> LENGTH: 9
<212> TYPE: PRT
<213> ORGANISM: Homo sapiens
<220> FEATURE:
<221> NAME/KEY: MISC_FEATURE
<223> OTHER INFORMATION: part of FIBB_HUMAN (P02675, fibrinogen beta
      chain precursor)

<400> SEQUENCE: 164

Gln Asp Gly Ser Val Asp Phe Gly Arg
1               5

<210> SEQ ID NO 165
<211> LENGTH: 13
<212> TYPE: PRT
<213> ORGANISM: Homo sapiens
<220> FEATURE:
<221> NAME/KEY: MISC_FEATURE
<223> OTHER INFORMATION: part of GPV_HUMAN (P40197, platelet
      glycoprotein V precursor GPV)

<400> SEQUENCE: 165

Gln His Leu Gly Leu Val Gly Gly Glu Glu Pro Pro Arg
1               5                   10

<210> SEQ ID NO 166
<211> LENGTH: 9
<212> TYPE: PRT
<213> ORGANISM: Homo sapiens
<220> FEATURE:
<221> NAME/KEY: MISC_FEATURE
<223> OTHER INFORMATION: part of HS27_HUMAN (P04792, heat shock 27 kDa
      protein HSP27)

<400> SEQUENCE: 166

Gln Asp Glu His Gly Tyr Ile Ser Arg
1               5

<210> SEQ ID NO 167
<211> LENGTH: 12
<212> TYPE: PRT
<213> ORGANISM: Homo sapiens
<220> FEATURE:
<221> NAME/KEY: MISC_FEATURE
<223> OTHER INFORMATION: part of ITAB_HUMAN (P08514, integrin alpha-IIB
      precursor platelet)

<400> SEQUENCE: 167

Gln Ile Phe Leu Pro Glu Pro Glu Gln Pro Ser Arg
1               5                   10

<210> SEQ ID NO 168
```

```
<211> LENGTH: 7
<212> TYPE: PRT
<213> ORGANISM: Homo sapiens
<220> FEATURE:
<221> NAME/KEY: MISC_FEATURE
<223> OTHER INFORMATION: part of MYH9_HUMAN (P35579, myosin heavy
      chain, nonmuscle type A)

<400> SEQUENCE: 168

Gln Leu Ala Ala Glu Asn Arg
1               5

<210> SEQ ID NO 169
<211> LENGTH: 11
<212> TYPE: PRT
<213> ORGANISM: Homo sapiens
<220> FEATURE:
<221> NAME/KEY: MISC_FEATURE
<223> OTHER INFORMATION: part of MYH9_HUMAN (P35579, myosin heavy
      chain, nonmuscle type A)

<400> SEQUENCE: 169

Gln Leu Glu Glu Ala Glu Glu Glu Ala Gln Arg
1               5                   10

<210> SEQ ID NO 170
<211> LENGTH: 12
<212> TYPE: PRT
<213> ORGANISM: Homo sapiens
<220> FEATURE:
<221> NAME/KEY: MISC_FEATURE
<223> OTHER INFORMATION: part of PSE1_HUMAN (Q06323, proteasome
      activator complex subunit 1)

<400> SEQUENCE: 170

Gln Leu Val His Glu Leu Asp Glu Ala Glu Tyr Arg
1               5                   10

<210> SEQ ID NO 171
<211> LENGTH: 10
<212> TYPE: PRT
<213> ORGANISM: Homo sapiens
<220> FEATURE:
<221> NAME/KEY: MISC_FEATURE
<223> OTHER INFORMATION: part of SORC_HUMAN (P30626, Sorcin 22kDa
      protein)

<400> SEQUENCE: 171

Gln His Phe Ile Ser Phe Asp Thr Asp Arg
1               5                   10

<210> SEQ ID NO 172
<211> LENGTH: 12
<212> TYPE: PRT
<213> ORGANISM: Homo sapiens
<220> FEATURE:
<221> NAME/KEY: MISC_FEATURE
<223> OTHER INFORMATION: part of TALI_HUMAN (Q9Y490, Talin)

<400> SEQUENCE: 172

Gln Glu Asp Val Ile Ala Thr Ala Asn Leu Ser Arg
1               5                   10

<210> SEQ ID NO 173
<211> LENGTH: 7
<212> TYPE: PRT
<213> ORGANISM: Homo sapiens
<220> FEATURE:
<221> NAME/KEY: MISC_FEATURE
```

```
<223> OTHER INFORMATION: part of UVRG_HUMAN Q9P2Y5, UV radiation
      resistance-associated gene)

<400> SEQUENCE: 173

Glu Ile Glu Glu Lys Leu Arg
1               5

<210> SEQ ID NO 174
<211> LENGTH: 11
<212> TYPE: PRT
<213> ORGANISM: Homo sapiens
<220> FEATURE:
<221> NAME/KEY: MISC_FEATURE
<223> OTHER INFORMATION: part of VASP_HUMAN (P50552,
      vasodilator-stimulated phosphoprotein)

<400> SEQUENCE: 174

Gln Gln Pro Gly Pro Ser Glu His Ile Glu Arg
1               5                   10

<210> SEQ ID NO 175
<211> LENGTH: 7
<212> TYPE: PRT
<213> ORGANISM: Homo sapiens
<220> FEATURE:
<221> NAME/KEY: MISC_FEATURE
<223> OTHER INFORMATION: part of VINC_HUMAN (P18206, vinculin
      metavinculin)

<400> SEQUENCE: 175

Gln Leu His Asp Glu Ala Arg
1               5

<210> SEQ ID NO 176
<211> LENGTH: 10
<212> TYPE: PRT
<213> ORGANISM: Homo sapiens
<220> FEATURE:
<221> NAME/KEY: MISC_FEATURE
<223> OTHER INFORMATION: part of VINC_HUMAN (P18206, vinculin
      metavinculin)

<400> SEQUENCE: 176

Gln Gln Glu Leu Thr His Gln Glu His Arg
1               5                   10

<210> SEQ ID NO 177
<211> LENGTH: 15
<212> TYPE: PRT
<213> ORGANISM: Homo sapiens
<220> FEATURE:
<221> NAME/KEY: MISC_FEATURE
<223> OTHER INFORMATION: part of ZYX_HUMAN (Q15942, Zyxin)

<400> SEQUENCE: 177

Gln His Pro Val Pro Pro Pro Ala Gln Asn Gln Asn Gln Val Arg
1               5                   10                  15

<210> SEQ ID NO 178
<211> LENGTH: 9
<212> TYPE: PRT
<213> ORGANISM: Homo sapiens
<220> FEATURE:
<221> NAME/KEY: MISC_FEATURE
<223> OTHER INFORMATION: fr5 - 882.36

<400> SEQUENCE: 178

Pro Ala Pro Gly Gly Ala Glu Gln Arg
```

-continued

```
1               5

<210> SEQ ID NO 179
<211> LENGTH: 4
<212> TYPE: PRT
<213> ORGANISM: Homo sapiens
<220> FEATURE:
<221> NAME/KEY: MISC_FEATURE
<223> OTHER INFORMATION: fr 5 - 899.34
<220> FEATURE:
<221> NAME/KEY: MISC_FEATURE
<222> LOCATION: (2)..(2)
<223> OTHER INFORMATION: M is a methionine-sulfoxide

<400> SEQUENCE: 179

Tyr Met Pro Arg
1

<210> SEQ ID NO 180
<211> LENGTH: 5
<212> TYPE: PRT
<213> ORGANISM: Homo sapiens
<220> FEATURE:
<221> NAME/KEY: MISC_FEATURE
<223> OTHER INFORMATION: fr5 - 911.31

<400> SEQUENCE: 180

Glu Ser Pro Gln Ala
1               5

<210> SEQ ID NO 181
<211> LENGTH: 7
<212> TYPE: PRT
<213> ORGANISM: Homo sapiens
<220> FEATURE:
<221> NAME/KEY: MISC_FEATURE
<223> OTHER INFORMATION: fr 5 - 920.36

<400> SEQUENCE: 181

Thr Gly Ala Gly Pro Ala Gly
1               5

<210> SEQ ID NO 182
<211> LENGTH: 7
<212> TYPE: PRT
<213> ORGANISM: Homo sapiens
<220> FEATURE:
<221> NAME/KEY: MISC_FEATURE
<223> OTHER INFORMATION: fr5 - 964.38

<400> SEQUENCE: 182

Ala Thr Gly Ala Gly Glx Pro
1               5

<210> SEQ ID NO 183
<211> LENGTH: 7
<212> TYPE: PRT
<213> ORGANISM: Homo sapiens
<220> FEATURE:
<221> NAME/KEY: MISC_FEATURE
<223> OTHER INFORMATION: fr5 - 964.39

<400> SEQUENCE: 183

Pro Gly Gly Ala Gly Gln Pro
1               5

<210> SEQ ID NO 184
<211> LENGTH: 5
```

-continued

```
<212> TYPE: PRT
<213> ORGANISM: Homo sapiens
<220> FEATURE:
<221> NAME/KEY: MISC_FEATURE
<223> OTHER INFORMATION: fr5 - 966.34

<400> SEQUENCE: 184

Ala Thr Gly Ala Gly
1               5

<210> SEQ ID NO 185
<211> LENGTH: 6
<212> TYPE: PRT
<213> ORGANISM: Homo sapiens
<220> FEATURE:
<221> NAME/KEY: MISC_FEATURE
<223> OTHER INFORMATION: fr5 - 986.39

<400> SEQUENCE: 185

Ala Ser Ser Thr Thr Ala
1               5

<210> SEQ ID NO 186
<211> LENGTH: 6
<212> TYPE: PRT
<213> ORGANISM: Homo sapiens
<220> FEATURE:
<221> NAME/KEY: MISC_FEATURE
<223> OTHER INFORMATION: fr5 - 996.32

<400> SEQUENCE: 186

Ala Ala Asn Pro Asp Gly
1               5

<210> SEQ ID NO 187
<211> LENGTH: 6
<212> TYPE: PRT
<213> ORGANISM: Homo sapiens
<220> FEATURE:
<221> NAME/KEY: MISC_FEATURE
<223> OTHER INFORMATION: fr5 - 1073.39

<400> SEQUENCE: 187

Ser Ser Gly Gly Ser Ile
1               5

<210> SEQ ID NO 188
<211> LENGTH: 7
<212> TYPE: PRT
<213> ORGANISM: Homo sapiens
<220> FEATURE:
<221> NAME/KEY: MISC_FEATURE
<223> OTHER INFORMATION: fr5 - 1466.53

<400> SEQUENCE: 188

Gln Glu Ala Gly Ser Thr Ser
1               5

<210> SEQ ID NO 189
<211> LENGTH: 5
<212> TYPE: PRT
<213> ORGANISM: Homo sapiens
<220> FEATURE:
<221> NAME/KEY: MISC_FEATURE
<223> OTHER INFORMATION: fr5 - 1466.54

<400> SEQUENCE: 189

Gln Glu Glu Ser Asp
```

1               5

<210> SEQ ID NO 190
<211> LENGTH: 8
<212> TYPE: PRT
<213> ORGANISM: Homo sapiens
<220> FEATURE:
<221> NAME/KEY: MISC_FEATURE
<223> OTHER INFORMATION: fr5 - 1522.41

<400> SEQUENCE: 190

Ala His Pro Asp Ser Glu Glu Gln
1               5

<210> SEQ ID NO 191
<211> LENGTH: 6
<212> TYPE: PRT
<213> ORGANISM: Homo sapiens
<220> FEATURE:
<221> NAME/KEY: MISC_FEATURE
<223> OTHER INFORMATION: fr5 - 1649.63

<400> SEQUENCE: 191

Gly Ser Gly Gly Ser Ile
1               5

<210> SEQ ID NO 192
<211> LENGTH: 5
<212> TYPE: PRT
<213> ORGANISM: Homo sapiens
<220> FEATURE:
<221> NAME/KEY: MISC_FEATURE
<223> OTHER INFORMATION: fr6 - 851.30

<400> SEQUENCE: 192

Ala Glu Asp Gly Ala
1               5

<210> SEQ ID NO 193
<211> LENGTH: 5
<212> TYPE: PRT
<213> ORGANISM: Homo sapiens
<220> FEATURE:
<221> NAME/KEY: MISC_FEATURE
<223> OTHER INFORMATION: fr6 - 851.32

<400> SEQUENCE: 193

Ala Gln Cys Glu Ala
1               5

<210> SEQ ID NO 194
<211> LENGTH: 5
<212> TYPE: PRT
<213> ORGANISM: Homo sapiens
<220> FEATURE:
<221> NAME/KEY: MISC_FEATURE
<223> OTHER INFORMATION: fr6 - 858.34

<400> SEQUENCE: 194

Pro Glu Asp Ile Ala
1               5

<210> SEQ ID NO 195
<211> LENGTH: 5
<212> TYPE: PRT
<213> ORGANISM: Homo sapiens
<220> FEATURE:
<221> NAME/KEY: MISC_FEATURE -continued
<223> OTHER INFORMATION: fr6 - 858.34

<400> SEQUENCE: 195

Pro Gln Asp Ile Ala
1               5

<210> SEQ ID NO 196
<211> LENGTH: 6
<212> TYPE: PRT
<213> ORGANISM: Homo sapiens
<220> FEATURE:
<221> NAME/KEY: MISC_FEATURE
<223> OTHER INFORMATION: fr6 - 899.39

<400> SEQUENCE: 196

Cys His Val Asn Pro Arg
1               5

<210> SEQ ID NO 197
<211> LENGTH: 6
<212> TYPE: PRT
<213> ORGANISM: Homo sapiens
<220> FEATURE:
<221> NAME/KEY: MISC_FEATURE
<223> OTHER INFORMATION: fr6 - 899.39

<400> SEQUENCE: 197

Pro Arg Cys Pro Pro Arg
1               5

<210> SEQ ID NO 198
<211> LENGTH: 7
<212> TYPE: PRT
<213> ORGANISM: Homo sapiens
<220> FEATURE:
<221> NAME/KEY: MISC_FEATURE
<223> OTHER INFORMATION: fr6 - 899.45

<400> SEQUENCE: 198

Cys Asn Ala Pro Ile Ala Arg
1               5

<210> SEQ ID NO 199
<211> LENGTH: 5
<212> TYPE: PRT
<213> ORGANISM: Homo sapiens
<220> FEATURE:
<221> NAME/KEY: MISC_FEATURE
<223> OTHER INFORMATION: fr6 - 904.37

<400> SEQUENCE: 199

Asn Pro Asn Gly Cys
1               5

<210> SEQ ID NO 200
<211> LENGTH: 7
<212> TYPE: PRT
<213> ORGANISM: Homo sapiens
<220> FEATURE:
<221> NAME/KEY: MISC_FEATURE
<223> OTHER INFORMATION: fr6 - 967.40

<400> SEQUENCE: 200

His Pro Ser Ala Asn Asn Arg
1               5

<210> SEQ ID NO 201

```
<211> LENGTH: 6
<212> TYPE: PRT
<213> ORGANISM: Homo sapiens
<220> FEATURE:
<221> NAME/KEY: MISC_FEATURE
<223> OTHER INFORMATION: fr6 - 973.43

<400> SEQUENCE: 201

Thr Ser Gln Asp Ala Arg
1               5

<210> SEQ ID NO 202
<211> LENGTH: 6
<212> TYPE: PRT
<213> ORGANISM: Homo sapiens
<220> FEATURE:
<221> NAME/KEY: MISC_FEATURE
<223> OTHER INFORMATION: fr6 - 984.37

<400> SEQUENCE: 202

Ser Ser Ala Asn Asn Arg
1               5

<210> SEQ ID NO 203
<211> LENGTH: 7
<212> TYPE: PRT
<213> ORGANISM: Homo sapiens
<220> FEATURE:
<221> NAME/KEY: MISC_FEATURE
<223> OTHER INFORMATION: fr6 - 1008.39

<400> SEQUENCE: 203

Gly Ser Ser Val Gln Thr Arg
1               5

<210> SEQ ID NO 204
<211> LENGTH: 5
<212> TYPE: PRT
<213> ORGANISM: Homo sapiens
<220> FEATURE:
<221> NAME/KEY: MISC_FEATURE
<223> OTHER INFORMATION: fr6 - 1028.40

<400> SEQUENCE: 204

Arg Thr Trp Met Gly
1               5

<210> SEQ ID NO 205
<211> LENGTH: 6
<212> TYPE: PRT
<213> ORGANISM: Homo sapiens
<220> FEATURE:
<221> NAME/KEY: MISC_FEATURE
<223> OTHER INFORMATION: fr6 - 1103.57

<400> SEQUENCE: 205

Pro Pro Pro Pro Pro Gly
1               5

<210> SEQ ID NO 206
<211> LENGTH: 7
<212> TYPE: PRT
<213> ORGANISM: Homo sapiens
<220> FEATURE:
<221> NAME/KEY: MISC_FEATURE
<223> OTHER INFORMATION: fr6 - 1168.48

<400> SEQUENCE: 206
```

```
Ile Thr Ser Gly Gln Met His
1               5

<210> SEQ ID NO 207
<211> LENGTH: 6
<212> TYPE: PRT
<213> ORGANISM: Homo sapiens
<220> FEATURE:
<221> NAME/KEY: MISC_FEATURE
<223> OTHER INFORMATION: fr6 - 1180.46

<400> SEQUENCE: 207

Asp Glu Glu Gln Tyr Ala
1               5

<210> SEQ ID NO 208
<211> LENGTH: 6
<212> TYPE: PRT
<213> ORGANISM: Homo sapiens
<220> FEATURE:
<221> NAME/KEY: MISC_FEATURE
<223> OTHER INFORMATION: fr6 - 1285.42

<400> SEQUENCE: 208

His Asp Glu Asn Gly Asp
1               5

<210> SEQ ID NO 209
<211> LENGTH: 8
<212> TYPE: PRT
<213> ORGANISM: Homo sapiens
<220> FEATURE:
<221> NAME/KEY: MISC_FEATURE
<223> OTHER INFORMATION: fr6 - 1303.49
<220> FEATURE:
<221> NAME/KEY: MISC_FEATURE
<222> LOCATION: (5)..(5)
<223> OTHER INFORMATION: M is a methionine-sulfoxide

<400> SEQUENCE: 209

His Asp Gly Asn Met Asp Ala Asn
1               5

<210> SEQ ID NO 210
<211> LENGTH: 6
<212> TYPE: PRT
<213> ORGANISM: Homo sapiens
<220> FEATURE:
<221> NAME/KEY: MISC_FEATURE
<223> OTHER INFORMATION: fr6 - 1345.54

<400> SEQUENCE: 210

His Asp Glu Asn Thr Ala
1               5

<210> SEQ ID NO 211
<211> LENGTH: 9
<212> TYPE: PRT
<213> ORGANISM: Homo sapiens
<220> FEATURE:
<221> NAME/KEY: MISC_FEATURE
<223> OTHER INFORMATION: fr6 - 1475.69

<400> SEQUENCE: 211

Ser Gln Val Thr Gln Val Ser Pro Gln
1               5

<210> SEQ ID NO 212
```

```
<211> LENGTH: 6
<212> TYPE: PRT
<213> ORGANISM: Homo sapiens
<220> FEATURE:
<221> NAME/KEY: MISC_FEATURE
<223> OTHER INFORMATION: fr6 - 1571.61

<400> SEQUENCE: 212

Gly Thr Gly Ser Glu Thr
1               5

<210> SEQ ID NO 213
<211> LENGTH: 11
<212> TYPE: PRT
<213> ORGANISM: Homo sapiens
<220> FEATURE:
<221> NAME/KEY: MISC_FEATURE
<223> OTHER INFORMATION: fr6 - 1571.63

<400> SEQUENCE: 213

Ser Glu Thr Glu Ser Gly Thr Cys Glu Ser Pro
1               5                   10

<210> SEQ ID NO 214
<211> LENGTH: 11
<212> TYPE: PRT
<213> ORGANISM: Homo sapiens
<220> FEATURE:
<221> NAME/KEY: MISC_FEATURE
<223> OTHER INFORMATION: fr6 - 1589.57

<400> SEQUENCE: 214

Ser Tyr Gly Thr Gly Ser Glu Thr Glu Ser Pro
1               5                   10

<210> SEQ ID NO 215
<211> LENGTH: 7
<212> TYPE: PRT
<213> ORGANISM: Homo sapiens
<220> FEATURE:
<221> NAME/KEY: MISC_FEATURE
<223> OTHER INFORMATION: fr6 - 1653.61

<400> SEQUENCE: 215

Ser Glu Thr Glu Ser Pro Arg
1               5

<210> SEQ ID NO 216
<211> LENGTH: 6
<212> TYPE: PRT
<213> ORGANISM: Homo sapiens
<220> FEATURE:
<221> NAME/KEY: MISC_FEATURE
<223> OTHER INFORMATION: fr7 - 761.34

<400> SEQUENCE: 216

Ser Asn Ser Pro Ser Asn
1               5

<210> SEQ ID NO 217
<211> LENGTH: 5
<212> TYPE: PRT
<213> ORGANISM: Homo sapiens
<220> FEATURE:
<221> NAME/KEY: MISC_FEATURE
<223> OTHER INFORMATION: fr7 - 848.39
<220> FEATURE:
<221> NAME/KEY: MISC_FEATURE
<222> LOCATION: (1)..(1)
```

```
<223> OTHER INFORMATION: M is a methionine-sulfoxide

<400> SEQUENCE: 217

Met Ala Gly Asp Asp
1               5

<210> SEQ ID NO 218
<211> LENGTH: 5
<212> TYPE: PRT
<213> ORGANISM: Homo sapiens
<220> FEATURE:
<221> NAME/KEY: MISC_FEATURE
<223> OTHER INFORMATION: fr7 - 855.36

<400> SEQUENCE: 218

Ile Ala Ile Asp Gly
1               5

<210> SEQ ID NO 219
<211> LENGTH: 7
<212> TYPE: PRT
<213> ORGANISM: Homo sapiens
<220> FEATURE:
<221> NAME/KEY: MISC_FEATURE
<223> OTHER INFORMATION: fr7 - 863.36

<400> SEQUENCE: 219

Glu Gly Ser Ser Val Gln Thr
1               5

<210> SEQ ID NO 220
<211> LENGTH: 6
<212> TYPE: PRT
<213> ORGANISM: Homo sapiens
<220> FEATURE:
<221> NAME/KEY: MISC_FEATURE
<223> OTHER INFORMATION: fr7 - 874.37

<400> SEQUENCE: 220

Gly Pro Gly Ile Glu Arg
1               5

<210> SEQ ID NO 221
<211> LENGTH: 4
<212> TYPE: PRT
<213> ORGANISM: Homo sapiens
<220> FEATURE:
<221> NAME/KEY: MISC_FEATURE
<223> OTHER INFORMATION: fr7 - 911.30

<400> SEQUENCE: 221

Asx Pro Tyr Cys
1

<210> SEQ ID NO 222
<211> LENGTH: 5
<212> TYPE: PRT
<213> ORGANISM: Homo sapiens
<220> FEATURE:
<221> NAME/KEY: MISC_FEATURE
<223> OTHER INFORMATION: fr7 - 955.42

<400> SEQUENCE: 222

Val Thr Ile Asn Ala
1               5

<210> SEQ ID NO 223
```

```
<211> LENGTH: 6
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: M is a methionine-sulfoxide
<220> FEATURE:
<221> NAME/KEY: MISC_FEATURE
<223> OTHER INFORMATION: fr7 - 1011.32

<400> SEQUENCE: 223

Pro Ser Ser Pro Ala Met
1               5

<210> SEQ ID NO 224
<211> LENGTH: 8
<212> TYPE: PRT
<213> ORGANISM: Homo sapiens
<220> FEATURE:
<221> NAME/KEY: MISC_FEATURE
<223> OTHER INFORMATION: fr7 - 1018.33

<400> SEQUENCE: 224

Gly Ser Ser Ser Ile Glu Ala Val
1               5

<210> SEQ ID NO 225
<211> LENGTH: 4
<212> TYPE: PRT
<213> ORGANISM: Homo sapiens
<220> FEATURE:
<221> NAME/KEY: MISC_FEATURE
<223> OTHER INFORMATION: fr7 - 1048.45

<400> SEQUENCE: 225

Glu Val Gln Ala
1

<210> SEQ ID NO 226
<211> LENGTH: 5
<212> TYPE: PRT
<213> ORGANISM: Homo sapiens
<220> FEATURE:
<221> NAME/KEY: MISC_FEATURE
<223> OTHER INFORMATION: fr7 - 1076.46

<400> SEQUENCE: 226

Tyr Val Asp Met Ser
1               5

<210> SEQ ID NO 227
<211> LENGTH: 7
<212> TYPE: PRT
<213> ORGANISM: Homo sapiens
<220> FEATURE:
<221> NAME/KEY: MISC_FEATURE
<223> OTHER INFORMATION: fr7 - 1092.46

<400> SEQUENCE: 227

Glu Val Asp Phe Ser Asp Arg
1               5

<210> SEQ ID NO 228
<211> LENGTH: 7
<212> TYPE: PRT
<213> ORGANISM: Homo sapiens
<220> FEATURE:
<221> NAME/KEY: MISC_FEATURE
```

<223> OTHER INFORMATION: fr7 - 1098.46

<400> SEQUENCE: 228

Val Glu Pro Gln Ile Glu Ala
1               5

<210> SEQ ID NO 229
<211> LENGTH: 6
<212> TYPE: PRT
<213> ORGANISM: Homo sapiens
<220> FEATURE:
<221> NAME/KEY: MISC_FEATURE
<223> OTHER INFORMATION: fr7 - 1099.39

<400> SEQUENCE: 229

Pro Asp Ser Ser Thr His
1               5

<210> SEQ ID NO 230
<211> LENGTH: 6
<212> TYPE: PRT
<213> ORGANISM: Homo sapiens
<220> FEATURE:
<221> NAME/KEY: MISC_FEATURE
<223> OTHER INFORMATION: fr7 - 1099.48

<400> SEQUENCE: 230

Glu Pro Gln Ile Glu Ala
1               5

<210> SEQ ID NO 231
<211> LENGTH: 6
<212> TYPE: PRT
<213> ORGANISM: Homo sapiens
<220> FEATURE:
<221> NAME/KEY: MISC_FEATURE
<223> OTHER INFORMATION: fr7 - 1113.38

<400> SEQUENCE: 231

Glu Thr Thr Thr Ala Glu
1               5

<210> SEQ ID NO 232
<211> LENGTH: 6
<212> TYPE: PRT
<213> ORGANISM: Homo sapiens
<220> FEATURE:
<221> NAME/KEY: MISC_FEATURE
<223> OTHER INFORMATION: fr7 - 1121.48

<400> SEQUENCE: 232

Trp Glu Ala Gly Ala Tyr
1               5

<210> SEQ ID NO 233
<211> LENGTH: 8
<212> TYPE: PRT
<213> ORGANISM: Homo sapiens
<220> FEATURE:
<221> NAME/KEY: MISC_FEATURE
<223> OTHER INFORMATION: fr7 - 1145.57

<400> SEQUENCE: 233

Gly Gly Gly Gly Ile Gly Ser Gly
1               5

<210> SEQ ID NO 234

```
<211> LENGTH: 8
<212> TYPE: PRT
<213> ORGANISM: Homo sapiens
<220> FEATURE:
<221> NAME/KEY: MISC_FEATURE
<223> OTHER INFORMATION: fr7 - 1147.54

<400> SEQUENCE: 234

Arg Ser Asn Gln Ile Ser Val Arg
1               5

<210> SEQ ID NO 235
<211> LENGTH: 6
<212> TYPE: PRT
<213> ORGANISM: Homo sapiens
<220> FEATURE:
<221> NAME/KEY: MISC_FEATURE
<223> OTHER INFORMATION: fr7 - 1213.51

<400> SEQUENCE: 235

Ala Gly Ala Gly Ile Gln
1               5

<210> SEQ ID NO 236
<211> LENGTH: 6
<212> TYPE: PRT
<213> ORGANISM: Homo sapiens
<220> FEATURE:
<221> NAME/KEY: MISC_FEATURE
<223> OTHER INFORMATION: fr7 - 1213.52

<400> SEQUENCE: 236

Glx Ala Glu Ile Gln Glu
1               5

<210> SEQ ID NO 237
<211> LENGTH: 8
<212> TYPE: PRT
<213> ORGANISM: Homo sapiens
<220> FEATURE:
<221> NAME/KEY: MISC_FEATURE
<223> OTHER INFORMATION: fr7 - 1215.43

<400> SEQUENCE: 237

Glx Ala Gln Thr Ala Ser Glu Asn
1               5

<210> SEQ ID NO 238
<211> LENGTH: 8
<212> TYPE: PRT
<213> ORGANISM: Homo sapiens
<220> FEATURE:
<221> NAME/KEY: MISC_FEATURE
<223> OTHER INFORMATION: fr7 - 1231.42

<400> SEQUENCE: 238

Glx Ala Gln Gly Gly Gln Glu Met
1               5

<210> SEQ ID NO 239
<211> LENGTH: 5
<212> TYPE: PRT
<213> ORGANISM: Homo sapiens
<220> FEATURE:
<221> NAME/KEY: MISC_FEATURE
<223> OTHER INFORMATION: fr7 - 1231.43

<400> SEQUENCE: 239
```

```
Gln Thr Arg Ile Glu
1               5

<210> SEQ ID NO 240
<211> LENGTH: 8
<212> TYPE: PRT
<213> ORGANISM: Homo sapiens
<220> FEATURE:
<221> NAME/KEY: MISC_FEATURE
<223> OTHER INFORMATION: fr7 - 1257.46

<400> SEQUENCE: 240

Glu Ala Gln Ser Ile Gly Ala Ser
1               5

<210> SEQ ID NO 241
<211> LENGTH: 5
<212> TYPE: PRT
<213> ORGANISM: Homo sapiens
<220> FEATURE:
<221> NAME/KEY: MISC_FEATURE
<223> OTHER INFORMATION: fr7 - 1282.67

<400> SEQUENCE: 241

Pro Ala Thr Pro Thr
1               5

<210> SEQ ID NO 242
<211> LENGTH: 5
<212> TYPE: PRT
<213> ORGANISM: Homo sapiens
<220> FEATURE:
<221> NAME/KEY: MISC_FEATURE
<223> OTHER INFORMATION: fr7 - 1295.40

<400> SEQUENCE: 242

Ala Gln Gly Ile Gln
1               5

<210> SEQ ID NO 243
<211> LENGTH: 6
<212> TYPE: PRT
<213> ORGANISM: Homo sapiens
<220> FEATURE:
<221> NAME/KEY: MISC_FEATURE
<223> OTHER INFORMATION: fr7 - 1375.52

<400> SEQUENCE: 243

Ser Phe Thr Thr Thr Ala
1               5

<210> SEQ ID NO 244
<211> LENGTH: 10
<212> TYPE: PRT
<213> ORGANISM: Homo sapiens
<220> FEATURE:
<221> NAME/KEY: MISC_FEATURE
<223> OTHER INFORMATION: fr7 - 1432.51

<400> SEQUENCE: 244

Ser Thr Gly Thr Trp Ser Ser Ala Thr Ala
1               5                   10

<210> SEQ ID NO 245
<211> LENGTH: 9
<212> TYPE: PRT
<213> ORGANISM: Homo sapiens
<220> FEATURE:
```

<221> NAME/KEY: MISC_FEATURE
<223> OTHER INFORMATION: fr7 - 1483.50

<400> SEQUENCE: 245

Thr Ser Val Glu Ser Asn Ser Asp Gly
1               5

<210> SEQ ID NO 246
<211> LENGTH: 7
<212> TYPE: PRT
<213> ORGANISM: Homo sapiens
<220> FEATURE:
<221> NAME/KEY: MISC_FEATURE
<223> OTHER INFORMATION: fr7 - 1483.51
<220> FEATURE:
<221> NAME/KEY: MISC_FEATURE
<222> LOCATION: (6)..(7)
<223> OTHER INFORMATION: XX is TT or SN

<400> SEQUENCE: 246

Val Thr Ser Val Glu Xaa Xaa
1               5

<210> SEQ ID NO 247
<211> LENGTH: 10
<212> TYPE: PRT
<213> ORGANISM: Homo sapiens
<220> FEATURE:
<221> NAME/KEY: MISC_FEATURE
<223> OTHER INFORMATION: fr7 - 1483.52

<400> SEQUENCE: 247

Val Thr Ser Val Glu Ser Asn Ser Asp Gly
1               5                   10

<210> SEQ ID NO 248
<211> LENGTH: 7
<212> TYPE: PRT
<213> ORGANISM: Homo sapiens
<220> FEATURE:
<221> NAME/KEY: MISC_FEATURE
<223> OTHER INFORMATION: fr7 - 1640.61

<400> SEQUENCE: 248

Glu Gln Ala Asp Glu Ala Pro
1               5

<210> SEQ ID NO 249
<211> LENGTH: 9
<212> TYPE: PRT
<213> ORGANISM: Homo sapiens
<220> FEATURE:
<221> NAME/KEY: MISC_FEATURE
<223> OTHER INFORMATION: fr7 - 1809.52

<400> SEQUENCE: 249

Asp Glu Ser Gly Pro Ser Ile Val His
1               5

<210> SEQ ID NO 250
<211> LENGTH: 8
<212> TYPE: PRT
<213> ORGANISM: Homo sapiens
<220> FEATURE:
<221> NAME/KEY: MISC_FEATURE
<223> OTHER INFORMATION: fr8 - 856.52

<400> SEQUENCE: 250

-continued

```
Ile Ala Thr Val Ile Ser Pro Arg
1               5

<210> SEQ ID NO 251
<211> LENGTH: 6
<212> TYPE: PRT
<213> ORGANISM: Homo sapiens
<220> FEATURE:
<221> NAME/KEY: MISC_FEATURE
<223> OTHER INFORMATION: fr8 - 923.38

<400> SEQUENCE: 251

Met Phe Asp Glu Ala Ile
1               5

<210> SEQ ID NO 252
<211> LENGTH: 6
<212> TYPE: PRT
<213> ORGANISM: Homo sapiens
<220> FEATURE:
<221> NAME/KEY: MISC_FEATURE
<223> OTHER INFORMATION: fr8 - 974.46

<400> SEQUENCE: 252

Pro Ala Ala Asn Phe Asp
1               5

<210> SEQ ID NO 253
<211> LENGTH: 6
<212> TYPE: PRT
<213> ORGANISM: Homo sapiens
<220> FEATURE:
<221> NAME/KEY: MISC_FEATURE
<223> OTHER INFORMATION: fr8 - 1002.42

<400> SEQUENCE: 253

Pro Glu Asp Phe Ile Arg
1               5

<210> SEQ ID NO 254
<211> LENGTH: 7
<212> TYPE: PRT
<213> ORGANISM: Homo sapiens
<220> FEATURE:
<221> NAME/KEY: MISC_FEATURE
<223> OTHER INFORMATION: fr8 - 1004.41

<400> SEQUENCE: 254

Pro Ala Ala Phe Ser Ser Pro
1               5

<210> SEQ ID NO 255
<211> LENGTH: 7
<212> TYPE: PRT
<213> ORGANISM: Homo sapiens
<220> FEATURE:
<221> NAME/KEY: MISC_FEATURE
<223> OTHER INFORMATION: fr8 - 1004.44

<400> SEQUENCE: 255

Thr Pro Ala Ala Phe Ser Ala
1               5

<210> SEQ ID NO 256
<211> LENGTH: 6
<212> TYPE: PRT
<213> ORGANISM: Homo sapiens
<220> FEATURE:
```

```
<221> NAME/KEY: MISC_FEATURE
<223> OTHER INFORMATION: fr8 - 1011.33

<400> SEQUENCE: 256

Met Asn Asn Ser His Gly
1               5

<210> SEQ ID NO 257
<211> LENGTH: 7
<212> TYPE: PRT
<213> ORGANISM: Homo sapiens
<220> FEATURE:
<221> NAME/KEY: MISC_FEATURE
<223> OTHER INFORMATION: fr8 - 1021.45

<400> SEQUENCE: 257

Thr Pro Glu Asp Phe Ile Arg
1               5

<210> SEQ ID NO 258
<211> LENGTH: 5
<212> TYPE: PRT
<213> ORGANISM: Homo sapiens
<220> FEATURE:
<221> NAME/KEY: MISC_FEATURE
<223> OTHER INFORMATION: fr8 - 1027.52

<400> SEQUENCE: 258

Thr Met Leu Ala Asp
1               5

<210> SEQ ID NO 259
<211> LENGTH: 8
<212> TYPE: PRT
<213> ORGANISM: Homo sapiens
<220> FEATURE:
<221> NAME/KEY: MISC_FEATURE
<223> OTHER INFORMATION: fr8 - 1035.44

<400> SEQUENCE: 259

Phe Ser Glu Val Glu Arg Ala Arg
1               5

<210> SEQ ID NO 260
<211> LENGTH: 9
<212> TYPE: PRT
<213> ORGANISM: Homo sapiens
<220> FEATURE:
<221> NAME/KEY: MISC_FEATURE
<223> OTHER INFORMATION: fr 8 - 1035.44

<400> SEQUENCE: 260

Gly Ser Ser Val Gly Val Glu Ala Arg
1               5

<210> SEQ ID NO 261
<211> LENGTH: 6
<212> TYPE: PRT
<213> ORGANISM: Homo sapiens
<220> FEATURE:
<221> NAME/KEY: MISC_FEATURE
<223> OTHER INFORMATION: fr8 - 1039.45

<400> SEQUENCE: 261

Asp Pro Glu Asn Phe Arg
1               5
```

```
<210> SEQ ID NO 262
<211> LENGTH: 5
<212> TYPE: PRT
<213> ORGANISM: Homo sapiens
<220> FEATURE:
<221> NAME/KEY: MISC_FEATURE
<223> OTHER INFORMATION: fr8 - 1048.31

<400> SEQUENCE: 262

Phe Ala Ser His Ile
1               5

<210> SEQ ID NO 263
<211> LENGTH: 5
<212> TYPE: PRT
<213> ORGANISM: Homo sapiens
<220> FEATURE:
<221> NAME/KEY: MISC_FEATURE
<223> OTHER INFORMATION: fr8 - 1077.39

<400> SEQUENCE: 263

Ile Gly Ala His Cys
1               5

<210> SEQ ID NO 264
<211> LENGTH: 7
<212> TYPE: PRT
<213> ORGANISM: Homo sapiens
<220> FEATURE:
<221> NAME/KEY: MISC_FEATURE
<223> OTHER INFORMATION: fr8 - 1077.44

<400> SEQUENCE: 264

Trp Pro Ala Ala Val Trp Arg
1               5

<210> SEQ ID NO 265
<211> LENGTH: 6
<212> TYPE: PRT
<213> ORGANISM: Homo sapiens
<220> FEATURE:
<221> NAME/KEY: MISC_FEATURE
<223> OTHER INFORMATION: fr8 - 1095.45

<400> SEQUENCE: 265

Ile Gly Ala Gly Val Gly
1               5

<210> SEQ ID NO 266
<211> LENGTH: 5
<212> TYPE: PRT
<213> ORGANISM: Homo sapiens
<220> FEATURE:
<221> NAME/KEY: MISC_FEATURE
<223> OTHER INFORMATION: fr8 - 1095.50

<400> SEQUENCE: 266

Ile Gly His Ala Gly
1               5

<210> SEQ ID NO 267
<211> LENGTH: 6
<212> TYPE: PRT
<213> ORGANISM: Homo sapiens
<220> FEATURE:
<221> NAME/KEY: MISC_FEATURE
<223> OTHER INFORMATION: fr8 - 1096.44

<400> SEQUENCE: 267
```

Gly Leu Asp Phe Asn Arg
1               5

<210> SEQ ID NO 268
<211> LENGTH: 7
<212> TYPE: PRT
<213> ORGANISM: Homo sapiens
<220> FEATURE:
<221> NAME/KEY: MISC_FEATURE
<223> OTHER INFORMATION: fr8 - 1113.49

<400> SEQUENCE: 268

Glu Thr Thr Thr Ala Glu Arg
1               5

<210> SEQ ID NO 269
<211> LENGTH: 7
<212> TYPE: PRT
<213> ORGANISM: Homo sapiens
<220> FEATURE:
<221> NAME/KEY: MISC_FEATURE
<223> OTHER INFORMATION: fr8 - 1131.33

<400> SEQUENCE: 269

Phe Thr Thr Thr Ala Glu Arg
1               5

<210> SEQ ID NO 270
<211> LENGTH: 7
<212> TYPE: PRT
<213> ORGANISM: Homo sapiens
<220> FEATURE:
<221> NAME/KEY: MISC_FEATURE
<223> OTHER INFORMATION: fr8 - 1137.41

<400> SEQUENCE: 270

Ser Gly Val Ser Glu Ile Arg
1               5

<210> SEQ ID NO 271
<211> LENGTH: 5
<212> TYPE: PRT
<213> ORGANISM: Homo sapiens
<220> FEATURE:
<221> NAME/KEY: MISC_FEATURE
<223> OTHER INFORMATION: fr8 - 1149.35

<400> SEQUENCE: 271

Glu Ile Gly Thr Thr
1               5

<210> SEQ ID NO 272
<211> LENGTH: 5
<212> TYPE: PRT
<213> ORGANISM: Homo sapiens
<220> FEATURE:
<221> NAME/KEY: MISC_FEATURE
<223> OTHER INFORMATION: fr8 - 1151.46

<400> SEQUENCE: 272

Pro Ala Ala Pro Asp
1               5

<210> SEQ ID NO 273
<211> LENGTH: 5
<212> TYPE: PRT
<213> ORGANISM: Homo sapiens

```
<220> FEATURE:
<221> NAME/KEY: MISC_FEATURE
<223> OTHER INFORMATION: fr8 - 1177.41

<400> SEQUENCE: 273

Ala Phe Thr Glu Glu
1               5

<210> SEQ ID NO 274
<211> LENGTH: 6
<212> TYPE: PRT
<213> ORGANISM: Homo sapiens
<220> FEATURE:
<221> NAME/KEY: MISC_FEATURE
<223> OTHER INFORMATION: fr8 - 1181.51

<400> SEQUENCE: 274

Gln Gly His Asn Glu Ser
1               5

<210> SEQ ID NO 275
<211> LENGTH: 8
<212> TYPE: PRT
<213> ORGANISM: Homo sapiens
<220> FEATURE:
<221> NAME/KEY: MISC_FEATURE
<223> OTHER INFORMATION: fr8 - 1199.54

<400> SEQUENCE: 275

Gln Gly His Ile Glu Ser Ser Arg
1               5

<210> SEQ ID NO 276
<211> LENGTH: 7
<212> TYPE: PRT
<213> ORGANISM: Homo sapiens
<220> FEATURE:
<221> NAME/KEY: MISC_FEATURE
<223> OTHER INFORMATION: fr8 - 1200.53

<400> SEQUENCE: 276

Pro Gly Ile Ser Trp Val Val
1               5

<210> SEQ ID NO 277
<211> LENGTH: 7
<212> TYPE: PRT
<213> ORGANISM: Homo sapiens
<220> FEATURE:
<221> NAME/KEY: MISC_FEATURE
<223> OTHER INFORMATION: fr8 - 1211.51

<400> SEQUENCE: 277

Thr Asp Pro Glu Asp Val Ile
1               5

<210> SEQ ID NO 278
<211> LENGTH: 5
<212> TYPE: PRT
<213> ORGANISM: Homo sapiens
<220> FEATURE:
<221> NAME/KEY: MISC_FEATURE
<223> OTHER INFORMATION: fr8 - 1216.36

<400> SEQUENCE: 278

Gly Asn Ser Val Gly
1               5
```

<210> SEQ ID NO 279
<211> LENGTH: 5
<212> TYPE: PRT
<213> ORGANISM: Homo sapiens
<220> FEATURE:
<221> NAME/KEY: MISC_FEATURE
<223> OTHER INFORMATION: fr8 - 1216.37
<220> FEATURE:
<221> NAME/KEY: MISC_FEATURE
<222> LOCATION: (4)..(4)
<223> OTHER INFORMATION: X is a Val or Tyr

<400> SEQUENCE: 279

Gly Ile Ser Xaa Gly
1               5

<210> SEQ ID NO 280
<211> LENGTH: 7
<212> TYPE: PRT
<213> ORGANISM: Homo sapiens
<220> FEATURE:
<221> NAME/KEY: MISC_FEATURE
<223> OTHER INFORMATION: fr8 - 1252.50

<400> SEQUENCE: 280

Pro Ala Ala Pro Pro Val Ala
1               5

<210> SEQ ID NO 281
<211> LENGTH: 6
<212> TYPE: PRT
<213> ORGANISM: Homo sapiens
<220> FEATURE:
<221> NAME/KEY: MISC_FEATURE
<223> OTHER INFORMATION: fr8 - 1257.59
<220> FEATURE:
<221> NAME/KEY: MISC_FEATURE
<222> LOCATION: (3)..(3)
<223> OTHER INFORMATION: X is an Ile or Asn

<400> SEQUENCE: 281

Thr Thr Xaa Glu Ala Val
1               5

<210> SEQ ID NO 282
<211> LENGTH: 5
<212> TYPE: PRT
<213> ORGANISM: Homo sapiens
<220> FEATURE:
<221> NAME/KEY: MISC_FEATURE
<223> OTHER INFORMATION: fr8 - 1258.40

<400> SEQUENCE: 282

Ala Val Asn Glu Ile
1               5

<210> SEQ ID NO 283
<211> LENGTH: 4
<212> TYPE: PRT
<213> ORGANISM: Homo sapiens
<220> FEATURE:
<221> NAME/KEY: MISC_FEATURE
<223> OTHER INFORMATION: fr8 - 1275.50

<400> SEQUENCE: 283

Asp Gly Trp Ile
1

```
<210> SEQ ID NO 284
<211> LENGTH: 5
<212> TYPE: PRT
<213> ORGANISM: Homo sapiens
<220> FEATURE:
<221> NAME/KEY: MISC_FEATURE
<223> OTHER INFORMATION: fr8 - 1284.49

<400> SEQUENCE: 284

Asp Ile Phe Ile Ile
1               5

<210> SEQ ID NO 285
<211> LENGTH: 4
<212> TYPE: PRT
<213> ORGANISM: Homo sapiens
<220> FEATURE:
<221> NAME/KEY: MISC_FEATURE
<223> OTHER INFORMATION: fr8 - 1299.59

<400> SEQUENCE: 285

Ile Ala Thr Ala
1

<210> SEQ ID NO 286
<211> LENGTH: 8
<212> TYPE: PRT
<213> ORGANISM: Homo sapiens
<220> FEATURE:
<221> NAME/KEY: MISC_FEATURE
<223> OTHER INFORMATION: fr8 - 1319.53

<400> SEQUENCE: 286

Asn Ile Thr Asn Thr Val Ala Arg
1               5

<210> SEQ ID NO 287
<211> LENGTH: 8
<212> TYPE: PRT
<213> ORGANISM: Homo sapiens
<220> FEATURE:
<221> NAME/KEY: MISC_FEATURE
<223> OTHER INFORMATION: fr8 - 1333.51

<400> SEQUENCE: 287

Gly Gln Thr Gly Phe Phe Pro Arg
1               5

<210> SEQ ID NO 288
<211> LENGTH: 4
<212> TYPE: PRT
<213> ORGANISM: Homo sapiens
<220> FEATURE:
<221> NAME/KEY: MISC_FEATURE
<223> OTHER INFORMATION: fr8 - 1337.58

<400> SEQUENCE: 288

Gln Met Asn Glu
1

<210> SEQ ID NO 289
<211> LENGTH: 6
<212> TYPE: PRT
<213> ORGANISM: Homo sapiens
<220> FEATURE:
<221> NAME/KEY: MISC_FEATURE
<223> OTHER INFORMATION: fr8 - 1353.51

<400> SEQUENCE: 289
```

Glu Met Asn Glu Phe Arg
1               5

<210> SEQ ID NO 290
<211> LENGTH: 10
<212> TYPE: PRT
<213> ORGANISM: Homo sapiens
<220> FEATURE:
<221> NAME/KEY: MISC_FEATURE
<223> OTHER INFORMATION: fr8 - 1353.53

<400> SEQUENCE: 290

Ile Gln Asp Thr Gly Ala Ser Asp Thr Arg
1               5                   10

<210> SEQ ID NO 291
<211> LENGTH: 8
<212> TYPE: PRT
<213> ORGANISM: Homo sapiens
<220> FEATURE:
<221> NAME/KEY: MISC_FEATURE
<223> OTHER INFORMATION: fr8 - 1360.53

<400> SEQUENCE: 291

Asp Thr Asp Ile Glu Ser Thr Arg
1               5

<210> SEQ ID NO 292
<211> LENGTH: 8
<212> TYPE: PRT
<213> ORGANISM: Homo sapiens
<220> FEATURE:
<221> NAME/KEY: MISC_FEATURE
<223> OTHER INFORMATION: fr8 - 1370.98

<400> SEQUENCE: 292

Asn Asp Pro Asn Trp Val Val Arg
1               5

<210> SEQ ID NO 293
<211> LENGTH: 7
<212> TYPE: PRT
<213> ORGANISM: Homo sapiens
<220> FEATURE:
<221> NAME/KEY: MISC_FEATURE
<223> OTHER INFORMATION: fr8 - 1376.56

<400> SEQUENCE: 293

Pro Ser Ile Ala Ala His Gly
1               5

<210> SEQ ID NO 294
<211> LENGTH: 6
<212> TYPE: PRT
<213> ORGANISM: Homo sapiens
<220> FEATURE:
<221> NAME/KEY: MISC_FEATURE
<223> OTHER INFORMATION: fr9 - 591.21
<220> FEATURE:
<221> NAME/KEY: MISC_FEATURE
<222> LOCATION: (2)..(2)
<223> OTHER INFORMATION: M is a methionine-sulfoxide

<400> SEQUENCE: 294

Glu Met Ala Ser His Ile
1               5

<210> SEQ ID NO 295
<211> LENGTH: 5
<212> TYPE: PRT
<213> ORGANISM: Homo sapiens
<220> FEATURE:
<221> NAME/KEY: MISC_FEATURE
<223> OTHER INFORMATION: fr9 - 1075.50

<400> SEQUENCE: 295

Glu Gln Val Glu Ile
1               5

<210> SEQ ID NO 296
<211> LENGTH: 6
<212> TYPE: PRT
<213> ORGANISM: Homo sapiens
<220> FEATURE:
<221> NAME/KEY: MISC_FEATURE
<223> OTHER INFORMATION: fr9 - 1149.44

<400> SEQUENCE: 296

Glu Met Ala Ser His Ile
1               5

<210> SEQ ID NO 297
<211> LENGTH: 7
<212> TYPE: PRT
<213> ORGANISM: Homo sapiens
<220> FEATURE:
<221> NAME/KEY: MISC_FEATURE
<223> OTHER INFORMATION: fr9 - 1187.56

<400> SEQUENCE: 297

Ile Ile Ser Thr Val Ser Ile
1               5

<210> SEQ ID NO 298
<211> LENGTH: 7
<212> TYPE: PRT
<213> ORGANISM: Homo sapiens
<220> FEATURE:
<221> NAME/KEY: MISC_FEATURE
<223> OTHER INFORMATION: fr9 - 1208.57
<220> FEATURE:
<221> NAME/KEY: MISC_FEATURE
<222> LOCATION: (5)..(5)
<223> OTHER INFORMATION: M is a methionine-sulfoxide

<400> SEQUENCE: 298

Gly Pro Ala Ala Met Ser Ala
1               5

<210> SEQ ID NO 299
<211> LENGTH: 5
<212> TYPE: PRT
<213> ORGANISM: Homo sapiens
<220> FEATURE:
<221> NAME/KEY: MISC_FEATURE
<223> OTHER INFORMATION: fr9 - 1290.65

<400> SEQUENCE: 299

Gly Ile Thr Ala Ile
1               5

<210> SEQ ID NO 300
<211> LENGTH: 7
<212> TYPE: PRT
<213> ORGANISM: Homo sapiens
<220> FEATURE:

```
<221> NAME/KEY: MISC_FEATURE
<223> OTHER INFORMATION: fr9 - 1298.72

<400> SEQUENCE: 300

Tyr Pro Ser Ile Val Pro
1               5

<210> SEQ ID NO 301
<211> LENGTH: 5
<212> TYPE: PRT
<213> ORGANISM: Homo sapiens
<220> FEATURE:
<221> NAME/KEY: MISC_FEATURE
<223> OTHER INFORMATION: fr9 - 1396.54

<400> SEQUENCE: 301

Gly Glu Glu Thr His
1               5

<210> SEQ ID NO 302
<211> LENGTH: 5
<212> TYPE: PRT
<213> ORGANISM: Homo sapiens
<220> FEATURE:
<221> NAME/KEY: MISC_FEATURE
<223> OTHER INFORMATION: fr9 - 1432.55

<400> SEQUENCE: 302

Gly Ala Gln Ile Val
1               5

<210> SEQ ID NO 303
<211> LENGTH: 10
<212> TYPE: PRT
<213> ORGANISM: Homo sapiens
<220> FEATURE:
<221> NAME/KEY: MISC_FEATURE
<223> OTHER INFORMATION: fr9 - 1478.71

<400> SEQUENCE: 303

Glu Ser Ala Gly Gly Ile Ile Gln Thr Ala
1               5                   10

<210> SEQ ID NO 304
<211> LENGTH: 8
<212> TYPE: PRT
<213> ORGANISM: Homo sapiens
<220> FEATURE:
<221> NAME/KEY: MISC_FEATURE
<223> OTHER INFORMATION: fr9 - 1537.59
<220> FEATURE:
<221> NAME/KEY: MISC_FEATURE
<222> LOCATION: (7)..(7)
<223> OTHER INFORMATION: M is a methionine-sulfoxide

<400> SEQUENCE: 304

Asp Glu Val Asn Gln Asp Met Thr
1               5

<210> SEQ ID NO 305
<211> LENGTH: 5
<212> TYPE: PRT
<213> ORGANISM: Homo sapiens
<220> FEATURE:
<221> NAME/KEY: MISC_FEATURE
<223> OTHER INFORMATION: fr9 - 1596.67

<400> SEQUENCE: 305
```

```
Ile Tyr Thr Ile Ile
1               5

<210> SEQ ID NO 306
<211> LENGTH: 6
<212> TYPE: PRT
<213> ORGANISM: Homo sapiens
<220> FEATURE:
<221> NAME/KEY: MISC_FEATURE
<223> OTHER INFORMATION: fr9 - 1615.67

<400> SEQUENCE: 306

Gln Arg Ile Gln Asn Val
1               5

<210> SEQ ID NO 307
<211> LENGTH: 5
<212> TYPE: PRT
<213> ORGANISM: Homo sapiens
<220> FEATURE:
<221> NAME/KEY: MISC_FEATURE
<223> OTHER INFORMATION: fr11 - 740.72

<400> SEQUENCE: 307

Glu Gln Phe Ile Arg
1               5

<210> SEQ ID NO 308
<211> LENGTH: 6
<212> TYPE: PRT
<213> ORGANISM: Homo sapiens
<220> FEATURE:
<221> NAME/KEY: MISC_FEATURE
<223> OTHER INFORMATION: fr11 - 767.50

<400> SEQUENCE: 308

Leu Leu Asn Glu Leu Arg
1               5

<210> SEQ ID NO 309
<211> LENGTH: 8
<212> TYPE: PRT
<213> ORGANISM: Homo sapiens
<220> FEATURE:
<221> NAME/KEY: MISC_FEATURE
<223> OTHER INFORMATION: fr11 - 900.54

<400> SEQUENCE: 309

Val Asp Ile Ile Asn Ala Gln Lys
1               5

<210> SEQ ID NO 310
<211> LENGTH: 7
<212> TYPE: PRT
<213> ORGANISM: Homo sapiens
<220> FEATURE:
<221> NAME/KEY: MISC_FEATURE
<223> OTHER INFORMATION: fr11 - 954.46

<400> SEQUENCE: 310

Met Ala Ser Met Asp Asp Arg
1               5

<210> SEQ ID NO 311
<211> LENGTH: 9
<212> TYPE: PRT
<213> ORGANISM: Homo sapiens
<220> FEATURE:
```

```
<221> NAME/KEY: MISC_FEATURE
<223> OTHER INFORMATION: fr11 - 954.46
<220> FEATURE:
<221> NAME/KEY: MISC_FEATURE
<222> LOCATION: (6)..(8)
<223> OTHER INFORMATION: X is an unassigned amino acid

<400> SEQUENCE: 311

Met Ala Ser Glu Glu Xaa Xaa Xaa Arg
1               5

<210> SEQ ID NO 312
<211> LENGTH: 8
<212> TYPE: PRT
<213> ORGANISM: Homo sapiens
<220> FEATURE:
<221> NAME/KEY: MISC_FEATURE
<223> OTHER INFORMATION: fr11 - 971.52

<400> SEQUENCE: 312

Gln Ser Ala Ser Ser Phe Phe Arg
1               5

<210> SEQ ID NO 313
<211> LENGTH: 4
<212> TYPE: PRT
<213> ORGANISM: Homo sapiens
<220> FEATURE:
<221> NAME/KEY: MISC_FEATURE
<223> OTHER INFORMATION: fr11 - 1027.48

<400> SEQUENCE: 313

Phe Ser Gln Glu
1

<210> SEQ ID NO 314
<211> LENGTH: 10
<212> TYPE: PRT
<213> ORGANISM: Homo sapiens
<220> FEATURE:
<221> NAME/KEY: MISC_FEATURE
<223> OTHER INFORMATION: fr11 - 1028.63

<400> SEQUENCE: 314

Leu Ala Gly Ala Val Ser Glu Ile Ile Arg
1               5                   10

<210> SEQ ID NO 315
<211> LENGTH: 6
<212> TYPE: PRT
<213> ORGANISM: Homo sapiens
<220> FEATURE:
<221> NAME/KEY: MISC_FEATURE
<223> OTHER INFORMATION: fr11 - 1105.60

<400> SEQUENCE: 315

Val Phe Ile Gly Gln Gly
1               5

<210> SEQ ID NO 316
<211> LENGTH: 7
<212> TYPE: PRT
<213> ORGANISM: Homo sapiens
<220> FEATURE:
<221> NAME/KEY: MISC_FEATURE
<223> OTHER INFORMATION: fr11 - 1110.56

<400> SEQUENCE: 316
```

```
Pro Glu Glu Gln Phe Ile Arg
1               5

<210> SEQ ID NO 317
<211> LENGTH: 4
<212> TYPE: PRT
<213> ORGANISM: Homo sapiens
<220> FEATURE:
<221> NAME/KEY: MISC_FEATURE
<223> OTHER INFORMATION: fr11 - 1126.62

<400> SEQUENCE: 317

Ile Val Asn Ile
1

<210> SEQ ID NO 318
<211> LENGTH: 4
<212> TYPE: PRT
<213> ORGANISM: Homo sapiens
<220> FEATURE:
<221> NAME/KEY: MISC_FEATURE
<223> OTHER INFORMATION: fr11 - 1177.61

<400> SEQUENCE: 318

Ala Ala His Tyr
1

<210> SEQ ID NO 319
<211> LENGTH: 9
<212> TYPE: PRT
<213> ORGANISM: Homo sapiens
<220> FEATURE:
<221> NAME/KEY: MISC_FEATURE
<223> OTHER INFORMATION: fr11 - 1190.48

<400> SEQUENCE: 319

Val Asn Arg Glu Glu Gln Phe Leu Arg
1               5

<210> SEQ ID NO 320
<211> LENGTH: 10
<212> TYPE: PRT
<213> ORGANISM: Homo sapiens
<220> FEATURE:
<221> NAME/KEY: MISC_FEATURE
<223> OTHER INFORMATION: fr11 - 1284.77

<400> SEQUENCE: 320

Asn Val Leu Glu Asp Gly Asp Val Leu Arg
1               5                   10

<210> SEQ ID NO 321
<211> LENGTH: 6
<212> TYPE: PRT
<213> ORGANISM: Homo sapiens
<220> FEATURE:
<221> NAME/KEY: MISC_FEATURE
<223> OTHER INFORMATION: fr11 - 1308.78

<400> SEQUENCE: 321

Ala Val Val Tyr Pro Trp
1               5

<210> SEQ ID NO 322
<211> LENGTH: 5
<212> TYPE: PRT
<213> ORGANISM: Homo sapiens
<220> FEATURE:
```

-continued

```
<221> NAME/KEY: MISC_FEATURE
<223> OTHER INFORMATION: fr11 - 1353.72

<400> SEQUENCE: 322

Val Phe Val Thr Ala
1               5

<210> SEQ ID NO 323
<211> LENGTH: 8
<212> TYPE: PRT
<213> ORGANISM: Homo sapiens
<220> FEATURE:
<221> NAME/KEY: MISC_FEATURE
<223> OTHER INFORMATION: fr11 - 1420.72

<400> SEQUENCE: 323

Gln Trp Ile Ile Pro Glu Ile Arg
1               5

<210> SEQ ID NO 324
<211> LENGTH: 6
<212> TYPE: PRT
<213> ORGANISM: Homo sapiens
<220> FEATURE:
<221> NAME/KEY: MISC_FEATURE
<223> OTHER INFORMATION: fr11 - 1449.80
<220> FEATURE:
<221> NAME/KEY: MISC_FEATURE
<222> LOCATION: (4)..(4)
<223> OTHER INFORMATION: X is an unassigned amino acid

<400> SEQUENCE: 324

Trp His Pro Xaa Pro Pro
1               5

<210> SEQ ID NO 325
<211> LENGTH: 5
<212> TYPE: PRT
<213> ORGANISM: Homo sapiens
<220> FEATURE:
<221> NAME/KEY: MISC_FEATURE
<223> OTHER INFORMATION: fr11 - 1500.80

<400> SEQUENCE: 325

Val Asp Ser Val Val
1               5

<210> SEQ ID NO 326
<211> LENGTH: 10
<212> TYPE: PRT
<213> ORGANISM: Homo sapiens
<220> FEATURE:
<221> NAME/KEY: MISC_FEATURE
<223> OTHER INFORMATION: fr11 - 1519.89

<400> SEQUENCE: 326

Val Phe Leu Gly Gln Ser Glu Gly Leu Arg
1               5                   10

<210> SEQ ID NO 327
<211> LENGTH: 11
<212> TYPE: PRT
<213> ORGANISM: Homo sapiens
<220> FEATURE:
<221> NAME/KEY: MISC_FEATURE
<223> OTHER INFORMATION: fr11 - 1645.96

<400> SEQUENCE: 327
```

```
Thr Gly Thr Asn Ile Val Val Ser His Thr
1               5                   10

<210> SEQ ID NO 328
<211> LENGTH: 11
<212> TYPE: PRT
<213> ORGANISM: Homo sapiens
<220> FEATURE:
<221> NAME/KEY: MISC_FEATURE
<223> OTHER INFORMATION: fr11 - 1965.98

<400> SEQUENCE: 328

Ser Glu Glu Ser Pro Ala Ile Glu Ala Ile His
1               5                   10

<210> SEQ ID NO 329
<211> LENGTH: 7
<212> TYPE: PRT
<213> ORGANISM: Homo sapiens
<220> FEATURE:
<221> NAME/KEY: MISC_FEATURE
<223> OTHER INFORMATION: fr11 - 1998.06

<400> SEQUENCE: 329

Ala Asp Leu Asp Phe Asp Phe
1               5

<210> SEQ ID NO 330
<211> LENGTH: 11
<212> TYPE: PRT
<213> ORGANISM: Homo sapiens
<220> FEATURE:
<221> NAME/KEY: MISC_FEATURE
<223> OTHER INFORMATION: fr11 - 2021.10

<400> SEQUENCE: 330

Pro Ser Ile Ile Ile Thr Gly Thr Gln Leu Tyr
1               5                   10

<210> SEQ ID NO 331
<211> LENGTH: 10
<212> TYPE: PRT
<213> ORGANISM: Homo sapiens
<220> FEATURE:
<221> NAME/KEY: MISC_FEATURE
<223> OTHER INFORMATION: fr11 - 2021.11

<400> SEQUENCE: 331

Ala Asn Thr Gly Thr Gln Ile Tyr Gly Arg
1               5                   10

<210> SEQ ID NO 332
<211> LENGTH: 10
<212> TYPE: PRT
<213> ORGANISM: Homo sapiens
<220> FEATURE:
<221> NAME/KEY: MISC_FEATURE
<223> OTHER INFORMATION: fr11 - 2021.11

<400> SEQUENCE: 332

Val Asn Thr Gly Thr Gln Ile Tyr Gly Arg
1               5                   10

<210> SEQ ID NO 333
<211> LENGTH: 5
<212> TYPE: PRT
<213> ORGANISM: Homo sapiens
<220> FEATURE:
```

```
<221> NAME/KEY: MISC_FEATURE
<223> OTHER INFORMATION: fr10 - 693.34

<400> SEQUENCE: 333

Phe Leu Glu Glu Arg
1               5

<210> SEQ ID NO 334
<211> LENGTH: 5
<212> TYPE: PRT
<213> ORGANISM: Homo sapiens
<220> FEATURE:
<221> NAME/KEY: MISC_FEATURE
<223> OTHER INFORMATION: fr10 - 709.36

<400> SEQUENCE: 334

Met Phe Leu Thr Arg
1               5

<210> SEQ ID NO 335
<211> LENGTH: 6
<212> TYPE: PRT
<213> ORGANISM: Homo sapiens
<220> FEATURE:
<221> NAME/KEY: MISC_FEATURE
<223> OTHER INFORMATION: fr10 - 848.42

<400> SEQUENCE: 335

Phe Glu Glu Leu Leu Arg
1               5

<210> SEQ ID NO 336
<211> LENGTH: 8
<212> TYPE: PRT
<213> ORGANISM: Homo sapiens
<220> FEATURE:
<221> NAME/KEY: MISC_FEATURE
<223> OTHER INFORMATION: fr10 - 920.52

<400> SEQUENCE: 336

Ser Gly Phe Leu Glu Gly Leu Arg
1               5

<210> SEQ ID NO 337
<211> LENGTH: 6
<212> TYPE: PRT
<213> ORGANISM: Homo sapiens
<220> FEATURE:
<221> NAME/KEY: MISC_FEATURE
<223> OTHER INFORMATION: fr10 - 988.55

<400> SEQUENCE: 337

Ile Ser Ile Ser Asp Arg
1               5

<210> SEQ ID NO 338
<211> LENGTH: 8
<212> TYPE: PRT
<213> ORGANISM: Homo sapiens
<220> FEATURE:
<221> NAME/KEY: MISC_FEATURE
<223> OTHER INFORMATION: fr10 - 1016.48

<400> SEQUENCE: 338

Pro Tyr Pro Phe Val Val Pro Arg
1               5
```

```
<210> SEQ ID NO 339
<211> LENGTH: 5
<212> TYPE: PRT
<213> ORGANISM: Homo sapiens
<220> FEATURE:
<221> NAME/KEY: MISC_FEATURE
<223> OTHER INFORMATION: fr10 - 1018.50

<400> SEQUENCE: 339

Pro Glu Ala Phe Arg
1               5

<210> SEQ ID NO 340
<211> LENGTH: 4
<212> TYPE: PRT
<213> ORGANISM: Homo sapiens
<220> FEATURE:
<221> NAME/KEY: MISC_FEATURE
<223> OTHER INFORMATION: fr10 - 1027.46

<400> SEQUENCE: 340

Phe Ser Gln Glu
1

<210> SEQ ID NO 341
<211> LENGTH: 7
<212> TYPE: PRT
<213> ORGANISM: Homo sapiens
<220> FEATURE:
<221> NAME/KEY: MISC_FEATURE
<223> OTHER INFORMATION: fr10 - 1064.50

<400> SEQUENCE: 341

Gln Ser Gly Thr Leu Phe Arg
1               5

<210> SEQ ID NO 342
<211> LENGTH: 7
<212> TYPE: PRT
<213> ORGANISM: Homo sapiens
<220> FEATURE:
<221> NAME/KEY: MISC_FEATURE
<223> OTHER INFORMATION: fr10 - 1080.67

<400> SEQUENCE: 342

Gln Val Leu Leu Asp Ser Leu
1               5

<210> SEQ ID NO 343
<211> LENGTH: 9
<212> TYPE: PRT
<213> ORGANISM: Homo sapiens
<220> FEATURE:
<221> NAME/KEY: MISC_FEATURE
<223> OTHER INFORMATION: fr10 - 1103.84

<400> SEQUENCE: 343

Pro Leu Val Glu Leu Thr Phe Glu Arg
1               5

<210> SEQ ID NO 344
<211> LENGTH: 9
<212> TYPE: PRT
<213> ORGANISM: Homo sapiens
<220> FEATURE:
<221> NAME/KEY: MISC_FEATURE
<223> OTHER INFORMATION: fr10 - 1168.70

<400> SEQUENCE: 344
```

```
Asn Leu Gly Gly Leu Ala Val Ala Arg
1               5

<210> SEQ ID NO 345
<211> LENGTH: 9
<212> TYPE: PRT
<213> ORGANISM: Homo sapiens
<220> FEATURE:
<221> NAME/KEY: MISC_FEATURE
<223> OTHER INFORMATION: fr10 - 1171.67

<400> SEQUENCE: 345

Met Asn Leu Asn Leu Ala Val Ala Arg
1               5

<210> SEQ ID NO 346
<211> LENGTH: 10
<212> TYPE: PRT
<213> ORGANISM: Homo sapiens
<220> FEATURE:
<221> NAME/KEY: MISC_FEATURE
<223> OTHER INFORMATION: fr10 - 1202.66

<400> SEQUENCE: 346

Gln Val Thr Thr Leu Gln Asp Ser Leu Arg
1               5                   10

<210> SEQ ID NO 347
<211> LENGTH: 8
<212> TYPE: PRT
<213> ORGANISM: Homo sapiens
<220> FEATURE:
<221> NAME/KEY: MISC_FEATURE
<223> OTHER INFORMATION: fr10 - 1204.56

<400> SEQUENCE: 347

Asn Leu Val Leu Asn Ala Ala Arg
1               5

<210> SEQ ID NO 348
<211> LENGTH: 8
<212> TYPE: PRT
<213> ORGANISM: Homo sapiens
<220> FEATURE:
<221> NAME/KEY: MISC_FEATURE
<223> OTHER INFORMATION: fr10 - 1219.61

<400> SEQUENCE: 348

Thr Thr Leu Gln Asp Ser Leu Arg
1               5

<210> SEQ ID NO 349
<211> LENGTH: 8
<212> TYPE: PRT
<213> ORGANISM: Homo sapiens
<220> FEATURE:
<221> NAME/KEY: MISC_FEATURE
<223> OTHER INFORMATION: fr10 - 1299.62

<400> SEQUENCE: 349

Gln Val Trp Thr Gln Leu Leu Arg
1               5

<210> SEQ ID NO 350
<211> LENGTH: 11
<212> TYPE: PRT
<213> ORGANISM: Homo sapiens
```

```
<220> FEATURE:
<221> NAME/KEY: MISC_FEATURE
<223> OTHER INFORMATION: fr10 - 1416.69

<400> SEQUENCE: 350

Met Thr Asp Phe Leu Phe Thr Leu Cys Ala Arg
1               5                   10

<210> SEQ ID NO 351
<211> LENGTH: 10
<212> TYPE: PRT
<213> ORGANISM: Homo sapiens
<220> FEATURE:
<221> NAME/KEY: MISC_FEATURE
<223> OTHER INFORMATION: fr10 - 1519.83

<400> SEQUENCE: 351

Leu Val Phe Leu Gly Gln Ser Glu Ala Arg
1               5                   10

<210> SEQ ID NO 352
<211> LENGTH: 10
<212> TYPE: PRT
<213> ORGANISM: Homo sapiens
<220> FEATURE:
<221> NAME/KEY: MISC_FEATURE
<223> OTHER INFORMATION: Q9H4M9 - EH-domain containing protein 1

<400> SEQUENCE: 352

Met Phe Ser Trp Val Ser Lys Asp Ala Arg
1               5                   10

<210> SEQ ID NO 353
<211> LENGTH: 11
<212> TYPE: PRT
<213> ORGANISM: Homo sapiens
<220> FEATURE:
<221> NAME/KEY: MISC_FEATURE
<223> OTHER INFORMATION: Q13045 - flightless-I protein homolog

<400> SEQUENCE: 353

Met Glu Ala Thr Gly Val Leu Pro Phe Val Arg
1               5                   10

<210> SEQ ID NO 354
<211> LENGTH: 11
<212> TYPE: PRT
<213> ORGANISM: Homo sapiens
<220> FEATURE:
<221> NAME/KEY: MISC_FEATURE
<223> OTHER INFORMATION: P17987 - T-complex protein 1, alpha subunit

<400> SEQUENCE: 354

Met Glu Gly Pro Leu Ser Val Phe Gly Asp Arg
1               5                   10

<210> SEQ ID NO 355
<211> LENGTH: 11
<212> TYPE: PRT
<213> ORGANISM: Homo sapiens
<220> FEATURE:
<221> NAME/KEY: MISC_FEATURE
<223> OTHER INFORMATION: P14174 - macrophage migration inhibitory factor

<400> SEQUENCE: 355

Pro Met Phe Ile Val Asn Thr Asn Val Pro Arg
1               5                   10
```

```
<210> SEQ ID NO 356
<211> LENGTH: 11
<212> TYPE: PRT
<213> ORGANISM: Homo sapiens
<220> FEATURE:
<221> NAME/KEY: MISC_FEATURE
<223> OTHER INFORMATION: P09211 - glutathione S-transferase P

<400> SEQUENCE: 356

Pro Pro Tyr Thr Val Val Tyr Phe Pro Val Arg
1               5                   10

<210> SEQ ID NO 357
<211> LENGTH: 12
<212> TYPE: PRT
<213> ORGANISM: Homo sapiens
<220> FEATURE:
<221> NAME/KEY: MISC_FEATURE
<223> OTHER INFORMATION: P00354 - glyceraldehyde 3-phosphate
      dehydrogenase

<400> SEQUENCE: 357

Gly Lys Val Lys Val Gly Val Asp Gly Phe Gly Arg
1               5                   10

<210> SEQ ID NO 358
<211> LENGTH: 13
<212> TYPE: PRT
<213> ORGANISM: Homo sapiens
<220> FEATURE:
<221> NAME/KEY: MISC_FEATURE
<223> OTHER INFORMATION: P07108 - Acyl-CoA-binding protein (ACBP)

<400> SEQUENCE: 358

Ser Gln Ala Glu Phe Glu Lys Ala Ala Glu Glu Val Arg
1               5                   10

<210> SEQ ID NO 359
<211> LENGTH: 14
<212> TYPE: PRT
<213> ORGANISM: Homo sapiens
<220> FEATURE:
<221> NAME/KEY: MISC_FEATURE
<223> OTHER INFORMATION: Q93084 - sarcoplasmic/endoplasmic reticulum
      calcium ATPase 3

<400> SEQUENCE: 359

Met Glu Ala Ala His Leu Leu Pro Ala Ala Asp Val Leu Arg
1               5                   10

<210> SEQ ID NO 360
<211> LENGTH: 7
<212> TYPE: PRT
<213> ORGANISM: Homo sapiens
<220> FEATURE:
<221> NAME/KEY: MISC_FEATURE
<223> OTHER INFORMATION: P55273 - cyclin-dependent kinase 4 inhibitor D

<400> SEQUENCE: 360

Met Leu Leu Glu Glu Val Arg
1               5

<210> SEQ ID NO 361
<211> LENGTH: 7
<212> TYPE: PRT
<213> ORGANISM: Homo sapiens
<220> FEATURE:
<221> NAME/KEY: MISC_FEATURE
```

-continued

```
<223> OTHER INFORMATION: P48739 - phosphatidylinositol transfer
      protein B

<400> SEQUENCE: 361

Val Leu Ile Lys Glu Phe Arg
1               5

<210> SEQ ID NO 362
<211> LENGTH: 8
<212> TYPE: PRT
<213> ORGANISM: Homo sapiens
<220> FEATURE:
<221> NAME/KEY: MISC_FEATURE
<223> OTHER INFORMATION: Q05209 - protein-tyrosine phosphatase

<400> SEQUENCE: 362

Met Glu Gln Val Glu Ile Leu Arg
1               5

<210> SEQ ID NO 363
<211> LENGTH: 8
<212> TYPE: PRT
<213> ORGANISM: Homo sapiens
<220> FEATURE:
<221> NAME/KEY: MISC_FEATURE
<223> OTHER INFORMATION: P06733 - alpha enolase (EC 4.2.1.11)

<400> SEQUENCE: 363

Ser Ile Leu Lys Ile His Ala Arg
1               5

<210> SEQ ID NO 364
<211> LENGTH: 9
<212> TYPE: PRT
<213> ORGANISM: Homo sapiens
<220> FEATURE:
<221> NAME/KEY: MISC_FEATURE
<223> OTHER INFORMATION: P18669 - phosphoglycerate mutase, brain form

<400> SEQUENCE: 364

Ala Ala Tyr Lys Leu Val Leu Ile Arg
1               5

<210> SEQ ID NO 365
<211> LENGTH: 9
<212> TYPE: PRT
<213> ORGANISM: Homo sapiens
<220> FEATURE:
<221> NAME/KEY: MISC_FEATURE
<223> OTHER INFORMATION: Q13418 - integrin-linked protein kinase 1

<400> SEQUENCE: 365

Met Asp Asp Ile Phe Thr Gln Cys Arg
1               5

<210> SEQ ID NO 366
<211> LENGTH: 9
<212> TYPE: PRT
<213> ORGANISM: Homo sapiens
<220> FEATURE:
<221> NAME/KEY: MISC_FEATURE
<223> OTHER INFORMATION: P17858 - 6-phosphofructokinase, liver type

<400> SEQUENCE: 366

Ala Ala Val Asp Leu Glu Lys Leu Arg
1               5
```

```
<210> SEQ ID NO 367
<211> LENGTH: 9
<212> TYPE: PRT
<213> ORGANISM: Homo sapiens
<220> FEATURE:
<221> NAME/KEY: MISC_FEATURE
<223> OTHER INFORMATION: Q05940 - synaptic vesicle amine transporter

<400> SEQUENCE: 367

Ala Leu Ser Glu Leu Ala Leu Val Arg
1               5

<210> SEQ ID NO 368
<211> LENGTH: 10
<212> TYPE: PRT
<213> ORGANISM: Homo sapiens
<220> FEATURE:
<221> NAME/KEY: MISC_FEATURE
<223> OTHER INFORMATION: P46966 - defender against cell death 1 (DAD-1)

<400> SEQUENCE: 368

Ser Ala Ser Val Val Ser Val Ile Ser Arg
1               5                   10

<210> SEQ ID NO 369
<211> LENGTH: 11
<212> TYPE: PRT
<213> ORGANISM: Homo sapiens
<220> FEATURE:
<221> NAME/KEY: MISC_FEATURE
<223> OTHER INFORMATION: P12324 - tropomyosin, cytoskeletal type

<400> SEQUENCE: 369

Ala Gly Ile Thr Thr Ile Glu Ala Val Lys Arg
1               5                   10

<210> SEQ ID NO 370
<211> LENGTH: 10
<212> TYPE: PRT
<213> ORGANISM: Homo sapiens
<220> FEATURE:
<221> NAME/KEY: MISC_FEATURE
<223> OTHER INFORMATION: P07226 - tropomyosin, fibroblast non-muscle
      type

<400> SEQUENCE: 370

Ala Gly Leu Asn Ser Leu Glu Ala Val Lys
1               5                   10

<210> SEQ ID NO 371
<211> LENGTH: 12
<212> TYPE: PRT
<213> ORGANISM: Homo sapiens
<220> FEATURE:
<221> NAME/KEY: MISC_FEATURE
<223> OTHER INFORMATION: P27708 - CAD protein

<400> SEQUENCE: 371

Ala Ala Leu Val Leu Glu Asp Gly Ser Val Leu Arg
1               5                   10

<210> SEQ ID NO 372
<211> LENGTH: 13
<212> TYPE: PRT
<213> ORGANISM: Homo sapiens
<220> FEATURE:
<221> NAME/KEY: MISC_FEATURE
<223> OTHER INFORMATION: P47756 - F-actin capping protein beta subunit
```

-continued

<400> SEQUENCE: 372

Ser Asp Gln Gln Leu Asp Cys Ala Leu Asp Leu Met Arg
1               5                   10

<210> SEQ ID NO 373
<211> LENGTH: 16
<212> TYPE: PRT
<213> ORGANISM: Homo sapiens
<220> FEATURE:
<221> NAME/KEY: MISC_FEATURE
<223> OTHER INFORMATION: O00151 - PDZ and LIM domain protein 1

<400> SEQUENCE: 373

Thr Thr Gln Gln Ile Asp Leu Gln Gly Pro Gly Pro Trp Gly Phe Arg
1               5                   10                  15

<210> SEQ ID NO 374
<211> LENGTH: 18
<212> TYPE: PRT
<213> ORGANISM: Homo sapiens
<220> FEATURE:
<221> NAME/KEY: MISC_FEATURE
<223> OTHER INFORMATION: O60234 - glia maturation factor gamma

<400> SEQUENCE: 374

Ser Asp Ser Leu Val Val Cys Glu Val Asp Pro Glu Leu Thr Glu Lys
1               5                   10                  15

Leu Arg

<210> SEQ ID NO 375
<211> LENGTH: 27
<212> TYPE: PRT
<213> ORGANISM: Homo sapiens
<220> FEATURE:
<221> NAME/KEY: MISC_FEATURE
<223> OTHER INFORMATION: P02570 - actin, cytoplasmic 1 (beta-actin)

<400> SEQUENCE: 375

Asp Asp Asp Ile Ala Ala Leu Val Val Asp Asn Gly Ser Gly Met Cys
1               5                   10                  15

Lys Ala Gly Phe Ala Gly Asp Asp Ala Pro Arg
                20                  25

<210> SEQ ID NO 376
<211> LENGTH: 19
<212> TYPE: PRT
<213> ORGANISM: Homo sapiens
<220> FEATURE:
<221> NAME/KEY: MISC_FEATURE
<223> OTHER INFORMATION: P02775 - low affinity platelet factor IV
      (LA-PF4)

<400> SEQUENCE: 376

Asn Leu Ala Lys Gly Lys Glu Glu Ser Leu Asp Ser Asp Leu Tyr Ala
1               5                   10                  15

Glu Leu Arg

<210> SEQ ID NO 377
<211> LENGTH: 7
<212> TYPE: PRT
<213> ORGANISM: Homo sapiens
<220> FEATURE:
<221> NAME/KEY: MISC_FEATURE
<223> OTHER INFORMATION: Q12768 - hypothetical protein KIAA0196

<400> SEQUENCE: 377

```
Met Leu Val Ser Tyr Tyr Arg
1               5

<210> SEQ ID NO 378
<211> LENGTH: 5
<212> TYPE: PRT
<213> ORGANISM: Homo sapiens
<220> FEATURE:
<221> NAME/KEY: MISC_FEATURE
<223> OTHER INFORMATION: FR9 - 999,46
<220> FEATURE:
<221> NAME/KEY: MISC_FEATURE
<222> LOCATION: (4)..(4)
<223> OTHER INFORMATION: K represents acetylated lysine

<400> SEQUENCE: 378

Ser Asn Asp Lys Arg
1               5

<210> SEQ ID NO 379
<211> LENGTH: 6
<212> TYPE: PRT
<213> ORGANISM: Homo sapiens
<220> FEATURE:
<221> NAME/KEY: MISC_FEATURE
<223> OTHER INFORMATION: FR9 - 1049,46

<400> SEQUENCE: 379

Pro Phe Val Val Pro Arg
1               5

<210> SEQ ID NO 380
<211> LENGTH: 5
<212> TYPE: PRT
<213> ORGANISM: Homo sapiens
<220> FEATURE:
<221> NAME/KEY: MISC_FEATURE
<223> OTHER INFORMATION: FR9 - 1085,42

<400> SEQUENCE: 380

Asp Val Asn Leu Ala
1               5

<210> SEQ ID NO 381
<211> LENGTH: 7
<212> TYPE: PRT
<213> ORGANISM: Homo sapiens
<220> FEATURE:
<221> NAME/KEY: MISC_FEATURE
<223> OTHER INFORMATION: FR9 - 1140,44
<220> FEATURE:
<221> NAME/KEY: MISC_FEATURE
<222> LOCATION: (2)..(2)
<223> OTHER INFORMATION: K represents acetylated lysine

<400> SEQUENCE: 381

Pro Lys Asp Val Leu Val Arg
1               5

<210> SEQ ID NO 382
<211> LENGTH: 8
<212> TYPE: PRT
<213> ORGANISM: Homo sapiens
<220> FEATURE:
<221> NAME/KEY: MISC_FEATURE
<223> OTHER INFORMATION: FR9 - 1152,46

<400> SEQUENCE: 382
```

-continued

```
Glu Leu Ser Ala Glu Tyr Leu Arg
1               5

<210> SEQ ID NO 383
<211> LENGTH: 4
<212> TYPE: PRT
<213> ORGANISM: Homo sapiens
<220> FEATURE:
<221> NAME/KEY: MISC_FEATURE
<223> OTHER INFORMATION: FR9 - 1157,48

<400> SEQUENCE: 383

Ala Ser His Arg
1

<210> SEQ ID NO 384
<211> LENGTH: 6
<212> TYPE: PRT
<213> ORGANISM: Homo sapiens
<220> FEATURE:
<221> NAME/KEY: MISC_FEATURE
<223> OTHER INFORMATION: FR9 - 1186,48

<400> SEQUENCE: 384

Asp Leu Leu Ser Thr Val
1               5

<210> SEQ ID NO 385
<211> LENGTH: 8
<212> TYPE: PRT
<213> ORGANISM: Homo sapiens
<220> FEATURE:
<221> NAME/KEY: MISC_FEATURE
<223> OTHER INFORMATION: FR9 - 1224,4

<400> SEQUENCE: 385

Thr Asn Phe Val Gln Val Leu Arg
1               5

<210> SEQ ID NO 386
<211> LENGTH: 9
<212> TYPE: PRT
<213> ORGANISM: Homo sapiens
<220> FEATURE:
<221> NAME/KEY: MISC_FEATURE
<223> OTHER INFORMATION: FR9 - 1245,54
<220> FEATURE:
<221> NAME/KEY: MISC_FEATURE
<222> LOCATION: (3)..(3)
<223> OTHER INFORMATION: K represents acetylated lysine

<400> SEQUENCE: 386

Leu Leu Lys Gly Leu Leu Ala Asn Arg
1               5

<210> SEQ ID NO 387
<211> LENGTH: 4
<212> TYPE: PRT
<213> ORGANISM: Homo sapiens
<220> FEATURE:
<221> NAME/KEY: MISC_FEATURE
<223> OTHER INFORMATION: FR9 - 1258,4

<400> SEQUENCE: 387

Asp Asp Leu Phe
1

<210> SEQ ID NO 388
```

```
<211> LENGTH: 4
<212> TYPE: PRT
<213> ORGANISM: Homo sapiens
<220> FEATURE:
<221> NAME/KEY: MISC_FEATURE
<223> OTHER INFORMATION: FR9 - 1294,46

<400> SEQUENCE: 388

Thr Trp Phe Val
1

<210> SEQ ID NO 389
<211> LENGTH: 8
<212> TYPE: PRT
<213> ORGANISM: Homo sapiens
<220> FEATURE:
<221> NAME/KEY: MISC_FEATURE
<223> OTHER INFORMATION: FR9 - 1299,48

<400> SEQUENCE: 389

Ala Ala Gln Glu Glu Pro Tyr Arg
1               5

<210> SEQ ID NO 390
<211> LENGTH: 5
<212> TYPE: PRT
<213> ORGANISM: Homo sapiens
<220> FEATURE:
<221> NAME/KEY: MISC_FEATURE
<223> OTHER INFORMATION: FR9 - 1347,59

<400> SEQUENCE: 390

Asn Ser His Leu Arg
1               5

<210> SEQ ID NO 391
<211> LENGTH: 11
<212> TYPE: PRT
<213> ORGANISM: Homo sapiens
<220> FEATURE:
<221> NAME/KEY: MISC_FEATURE
<223> OTHER INFORMATION: FR9 - 1354,6
<220> FEATURE:
<221> NAME/KEY: MISC_FEATURE
<222> LOCATION: (1)..(1)
<223> OTHER INFORMATION: K represents acetyled lysine
<220> FEATURE:
<221> NAME/KEY: MISC_FEATURE
<222> LOCATION: (5)..(5)
<223> OTHER INFORMATION: K represents acetyled lysine

<400> SEQUENCE: 391

Lys Leu Gly Thr Lys Leu Val Ser Val Glu Arg
1               5                   10

<210> SEQ ID NO 392
<211> LENGTH: 7
<212> TYPE: PRT
<213> ORGANISM: Homo sapiens
<220> FEATURE:
<221> NAME/KEY: MISC_FEATURE
<223> OTHER INFORMATION: FR9 - 1372,66
<220> FEATURE:
<221> NAME/KEY: MISC_FEATURE
<222> LOCATION: (4)..(4)
<223> OTHER INFORMATION: X can be any amino acid

<400> SEQUENCE: 392

Leu Thr Ala Xaa Met Val Leu
1               5
```

<210> SEQ ID NO 393
<211> LENGTH: 9
<212> TYPE: PRT
<213> ORGANISM: Homo sapiens
<220> FEATURE:
<221> NAME/KEY: MISC_FEATURE
<223> OTHER INFORMATION: FR9 - 1383,54

<400> SEQUENCE: 393

Glu Val Glu Pro Gln Leu Leu Thr Arg
1               5

<210> SEQ ID NO 394
<211> LENGTH: 8
<212> TYPE: PRT
<213> ORGANISM: Homo sapiens
<220> FEATURE:
<221> NAME/KEY: MISC_FEATURE
<223> OTHER INFORMATION: FR9 - 1401,6
<220> FEATURE:
<221> NAME/KEY: MISC_FEATURE
<222> LOCATION: (3)..(4)
<223> OTHER INFORMATION: X can be any amino acid

<400> SEQUENCE: 394

Val Glu Xaa Xaa Val His Thr Arg
1               5

<210> SEQ ID NO 395
<211> LENGTH: 8
<212> TYPE: PRT
<213> ORGANISM: Homo sapiens
<220> FEATURE:
<221> NAME/KEY: MISC_FEATURE
<223> OTHER INFORMATION: FR9 - 1435,76
<220> FEATURE:
<221> NAME/KEY: MISC_FEATURE
<222> LOCATION: (4)..(4)
<223> OTHER INFORMATION: K represents acetylated lysine

<400> SEQUENCE: 395

Ser Ala Gly Lys Leu Trp Asn Arg
1               5

<210> SEQ ID NO 396
<211> LENGTH: 9
<212> TYPE: PRT
<213> ORGANISM: Homo sapiens
<220> FEATURE:
<221> NAME/KEY: MISC_FEATURE
<223> OTHER INFORMATION: FR9 - 1442,54

<400> SEQUENCE: 396

Glu Val Glu Asn Gln Leu Leu Thr Arg
1               5

<210> SEQ ID NO 397
<211> LENGTH: 9
<212> TYPE: PRT
<213> ORGANISM: Homo sapiens
<220> FEATURE:
<221> NAME/KEY: MISC_FEATURE
<223> OTHER INFORMATION: FR9 - 1480,38

<400> SEQUENCE: 397

Gln Tyr Val Tyr Asn Val Asp Gln Arg
1               5

-continued

```
<210> SEQ ID NO 398
<211> LENGTH: 10
<212> TYPE: PRT
<213> ORGANISM: Homo sapiens
<220> FEATURE:
<221> NAME/KEY: MISC_FEATURE
<223> OTHER INFORMATION: FR9 - 1497,58
<220> FEATURE:
<221> NAME/KEY: MISC_FEATURE
<222> LOCATION: (6)..(6)
<223> OTHER INFORMATION: k represents acetylated lysine

<400> SEQUENCE: 398

Asp Thr Phe Thr Val Lys Tyr Thr Pro Arg
1               5                   10

<210> SEQ ID NO 399
<211> LENGTH: 10
<212> TYPE: PRT
<213> ORGANISM: Homo sapiens
<220> FEATURE:
<221> NAME/KEY: MISC_FEATURE
<223> OTHER INFORMATION: FR9 - 1551,62

<400> SEQUENCE: 399

Asp Asn Glu Glu Gly Phe Phe Ser Ala Arg
1               5                   10

<210> SEQ ID NO 400
<211> LENGTH: 12
<212> TYPE: PRT
<213> ORGANISM: Homo sapiens
<220> FEATURE:
<221> NAME/KEY: MISC_FEATURE
<223> OTHER INFORMATION: FR9 - 1562,48

<400> SEQUENCE: 400

Ala Pro Glu Glu Glu Asp His Val Leu Val Leu Arg
1               5                   10

<210> SEQ ID NO 401
<211> LENGTH: 12
<212> TYPE: PRT
<213> ORGANISM: Homo sapiens
<220> FEATURE:
<221> NAME/KEY: MISC_FEATURE
<223> OTHER INFORMATION: FR9 - 1575,86

<400> SEQUENCE: 401

Tyr Val Thr Leu Ala Gln Ala Glu Gln Ala Glu Arg
1               5                   10

<210> SEQ ID NO 402
<211> LENGTH: 10
<212> TYPE: PRT
<213> ORGANISM: Homo sapiens
<220> FEATURE:
<221> NAME/KEY: MISC_FEATURE
<223> OTHER INFORMATION: FR9 - 1576,72
<220> FEATURE:
<221> NAME/KEY: MISC_FEATURE
<222> LOCATION: (4)..(4)
<223> OTHER INFORMATION: k represents acetylated lysine

<400> SEQUENCE: 402

Glu Phe Glu Lys Ala Ala Glu Glu Val Arg
1               5                   10
```

```
<210> SEQ ID NO 403
<211> LENGTH: 6
<212> TYPE: PRT
<213> ORGANISM: Homo sapiens
<220> FEATURE:
<221> NAME/KEY: MISC_FEATURE
<223> OTHER INFORMATION: FR9 - 1585,96

<400> SEQUENCE: 403

Glu Trp Pro Leu Asn Ala
1               5

<210> SEQ ID NO 404
<211> LENGTH: 11
<212> TYPE: PRT
<213> ORGANISM: Homo sapiens
<220> FEATURE:
<221> NAME/KEY: MISC_FEATURE
<223> OTHER INFORMATION: FR9 - 1628,68

<400> SEQUENCE: 404

Leu Thr Asp Ala Ala Thr Val Ser Gln Glu Arg
1               5                   10

<210> SEQ ID NO 405
<211> LENGTH: 8
<212> TYPE: PRT
<213> ORGANISM: Homo sapiens
<220> FEATURE:
<221> NAME/KEY: MISC_FEATURE
<223> OTHER INFORMATION: FR9 - 1646,72
<220> FEATURE:
<221> NAME/KEY: MISC_FEATURE
<222> LOCATION: (2)..(2)
<223> OTHER INFORMATION: X can be any amino acid
<220> FEATURE:
<221> NAME/KEY: MISC_FEATURE
<222> LOCATION: (7)..(7)
<223> OTHER INFORMATION: k represents acetylated lysine

<400> SEQUENCE: 405

Val Xaa Glu Ala Gln Ser Lys Arg
1               5

<210> SEQ ID NO 406
<211> LENGTH: 11
<212> TYPE: PRT
<213> ORGANISM: Homo sapiens
<220> FEATURE:
<221> NAME/KEY: MISC_FEATURE
<223> OTHER INFORMATION: FR9 - 1680,52

<400> SEQUENCE: 406

Leu Glu Leu Thr Asp Asp Asn Phe Glu Ser Arg
1               5                   10

<210> SEQ ID NO 407
<211> LENGTH: 14
<212> TYPE: PRT
<213> ORGANISM: Homo sapiens
<220> FEATURE:
<221> NAME/KEY: MISC_FEATURE
<223> OTHER INFORMATION: FR9 - 1719,6

<400> SEQUENCE: 407

Gln Thr Gly Thr Ala Glu Phe Ser Ser Leu Leu Glu Glu Arg
1               5                   10

<210> SEQ ID NO 408
```

```
<211> LENGTH: 11
<212> TYPE: PRT
<213> ORGANISM: Homo sapiens
<220> FEATURE:
<221> NAME/KEY: MISC_FEATURE
<223> OTHER INFORMATION: FR9 - 1770,84
<220> FEATURE:
<221> NAME/KEY: MISC_FEATURE
<222> LOCATION: (4)..(4)
<223> OTHER INFORMATION: k represents acetylated lysine
<220> FEATURE:
<221> NAME/KEY: MISC_FEATURE
<222> LOCATION: (5)..(5)
<223> OTHER INFORMATION: X can be any amino acid
<220> FEATURE:
<221> NAME/KEY: MISC_FEATURE
<222> LOCATION: (8)..(9)
<223> OTHER INFORMATION: X can be any amino acid

<400> SEQUENCE: 408

Val Thr Ser Lys Xaa Val Leu Xaa Xaa Leu Arg
1               5                   10

<210> SEQ ID NO 409
<211> LENGTH: 5
<212> TYPE: PRT
<213> ORGANISM: Homo sapiens
<220> FEATURE:
<221> NAME/KEY: MISC_FEATURE
<223> OTHER INFORMATION: FR10 - 1017,48

<400> SEQUENCE: 409

Pro Glu Ala Phe Arg
1               5

<210> SEQ ID NO 410
<211> LENGTH: 6
<212> TYPE: PRT
<213> ORGANISM: Homo sapiens
<220> FEATURE:
<221> NAME/KEY: MISC_FEATURE
<223> OTHER INFORMATION: FR10 - 1102,56

<400> SEQUENCE: 410

Pro Leu Val Glu Thr Leu
1               5

<210> SEQ ID NO 411
<211> LENGTH: 7
<212> TYPE: PRT
<213> ORGANISM: Homo sapiens
<220> FEATURE:
<221> NAME/KEY: MISC_FEATURE
<223> OTHER INFORMATION: FR10 - 1187,56
<220> FEATURE:
<221> NAME/KEY: MISC_FEATURE
<222> LOCATION: (4)..(5)
<223> OTHER INFORMATION: k represents acetylated lysine

<400> SEQUENCE: 411

Pro Leu Gly Lys Lys Ala Arg
1               5

<210> SEQ ID NO 412
<211> LENGTH: 6
<212> TYPE: PRT
<213> ORGANISM: Homo sapiens
<220> FEATURE:
<221> NAME/KEY: MISC_FEATURE
<223> OTHER INFORMATION: FR10 - 1298,7
```

```
<400> SEQUENCE: 412

Trp Thr Gln Leu Leu Arg
1               5

<210> SEQ ID NO 413
<211> LENGTH: 5
<212> TYPE: PRT
<213> ORGANISM: Homo sapiens
<220> FEATURE:
<221> NAME/KEY: MISC_FEATURE
<223> OTHER INFORMATION: FR10 - 1306,72

<400> SEQUENCE: 413

Thr Val Phe Asp Glu
1               5

<210> SEQ ID NO 414
<211> LENGTH: 7
<212> TYPE: PRT
<213> ORGANISM: Homo sapiens
<220> FEATURE:
<221> NAME/KEY: MISC_FEATURE
<223> OTHER INFORMATION: FR10 - 1441,64

<400> SEQUENCE: 414

Leu Gly Glu Phe Val Ser Glu
1               5

<210> SEQ ID NO 415
<211> LENGTH: 5
<212> TYPE: PRT
<213> ORGANISM: Homo sapiens
<220> FEATURE:
<221> NAME/KEY: MISC_FEATURE
<223> OTHER INFORMATION: FR10 - 1518,8

<400> SEQUENCE: 415

Leu Val Phe Leu Gly
1               5

<210> SEQ ID NO 416
<211> LENGTH: 13
<212> TYPE: PRT
<213> ORGANISM: Homo sapiens
<220> FEATURE:
<221> NAME/KEY: MISC_FEATURE
<223> OTHER INFORMATION: FR10 - 1523,36
<220> FEATURE:
<221> NAME/KEY: MISC_FEATURE
<222> LOCATION: (3)..(3)
<223> OTHER INFORMATION: k represents acetylated lysine
<220> FEATURE:
<221> NAME/KEY: MISC_FEATURE
<222> LOCATION: (5)..(5)
<223> OTHER INFORMATION: k represents acetylated lysine

<400> SEQUENCE: 416

Val Gln Lys Ala Lys Leu Ala Glu Ala Gln Ala Glu Arg
1               5                   10

<210> SEQ ID NO 417
<211> LENGTH: 9
<212> TYPE: PRT
<213> ORGANISM: Homo sapiens
<220> FEATURE:
<221> NAME/KEY: MISC_FEATURE
<223> OTHER INFORMATION: FR10 - 1546,06

<400> SEQUENCE: 417
```

```
Glu Ala Leu Glu Glu Thr Glu Gln Pro
1               5

<210> SEQ ID NO 418
<211> LENGTH: 6
<212> TYPE: PRT
<213> ORGANISM: Homo sapiens
<220> FEATURE:
<221> NAME/KEY: MISC_FEATURE
<223> OTHER INFORMATION: FR10 - 1564,76

<400> SEQUENCE: 418

Glu Ala Ala His Leu Leu
1               5

<210> SEQ ID NO 419
<211> LENGTH: 11
<212> TYPE: PRT
<213> ORGANISM: Homo sapiens
<220> FEATURE:
<221> NAME/KEY: MISC_FEATURE
<223> OTHER INFORMATION: FR10 - 1570,7
<220> FEATURE:
<221> NAME/KEY: MISC_FEATURE
<222> LOCATION: (1)..(1)
<223> OTHER INFORMATION: k represents acetylated lysine
<220> FEATURE:
<221> NAME/KEY: MISC_FEATURE
<222> LOCATION: (4)..(5)
<223> OTHER INFORMATION: k represents acetylated lysine

<400> SEQUENCE: 419

Lys Ser Leu Lys Lys Leu Val Glu Glu Ser Arg
1               5                   10

<210> SEQ ID NO 420
<211> LENGTH: 9
<212> TYPE: PRT
<213> ORGANISM: Homo sapiens
<220> FEATURE:
<221> NAME/KEY: MISC_FEATURE
<223> OTHER INFORMATION: FR10 - 1609,6

<400> SEQUENCE: 420

Glu Pro Glu Leu Trp Phe Val Ser Glu
1               5

<210> SEQ ID NO 421
<211> LENGTH: 9
<212> TYPE: PRT
<213> ORGANISM: Homo sapiens
<220> FEATURE:
<221> NAME/KEY: MISC_FEATURE
<223> OTHER INFORMATION: FR10 - 1624,68

<400> SEQUENCE: 421

Ala Phe Leu Leu Asp Asp Leu Ser Glu
1               5

<210> SEQ ID NO 422
<211> LENGTH: 9
<212> TYPE: PRT
<213> ORGANISM: Homo sapiens
<220> FEATURE:
<221> NAME/KEY: MISC_FEATURE
<223> OTHER INFORMATION: FR10 - 1703,84
<220> FEATURE:
<221> NAME/KEY: MISC_FEATURE
<222> LOCATION: (9)..(9)
```

<223> OTHER INFORMATION: k represents acetylated lysine

<400> SEQUENCE: 422

Glu Val Leu Phe Asp Glu Val Val Lys
1               5

<210> SEQ ID NO 423
<211> LENGTH: 9
<212> TYPE: PRT
<213> ORGANISM: Homo sapiens
<220> FEATURE:
<221> NAME/KEY: MISC_FEATURE
<223> OTHER INFORMATION: FR10 - 1705,9
<220> FEATURE:
<221> NAME/KEY: MISC_FEATURE
<222> LOCATION: (9)..(9)
<223> OTHER INFORMATION: k represents acetylated lysine

<400> SEQUENCE: 423

Glu Asp Leu Met Leu Glu Val Val Lys
1               5

<210> SEQ ID NO 424
<211> LENGTH: 13
<212> TYPE: PRT
<213> ORGANISM: Homo sapiens
<220> FEATURE:
<221> NAME/KEY: MISC_FEATURE
<223> OTHER INFORMATION: FR10 - 1730,7

<400> SEQUENCE: 424

Pro Ala Ser Leu Val Val Ala Ala Glu Glu Gly Glu Arg
1               5                   10

<210> SEQ ID NO 425
<211> LENGTH: 15
<212> TYPE: PRT
<213> ORGANISM: Homo sapiens
<220> FEATURE:
<221> NAME/KEY: MISC_FEATURE
<223> OTHER INFORMATION: FR10 - 2044,88
<220> FEATURE:
<221> NAME/KEY: MISC_FEATURE
<222> LOCATION: (11)..(11)
<223> OTHER INFORMATION: k represents acetylated lysine

<400> SEQUENCE: 425

Val Glu Trp Leu Ala Glu Glu Ala Ala Glu Lys Ala Thr Ser Arg
1               5                   10                  15

<210> SEQ ID NO 426
<211> LENGTH: 5
<212> TYPE: PRT
<213> ORGANISM: Homo sapiens
<220> FEATURE:
<221> NAME/KEY: MISC_FEATURE
<223> OTHER INFORMATION: Table XIX - 999.46
<220> FEATURE:
<221> NAME/KEY: MISC_FEATURE
<222> LOCATION: (4)..(4)
<223> OTHER INFORMATION: k represents acetylated lysine

<400> SEQUENCE: 426

Ser Asn Asp Lys Arg
1               5

<210> SEQ ID NO 427
<211> LENGTH: 5
<212> TYPE: PRT

<213> ORGANISM: Homo sapiens
<220> FEATURE:
<221> NAME/KEY: MISC_FEATURE
<223> OTHER INFORMATION: Table XIX - 1017.48

<400> SEQUENCE: 427

Pro Glu Ala Phe Arg
1               5

<210> SEQ ID NO 428
<211> LENGTH: 6
<212> TYPE: PRT
<213> ORGANISM: Homo sapiens
<220> FEATURE:
<221> NAME/KEY: MISC_FEATURE
<223> OTHER INFORMATION: Table XIX - 1049.46

<400> SEQUENCE: 428

Pro Phe Val Val Pro Arg
1               5

<210> SEQ ID NO 429
<211> LENGTH: 5
<212> TYPE: PRT
<213> ORGANISM: Homo sapiens
<220> FEATURE:
<221> NAME/KEY: MISC_FEATURE
<223> OTHER INFORMATION: Table XIX - 1085.42

<400> SEQUENCE: 429

Asp Val Asn Leu Ala
1               5

<210> SEQ ID NO 430
<211> LENGTH: 6
<212> TYPE: PRT
<213> ORGANISM: Homo sapiens
<220> FEATURE:
<221> NAME/KEY: MISC_FEATURE
<223> OTHER INFORMATION: Table XIX - 1102.56

<400> SEQUENCE: 430

Pro Leu Val Glu Thr Leu
1               5

<210> SEQ ID NO 431
<211> LENGTH: 7
<212> TYPE: PRT
<213> ORGANISM: Homo sapiens
<220> FEATURE:
<221> NAME/KEY: MISC_FEATURE
<223> OTHER INFORMATION: Table XIX - 1140.44
<220> FEATURE:
<221> NAME/KEY: MISC_FEATURE
<222> LOCATION: (2)..(2)
<223> OTHER INFORMATION: k represents acetylated lysine

<400> SEQUENCE: 431

Pro Lys Asp Val Leu Val Arg
1               5

<210> SEQ ID NO 432
<211> LENGTH: 8
<212> TYPE: PRT
<213> ORGANISM: Homo sapiens
<220> FEATURE:
<221> NAME/KEY: MISC_FEATURE
<223> OTHER INFORMATION: Table XIX - 1152.46

```
<400> SEQUENCE: 432

Glu Leu Ser Ala Glu Tyr Leu Arg
1               5

<210> SEQ ID NO 433
<211> LENGTH: 4
<212> TYPE: PRT
<213> ORGANISM: Homo sapiens
<220> FEATURE:
<221> NAME/KEY: MISC_FEATURE
<223> OTHER INFORMATION: Table XIX - 1157.48

<400> SEQUENCE: 433

Ala Ser His Arg
1

<210> SEQ ID NO 434
<211> LENGTH: 6
<212> TYPE: PRT
<213> ORGANISM: Homo sapiens
<220> FEATURE:
<221> NAME/KEY: MISC_FEATURE
<223> OTHER INFORMATION: Table XIX - 1186.48

<400> SEQUENCE: 434

Asp Leu Leu Ser Thr Val
1               5

<210> SEQ ID NO 435
<211> LENGTH: 7
<212> TYPE: PRT
<213> ORGANISM: Homo sapiens
<220> FEATURE:
<221> NAME/KEY: MISC_FEATURE
<223> OTHER INFORMATION: Table XIX - 1187.56
<220> FEATURE:
<221> NAME/KEY: MISC_FEATURE
<222> LOCATION: (4)..(5)
<223> OTHER INFORMATION: k represents acetylated lysine

<400> SEQUENCE: 435

Pro Leu Gly Lys Lys Ala Arg
1               5

<210> SEQ ID NO 436
<211> LENGTH: 8
<212> TYPE: PRT
<213> ORGANISM: Homo sapiens
<220> FEATURE:
<221> NAME/KEY: MISC_FEATURE
<223> OTHER INFORMATION: Table XIX - 1224.40

<400> SEQUENCE: 436

Thr Asn Phe Val Gln Val Leu Arg
1               5

<210> SEQ ID NO 437
<211> LENGTH: 9
<212> TYPE: PRT
<213> ORGANISM: Homo sapiens
<220> FEATURE:
<221> NAME/KEY: MISC_FEATURE
<223> OTHER INFORMATION: Table XIX - 1245.54
<220> FEATURE:
<221> NAME/KEY: MISC_FEATURE
<222> LOCATION: (3)..(3)
<223> OTHER INFORMATION: k represents acetylated lysine

<400> SEQUENCE: 437
```

```
Leu Leu Lys Gly Leu Leu Ala Asn Arg
1               5

<210> SEQ ID NO 438
<211> LENGTH: 4
<212> TYPE: PRT
<213> ORGANISM: Homo sapiens
<220> FEATURE:
<221> NAME/KEY: MISC_FEATURE
<223> OTHER INFORMATION: FR10 - 1258.40

<400> SEQUENCE: 438

Asp Asp Leu Phe
1

<210> SEQ ID NO 439
<211> LENGTH: 4
<212> TYPE: PRT
<213> ORGANISM: Homo sapiens
<220> FEATURE:
<221> NAME/KEY: MISC_FEATURE
<223> OTHER INFORMATION: Table XIX - 1294.46

<400> SEQUENCE: 439

Thr Trp Phe Val
1

<210> SEQ ID NO 440
<211> LENGTH: 6
<212> TYPE: PRT
<213> ORGANISM: Homo sapiens
<220> FEATURE:
<221> NAME/KEY: MISC_FEATURE
<223> OTHER INFORMATION: Table XIX - 1298.70

<400> SEQUENCE: 440

Trp Thr Gln Leu Leu Arg
1               5

<210> SEQ ID NO 441
<211> LENGTH: 8
<212> TYPE: PRT
<213> ORGANISM: Homo sapiens
<220> FEATURE:
<221> NAME/KEY: MISC_FEATURE
<223> OTHER INFORMATION: Table XIX - 1299.48

<400> SEQUENCE: 441

Ala Ala Gln Glu Glu Pro Tyr Arg
1               5

<210> SEQ ID NO 442
<211> LENGTH: 5
<212> TYPE: PRT
<213> ORGANISM: Homo sapiens
<220> FEATURE:
<221> NAME/KEY: MISC_FEATURE
<223> OTHER INFORMATION: Table XIX - 1306.72

<400> SEQUENCE: 442

Thr Val Phe Asp Glu
1               5

<210> SEQ ID NO 443
<211> LENGTH: 5
<212> TYPE: PRT
<213> ORGANISM: Homo sapiens
```

```
<220> FEATURE:
<221> NAME/KEY: MISC_FEATURE
<223> OTHER INFORMATION: Table XIX - 1347.48

<400> SEQUENCE: 443

Asn Ser His Leu Arg
1               5

<210> SEQ ID NO 444
<211> LENGTH: 11
<212> TYPE: PRT
<213> ORGANISM: Homo sapiens
<220> FEATURE:
<221> NAME/KEY: MISC_FEATURE
<223> OTHER INFORMATION: Table XIX - 1354.60
<220> FEATURE:
<221> NAME/KEY: MISC_FEATURE
<222> LOCATION: (1)..(1)
<223> OTHER INFORMATION: k represents acetylated lysine
<220> FEATURE:
<221> NAME/KEY: MISC_FEATURE
<222> LOCATION: (5)..(5)
<223> OTHER INFORMATION: k represents acetylated lysine

<400> SEQUENCE: 444

Lys Leu Gly Thr Lys Leu Val Ser Val Glu Arg
1               5                   10

<210> SEQ ID NO 445
<211> LENGTH: 7
<212> TYPE: PRT
<213> ORGANISM: Homo sapiens
<220> FEATURE:
<221> NAME/KEY: MISC_FEATURE
<223> OTHER INFORMATION: Table XIX - 1372.66
<220> FEATURE:
<221> NAME/KEY: MISC_FEATURE
<222> LOCATION: (4)..(4)
<223> OTHER INFORMATION: X is an unassigned amino acid

<400> SEQUENCE: 445

Leu Thr Ala Xaa Met Val Leu
1               5

<210> SEQ ID NO 446
<211> LENGTH: 9
<212> TYPE: PRT
<213> ORGANISM: Homo sapiens
<220> FEATURE:
<221> NAME/KEY: MISC_FEATURE
<223> OTHER INFORMATION: Table XIX - 1383.54

<400> SEQUENCE: 446

Glu Val Glu Pro Gln Leu Leu Thr Arg
1               5

<210> SEQ ID NO 447
<211> LENGTH: 8
<212> TYPE: PRT
<213> ORGANISM: Homo sapiens
<220> FEATURE:
<221> NAME/KEY: MISC_FEATURE
<223> OTHER INFORMATION: Table XIX - 1401.60
<220> FEATURE:
<221> NAME/KEY: MISC_FEATURE
<222> LOCATION: (3)..(4)
<223> OTHER INFORMATION: X is an unassigned amino acid

<400> SEQUENCE: 447

Val Glu Xaa Xaa Val His Thr Arg
```

```
<210> SEQ ID NO 448
<211> LENGTH: 8
<212> TYPE: PRT
<213> ORGANISM: Homo sapiens
<220> FEATURE:
<221> NAME/KEY: MISC_FEATURE
<223> OTHER INFORMATION: Table XIX - 1435.76
<220> FEATURE:
<221> NAME/KEY: MISC_FEATURE
<222> LOCATION: (4)..(4)
<223> OTHER INFORMATION: k represents acetylated lysine

<400> SEQUENCE: 448

Ser Ala Gly Lys Leu Trp Asn Arg
1               5

<210> SEQ ID NO 449
<211> LENGTH: 7
<212> TYPE: PRT
<213> ORGANISM: Homo sapiens
<220> FEATURE:
<221> NAME/KEY: MISC_FEATURE
<223> OTHER INFORMATION: Table XIX - 1441.64

<400> SEQUENCE: 449

Leu Gly Glu Phe Val Ser Glu
1               5

<210> SEQ ID NO 450
<211> LENGTH: 9
<212> TYPE: PRT
<213> ORGANISM: Homo sapiens
<220> FEATURE:
<221> NAME/KEY: MISC_FEATURE
<223> OTHER INFORMATION: Table XIX - 1442.54

<400> SEQUENCE: 450

Glu Val Glu Asn Gln Leu Leu Thr Arg
1               5

<210> SEQ ID NO 451
<211> LENGTH: 9
<212> TYPE: PRT
<213> ORGANISM: Homo sapiens
<220> FEATURE:
<221> NAME/KEY: MISC_FEATURE
<223> OTHER INFORMATION: Table XIX - 1480.38

<400> SEQUENCE: 451

Gln Tyr Val Tyr Asn Val Asp Gln Arg
1               5

<210> SEQ ID NO 452
<211> LENGTH: 10
<212> TYPE: PRT
<213> ORGANISM: Homo sapiens
<220> FEATURE:
<221> NAME/KEY: MISC_FEATURE
<223> OTHER INFORMATION: Table XIX - 1497.58
<220> FEATURE:
<221> NAME/KEY: MISC_FEATURE
<222> LOCATION: (6)..(6)
<223> OTHER INFORMATION: k represents acetylated lysine

<400> SEQUENCE: 452

Asp Thr Phe Thr Val Lys Tyr Thr Pro Arg
1               5                   10
```

-continued

```
<210> SEQ ID NO 453
<211> LENGTH: 5
<212> TYPE: PRT
<213> ORGANISM: Homo sapiens
<220> FEATURE:
<221> NAME/KEY: MISC_FEATURE
<223> OTHER INFORMATION: Table XIX - 1518.80

<400> SEQUENCE: 453

Leu Val Phe Leu Gly
1               5

<210> SEQ ID NO 454
<211> LENGTH: 13
<212> TYPE: PRT
<213> ORGANISM: Homo sapiens
<220> FEATURE:
<221> NAME/KEY: MISC_FEATURE
<223> OTHER INFORMATION: Table XIX - 1523.36
<220> FEATURE:
<221> NAME/KEY: MISC_FEATURE
<222> LOCATION: (3)..(3)
<223> OTHER INFORMATION: k represents acetylated lysine
<220> FEATURE:
<221> NAME/KEY: MISC_FEATURE
<222> LOCATION: (5)..(5)
<223> OTHER INFORMATION: k represents acetylated lysine

<400> SEQUENCE: 454

Val Gln Lys Ala Lys Leu Ala Glu Ala Gln Ala Glu Arg
1               5                   10

<210> SEQ ID NO 455
<211> LENGTH: 9
<212> TYPE: PRT
<213> ORGANISM: Homo sapiens
<220> FEATURE:
<221> NAME/KEY: MISC_FEATURE
<223> OTHER INFORMATION: Table XIX - 1546.06

<400> SEQUENCE: 455

Glu Ala Leu Glu Glu Thr Glu Gln Pro
1               5

<210> SEQ ID NO 456
<211> LENGTH: 10
<212> TYPE: PRT
<213> ORGANISM: Homo sapiens
<220> FEATURE:
<221> NAME/KEY: MISC_FEATURE
<223> OTHER INFORMATION: Table XIX - 1551.62

<400> SEQUENCE: 456

Asp Asn Glu Glu Gly Phe Phe Ser Ala Arg
1               5                   10

<210> SEQ ID NO 457
<211> LENGTH: 12
<212> TYPE: PRT
<213> ORGANISM: Homo sapiens
<220> FEATURE:
<221> NAME/KEY: MISC_FEATURE
<223> OTHER INFORMATION: Table XIX - 1562.48

<400> SEQUENCE: 457

Ala Pro Glu Glu Glu Asp His Val Leu Val Leu Arg
1               5                   10
```

```
<210> SEQ ID NO 458
<211> LENGTH: 6
<212> TYPE: PRT
<213> ORGANISM: Homo sapiens
<220> FEATURE:
<221> NAME/KEY: MISC_FEATURE
<223> OTHER INFORMATION: Table XIX - 1564.76

<400> SEQUENCE: 458

Glu Ala Ala His Leu Leu
1               5

<210> SEQ ID NO 459
<211> LENGTH: 11
<212> TYPE: PRT
<213> ORGANISM: Homo sapiens
<220> FEATURE:
<221> NAME/KEY: MISC_FEATURE
<223> OTHER INFORMATION: Table XIX - 1570.70
<220> FEATURE:
<221> NAME/KEY: MISC_FEATURE
<222> LOCATION: (1)..(1)
<223> OTHER INFORMATION: k represents acetylated lysine
<220> FEATURE:
<221> NAME/KEY: MISC_FEATURE
<222> LOCATION: (4)..(5)
<223> OTHER INFORMATION: k represents acetylated lysine

<400> SEQUENCE: 459

Lys Ser Leu Lys Lys Leu Val Glu Glu Ser Arg
1               5                   10

<210> SEQ ID NO 460
<211> LENGTH: 12
<212> TYPE: PRT
<213> ORGANISM: Homo sapiens
<220> FEATURE:
<221> NAME/KEY: MISC_FEATURE
<223> OTHER INFORMATION: Table XIX - 1575.86

<400> SEQUENCE: 460

Tyr Val Thr Leu Ala Gln Ala Glu Gln Ala Glu Arg
1               5                   10

<210> SEQ ID NO 461
<211> LENGTH: 10
<212> TYPE: PRT
<213> ORGANISM: Homo sapiens
<220> FEATURE:
<221> NAME/KEY: MISC_FEATURE
<223> OTHER INFORMATION: Table XIX - 1576.72
<220> FEATURE:
<221> NAME/KEY: MISC_FEATURE
<222> LOCATION: (4)..(4)
<223> OTHER INFORMATION: k represents acetylated lysine

<400> SEQUENCE: 461

Glu Phe Glu Lys Ala Ala Glu Glu Val Arg
1               5                   10

<210> SEQ ID NO 462
<211> LENGTH: 6
<212> TYPE: PRT
<213> ORGANISM: Homo sapiens
<220> FEATURE:
<221> NAME/KEY: MISC_FEATURE
<223> OTHER INFORMATION: Table XIX - 1585.96

<400> SEQUENCE: 462
```

```
Glu Trp Pro Leu Asn Ala
1               5

<210> SEQ ID NO 463
<211> LENGTH: 9
<212> TYPE: PRT
<213> ORGANISM: Homo sapiens
<220> FEATURE:
<221> NAME/KEY: MISC_FEATURE
<223> OTHER INFORMATION: Table XIX - 1609.60

<400> SEQUENCE: 463

Glu Pro Glu Leu Trp Phe Val Ser Glu
1               5

<210> SEQ ID NO 464
<211> LENGTH: 9
<212> TYPE: PRT
<213> ORGANISM: Homo sapiens
<220> FEATURE:
<221> NAME/KEY: MISC_FEATURE
<223> OTHER INFORMATION: Table XIX - 1624.68

<400> SEQUENCE: 464

Ala Phe Leu Leu Asp Asp Leu Ser Glu
1               5

<210> SEQ ID NO 465
<211> LENGTH: 11
<212> TYPE: PRT
<213> ORGANISM: Homo sapiens
<220> FEATURE:
<221> NAME/KEY: MISC_FEATURE
<223> OTHER INFORMATION: Table XIX - 1628.68

<400> SEQUENCE: 465

Leu Thr Asp Ala Ala Thr Val Ser Gln Glu Arg
1               5                   10

<210> SEQ ID NO 466
<211> LENGTH: 8
<212> TYPE: PRT
<213> ORGANISM: Homo sapiens
<220> FEATURE:
<221> NAME/KEY: MISC_FEATURE
<223> OTHER INFORMATION: Table XIX - 1646.72
<220> FEATURE:
<221> NAME/KEY: MISC_FEATURE
<222> LOCATION: (2)..(2)
<223> OTHER INFORMATION: X is an unassigned amino acid
<220> FEATURE:
<221> NAME/KEY: MISC_FEATURE
<222> LOCATION: (7)..(7)
<223> OTHER INFORMATION: k represents acetylated lysine

<400> SEQUENCE: 466

Val Xaa Glu Ala Gln Ser Lys Arg
1               5

<210> SEQ ID NO 467
<211> LENGTH: 11
<212> TYPE: PRT
<213> ORGANISM: Homo sapiens
<220> FEATURE:
<221> NAME/KEY: MISC_FEATURE
<223> OTHER INFORMATION: Table XIX - 1680.52

<400> SEQUENCE: 467

Leu Glu Leu Thr Asp Asp Asn Phe Glu Ser Arg
```

```
<210> SEQ ID NO 468
<211> LENGTH: 9
<212> TYPE: PRT
<213> ORGANISM: Homo sapiens
<220> FEATURE:
<221> NAME/KEY: MISC_FEATURE
<223> OTHER INFORMATION: Table XIX - 1703.84
<220> FEATURE:
<221> NAME/KEY: MISC_FEATURE
<222> LOCATION: (9)..(9)
<223> OTHER INFORMATION: k represents acetylated lysine

<400> SEQUENCE: 468

Glu Val Leu Phe Asp Glu Val Val Lys
1               5

<210> SEQ ID NO 469
<211> LENGTH: 9
<212> TYPE: PRT
<213> ORGANISM: Homo sapiens
<220> FEATURE:
<221> NAME/KEY: MISC_FEATURE
<223> OTHER INFORMATION: Table XIX - 1705.90
<220> FEATURE:
<221> NAME/KEY: MISC_FEATURE
<222> LOCATION: (9)..(9)
<223> OTHER INFORMATION: k represents acetylated lysine

<400> SEQUENCE: 469

Glu Asp Leu Met Leu Glu Val Val Lys
1               5

<210> SEQ ID NO 470
<211> LENGTH: 14
<212> TYPE: PRT
<213> ORGANISM: Homo sapiens
<220> FEATURE:
<221> NAME/KEY: MISC_FEATURE
<223> OTHER INFORMATION: Table XIX - 1719.60

<400> SEQUENCE: 470

Gln Thr Gly Thr Ala Glu Phe Ser Ser Leu Leu Glu Glu Arg
1               5                   10

<210> SEQ ID NO 471
<211> LENGTH: 13
<212> TYPE: PRT
<213> ORGANISM: Homo sapiens
<220> FEATURE:
<221> NAME/KEY: MISC_FEATURE
<223> OTHER INFORMATION: Table XIX - 1730.70

<400> SEQUENCE: 471

Pro Ala Ser Leu Val Val Ala Ala Glu Glu Gly Glu Arg
1               5                   10

<210> SEQ ID NO 472
<211> LENGTH: 11
<212> TYPE: PRT
<213> ORGANISM: Homo sapiens
<220> FEATURE:
<221> NAME/KEY: MISC_FEATURE
<223> OTHER INFORMATION: Table XIX - 1770.84
<220> FEATURE:
<221> NAME/KEY: MISC_FEATURE
<222> LOCATION: (4)..(4)
<223> OTHER INFORMATION: k represents acetylated lysine
<220> FEATURE:
```

-continued

```
<221> NAME/KEY: MISC_FEATURE
<222> LOCATION: (5)..(5)
<223> OTHER INFORMATION: X is an unassigned amino acid
<220> FEATURE:
<221> NAME/KEY: MISC_FEATURE
<222> LOCATION: (8)..(9)
<223> OTHER INFORMATION: X is an unassigned amino acid

<400> SEQUENCE: 472

Val Thr Ser Lys Xaa Val Leu Xaa Xaa Leu Arg
1               5                   10

<210> SEQ ID NO 473
<211> LENGTH: 15
<212> TYPE: PRT
<213> ORGANISM: Homo sapiens
<220> FEATURE:
<221> NAME/KEY: MISC_FEATURE
<223> OTHER INFORMATION: Table XIX - 2044.88
<220> FEATURE:
<221> NAME/KEY: MISC_FEATURE
<222> LOCATION: (11)..(11)
<223> OTHER INFORMATION: k represents acetylated lysine

<400> SEQUENCE: 473

Val Glu Trp Leu Ala Glu Glu Ala Ala Glu Lys Ala Thr Ser Arg
1               5                   10                  15
```